US008765377B2

(12) United States Patent
Schaefer et al.

(10) Patent No.: US 8,765,377 B2

(45) Date of Patent: Jul. 1, 2014

(54) COMPOSITIONS AND METHODS FOR TREATING AND PREVENTING CORONARY HEART DISEASE

(71) Applicants: Ernst J. Schaefer, Natick, MA (US); Eliana Polisecki, Framingham, MA (US)

(72) Inventors: Ernst J. Schaefer, Natick, MA (US); Eliana Polisecki, Framingham, MA (US)

(73) Assignee: Boston Heart Diagnostics Corporation, Framingham, MA (US)

( * ) Notice: Subject to any disclaimer, the term of this patent is extended or adjusted under 35 U.S.C. 154(b) by 0 days.

(21) Appl. No.: 13/650,948

(22) Filed: Oct. 12, 2012

(65) Prior Publication Data

US 2013/0102582 A1 Apr. 25, 2013

Related U.S. Application Data

(60) Provisional application No. 61/546,802, filed on Oct. 13, 2011.

(51) Int. Cl.
*C12Q 1/68* (2006.01)
*C12Q 1/60* (2006.01)

(52) U.S. Cl.
CPC ........ *C12Q 1/6883* (2013.01); *C12Q 2600/106* (2013.01); *C12Q 2600/172* (2013.01); *C12Q 2600/156* (2013.01); *C12Q 1/6827* (2013.01)
USPC ............................ 435/6.11; 435/6.13; 435/11

(58) Field of Classification Search
None
See application file for complete search history.

(56) References Cited

U.S. PATENT DOCUMENTS

2005/0281868 A1 12/2005 Lane
2007/0031838 A1 2/2007 Ambrose et al.
2008/0293054 A1 11/2008 Medina et al.
2009/0197242 A1* 8/2009 Kaddurah-Daouk et al. .... 435/4
2010/0190172 A1 7/2010 Cargill et al.
2011/0269735 A1 11/2011 Shiffman et al.

OTHER PUBLICATIONS

Romaine SPR et al, The Influence of SLCO1B1 (OATP1B1) Gene Polymorphisms on Response to Statin Therapy, Pharmacogenom J 10: 1-11, 2010.*
Ordovas JM et al, The APOE Locus and the Pharmacogenetics of Lipid Response, Cur Opin Lipidol 13: 113-117, 2002.*
Uusitupa MIJ et al, Lathosterol and Other Noncholesterol Sterols During Treatment of Hypercholesterolemia With Lovastatin Alone and With Cholestyramine or Guar Gum, Arterioscler Thromb 12: 807-813, 1992.*
Gazi IF et al, Effect of Ezetimibe in Patients Who cannot Tolerate Statins or cannot Get to the Low Density Lipoprotein Cholesterol Target Despite Taking a Statin, Crur Med Res Opin 23: 2183-2192, 2007.*
Dullaart RPF et al, The Serum Lathosterol to Cholesterol Ratio, an Index of Cholesterol Synthesis,is Not Elevated in Patients With Glomerular Proteinuria and Is Not Associated With Improvement of Hyperlipidemia in Response to Antiproteinuric Treatment, Metabolism 45: 723-730, 1996.*
Generaux GT et al, Impact of SLCO1B1 (OATP1B1) and ABCG2 (BCRP) Genetic Polymorphisms and Inhibition on LDL-C Lowering and Myopathy of Statins, Xenobiot 41: 639-651, 2011.*
Couvert P et al, Association between a Frequent Allele of the Gene Encoding OATP1B1 and the Enhanced LDL-Lowering Response to Fluvastatin Therapy, Pharmacogenomics 9: 1217-1227, 2008.*
International Search Report and Written Opinion for PCT/US12/60014, dated Apr. 5, 2013, 9 pages.

* cited by examiner

*Primary Examiner* — Chris R Tate
*Assistant Examiner* — Douglas F White
(74) *Attorney, Agent, or Firm* — Thomas C. Meyers; Brown Rudnick LLP

(57) ABSTRACT

The invention pertains to a method of determining a statin dosage for an individual in need of treatment with a statin, comprising determining a SLCO1B1 genotype from a nucleic acid sample of the individual, said genotype comprising the presence or absence of the SLCO1B1-056 polymorphism, and determining an ApoE genotype or phenotype identifying an ApoE polymorphism selected from the group consisting of ApoE2, ApoE3, ApoE4, and any combination thereof, wherein the combination of a SLCO1B1 genotype identifying the presence of the SLCO1B1-056 C polymorphism and the ApoE genotype or phenotype identifying one of the ApoE3/4 or ApoE4/4 genotypes indicates the statin dosage.

13 Claims, 37 Drawing Sheets

FIG. 1 ApoE nucleic acid sequence (NCBI Accession No. NM_000041.2) (SEQ ID No. 68)

GGGATCCTTGAGTCCTACTCAGCCCCAGCGGAGGTGAAGGACGTCCTTCCCCAGGAGCCGACTGGCCAAT
CACAGGCAGGAAGATGAAGGTTCTGTGGGCTGCGTTGCTGGTCACATTCCTGGCAGGATGCCAGGCCAAG
GTGGAGCAAGCGGTGGAGACAGAGCCGGAGCCCGAGCTGCGCCAGCAGACCGAGTGGCAGAGCGGCCAGC
GCTGGGAACTGGCACTGGGTCGCTTTTGGGATTACCTGCGCTGGGTGCAGACACTGTCTGAGCAGGTGCA
GGAGGAGCTGCTCAGCTCCCAGGTCACCCAGGAACTGAGGGCGCTGATGGACGAGACCATGAAGGAGTTG
AAGGCCTACAAATCGGAACTGGAGGAACAACTGACCCCGGTGGCGGAGGAGACGCGGGCACGGCTGTCCA
AGGAGCTGCAGGCGGCGCAGGCCCGGCTGGGCGCGGACATGGAGGACGTGTGCGGCCGCCTGGTGCAGTA
CCGCGGCGAGGTGCAGGCCATGCTCGGCCAGAGCACCGAGGAGCTGCGGGTGCGCCTCGCCTCCCACCTG
CGCAAGCTGCGTAAGCGGCTCCTCCGCGATGCCGATGACCTGCAGAAGCGCCTGGCAGTGTACCAGGCCG
GGGCCCGCGAGGGCGCCGAGCGCGGCCTCAGCGCCATCCGCGAGCGCCTGGGGCCCCTGGTGGAACAGGG
CCGCGTGCGGGCCGCCACTGTGGGCTCCCTGGCCGGCCAGCCGCTACAGGAGCGGGCCCAGGCCTGGGGC
GAGCGGCTGCGCGCGCGGATGGAGGAGATGGGCAGCCGGACCCGCGACCGCCTGGACGAGGTGAAGGAGC
AGGTGGCGGAGGTGCGCGCCAAGCTGGAGGAGCAGGCCCAGCAGATACGCCTGCAGGCCGAGGCCTTCCA
GGCCCGCCTCAAGAGCTGGTTCGAGCCCCTGGTGGAAGACATGCAGCGCCAGTGGGCCGGGCTGGTGGAG
AAGGTGCAGGCTGCCGTGGGCACCAGCGCCGCCCCTGTGCCCAGCGACAATCACTGAACGCCGAAGCCTG
CAGCCATGCGACCCCACGCCACCCCGTGCCTCCTGCCTCCGCGCAGCCTGCAGCGGGAGACCCTGTCCCC
GCCCCAGCCGTCCTCCTGGGGTGGACCCTAGTTTAATAAAGATTCACCAAGTTTCACGCAAAAAAAAAAA
AAAAAAAAAAAAAAAAAAAAAAAAAAAAAAAAA

FIG. 2: Wild-type ApoE nucleic acid sequence (NCBI Accession No. NG_007084.2)(SEQ ID No. 69)

TGGAGAGCTGGTCTACCACCGGCGGCCTGGAGAGGAGGGCACTGTCATGTCTCTAGCTGGGAAATACACA
TGTGAGCCTGGCGCCTGGGTCCGAGGGTGGAGGGGCTGGGCCCCTGGACTCCTCCTGGGTCTGAGGGAGG
ACGGGCTAGGGCCCTGGACACTCAGGTCTGAGGGAGGAGGCCTGGGTTCCCAGATGCCCAAATCCCCTTG
GTAATGAGACCCCGCCTCCACCCCACTCTCTGACAGTGAACAACTGGTTGGCAACGGTAACGTTGGGCCA
GGCGGGCATGCACGCAACATACTACCACAAAGCCAGTGACCAGGTGAGTGGGTGCAGGGACTAGCTGGTG
CTGCCAGGGGCTGCTGGGCCTGGAAGTCCAGGTGGGGCCACTTGCTAATTCTCATGTGTTGCTCCGGCCC
CTCCAGCTGCAGGTGGGTGTGGAGTTTGAGGCCAGCACAAGGATGCAGGACACCAGCGTCTCCTTCGGGT
ACCAGCTGGACCTGCCCAAGGCCAACCTCCTCTTCAAAGGTAAAGGTCTCGGTTCCCCTACGCGGGAAAC
AGGCAGGAGGTGACTCAACTCTGAGTGGATGTGTGGCCACCACAGGTGCTGGAGGACAGTGTGCTGCCA
CCCTGTGGGCCTCCACATTACCAGGGAACACTTGTTAAAAGGTAGGTGGGGCCGGGTGCGGTGGCTCACG
CCTGTAATCCCAGCACTTTGGGAGGCCAAGGCGGGCCGAGGTAAGGAGATTGAGACCATCCTGGCTAACA
CGGTGAAACTCCGTCTCTACTAAAAATACAAAAACAAAATTAGCCGGGTGTGGTTGCGGGTGCCTATAGT
CCCAACTACTGAGGCTGAGGCGGGAAAATGGTATGAACCCAGGAGGCGGAGCTTGCGGTGAGCCGAGATC
GTGCCACCGCACTCCAGCCTGGGTGACAGAGCAAGACTCCATCTCAAAAAAAAAAAAAGTAGGTGGACAAC
CCTCTACTATGTTTTATGCTTGGAAAAAAAAAGTAGGTAGAGCAGCCAGGCGTGGTGACTCACGCCTGTA
ATCCCAGCATTTTGGGAGGCCAAGCCAGGTAGAATACTTGAGGCCAGGAGTTGGAGACCAGCCTGGCCAA
CGTGGTGAAATCCCCTCTCTACTAAAAGTACAAAAATTAGCCAGGTGTGGTAGCGTGCTGCAACTGTAGT
CCCCGCTACTTAGGAGGCTGAGGCACAAGAATCACTTGAACCTGGGAGGCGGAGGTTGCAGGGAGTTGAG
ACTGCACCACTGCACTCCAGCCTGGGTGACAGAGTGAGACTCCATCTCCAAAAAAAATAAAATGAAATAA
ATAAATAAATGTTAAAAAAAATCTGGTGGAGCATCTGATGGGTGTTTGGGCCAAGCTGGAGCTTTGTCCA
TCCCCTCTTATTTTTCTGCACTTGACTCTCTTATTTTTCTGAGACTGGTCTCCCTCTGTCGCCCAGGCTA
GAGTGCAGCAGTGCAACTGCGGCTCACTGCAGCCTCCACCTCCCGGGCTCAAGCAGCCTTCCCACCTCAG
CCTCCTGAGTAGCTAGGACCACAGGTGTATGCCACCAGGCCCAGCTAATTTTTTTGATAGTTTTGGGAGA
CATGGGGGTTTCACCATGTTGCCCAGGCTGGTCTCGAACTCCTGGACTCAAGCCTTGGCCTCCCAAAGTG
CTGGGATTATAGGTGTGAGCCACCACACCCAGCCAGGGTAGAAGGCACTTTGGAAGCCTCGAGCCTGCCC
CATTCATCTTACGTTAGTGGAAACTGAGGCTTCCAGAGGTTTCAAGGTCACAACTAAATCCAGAACCTCA
TCTCAGGCACACTGGTCGTAGTCCCAATGTCCAGTCTTAAGTCTTCTTGGATATCTGTGGCTCACAGATT
TTGGGTGTTTGAGCCTCCTGCTGAGCACTGCTGGGGCCACAGCGGTGACCAGCCCTGTCTTCACGGGACT
CAGTGAGAGGAACAGATTCATCCGCAGAGTGGGCAGGACTAGGTTGGGGGAACCCAGGGGTCTAGAGGGC
TTTTCAGAGGGCAGGGGTCACTGAGCGGAGAGCAGAGGAGGAGTGAGCCATTTGCTCCAGCGTGAAGTTG
TTGGTGTGATGGGGTTTCAGGGTGGCAGGAGCAGTGTGGTTAAAGGTCTGGAAGCTGTCGGCATGTGGCT
GGTATCCAAGGTGGCCAGGAACTCTGCATGGATATGGTGGGAAGCTGGCACGCCTCTCACCTCAGCTCTT
CCCTGCAGGCTCTGTGGATAGCAACTGGATCGTGGGTGCCACGCTGGAGAAGAAGCTCCCACCCCTGCCC
CTGACACTGGCCCTTGGGGCCTTCCTGAATCACCGCAAGAACAAGTTTCAGTGTGGCTTTGGCCTCACCA
TCGGCTGAGCCCTCCTGGCCCCCGCCTTCCACGCCCTTCCGATTCCACCTCCACCTCCACCTCCCCCTGC
CACAGAGGGGAGACCTGAGCCCCCCTCCCTTCCCTCCCCCCTTGGGGGTCGGGGGGGACATTGGAAAGGA
GGGACCCCGCCACCCCAGCAGCTGAGGAGGGGATTCTGGAACTGAATGGCGCTTCGGGATTCTGAGTAGC
AGGGGCAGCATGCCCAGTGGGCCTGGGGTCCCGGGAGGGATTCCGGAATTGAGGGGCACGCAGGATTCTG
AGCACCAGGGGCAGAGGCGGCCAGACAACCTCAGGGAGGAGTGTCCTGGCGTCCCCATCCTCCAAAGGGC
CTGGGCCCGCCCCGAGGGGGCAGCGAGAGGAGCTTCCCCATCCCCGGTCAGTCCACCCTGCCCCGTCCAC
TTTCCCATCTCCTCGGTATAAATCATGTTTATAAGTTATGGAAGAACCGGGACATTTTACAGAAAAAAAA
CAAAAAACAACAAAAAATATACGTGGAAAAAAAACGATGGAGGCCTCCGTTTTCTCAAGTGTGTCTGG
CCTGTTTTGAGCATTTCATCCGGAGTCTGGCCGCCCTGACCTTCCCCCAGCCGCCTGCAGGGGGCGCCAG
AGGGCCGGAGCACGGAAAGCAGCGGATCCTTGATGCTGCCTTAAGTCCGGCTCAGAGGGGCGCAGCGTGG
CCTGGGGTCGCTATCTTCCCATCCGGAACATCTGCCCTGCTGGGGGACACTACGGGCCTTCCCTTGCCTG
AGGGTAGGGTCTCAAGGTCACTTGCCCCCAGCTTGACCTGGCCGGAGTGGCTATAGAGGACTTTGTCCCT
GCAGACTGCAGCAGCAGAGATGACACTGTCTCTGAGTGCAGAGATGGGGGCAGGGAGCTGGGAGAGGGTT
CAAGCTACTGGAACAGCTTCAGAACAACTAGGGTACTAGGAACTGCTGTGTCAGGGAGAAGGGGCTCAAG
GACTCGCAGGCCTGGGAGGAGGGGCCTAGGCCAGCCATGGGAGTTGGGTCACCTGTGTCTGAGGACTTGG
TGCTGTCTGGATTTTGCCAACCTAGGGCTGGGGTCAGCTGATGCCCACCACGACTCCCGAGCCTCCAGGA
ACTGAAACCCTGTCTGCCCCCAGGGTCTGGGGAAGGAGGCTGCTGAGTAGAACCAACCCCAGGTTACCAA
CCCCACCTCAGCCACCCCTTGCCAGCCAAAGCAAACAGGCCCGGCCCGGCACTGGGGGTTCCTTCTCGAA
CCAGGAGTTCAGCCTCCCCTGACCCGCAGAATCTTCTGATCCCACCCGCTCCAGGAGCCAGGAATGAGTC

FIG. 2 (continued)

CCAGTCTCTCCCAGTTCTCACTGTGTGGTTTTGCCATTCGTCTTGCTGCTGAACCACGGGTTTCTCCTCT
GAAACATCTGGGATTTATAACAGGGCTTAGGAAAGTGACAGCGTCTGAGCGTTCACTGTGGCCTGTCCAT
TGCTAGCCCTAACATAGGACCGCTGTGTGCCAGGGCTGTCCTCCATGCTCAATACACGTTAGCTTGTCAC
CAAACATACCCGTGCCGCTGCTTTCCCAGTCTGATGAGCAAAGGAACTTGATGCTCAGAGAGGACAAGTC
ATTTGCCCAAGGTCACACAGCTGGCAACTGGCAGAGCCAGGATTCACGCCCTGGCAATTTGACTCCAGAA
TCCTAACCTTAACCCAGAAGCACGGCTTCAAGCCCCTGGAAACCACAATACCTGTGGCAGCCAGGGGGAG
GTGCTGGAATCTCATTTCACATGTGGGGAGGGGGCTCCCCTGTGCTCAAGGTCACAACCAAAGAGGAAGC
TGTGATTAAAACCCAGGTCCCATTTGCAAAGCCTCGACTTTTAGCAGGTGCATCATACTGTTCCCACCCC
TCCCATCCCACTTCTGTCCAGCCGCCTAGCCCCACTTTCTTTTTTTCTTTTTTTGAGACAGTCTCCCTC
TTGCTGAGGCTGGAGTGCAGTGGCGAGATCTCGGCTCACTGTAACCTCCGCCTCCCGGGTTCAAGCGATT
CTCCTGCCTCAGCCTCCCAAGTAGCTAGGATTACAGGCGCCCGCCACCACGCCTGGCTAACTTTTGTATT
TTTAGTAGAGATGGGGTTTCACCATGTTGGCCAGGCTGGTCTCAAACTCCTGACCTTAAGTGATTCGCCC
ACTGTGGCCTCCCAAAGTGCTGGGATTACAGGCGTGAGCTACCGCCCCCAGCCCCTCCCATCCCACTTCT
GTCCAGCCCCCTAGCCCTACTTTCTTTCTGGGATCCAGGAGTCCAGATCCCCAGCCCCCTCTCCAGATTA
CATTCATCCAGGCACAGGAAAGGACAGGGTCAGGAAAGGAGGACTCTGGGCGGCAGCCTCCACATTCCCC
TTCCACGCTTGGCCCCCAGAATGGAGGAGGGTGTCTGTATTACTGGGCGAGGTGTCCTCCCTTCCTGGGG
ACTGTGGGGGGTGGTCAAAAGACCTCTATGCCCCACCTCCTTCCTCCCTCTGCCCTGCTGTGCCTGGGGC
AGGGGGAGAACAGCCCACCTCGTGACTGGGGGCTGGCCCAGCCCGCCCTATCCCTGGGGGAGGGGGCGGG
ACAGGGGGAGCCCTATAATTGGACAAGTCTGGGATCCTTGAGTCCTACTCAGCCCCAGCGGAGGTGAAGG
ACGTCCTTCCCCAGGAGCCGGTGAGAAGCGCAGTCGGGGGCACGGGGATGAGCTCAGGGGCCTCTAGAAA
GAGCTGGGACCCTGGGAACCCCTGGCCTCCAGGTAGTCTCAGGAGAGCTACTCGGGGTCGGGCTTGGGGA
GAGGAGGAGCGGGGGTGAGGCAAGCAGCAGGGGACTGGACCTGGGAAGGGCTGGGCAGCAGAGACGACCC
GACCCGCTAGAAGGTGGGGTGGGGAGAGCAGCTGGACTGGGATGTAAGCCATAGCAGGACTCCACGAGTT
GTCACTATCATTTATCGAGCACCTACTGGGTGTCCCCAGTGTCCTCAGATCTCCATAACTGGGGAGCCAG
GGGCAGCGACACGGTAGCTAGCCGTCGATTGGAGAACTTTAAAATGAGGACTGAATTAGCTCATAAATGG
AACACGGCGCTTAACTGTGAGGTTGGAGCTTAGAATGTGAAGGGAGAATGAGGAATGCGAGACTGGGACT
GAGATGGAACCGGCGGTGGGGAGGGGGTGGGGGGATGGAATTTGAACCCCGGGAGAGGAAGATGGAATTT
TCTATGGAGGCCGACCTGGGGATGGGGAGATAAGAGAAGACCAGGAGGGAGTTAAATAGGGAATGGGTTG
GGGGCGGCTTGGTAAATGTGCTGGGATTAGGCTGTTGCAGATAATGCAACAAGGCTTGGAAGGCTAACCT
GGGGTGAGGCCGGGTTGGGGCCGGGCTGGGGGTGGGAGGAGTCCTCACTGGCGGTTGATTGACAGTTTCT
CCTTCCCCAGACTGGCCAATCACAGGCAGGAAGATGAAGGTTCTGTGGGCTGCGTTGCTGGTCACATTCC
TGGCAGGTATGGGGGCGGGGCTTGCTCGGTTCCCCCCGCTCCTCCCCCCTCTCATCCTCACCTCAACCTCC
TGGCCCCATTCAGGCAGACCCTGGGCCCCCTCTTCTGAGGCTTCTGTGCTGCTTCCTGGCTCTGAACAGC
GATTTGACGCTCTCTGGGCCTCGGTTTCCCCCATCCTTGAGATAGGAGTTAGAAGTTGTTTTGTTGTTGT
TGTTTGTTGTTGTTGTTTTGTTTTTTTGAGATGAAGTCTCGCTCTGTCGCCCAGGCTGGAGTGCAGTGGC
GGGATCTCGGCTCACTGCAAGCTCCGCCTCCCAGGTCCACGCCATTCTCCTGCCTCAGCCTCCCAAGTAG
CTGGGACTACAGGCACATGCCACCACACCCGACTAACTTTTTTGTATTTTCAGTAGAGACGGGGTTTCAC
CATGTTGGCCAGGCTGGTCTGGAACTCCTGACCTCAGGTGATCTGCCCGTTTCGATCTCCCAAAGTGCTG
GGATTACAGGCGTGAGCCACCGCACCTGGCTGGGAGTTAGAGGTTTCTAATGCATTGCAGGCAGATAGTG
AATACCAGACACGGGGCAGCTGTGATCTTTATTCTCCATCACCCCCACACAGCCCTGCCTGGGGCACACA
AGGACACTCAATACATGCTTTTCCGCTGGGCGCGGTGGCTCACCCCTGTAATCCCAGCACTTTGGGAGGC
CAAGGTGGGAGGATCACTTGAGCCCAGGAGTTCAACACCAGCCTGGGCAACATAGTGAGACCCTGTCTCT
ACTAAAAATACAAAAATTAGCCAGGCATGGTGCCACACACCTGTGCTCTCAGCTACTCAGGAGGCTGAGG
CAGGAGGATCGCTTGAGCCCAGAAGGTCAAGGTTGCAGTGAACCATGTTCAGGCCGCTGCACTCCAGCCT
GGGTGACAGAGCAAGACCCTGTTTATAAATACATAATGCTTTCCAAGTGATTAAACCGACTCCCCCCTCA
CCCTGCCCACCATGGCTCCAAAGAAGCATTTGTGGAGCACCTTCTGTGTGCCCCTAGGTACTAGATGCCT
GGACGGGGTCAGAAGGACCCTGACCCACCTTGAACTTGTTCCACACAGGATGCCAGGCCAAGGTGGAGCA
AGCGGTGGAGACAGAGCCGGAGCCCGAGCTGCGCCAGCAGACCGAGTGGCAGAGCGGCCAGCGCTGGGAA
CTGGCACTGGGTCGCTTTTGGGATTACCTGCGCTGGGTGCAGACACTGTCTGAGCAGGTGCAGGAGGAGC
TGCTCAGCTCCCAGGTCACCCAGGAACTGAGGTGAGTGTCCCCATCCTGGCCCTTGACCCTCCTGGTGGG
CGGCTATACCTCCCCAGGTCCAGGTTTCATTCTGCCCCTGTCGCTAAGTCTTGGGGGGCCTGGGTCTCTG
CTGGTTCTAGCTTCCTCTTCCCATTTCTGACTCCTGGCTTTAGCTCTCTGGAATTCTCTCTCTCAGCTTT
GTCTCTCTCTCTTCCCTTCTGACTCAGTCTCTCACACTCGTCCTGGCTCTGTCTCTGTCCTTCCCTAGCT
CTTTTATATAGAGACAGAGAGATGGGGTCTCACTGTGTTGCCCAGGCTGGTCTTGAACTTCTGGCTCAA
GCGATCCTCCCGCCTCGGCCTCCCAAAGTGCTGGGATTAGAGGCATGAGCCACCTTGCCCGGCCTCCTAG
CTCCTTCTTCGTCTCTGCCTCTGCCCTCTGCATCTGCTCTCTGCATCTGTCTCTGTCTCCTTCTCTCGGC
CTCTGCCCCGTTCCTTCTCTCCCTCTTGGGTCTCTCTGGCTCATCCCCATCTCGCCCGCCCCATCCCAGC

FIG. 2 (continued)

CCTTCTCCCCGCCTCCCACTGTGCGACACCCTCCCGCCCTCTCGGCCGCAGGGCGCTGATGGACGAGACC
ATGAAGGAGTTGAAGGCCTACAAATCGGAACTGGAGGAACAACTGACCCCGGTGGCGGAGGAGACGCGGG
CACGGCTGTCCAAGGAGCTGCAGGCGGCGCAGGCCCGGCTGGGCGCGGACATGGAGGACGTGTGCGGCCG
CCTGGTGCAGTACCGCGGCGAGGTGCAGGCCATGCTCGGCCAGAGCACCGAGGAGCTGCGGGTGCGCCTC
GCCTCCCACCTGCGCAAGCTGCGTAAGCGGCTCCTCCGCGATGCCGATGACCTGCAGAAGCGCCTGGCAG
TGTACCAGGCCGGGGCCCGCGAGGGCGCCGAGCGCGGCCTCAGCGCCATCCGCGAGCGCCTGGGGCCCCT
GGTGGAACAGGGCCGCGTGCGGGCCGCCACTGTGGGCTCCCTGGCCGGCCAGCCGCTACAGGAGCGGGCC
CAGGCCTGGGGCGAGCGGCTGCGCGCGCGGATGGAGGAGATGGGCAGCCGGACCCGCGACCGCCTGGACG
AGGTGAAGGAGCAGGTGGCGGAGGTGCGCGCCAAGCTGGAGGAGCAGGCCCAGCAGATACGCCTGCAGGC
CGAGGCCTTCCAGGCCCGCCTCAAGAGCTGGTTCGAGCCCCTGGTGGAAGACATGCAGCGCCAGTGGGCC
GGGCTGGTGGAGAAGGTGCAGGCTGCCGTGGGCACCAGCGCCGCCCCTGTGCCCAGCGACAATCACTGAA
CGCCGAAGCCTGCAGCCATGCGACCCCACGCCACCCCGTGCCTCCTGCCTCCGCGCAGCCTGCAGCGGGA
GACCCTGTCCCCGCCCCAGCCGTCCTCCTGGGGTGGACCCTAGTTTAATAAAGATTCACCAAGTTTCACG
CATCTGCTGGCCTCCCCCTGTGATTTCCTCTAAGCCCCAGCCTCAGTTTCTCTTTCTGCCCACATACTGG
CCACACAATTCTCAGCCCCCTCCTCTCCATCTGTGTCTGTGTGTATCTTTCTCTCTGCCCTTTTTTTTTT
TTTTAGACGGAGTCTGGCTCTGTCACCCAGGCTAGAGTGCAGTGGCACGATCTTGGCTCACTGCAACCTC
TGCCTCTTGGGTTCAAGCGATTCTGCTGCCTCAGTAGCTGGGATTACAGGCTCACACCACCACACCCGGC
TAATTTTTGTATTTTTAGTAGAGACGAGCTTTCACCATGTTGGCCAGGCAGGTCTCAAACTCCTGACCAA
GTGATCCACCCGCCGGCCTCCCAAAGTGCTGAGATTACAGGCCTGAGCCACCATGCCCGGCCTCTGCCCC
TCTTTCTTTTTTAGGGGGCAGGGAAAGGTCTCACCCTGTCACCCGCCATCACAGCTCACTGCAGCCTCCA
CCTCCTGGACTCAAGTGATAAGTGATCCTCCCGCCTCAGCCTTTCCAGTAGCTGAGACTACAGGCGCATA
CCACTAGGATTAATTTGGGGGGGGGGTGGTGTGTGTGGAGATGGGGTCTGGCTTTGTTGGCCAGGCTGA
TGTGGAATTCCTGGGCTCAAGCGATACTCCCACCTTGGCCTCCTGAGTAGCTGAGACTACTGGCTAGCAC
CACCACACCCAGCTTTTTATTATTATTTGTAGAGACAAGGTCTCAATATGTTGCCCAGGCTAGTCTCAAA
CCCCTGGGCTCAAGAGATCCTCCGCCATCGGCCTCCCAAAGTGCTGGGATTCCAGGCATGGGGCTCCGAG
CCCGGCCTGCCCAACTTAATAATACTTGTTCCTCAGAGTTGCAACTCCAAATGACCTGAGATTGGTGCCT
TTATTCTAAGCTATTTTCATTTTTTTTCTGCTGTCATTATTCTCCCCCTTCTCTCCTCCAGTCTTATCTG
ATATCTGCCTCCTTCCCACCCACCCTGCACCCCATCCCACCCCTCTGTCTCTCCCTGTTCTCCTCAGGAG
ACTCTGGCTTCCTGTTTTCCTCCACTTCTATCTTTTATCTCTCCCTCCTACGGTTTCTTTTCTTTCTCCC
CGGCCTGCTTGTTTCTCCCCCAACCCCCTTCATCTGGATTTCTTCTTCTGCCATTCAGTTTGGTTTGAGC
TCTCTGCTTCTCCGGTTCCCTCTGAGCTAGCTGTCCCTTCACCCACTGTGAACTGGGTTTCCCTGCCCAA
CCCTCATTCTCTTTCTTTCTTTCTTTTTTTTTTTTTTTTTTTTTTTTTTTTTTTGAGACAGAGTCTTGCT
CTGTTGCCCAGCCTGGAGTGCAGTGGTGCAATCTTGGTTCACTGCAACCTCCACTTCCCAGATTCAAGCA
ATTCTCCTGCCTCAGCCTCCAGAGTAGCTGGGATTACAGGCGTGTCCCACCACACCCGACTAATTTTTGT
ATTTTTGGTAGAGACAAGGCTTCGGCATTGTTGGCCAGGCAGGTCTCGAACTCCTGACCTCAAGTAATCT
GCCTGCCTCACCCTCCCAAAGTGCTGGGATTACAGGCATGAGCCACCTCACCCGGACCATCCCTCATTCT
CCATCCTTTCCTCCAGTTGTGATGTCTACCCCTCATGTTTCCCAACAAGCCTACTGGGTGCTGAATCCAG
GCTGGGAAGAGAAGGGAGCGGCTCTTCTGTCGGAGTCTGCACCAGGCCCATGCTGAGACGAGAGCTGGCG
CTCAGAGAGGGGAAGCTTGGATGGAAGCCCAGGAGCCGCCGGCACTCTCTTCTCCTCCCACCCCCTCAGT
TCTCAGAGACGGGGAGGAGGGTTCCCACCAACGGGGGACAGGCTGAGACTTGAGCTTGTATCTCCTGGGC
CAGCTGCAACATCTGCTTGTCCCTCTGCCCATCTTGGCTCCTGCACACCCTGAACTTGGTGCTTTCCCTG
GCACTGCTCTGATCACCCACGTGGAGGCAGCACCCCTCCCCT

FIG. 3 ApoE polypeptide wildtype sequence (NCBI Accession No. NP_000032.1) (SEQ ID No. 70)

MKVLWAALLVTFLAGCQAKVEQAVETEPEPELRQQTEWQSGQRWELALGRFWDYLRWVQTLSEQVQEELL
SSQVTQELRALMDETMKELKAYKSELEEQLTPVAEETRARLSKELQAAQARLGADMEDVCGRLVQYRGEV
QAMLGQSTEELRVRLASHLRKLRKRLLRDADDLQKRLAVYQAGAREGAERGLSAIRERLGPLVEQGRVRA
ATVGSLAGQPLQERAQAWGERLRARMEEMGSRTRDRLDEVKEQVAEVRAKLEEQAQQIRLQAEAFQARLK
SWFEPLVEDMQRQWAGLVEKVQAAVGTSAAPVPSDNH

FIG. 4 SLCO1B1 nucleic acid sequence (NCBI Accession No. NM_006446.4) (SEQ ID No. 71)

AAAGGGTGGACTTGTTGCAGTTGCTGTAGGATTCTAAATCCAGGTGATTGTTTCAAACTGAGCATCAACA
ACAAAAACATTTGTATGATATCTATATTTCAATCATGGACCAAAATCAACATTTGAATAAAACAGCAGAG
GCACAACCTTCAGAGAATAAGAAAACAAGATACTGCAATGGATTGAAGATGTTCTTGGCAGCTCTGTCAC
TCAGCTTTATTGCTAAGACACTAGGTGCAATTATTATGAAAAGTTCCATCATTCATATAGAACGGAGATT
TGAGATATCCTCTTCTCTTGTTGGTTTTATTGACGGAAGCTTTGAAATTGGAAATTTGCTTGTGATTGTA
TTTGTGAGTTACTTTGGATCCAAACTACATAGACCAAAGTTAATTGGAATCGGTTGTTTCATTATGGGAA
TTGGAGGTGTTTTGACTGCTTTGCCACATTTCTTCATGGGATATTACAGGTATTCTAAAGAAACTAATAT
CAATTCATCAGAAAATTCAACATCGACCTTATCCACTTGTTTAATTAATCAAATTTTATCACTCAATAGA
GCATCACCTGAGATAGTGGGAAAAGGTTGTTTAAAGGAATCTGGGTCATACATGTGGATATATGTGTTCA
TGGGTAATATGCTTCGTGGAATAGGGGAGACTCCCATAGTACCATTGGGGCTTTCTTACATTGATGATTT
CGCTAAAGAAGGACATTCTTCTTTGTATTTAGGTATATTGAATGCAATAGCAATGATTGGTCCAATCATT
GGCTTTACCCTGGGATCTCTGTTTTCTAAAATGTACGTGGATATTGGATATGTAGATCTAAGCACTATCA
GGATAACTCCTACTGATTCTCGATGGGTTGGAGCTTGGTGGCTTAATTTCCTTGTGTCTGGACTATTCTC
CATTATTTCTTCCATACCATTCTTTTTCTTGCCCCAAACTCCAAATAAACCACAAAAAGAAAGAAAAGCT
TCACTGTCTTTGCATGTGCTGGAAACAAATGATGAAAAGGATCAAACAGCTAATTTGACCAATCAAGGAA
AAAATATTACCAAAAATGTGACTGGTTTTTCCAGTCTTTTAAAAGCATCCTTACTAATCCCCTGTATGT
TATGTTTGTGCTTTTGACGTTGTTACAAGTAAGCAGCTATATTGGTGCTTTTACTTATGTCTTCAAATAC
GTAGAGCAACAGTATGGTCAGCCTTCATCTAAGGCTAACATCTTATTGGGAGTCATAACCATACCTATTT
TTGCAAGTGGAATGTTTTTAGGAGGATATATCATTAAAAAATTCAAACTGAACACCGTTGGAATTGCCAA
ATTCTCATGTTTTACTGCTGTGATGTCATTGTCCTTTTACCTATTATATTTTTTCATACTCTGTGAAAAC
AAATCAGTTGCCGGACTAACCATGACCTATGATGGAAATAATCCAGTGACATCTCATAGAGATGTACCAC
TTTCTTATTGCAACTCAGACTGCAATTGTGATGAAAGTCAATGGGAACCAGTCTGTGGAAACAATGGAAT
AACTTACATCTCACCCTGTCTAGCAGGTTGCAAATCTTCAAGTGGCAATAAAAAGCCTATAGTGTTTTAC
AACTGCAGTTGTTTGGAAGTAACTGGTCTCCAGAACAGAAATTACTCAGCCCATTTGGGTGAATGCCCAA
GAGATGATGCTTGTACAAGGAAATTTTACTTTTTTGTTGCAATACAAGTCTTGAATTTATTTTTCTCTGC
ACTTGGAGGCACCTCACATGTCATGCTGATTGTTAAAATTGTTCAACCTGAATTGAAATCACTTGCACTG
GGTTTCCACTCAATGGTTATACGAGCACTAGGAGGAATTCTAGCTCCAATATATTTTGGGGCTCTGATTG
ATACAACGTGTATAAAGTGGTCCACCAACAACTGTGGCACACGTGGGTCATGTAGGACATATAATTCCAC
ATCATTTTCAAGGGTCTACTTGGGCTTGTCTTCAATGTTAAGAGTCTCATCACTTGTTTTATATATTATA
TTAATTTATGCCATGAAGAAAAAATATCAAGAGAAAGATATCAATGCATCAGAAAATGGAAGTGTCATGG
ATGAAGCAAACTTAGAATCCTTAAATAAAAATAAACATTTTGTCCCTTCTGCTGGGGCAGATAGTGAAAC
ACATTGTTAAGGGGAGAAAAAAAGCCACTTCTGCTTCTGTGTTTCCAAACAGCATTGCATTGATTCAGTA
AGATGTTATTTTTGAGGAGTTCCTGGTCCTTTCACTAAGAATTTCCACATCTTTTATGGTGGAAGTATAA
ATAAGCCTATGAACTTATAATAAAACAAACTGTAGGTAGAAAAAATGAGAGTACTCATTGTTACATTATA
GCTACATATTTGTGGTTAAGGTTAGACTATATGATCCATACAAATTAAAGTGAGAGACATGGTTACTGTG
TAATAAAAGAAAAAATACTTGTTCAGGTAATTCTAATTCTTAATAAAACAAATGAGTATCATACAGGTAG
AGGTTAAAAAGGAGGAGCTAGATTCATATCCTAAGTAAAGAGAAATGCCTAGTGTCTATTTTATTAAACA
AACAAACACAGAGTTTGAACTATAATACTAAGGCCTGAAGTCTAGCTTGGATATATGCTACAATAATATC
TGTTACTCACATAAAATTATATATTTCACAGACTTTATCAATGTATAATTAACAATTATCTTGTTTAAGT
AAATTTAGAATACATTTAAGTATTGTGGAAGAAATAAAGACATTCCAATATTTGCAAAAAAAAAAAAAAA

FIG. 5 Wildtype SLCOB1B1 nucleic acid molecule (NCBI Accession No. NG_011745.1) (SEQ ID No. 72)

GATTCCTCTGCAGTGTAACTTCATGGTTTTTGAGGCAAAGGAAGGCTGGCAGTAAACAAAATATGTGAGT
AAAATTTATAGTATGATGGTGAGAGAATAAAAATTGAGTGTCAAAGGGAGTAATATTAAAAAATTGTTAG
AGAAGACTTCGCTGGGAAAGTGTCATTTGTTTGGGTACTAGAATATGGTGAGGGAGTAAGTTATGCAGCT
ATAGGGAAAGAACATTCCAGACAGAAAGAAAAATAGGAACAAAGATTCTCAGTAGAGGATCTATAACTTA
TAAGGCCTTAAAGCTGTTCTTTGGATTTTTGAGTGATATGTGAAGCCAATGGGGGATTTGAGCAGAGCTA
TGACATGGTATGACCCTCACTTATATGTTAAGATTTACACAGGGGAAGGAGGTTGGGGAAGAGGGGCTGT
GAGTGGTCAGGAGGAAAGCTGAGATACAAGTATGAGGGTATTGCAATAATTCAGGACCAGCCTGAAAGTT
GTGGAGGAGGTAAGAAATCATCAGATTCTGGGTATATTTGGAAATTAGAGCCTAATGTGAGTGTGAGAAA
TAGAGAAGAATGATTCTAATATTGTATGTGGCTGTGCATGTGCACGCATGTGTGCAACTGGAATGACAGA
ATTACAATGTATGGGGATTATTGTCTTCCCTGGACAATAATCCCTGGAAATGGGGATTATTACAAGAGGA
GAGGTTGGGGAAGGAAAGACAAAGATACCATGTTAGAAAATATTAAGTGTAAGATGCCTATTAGAGATAT
ATAGGAAGATGGTGAGAAGTCAATGGATAAATCTAGAGTTCATGAGTAACTTGGCTAGAGAAAAAATTTT
GGAATTATCAACGTATGGATAAGATTTAAAGACATGAGAATAGATGAGGTCACAAACACACACAGTAAGG
TTATTGTCTGACATGCTTCAATTTAGAAGACAAAGATAAAGAATTTAGAGTAAATGAAGTGTAAATAAGT
AAGTCAGTGAGTTAGAAGGCAAACCACAAAGGGTAGTGTCCTGCAAAGTTTTGCTTAGGGAGGGAATTCT
CAGTTCTGAAAAATGCTGCTAATAGTTCAAGTCAGATGAGGACTATTAGATGTAGCATTTAGGTAATTTA
TGACTTAGGAAAAGTAGTTTCAGTGGAAATTTGGGGGCAAAAGCCTGATAAGAGTGTGCTCAAGAGAGAA
TGTAGAGAGAGAGATTGAAAGCAATAATTAGACAAGCTATTTCTCTGTAAAAATAGCACAGAAATAGGGC
AATATTAGGAAAAAATGGGATCAAAAGAGAGATTTTTGGAAGATGAAAAAGTGACAGCATTCTTACATGC
TGATGGAAACATTTAAAAAGAGGATAGTGCTATCCTTAAAAACACAAGGGGAGGAGTCAATGTCATATGC
AAGTGGAGATTGGCCTTAGCTTAAACTTGGGTAGTTCACTAAGGCAGACCATGTGGTGGTACTGGGGCTT
TACATAGATAAATGTGGTCAAGGGAGCTTTTGAAGTTTCTTCTTTATTTATTTATTTTTTCAGTAAAATA
ATTCATCAGCTGAAGGTGGGGAAGGGATGTATTAGAATTTCAAAAAAAAAAAAAAAAAGATGAAGGCACAA
AATGCTCAGAGTGCAAAATGGCGTGAATGATTTCTTGGCAAAATGAAAGGTCCATTTGGGCTTCCTAATC
ATACGTTTAAAGTCAGCATGGTTGAGAGATTTTCCTCAGTTACATTTAGCTTCATAAGGGAAATGTGCAG
AGTTATTTGAGAGTTAAATTTAATCAAGATTGTGGCTTTGACATGCAATTAAAATAATGCAAAACAGTCA
AAATTATATGAAGTTATATAGAAGAGAGTGATTACCGTGACCATTAAATTAACCCAGATGTATAGATAAG
GAACACCGAAATCTCTGGCAAAATCAAATTGTAGGTTATACATCCTGGTCAGTGGAAGCATGTGGATCTA
GGGTGTTACTGAGTGTGAGCTAGGAGTGATAAAGAGTGGTGCTCCAATCTTTGATATTATGGAGAGATTA
CAGTGGTGTGAAAAGCATAGGATATGCCCATAGCAGTAGGTAGAAGCCAAGATCATTGAGGAGAAGGCTA
AAAAATAAAAAGAAAATAAAAAGAAAACAGAGAATTAAAAAGATTCTCTTCATGGTCATTACCATCATGA
ATAATTAAAATAGTAGTAGCATTTTGAGAGAATGGCTTTGGATCGAGAGCTAAAATTGTCATGAAATGAG
TGGGAGTGACTGAGCGTTGATAGATGATTTCAACAAGAGGAATAAGTGATAGAGTCTTTCAATATGAGAT
CCAAAACTATGGATTATGAGTGTAAAGGGTGGGGAAATGTAAAGAAACTAGCAAAGTGAGGCACATTGGA
AACCAGCCCATCTGGTTTGCAGCAATATGGGGGATAAGGCAACCCCTATGTATCACTGCTGCAGGAGAGG
GAGTGTCTCAGGGAAGACCAATTTTTAAGTTCAAGGCAGAAGTGAAGCAGAATAACTCAGAGAAGAGGTA
AAGGTAAGGGGAGTTTCAGTCATGACTAGTGATGGGTTCCAGAAAACTCAAGAGAAGAATTTCAGTCCAG
GATTGGGAGAAAGAGAGAAGATGGGGGCAAACATAGGAATGTGCAGAGCCCTGTGGGGATTAGAGAAGAG
GTGATGAGTCATCAGGGAATCCCTACCTTCTTATGGTGGTCACTACCATAAGAGCGATAATTGCCATGGT
AATATTAGTCTTGATGATGCCAGAGCTTTGATCATTGGTGGGTATAGAAACATGTTTGGAGAATAATATG
TAGAATAGGAGTTCTTTCCAGGAGAGTGTAGCTTTCTGGAGCTGTCTCTTAATCAGCACCAACAGAAGTG
AAATGTTCGGGTAAGGGCGGATCTGCTTGGAGCCTGACGGTTCCCTCTTGAGGTGTGCCTGTGGTACACA
CCTGAGAACTCTGGGGCTAAAACCTATTGGACATAGGTTTTACAGATCTACAGGATACAGATCTCAGAGA
TTTTATTTGTATTCATTTAATATAAATTAACTGCTCTAAAATTTATAATATGCAAATATCATACAATTAA
TCTAATTAGGTGTTGAATCTATAATGTGCCAGGCATTATGTAAGGCACTTTACATACACTAAATCTTTAT
TCCAAATATAGACTTCTTACTTTATAGATGAGTGCACTGATGCTCAGAAATGGTAAATAACCTACTGATG
TTTATACTGCTGGCAGGTAGCAGAGACATATCGGCATTTAAGTCTTTCAGACTTCAAAGGCCATGATATT
TCATCAGAGCTGTGATAGCCGTTCCTGAAAAAAATATCAGCTGATTCTTTAAATCAATTTTTGTCATCTA
ACTGATGCGTGGCTGTTAGCATAATATTGATCTTGAAAGATGTTTTGCAACATCTTTCCCCTGGTGTACT
CTTGTTTTTCCATGATCCCACAAAATGAGCAGTCTAATTATTTACACAATTAGGAAGAGAAAAGGGGCAC
AGAGAATGCTCTTTGACCTCTGAAAATATTGGAGAATTTTACAACTGGCACCTTTAGCTCAGGATTATAA
AGGTTGTTAGTTAGTTTGTACTGTTTTATCTTCATTGTATATAATATATATATTAGTCTCCAAACATGTT
GATGTGTTTTCAATGAAATGGATGTCTGAGGAGAAAACCATTAGCCTGAGAAAACCCAAACTGTATTCCC

FIG. 5 (continued)

ATTGTGAATAAAAGGAAGTCCATAAAAATGATGGAAAATGTTCTGCATTCCTGTTATGATATCAAAATCT
GGCAGTACATGAAAATTTTTCAAAGTGCTTATTTAACAGGCATAATCTTTGGTCTCCTGAGCCAGAATCT
GCTGGGTATGGGACTGGATTGCTATTTTGACAACTCGCCAGTAGATTCTTACTCAGCAGAGTATTTGGAA
GCCTTACTCTAATATTTTGGCCTTGGGTCTACATTTCTCAGTTCTGCACAGTCATTCTTCCCCTCTACAC
TACTCTTTAGTTTGTCTCATGATTCCAATACTCTCAATAATTAACCAAGAATAGAACTAATCAATCAGAT
AACTGTGGCACAGACATCAAATACATTTTGCTGCAACCATATCAACAAATGTCCCATGAATGATAAGGGG
TAACCATATTCTCATATATGCATCCTCACATTACCACATATATATATGTGCATATGTGTATACAGGTAAA
AGTGTGTATATATGTATACATGTATGTTTGTGTGTATATACATACATATATCTTCACACTTTTCTGAAAT
ATATATATTTATGTGAGAGAAGGGTCTGTACTTTATTTCAGAAGAGAGCTTAATGTCCAAGGTATAATTG
AGAGTCTAAAATGTTTGAGTTATTGAATTAATTAAACTTCATCTCTACTCAAGAAAACTTTTAACTGAGT
TAAGCTCTTCCTTTCTCCACAAGTCAAGTCAATAAAAGGAAACTGTGATATTAATAATTCTTTCCTGTTT
TGATGTAAAGAATCTATCGCATAAAGCAGTCTTAATTTTCATCATTCAGAAAAATGGTCTTGCAGTTAAT
TGGGACTCTCTTATTCCAGGTGGTATCTCCAGTCTCCATACATACCACGTTAGAACCATACTTATGTACC
AAGCAAAGAGGGTATATTTTAATTTTTAAATGCCAATGTAACCTGTAGGCATATTTTTTATTTGTCTTAA
ATTATTTCCTATTTGGAAGTTTTAAATACCTGGAATAATTTATTGTACTCATATTTTTAAAGAAAAAAAT
CTTATGCCACCAACTTAATTGAATAAACAAGTAAAAGCCATTCCCAAAAGTAAGGTTTACTTGTTAAGAT
TAACAAAAAATAATGTGAGAATTCTGAGAAATATAATCTTTAAATATTGGCAACTGGAGTGAACTCTTAA
AACTAACTAGGTTTTATATGTTTGACTAGAGCAATGACATAATAAGGTGGTTAATCATCACTGGACTTGT
TTTCAAAAAGCCAACTACTTTAAGAGGAATAAAGGGTGGACTTGTTGCAGTTGCTGTAGGATTCTAAATC
CAGGTAAGAACCATTGAGATTCTCTAATTTTTACATATATTTTATGTAAGAAATTTTCACGGAAGAAGAT
TTTGATGGTCTTGAAAAATATTACGAATTTTATGCTCTGTGTCTTCCACACGCTTACATTCTGAGCCCTT
AAAACATAGTAAATATTCCTTCTGGGAGTAGAAGAGCCTCAGGTTTATATACTGTTAAAAATAAAGTAGA
GAAAATAATACCTTTATATATTTAAATATAAAGTTTCAAATCTTGGTCTTATTAATTTCCAAACAAATAA
AAATCAAGTCTCAAAAATGAAGCTCTAGTTACCTTCTTAAAATATGCTACAGGATAATTATTTTTGTCAA
CTACATTGACTGATCACACTAGACTCCTTATTTCTTTGATGTCTTCTTAACTGGATGAAGGCAGCCAAGG
GTGGGAGTAGAGGGAAGAGTTAATTGGCAAACATAAAAAACAGGTGTCTCAAAGTCACATAACCACCTCA
GTTTCCTTGTTTCAACTCAAGTTTGATACAGGGTGAAGGGAAATATATTTTCTAGATAATTTATCTCCAA
TTAAATAAGCAAAAAGTCTTCTCAGTACAGTTTTTTTCTTTTTTTATTTCATTATTATTATACTTTAAGT
TTTAGGGTACATGTGCACAACATGCAGGTTTGTTACATATGTATACATGTGCCATGTTGGTGTGCTGCAC
CCATTAACTCATCATTTAACATTGGGCATATCTCCTAATGCTATCCCTCCCCTCTCCCCCACCCCACAAC
AGTCCCCGGTGTGTGATGTTCCCTTTCCTGTGTCCATGTGTTCTCATTGTTCAGTTCCCACCTATGAGTG
AGAACATGCGGTGTTTGGTTTTTTGTCCTTGCGATAGTTTGTTGAGAATGATGGTTTCCAGTTTCATCCA
TGTCCCTACAAAGGACATAAACTCATCATTTTTATGGCTGCATAGTATTCCATGGTGTATGTGTGCCACA
TTTTCTTAATCCACTCTATCGTTGTTGGACATTTAGGTTGGTTCCAAGTCTTTGCTACTGTGAATAGTGC
CGCTATAAACATACGTGTGCATGTGTCTTTATAGCAGCATGATTTATAATCCCTTGGGTATATATCCACT
TATGGGATGGCTGGGTCAAATGGTATTTCCAGTTCTAGATCCCTGAGGAATCGCCACACTGTCTTCCACA
ATGGTTGAACTAGTTTACAGTCCCACCAACAGTGTAAAAGTGTTCCTATTTCTCCACATCCTCTCCAGCA
CCTGTTGTTTCCTGACTTTTTAATGATCGCTATTCTAACTGGTGTGAGATAGTATCTCATTGTGGTTTTG
ATTTGCATTTCTCTGATGGCCAGTGATGATGAGCATTTTTTCACGTGTTTTTTGGCTGCATAAATGTCTT
CTGTTGAGAAGTGTCTGTTCATGTCCTTCACCCACTTCTTGATGGGGTCGTTTGTCTTTTGTAAATTTGT
TTGAGTTCATTGTAGATTTTGGGTATTAGCCTTTTGTCAGATGAGTAGGTTGCAAAAATTTTCTCCCATT
CTGTAGGTTGCCTGTTCACTCTGATGGTAGTTTCTTTTGCTGTGCAGAAGCTCTTTAGTTTAATTATATC
TCATTTGTCATTTTTGGCTTTTGTTGCCATTGCTTTTGGTGTTTTAGACATGAAGTCCTTGCCCATGCCT
ATGTCCTGAATGGTATTGCCTAGGTTTTCTTCTAGGGTTTTTATGGTTTTAGGTCTAACATTTAAGTCTT
TAATCCATCTTGAATTAATTTTTGTGTAAGGTGTAAGGAAGGGATCCAGTTTCAGCTTTCTACATATGGC
TTGCCAGTTTTCCCAGCATCATTTATTAAATAGGGAATCCTTTCCCCATTGCTTGTTTTTCTCAGGTTTG
TCAAAGATCAGATAGTTGTAGATATGCGGCACTATTTCTGAGGGCTCTGTTCTGTTCCATTGGTCTATAT
CTCTGTTTTGGTACCAGTACCATGCTGTTTTGGTTACTGTAGCCTTGTAGTATAGTTTGAAGTCAGGTAG
GGTGATGCCTCCAGCTTTGTTCTTTTCGCTTAGGATTGACTTGGTATGCGGGCTCTTTTTTGGTTCCATA
TGAACTTTAAAGTAGTTTTTTCCAATTCTGTGAAGAAAGTCATTGGTAGCTTGATGGGGATGGCATTGAA
TCTATAAATTACCTTGGACAGTATGGCCATTTTCATGATATTGATTCTTCCTGCCCATGAGCATGGAATG
TTCTTCTATTTGTTCGTATCCTCTTTTATTTCATTGAGCAGTGGTTTGTAGTTCTCCTTGAAGAGGTCCT
TCACATCCCTTGTAAGTTGGATTCCTAGGTATTTTATTCTCTTTGAAGCAATTGTGAATGGGAGTTCACT
CATGATTTGGCTCTCTGTTTGTCTGTTATTGGTGTATAAGAATGCTTGTGATTTTTATACATTGATTTTG
TATTCTGAGACTTTGCTGAAGTTGCTTATCAACTTGAGGAAATTTTGGGCTGAGATGATGGGGTTTTCTA
GATATACAATCATGTGATCTGCAAACAGGGACAATTTGACTTCCTCTTTTCCTAATTGAATACCCTTTAT
TTTCTTCTCCTGCCTGATTGCCCTGGCCAGAACTTCCAACATTATGTTGAATAGGAGCAGTGAGAGAGGG

FIG. 5 (continued)

CATCCCTGTCTTGTGCCCGTTTTCAAAGGGAATGCTTCCAGTTTTTGCCCATTCAGTATCATATTGGCTG
CAGGTTTGTCATAGATAGCTCTTATTATTTTGAGATACATCCCATCAATACCTAATTTATTGAGAGTTTT
TAGCATGAAGGGTTGTTGAATTTTGTCAAAGGCCTTTTCTGCATCTATTGAGATGATCATGTAGTTTTTG
TCTTTGGTTCTGTTTATATGCTGGATTACATTTATTGATTTGCGTATGTTGAACCAGCCTTGCATCCCAG
GGATGAATCCCACTTGGTCATGTTGGATAAGCTTTTTGATGTGCTGTTGGATTTGGTTTGCCAGTATTTT
ATTGAGGATTTTTGCATCAATGTTCATCAAGGATATTGGTCTAAAATTCTCTTTTTTTGTTGTTTCTCTG
CCAGGCTTTGGTATCAGGATGATGCTGGCCTCATAAAATGAGTTAGGGAGGATTCCCTCTTTTTCTATTG
ATTGGAATAGTTTCAGAAGTATTGGTACCAGTTCCTCCTTGTACCTCTGGTAGAATTCGGCTGTGAATCC
ATCTGGTCCTGGACTTTTTTTTGTTGGTAAGCTATTGAGTATTGCCTCAATTTCAGAGCCTGTTATTGGT
CTATTCAGAGATGCAACTTCTTCCTGGTTTAGTCTTGGGAGGATGTATGTGTCAAGGAATTTATCCATTT
CTGCTAGATTTTCTAGTTTATTTGCCTAGAGGTGTTTATAGTATTCTCTGATGGTAGTTTGTATTTCTGT
GGGATCGGTGGTTATATCCTCTTTATCATTTTTTATTGCATCTATTTGATTCTTCTCTGTTTTCTTCTTT
ATTAGTCTTGCTAGTGGTCTATCAATTTTGTTGATGCTTTCAAAAAACCAGCTCCTGGATTCATTAATTT
TTTGAAGGGTTTTTTGTGTCTCTATTTCCTTCAGTTCTGCTCTGATGGTAGTTATTTCTTGCCTTCTGCT
AGCTTTTGAATGTGTTTGCTCTTGCTTTTCTAGTTCTTTTAATTGTGATGTTGGGGTGTCAATTTTGGAT
CTTTCCTGCTTTCTCTTGTGGGCATTTAGTGCTATAAATTTCCCTCTACACACTGCTTTAAATGTGTCCC
AGAGATTCTCGTATGTTGTGTGTTTGTTCTCATTGGTTTCAAAGAACATCTTTATTTATGCCTTCATTTC
ATTATGTACCCAGTAGTCATTCAGTAGCAGATTGTTCAGTTTCCATGCAGTTGAGCAGTTTTGAGTGAGT
TTCTTAATCCTGAGTTCTAGTTTGATTGCGCTGTGGTCTGAGAAACAGTTTGTTATAATTTCTGTTCTTT
TCCATTTGCTGAGGAGAGCTTTACTTCCAACTATGTGGTCAATTTCAGAGTAGGTGTGGTGTGGTGCTGA
AAAGAATGTATATTCTGTTGATTTGGGGTGGAGAGTTCTGTAGATGTCTATTAGGTCCGCTTGGTGCAGA
GCTGAGTTCAATTCCTGGGTATCCTTGTTAACTTTCTGTCTCATTGATCTGTCTAATGTTGACAGTGGGG
TGTTAAAGTCTCCCATTATTATTGAGTGGAATTCTAAGTCTCTTTGTAGGTCACTAAGGACTTGCTTTAT
GAATCTGGGTGCTCCTGTATTGGGTGCATATATATTTAGGATAGTTAGCGCTTCTTGTTGAATTGATCCC
TTTACCATTAGGTAATGGCCTTCTTTGTCTCTTTTGATCTTTGTTGGTATAAAGTCTGTTTTATCAGAGA
CTAGGATTGCAACCCCTGCCTTTTTTTGTTTTCCATTTGCTTGGTAGATCTTCCTCCATCCCTTTATTTT
GAGCCTATGTGTGTCTCTGCATGTGAGATGGATTTCCTGACTACAGTGCACTGATTGGTCTTGACTCTTT
ATCCAATTTGCCAGTCTGTGTCTTTTAATTGCAGCATTTAGCCCATTTACATTTAAAGTTAATATTGTTA
TGTGTGAATTTGATCCTGTCATTGTGATGTTAGCTGGTTATTTTGCTCATTAGTTGATGCAGTTTCTTCC
TAGCCTTGATGGTCTTTACAATTTGGCATGTTTTTGCAGTGGCTGGTACCAGTTGTTCCTTTCCATGTTT
AGTGCTTCCTTCAGGAGCTCTTTTAGGGCAGGCCTGGTGGTGACAAAATCAGCATTTGCTTGTCTGTGAA
GGATTTTGTTTCTCCTTCACTTATGAAGCTTCGTTTGGCTGGATATGAAATTCTGGGTTGAAAATTCTTT
TCTTTAAGAATGTTGAATATTGGTCCCCACTCTCTTCTGGCTTGTAGAGTTTCTGCCGAGAGATCAGCTG
TTAGTCTGATGGGCTTCCCTTTGTGGGTAACCCAACCTTTCTCTCTGGCTGCCCTTAATATTTTTTCCTT
CATTTCAACTTTGGTGAATCTGACAATTATGTGTCTTGGAGTTGCTCTTCTCGAGGAGTATCTTTGTGGC
GTACTCTGTATTTCCTGAATCTGAACGTTGGCCTGCCTTGCTAGATTGGGGAAGTTCTCCTGGATAATAT
CCTGCAGAGTGTTTTCCAACTTGGTTCCCTTCTCCCCATCACTTTCAGGTACACCAATCAGACGTAGATT
TGGTCTTTTCACATAGTCCCATATTTCTTGGAGGCTTTGTTCGTTTCTTTTTATTCTTTTTTCTCTAAAC
TTCTCTTCTCACTTCATTTCATTCATTTCGTCTTCCATCACTGATAACCTTTCTTCCAGTTGATCCTATC
AGCTACTGAGGCTTCTGCATTTGTCATGTGGCTCTCTTGCCTTGGTTTTCAGCTCCATCAAGTCCTTTAA
GAACTTCTCTGCATTGGTTATTCTAGTTATCCATTTGTCTGATTTTTTTTCAAAGCTTTTAACTTCTTTG
CCATTGGTTTGAATTTCCACCTGTAGCTCAGAGTAGTTTGATCATCTGAAGCCTTCTTCTCTCAACTTGT
CAAAGTCATTCTCCATCCAGCTTTGTTCCGTTGCTGGTGAGGAGCTGCATTCCTTTGGAGGAGGAGAGGC
GCTCTGATCTTTAGAGTTTCCAGTTTTTCTGCTCTGTTTTTTTCTCATCTTTGTGGTTTCATCTATCTTT
GGTCTTTGATGATGGTGACGTACAGATGGGTTTTTGGTGCGGATGTCCTTTCTGTTTGTTAGTTTTCCTT
CTAACAGACAGGACCCTCAGCTGCAGGTCTGTTAGAGTTTGCTAGAGGTCCACTGCAGACCCTGTTTGCC
TGGGTTTCAGCCTCAGTGGCTGTAGAAGAGCGGATATTGGTGAACCACAAATGCTGCTGCCTGATCGTTC
CTCTGGAAGTTTTGTCTCAGAGGAGTACCCGACCGTGTGAGGTGTCAGTCCGCCCCTACTGGGGGTGCC
TCCCAGTTAGGCTACTCGGGGGTCAGGGACCCACTTGAGGAGGCAGTCTGCCTGTTCTCAGATCTCAAGC
TGCGTGCTGGGAGAACCACTGCTCTCTTCAAAGCTGTCAGAGAGGGACATTTAAGTCTGCAGAGGTTACT
GCTGTCTTTTTGTTTGTCTGTGCCCTGCCCCCAGAGATGGAGCCTACAGAGGCAGGCAGGTGTCCTTGAG
CTGTGGTGGGCTCCACCCAGTTCGAGCTTCCCAGCCGCTTTGTTTACCTAATCAAACAACTAACTCAGCA
ATGGTGGCCGCCCCTCCCCCAGCCTCGCTGCCACCTTGCAGTTTGATCTTGGATGGCTGTGCTTGCAATG
AGCGAGACTCTGTGGGCATAGGACCCTCCAAGCCAGGTGCAGGATATAATCTCCTGGTGTGCTGTTTTTT
AAGCCGGTTGGAAAAGCACAGTATTAGGGTGGGAGTGACCCAATTTTCCAGGTGCCGTCTGTCACCCCTT
TCTCTGACTAGGAAAGGGAATTCCCTGACCCCTTGTGCTTCCCGGGTGAGGCAATGCCTCGCCCTGCTTT
GGCTTGCGCACGGTGCGCTTCACCCACTGTCCTGCACCTACTGTCTGGCACTCCCCAGTGAGATGAACCC

FIG. 5 (continued)

GGTACCTCAGTTGGAAATGCAGAAATCACCAGTCTTCTGTGTTGCTCATGCTGGGAGCTGTAGACCAGAG
CTGTTCCTATTTGGCCATCTTGGCTCCTCCCCTCAGCACAGTTTTTAGCATGAACTAAGGCCTCAATAAA
TATTAGTTCCCTTCTCCAATTCAGAAAGTTGTCTGCCTTGATAAGACAATTGTTTTTATTGTGAAAGTGA
GGTGGAGATGGGGGATTGTCTCTCCTATAAAAGGTCTAAGAAGTTAGCAAATGCTGTTTTTCCTTTTTGC
TCCTCAGTTGCATAAGTACATGGTAGAAATTGGGTCACTTTGCCTAAACCGGTTTTCTATAACCTATTAA
GTATTAAAAGCTTGACACAGATAAGTAGAGGCTGATAAGATTCTGTCCTGCACCCCACTCCTATCAAATT
TGGAAGAACTGACCTCTTCCGGGAAGAATTGCAATGCTAAATCCAAATGCCTATGGTTCTATCTTATAAA
CAAATGGTGTCCTCAAAATTCATTTATGTAAATCATTTGAAATTTAAGAAAAAAATATGTTCAGAGAAAA
ATATGTTAAATGTCAAGGTGAATTAGAAAGTGTGGCATTTAGTCAAGCATAAATTAATATTCCAACTTTC
TAGTTACTTTGTAGTAACTTATTTAACATTTTGGTGAAATGAGGAACAAAGTGTCCACCTTTTTTTCCTG
AATATTTTATCTGAAGATCTAGGAGAGAGATGTGAAATAGTATTTTTCTGGGGAAGTAGGGGAAATACAA
AGAAAAGTAATGACTTCAGGTATATTCTCCACTGGTACAGCAGGATGGGAGATATTATCAACAGGTGGTA
AGTATAAAAATATTGAAGAGGTACAATTTGGATCAGCATTACAACCAAGAATGGAGAATGACATTCAGGA
TTGAAAGAAACATACAAGAGGGCAGAAAGCTTTCTTCTTGGGACTGTGGTTTCATGTGTCTGCAGGTGCT
ATGGGTATATTGAGAATGGTTCTAAAAACAGGGGCTTGGTTTAGGTTGTGAAGACCATCAAATAGAAACT
GTGAATTTTATTTTGTGTCGTTAAAGGGATCTTTGAAAGATTCTTAGGATAAATATGATATGCATAGGAT
AGAAAGAAAGGTGGGAGACAGGACAAACAGAAGTTAATCAATTGAAATAAACCAGGTTTGGAGTGGTGGG
ACAATAGCCTTCAAGACATCAAGAATATTTGTTAGTAGAAAGAAAATCGAAGCCTAAAACTAAAGGAAGA
CTATCCACCTTGCAAGTCATACAGAGATATTTGCTATTATATAATTTTTTTAAAAAAAGATTTCCTAATA
TTTAAATTATGAAGAAAGAGATAGAAACAGATATTCATGGAAAAAATGGGGTGAAATTAATCAAAGGGCA
GCTTATTACCTTGAGACTAAACAGCCATTGACTTTTTTCTTACCTCACTGAACCCAGAAACCCGACATAT
CTAGGTACAGGCATGCATAAAACATGTACACACACAAAATGTAATAATTGGAGTTCACTTAGAGGTACAC
ATGTATGGGTTTCTGTATTCAACCATATGTTGATATATACTCACATATATGTAAGTGATAATATCCTGTT
TGTTACTTCCACATTTATGCACTATCCCTTAAATATGTATTATATATATTTATATTATTCAGAATCCATC
AGCCCTTGTTGAATAAATTAGTGAATAAAATATAGAGTCGAGTCTCATTATTCACAGATTCTATATAAGA
AAATTTGTCTATTCACTAAAATTCCTTTGTAACACCAAAATCAATACTGCTGGACTTTCATGGGCATTCA
CATGCATGTGCAAAGTGGTGAAAAATTTGAGCTGCCATGTTCCCAACTAAGGTTGAACAAAATGAAGCTC
TGTCTTCTTGTTTCTGCTCACATATGATAAAGAAATATCCTTTTCACACTGTATTTATTGCCACATTTTT
GGCATTTTTGTGTTTTGTGTTTCTGAGTTGAATGTTTCGAATGGGCCCCAAAGATAGTGCTGAAGTGCTC
TCCGGTGCACAAGAGTATCTGAGGGAAAAGATACATATGCTGTATAAGCTTCCTCCAGGCCTGAACTACA
GTGTTGTTGACAACTAATTCAATGTTAATGAATCAATAGTATGTATTAAATAAAGTGTCTTTAAACAAAA
CATACATAAAACACAGTTCTATATTGAACAATTTACCAAAATATTGTGACCAGAGGCAGACAGGCATATA
ACTAACCCCACATCTCTCCAAGGAACAATGGTTCAATATTTGCTAATTCAGTGTTCCCAGCAACTTTATA
AAACATAACTACTGCAACAAGTATCAACTGTACATATAATATATATTAGACATATTGTATAATTACTGCC
CTATTAAAAATCATGTATCTATGCTGTGTCTGCTTATATAGATATCTTAGATACATAAATATGTATTGTT
TACATACATAGGAGCAAGAATGTATTTCTAAAACTCCATGAAGAACACATTATATTCTATATAAAAGAGT
CAGTTGAAGTAAAAAGTTAACTCATTTTACTAGTCTTTAAAGTAGGACTTTAATGACTCTCAAAATAACA
ATTTCTCTCATACATTGACTCCAAAACTTTAGTTGTTGAATTTATTCTGCAGATATGGCCACATAAAACC
AAAATGGCATATGATATATTAAGAACATCTTTAATATGAAATGATTAGATACAACCTAAAAGCTGATGAA
TATAGAACCAGTTGCATATATTATGGACAACTTAATACCCTGCTACCATAAGAAAAATGAGAAAGACTTA
TTAAGATTAAGTATATAGAGAAGATAAAAAGGTAGAGAATGATGTTTAAGGTATGCTACCATTTGCATTG
AAAAGGAAAATATTATGTACTTAATGAAAAATCCATATTATATTTCTGGATAATGGGACAAGAGTTAGAG
GAAGAATCTTTGTTTTATTTTTTTAATTTGCATTTTCAACTATATGCATTTTCTCTTGGAAAAGAAATGA
ACAAAATCAAAATAAAGTAACATCATGATGGTGGTAAGGTCAAGCAATACCAGAGTTGCTCTGAGAAGTA
CTTGGAGTACACTTTGCTCTTTTTAACAAATCCAAATTCTGTTTGCTTTTTGAGCCTGATTCCAGTGGTG
TCTCCTTTATAAAACTGAGGCCATTCTAATTTAATTCTTTATATTATTTTTGTATCTGTTTTGAATATCT
ACTCTGTGCAAGGGGCTAATAGGCACATTTTAAAACTAGAAGGATAAAGAAAACATATATTTGCTTTTAT
AAATTTTACAATATAGGTGTGTAGAAAAGATAATAATTTAAATTTCTATAATTTAAAATGTTCATGTAAT
CTGGTGTGTGATTCTATATTACTTACTTGTTTCAAATTTCTCTCCACAAATTTATTTTTCTATTAAATTG
TAATCTCCTTAGGCTAGAATTTGTGTCTGTCTTTCCTACTTTTGTTTCCAGCATTGACCTAGCAGAGTGG
TAACGACATAGTAGACCCTGAGTGAATGTTAGTGAATGGTTGATTGATTGATGATGATCTTGTGGCTTTT
CTTATTTCTAAATTATATATTGTAAAAATAAAATAAACTATACTTTTTCTTCCTTAATAGGTGATTGTTT
CAAACTGAGCATCAACAACAAAAACATTTGTATGATATCTATATTTCAATCATGGACCAAAATCAACATT
TGAATAAAACAGCAGAGGCACAACCTTCAGAGAATAAGAAAACAAGATACTGCAATGGATTGAAGGTAGA
ATAAGTTTTATGTTTTTGAGCTAAAATAAGTAAATAGGGAACTTTAATGTATAGAAAAGCAAGTTGTTAA
AAAGAACATTATGTTTCAAATTATAATTTTCAATTGAAGCATATATTGAAATATTAACATAATGATTCAT
ACCTTGATTTAAACCAGTCTTTTAATCTGATTAAGTATTTCTTTGGCGAAATTTTTGATGCTTAATAGTT

FIG. 5 (continued)

TATCAATGTAGAAAATTTAGAAATATTTTGATAGCTTCTCTTTGGTTTTGGATTGATCACGACATATTTA
GGAATGTGATTAAAATAAAAAATGCATAATGAATAATATTTTAAAATTCTTAGAATTGACTTATAAACTT
AGAATATTAATGTCTTGAGACTCACTTTGTGATACTGACTTATTTAAAAATTCTTTTAAAAAAAAAAACA
AAAAACAGGATTTAAAAAAGTTCTGATAAGTAATTTAGGCTCATGGAACGGAGGTCTATGATAGTCAAAA
ACTTGGCCAAAAGACCTGTTTGACGATTTAGAAAAGCCATTTAATGTTTTCATTTGCCAGCTGGTAAAAG
TAATAATTCTGCTTTTTGCTTTTGGCACAAACTGTATTAAATGATACAGTTGAGGTATTAAGTGATGCTG
GCATTTTTATAAACAGGAATGAGTACTCCTAAGCACAATGCTAAATGAGAAGCCAAGACTCAGAAAAGTT
AAGAAATTTTCCTGAAGTCATCTACATTGTGAATTGAAAACCCTGGAACCCAAGACAAAGCCTTTAAATC
CCCATATGGAAGTCTTGAGGAAATCAAGAAATAAGGGTCACCTTTTATCAATGTTTTAACTTTTTTATTT
AGTCAAATTTGTAGTCTTATACAGCTGAATAAAGGCCACCAAGATTGGAGTCAATTACAATAATGTTATA
AAAGGTTCCTTTTAGCTCCTTCCAGGGAACATAAAATTTGTTTGTTTTCTGAGATTACTGATAAAGCCTT
CTCTGATGAAATATTTGAGTAACATTTAGGCCAAGTGGCAGTCATAAGGAAAAAGTATTGGTTAATGCAA
GTGAATTATGTTCTATATTCTAAGGATAATATAATGTACTGAATTGTTTTTATTTTTAAATACTGAGTGT
TACAGTAATTTCACTGACATGTGCATAGCAAAATGGCAGCAAACTGCCTGAAGCAATAAAATTTCCAGAG
TGATCCCTTATAGCATATCTGGAGAAGCTGGGAGTTAGGGAATTAGCAGTGTGTGGAAAGGACATTAACT
GCAGCCCAATAAAGAAGACTAGAGCTAGAGGAAGATACTGGGATAAGACTGGCATCCCTAATGCTGGTAT
TTCAGAAACATCGCTAAATTGGTTAATCATGTCTACAAGTGATATTTAAAATAATATTTTCACTCACTTA
AATTGTTAACATTGATATGTTGTTGATAAAGAATATTAAACTCAACAATCATTTTACAATAATTCTGTAA
AGACTTGCGTGCCTGTAGTTGAGGTTTGTTGCATTTCTGAGCTTACTTTTTATTCATGAGAAATGAAAAC
ATAATGGGAGAAAATTTTTTAAATAAAGGGTATTTTAATTTTTTATGAAGTTTGGGACTTCAAAGTATTA
ACAAAAGTTGCTGAAAATATATTGACTTTTACTTTCATTAAATTACATTTTATCATCTAATTTCTTAATT
TTCTGTATTTGAAATATTATGATTTAGAGATATCTCTGTAGATAGAAAGATAATGAAAACAATAGTAAAA
CAAATGTAATTCAGGAGCATAAAAAAAAGATGAGAGAAACCTTAATAATAGTAGCTAACATTTATCAAGCA
TTTACTATATGCCAGACATTGATTTAGTGTTTTACTTTTGCTAACAGATTTTTTCCTTACCATAATTCTA
TCAACTGGATGGTATTATCTCCCCTTTTCAGATGAAAAAACCTAGATATAGACAGGGCAAATGTCTTCTC
CTAGGTCTCAAAGTTGGTAATTGGTACACTGAAGGTCTGAACTCAGGCAATCTGATTCCAAATCCTATGC
TCTCAACTGTATTCCATATTGCTAAAATAAATGTGGATTTTTGTAATATTAGTACCCTCAAGATGTTATG
GCAAGCAGGCTTTTATAAGTGGTGTCTTTAATAACTTTCCTCATTCCATACTTCTAAAAAATTATCTTAA
GGTTAAATTATTGAGTGTCAAGCAACTGTGGATTCTAACACTTGCTAACATGCATGCACACACCCAAATA
TACATGTTGTTACTGACTTACATATACAGACACAGCAGGTGGCAATATATAAGTGCAAATTGATAATATA
TCCGTGGAAATACAAACAAAACTTTGAGAAATCAAATACTTGAATTCTTTTCTACCCCTTCTCCTCAATT
TTTGTACTGAACTAACTACATTACATAGAACCTGCTAGTATATGTTTCATCATTACACTTGTCATTTCTT
CTCTTCAAATTTAAACCCAACAAGATACAGGGGAAGATTTAAATGCAATCCAAAGAAAACAGGAAAACAA
TTCAAGAGTTTAAAGATGACATAGTCATTTTAAGAAAGAACCAAAATTAACTTCTGAAATTAAATATTTT
ACTACAGGAATTTCATAATACAATTATAGTAATTAACAACAAAATAGACCAAGCTTAAGAAAGAATCTCA
GAGTTTGAAGATTACCCCTTTGAATCAACACAAGCAGACAAAATTAAAGGAAAAATATTAATGAAAAAAA
CCTCTGAGAAATATGGGATTATGTAAAGAGACCAAGCCTGTGACTCATTGGCATTCCTGAAAGAGGAGAA
AGAGTAAGCAACTTGGAAAATGTCTTTGAGGATAAAGTCCATGAAAAATTTCCCAGTCTTGCTAGAGAGG
TGGATATGCAAGTTCAAAAAAATTCAAAGAATCCCTTCAAGATACTATACAAGATGGTCATCCACAAGACA
CATAATCATCAGATTCTCCAAGGTAAACAAGAAAGAAAAAAACCTTAAAGGCAGCTAGAGAGAAGGGGCA
GGTCACTTACAAAAGGAGCCCCATCAGTCTAACAATAGATCTTTCAGCAGAAAGCTTACAAGCTAGAAGA
GATTGGGGACCTATTTTCACCATCCTTAAAGAAAAGAAATTGCAACTAAGAATTTTATATTCTGCCAAAC
TAAGCTTCATAAGTAAAGAAAAAATATTATTTTCGGTCAAGCAAATGCTAACAGAATTTGTTACCATTAG
ACCTGCCTTACCAGAGATGCTTAAGGGAGTCCTAAACATGGAAATGAAAGAATGATACCTGTCACCACAA
AAATAGACTTAACTACAGAGCCCACAGACATTATAAAGCAATTATGCAATCAAGCCAACATAATAACCAG
CTAACAACACTATGACAGAATCAAATCCTCACATATCAGTATTAATCTTGAATGTAAATGGGTTAAATGC
CTACACTTAAAAGGCATAGAATAGCAAGTTGGATAAAGAAGCAAGACCCAACCGTTTGTTGTCTTCATG
ACTCATGTATCATGACATCCATAAGATAGAAAATGAATAAATTGAAATAATATTTATCTCAGAGTTGTCA
GGATATTTATAAGGTGCTTAGCACAGTGTTACATAGAAACTCAATAAATTGGAAAGTTCCAACATAGTAG
CATTATAGTTGCTGCACTTTTTTTGAGACAGGGCCTCTGTCACCCAGGCTGGAGTGCAGTGGCATAATCT
TGGCTCACTGCAAACTCCACCTCCCAGGCTCAAGTGATTCTCCCACCTCCTGAGTAGCTGGAACTACAGG
CACATGCCACTTCACCCAGCATTTTTTTCATTTTTTTTTTTTTTTTTTTTTTTTTAGTAGAGATGAGGT
CTTACCTTGTTGCCAGGCTGGTCTTAAATTCCTAGGCTCAAGCAATCAGCCCGCCTTGGCCTCCTAAAGT
GCTGGAATTACAGGTATGAGCCATCACATCTGGAAGCTGTTTCTTTTTAAAGTGACTACATTAATTTACT
TGATCACGAGTAATACATAAATGAAAATTTGAGAATACATTCACTCCAATATTTGGAATTATGTGACTTC
TAGATTTTTGCAATTTAAGTAGGCATAAAATGGTACTTTGTTTTAGTATTTGTCTGTGCTCCTTGATTCT
TATAAATATTATATTTTGTGAAATCCATTGCTGAATGCAAGTGGTGCTGGTTACATTTGCCTATTTCCAA

FIG. 5 (continued)

GTTTTAGTACATTTATTTTTGAAATATATTTTATCAGTTTAAGGACTTACTTGTAATATCTTTGTGTGGT
CTTGGTATTAGGTTAATGTTGGCCTCAATAAATGAGATAGGAAGTATTTTTTTCTGCTTCTAACCTCTGA
AAAAAACTGTAGAGAATTGATATAAATTAATTCTTAGGTATTTGGTAGAATTCAACAGTGAAACCATGTA
GGCCTGTTTCTTTCTGTTTTGGAAAGTTATTAAAATCAGTTCAATTTCTTAAACAGAAATAGTCCTTTTA
ATATTGTCTATTTATTCTTGTACAAAATTGGGTAGATCGTGTCTTTCAATATATTGGTCTATTTTATATA
GGTTATCATAGTTGTAGGCAGAGTGTTGCTTATAGTATTTCTTTATTATCCTTTTCATGTATATTGGATC
TGTAGTTATGTCCCCGCCTTTATTTCTGTTATTAGTAATTTGTGCCTTCCCTCATCTTCTTAGGTAACCT
GGCTGGGTCAATTTTATTAATCTTTCTAAAGAATTAACTTGTGGTTTTGTCAATTTCCTCTATTGATTTC
CTGTTTATGATTTAATTGATTTCAGGTCCAATTTTTATTCTATTTTTTCTTGTGCTTACTTAAAATTTAA
TTTGCTTTTCTTTTTGATTTTCCCAAGGTGGAAACTTAGATATTGATTTTAGCATTTTCTTGTTTTCTAA
CATATGCATTCAGTGCAATAAATCTCTAAGTCTTGATTTTGCTACCTTTCACAAATTTTGATCACTTGTA
TGTTTAATTTTATTTTTTTCAAGATGTTTTAAAATTTTTCTTCAGATTTCTTTTGACTCATAAGTTACTT
AAAAGTGTGGTAGTTAATCTCCACATATTTTGGTATTTTTCCAGTTATCTTTCTGTTATATTCTAGCTTA
ATTTCATTGTCATCTAAGAGAAGACATTATTAGTTTAAATGTGTTAAGGTGTGTTTTATGGCTTAGGCTG
TGGTATATATTGGTGAATATTCCATGTAAGCTTAAGAAGAATGTGTATTCTGTTGTTGTTGGATGAAATA
ACATATAGATGTTTATTATATCCAGTTAATTGATGATGTTGTTAAGGTCAATCATGTTCTTCCTGTTTTT
ACCTGCTGGATCTTTCCATTTCTAGAGAGATGTAGAGTCTCCAAATACCATAGTGTATTCATTTATTTCT
CCTTGTATTTCTACTGGCTTTTACTTCAGATAGTTTGCAGCTCTGTTGTTTGGTGCCTCTATGTTAAGAA
GTGTTATGTTTTCTTAAGAATTGACCCCTTTAACATTTTGTAATGCCCCGTTTTTACCTCTGTTAATTTC
CTTGCTTTAGAGTCTGCTGTGTCCAAAATTAATTTAGATTGTCTTGCTTTGTTTTGGTTATTGTTACCAT
GGAATGTTTTTCTCCACTTCTTTACTTTTTTAAAAAATTACACTTTAAGTTCTGGGATACATGTGCAGAA
TGTGCACATTTGTTACATAGGTAAACACATGCCATGGTGGTTTGCTGCACCCATCAACCCGTCATCTACA
TTAGGAATTTCTCCTAATGCTACTCCCTAGCCCCCCAACCCCCAACAGGTGCTGGTGTGTAATGTTCCCC
TCCCTGTGTCCATGTGTTCTCATTGTTCAACTCCCACTTATGAGTGGGAACATGCAGTGTTTGGATTTCT
GCTCCTATGTTAGTTTACTGAGAATGATGGTTTCCAGCTTCATCCATGTCCCTGCAAAGGACATAAACTC
ATTCTTTCTTTTGGCTGCATAGTATTCCATGGTGTATATGTGCCACATTTTATTTATCCATTCAATTATT
GATGGGCATTTGGGTTGGTTCCAAGTCTTTGCTATTGTGAATAGTGCTGCAATAAACATACATGTGCATG
TGTCTTTATAGTAGAATGATTTATAATCCTATGGATACATTCAACAATGGTTGAATTAATTTACACTCCC
ACCAACAGGGTAAAAGCATTCCTATTTCTCCACATCCTCTCCAGCATCTGTTGTTTCCTGACTTTTTAAT
GATCGCTTCCAACTGGCGTGAGATAGTATCTCATTGCAGTTTTGATTTGCATTCTCTAATGACCAGTGAT
GATGAGCTTTTTTAATATGTTTGTTGGCCACATAAATGTCTTATTTTGAGAAGTGTCTGTTCATATCCTT
GGCCCACTTTTTGATGGCATTGTTTGTTTCTTTCTTGTAAATTTGTTTAAGTTCCTTGTAGATTCTGGAT
ATTAGCTCTTTGTCAGATGGATAGATTGTAAAAATTTTCTCCCATTCTGTAGGTTGCCTGTTCACTCTGA
TGATAGTTTCTTTTGCTATGCAGGAGCTTTTTAGTTTAATTAGATCCCATTTGTCAATCTGGGTTTTTGT
TGCCATTGCTTTTTGTGTTTTAGTCATGAAGTATTTGTCCATGCCTATGTCCTGAATGGTATTGCCTAGG
TTTTGTTCTAGGGTTTTTATGGTGTTAGGTCTTACATTTAAGTCTTTAATCCATCTTGAGTTAATTTTTG
AATAAGGTGTAAGAAAGGGGTCCAGTTTCAATTTTCTGCATATGGCTAGCCAGTTTTCCCAACATCATAT
ATATTAAGAAGGGAATCCTTTTTCCATTGCTTTTTTTGGTCAGACTTGTCAAAGATCGGATGGTTGTAGA
TATGTGGCATTATTTCTGAGGTCTCTGTTCTGTTCCATTGGTCTATATATCTGTTTTGGTAAAAGTACCA
TGCTGTGTTGGTTACTGGAGGCTTGTAGTATCATTTAAAGTCAGGAAGCATGATGCCTCCAGCTTTGTTC
TTTTTGCTTAGGATTGTCTTGGCTATATGGGCTTTTTTTTTTTTTTTTTTTTTGGTTCCATATGAAATTTA
AAGTAGTTTTTTCCAATTCTGTGATGAAAGTCAATGGTAGCTTGATGGGGATAGCATTGAATCTATAAAT
TACTTTGGGCAGTATGGCCATTTTTACAATATTGATTCTTCCTATCCATGAGCATAGAATGTTTTTCCAT
TTATTTGTGTCCTCTCTTATTTCATTGAGCAGTGGTTTGTAGTTCTCGTTGAAGAGGTCCCTCACACCCC
TTGTAAGTTGTATTCCTAGGTATTTTATTCTCATTGTAGCAATTGTGAATGGAAGTTCACTCATGATTTG
GCTCTCTGTTTGTCTATTATTGGTGTATAGGAATGCTTGTGATTTTTACACATTGATTTTGTATCCTGAG
ACTTTGCTGAAGTTGCTTATCAGCTTAAGGAGATTTTGGGCTGAGACAATGGGGTTTTCTAAATATACAA
TCATATCATCTGCAAACAAAGACAATTTGACTTCCTCTCTTCTTATTTGAGTATCTTTTATTTATTTCTC
TTGCCTGATTGCCCTGGCCAGAACTTCCAATACTATGTTGAATAGGAGTGGTGAGAGAGGGCATCCTTGT
CTTGTGCCGGTTTTCAAAGGGAATGCTTCCAGCTTTCACCCATTCAGTATGATATTGGCTGTGGGTTTGT
TATAGATAGCTCTTATTATTTTGAGATATATTCCATCAATACCTAGTTTATTGAGAGATTTTAGCACAGC
TCCAGTGTGCAGCTCCCAAAAAGATCAACGCAGAAGGTGGGTGATTTCTGCATTTCCAACTGAGGTACCC
AGCTCATCTCTTTGAGACTGGTTAGACAGTGGGTGCAGCCAACAGGGGGCAAGCCGAAGCAGGGTAGGGT
GTCACCTAACCTGGGAAGTGCAAGTTGTCAGGAAACTTCCTCCCCTAGCCAAGGGAAGCCACGAGGGACT
GTGCCCTGAGGAAAAGTGCATTCTGGTCCAGATACTATGCTTTTCCCAGTCTTTGCCACTGGCAGACCAG
GAGATTCCCTCGGGTGCCTACACCACCAGGGCCCTGGGTTGCAAGCACAAAACTGGGTGGCTGTTTGGGC
AGACACTGAGATAGCTGCAGGATTTTCTTTTTAAACCCCAGTGGTGCCTGGGACACCAGCAAGACAGAAC

FIG. 5 (continued)

CCTTCACTCCCCTGGAAAAGGGGCTGAAGCTAGGGAACCAAGTGGTCTAGCTCAGTGGATCCCACCCCCA
TAGAGCCCAGCAAGCTGAGATCCACTGGCTTGAAATTCTCCTTGCCAGCCGAGCAGTCTGAAGTCAACCC
GGGATGCTCGAGCTTGGTAGGGGGAGGGGTGTCTGCCATTACTGAGGCTTGAGTAGGTGCTTTTCCCTCA
CAATGCAAACAAAGCCACTAGGAACTGGGTGGAGCCCACCGCAGCTCCACAAAGCCCCTGTAGCCAGACT
GCCTCTCTAGATTCCTCCTCTCTGGGCAGGGCATCTCTTAAAGAAAGGCAGCAGCCCCAGTCACGGGCTT
ATATATAAAATTCCCTCTATCTGGGACAGAGCACCTGGGAGAAGGGGCAGCTGTGGGCGCAGCTTCAGCA
GACTTAAACTATCCTGCCTGCTGGCTCTGAAGAGGGCAGTGGATCTCCTAGCACCATTCTCAAGCTCTGC
TAAGGGACAGACTGCCTCCTTAAGTGGGTCCCTGACTCCCGTGCCTCCTGACTGGGAGACACCTCACAGC
AGGGTTCAACAGACACCTCATGCAGGAGAGTTCTGGCTGGCATCTGGTGGGTGCCCCTCTGGAATGAAGC
TTCCAGAGGAAGGAACAGGCCGCAATCTCTGCTGTTCTGCAGCCACTGCTGGTGATACCTAGGCAAACAG
GGTCTGGAGTGGACCTCCAGCAAACTCCAGCAGACCTGCAGCTGAGGGGCCTGACTGTTAGAAGAAAAAC
CTACAAACAGAAAGGAATAGCATCAACATCAACAAAAAGGATGTCCACACAAAAACCCCATCTGAAAGGC
ACCAACATCAAAGACCAAAGGTAGATAAATCCACGAAGATGAGGAAAAACAAGTGCAAAAAGGCTGAAAA
TTCCAAAACCCAGAATGCCTCATCTCCTCCAAAGGATCATGTTTACTTTTAATCTATATGTGTTTATATA
TTTAAAGTGGGTTTCATGTAGACAACATATAGTTGGTTCTTGTTACTTGATCTACTGTGTCAATTTCAAT
CTTTTAATTAATACATTTAGATCATTTGCGTTAAAAGTGATTACTGATATATAGTCATGTGTCATTTAAC
AACAGGAATGCATTATGAGAAATGCATTGTTAGATAATTTTGTCATTGTGCAAACATCTTAGCGTGTACA
TACATAAACCTAGATATTATAGCCTACTACACACCTAAGCTTATGGTATAGGCTATTACTTTGATGCTAC
CAAAACCTGTACATTATTGTAGTTTACTAAATACTAATTACAACACAGTGATATTGGTGTATCTAAACAT
ATCTGAGCACAGAAAAGATAAAGTAAAAATATGGTATTATAATCTTATGGGACCATCATTGTATATGCTC
TCCAACATTGACTTAAATGTCATTATGACATGTGTGACTGTAGTTAGATTAGTATCTACCATAGCGGTTG
GGTTGCCTGGGTGTTTGCAAGATAAATTTACAAATAATTCAAGTCCACTTTCACGTGACGTCATACCACT
TCATGGGTAGTATGAGTACCTGATAATAGCAAATTATTTATAATACTTTCCTTCCATTTCTTGTATCATT
ATTGTCATTCATTTCAATTTTGTGTCAGCATACATAATCAAATACATTATAGATATTATTTTAAAAACAG
TTATGTCTTAGATTAAGAATAAGAAAAGTAATAATTTATATTTTATGCTCACTTATTTCTCCTCCAATGT
TTTCCTTGCTTTAAGTAGATCTGAGTTTCTGATTTATATTATTTTATCTTTCTGTAAAGAACTCCTTTTA
ACACCTTGCAAGGCTGATCTAAAGGCAAAACATTTCTTTCAGTTTCATTTCTCAGAGGAAGTTTTATTTC
TCCTTCATGTTAGATGGATAAATACACAGGGTATGGGGAAGGTATTTTTTTCCTCTGTATTCTTTTGGGAT
TTTTTTCCTTTGTCTGTGATTTTCTATAGTTTTAAAATGACATGACTAGGTGTAACTTTTTGGGCATTTA
TACAACTTGTTATTCTATGGACTTCCAGGATCTGTGGTTTGTTGTCTGATACTAATTTGGGGAAATTCTC
GGTTGTTATTGTTTCAAATATTTCTTTAGTCTCTATTTCTCCTTCTAGTGATTCCATTATGTATATGCTA
TACCTTTTTTAGTTGGCCCACAGTTTTTTGATACTTTGTTCTGATTTTTTTGTCTTTGTTATTTTTATTT
GCTTTTTAGTTTTGCAGATTTTAATTCATATATCCTGAATCTCAGATATCCTGTTTTCAGTCTTGTGCAG
TATACTGATGTGTTTACCAAAGGCATTCTTCATTTCTGCTACGATGTTGTGACATTATAATTTTTTTAAT
GAAATTTTTATCTGTCTGCTTACATTGCTCTGTTCTTGTGTGCTTCTTTATTTTACCACTAGAACACTTA
GCATATTAATCACAGTTGTTTTAAATTCTCAGTCCAATAAATCCAACATCCTTTCTGTATCTGAGTTTGG
TTCTGATTCTTGCTCTGTCTCTTCAAAATTATATATATATTTTTTTTCTTTTAGATGACTGGTAATATATTC
TGGATATCCAGACATAATGTATTGAGTTTTGTAAAACCTGCTATACATAGGCCTTCAATAATTGTTGCTA
AGGTGTGGAGAGGAGAGGCTTTTTTTTTTTTTTTTTTGCCTCTGGACTGTAACCTTCACAAGTGTTTTT
TTAGTATTTTTTTTCCTTCTTGGTCAGAATGGGTTTGGTAGAGTGAGATGGATTTTGGTATTTTCCTTCT
GTCACATGGAAGACTAGAATTGGCTGGAGCTGGGTATTTCCTTTCCCTTCGGTCAGTTAGGCTCTAATAA
CACACCATCTTATGAGGCTCTGATAAACTAGTTCTGCCTAAGGGCAAGCACTAAAAGTCCTATTAAAAAC
AGAGGGCTCTAGTCTATTTCAAAAATGAGTCTTGTCTCCTCATGCTACTGAAAGAACAAGATAATTTTTC
TCCAACATTTACTATAAGAACCTGGTCAAGCTCCTGGAGGGAAAACTCAAAATGTGGAGGTCACCGACTG
GGTTCCCTTGGAGTGTTTAGTGCTCAGACTTAACCACACTGAGTGAGACTCTAGCAGTTTATCAATTATA
GTGAAGGTATTTCTACCTTGTCACTGGTTCCTGTGCAGTTTCTGTTCATGAGTCTCTACTGCTATAAGCT
GTGACACTTTGTAATCACCTATTTGTCTCTCCAATCTTGAAGGCAGTCGATTGCCATTGGTCCTCACCTC
TTTTACAGATCCAGAAAGAGTTGCTGCATTTTAAATTGGTTCAGTGTTTTTCTTGTTGTTACTATAAAAT
GGCAAGCTCCAAGCTCCTTGAAGGTTTCCAGAGCCTAGAAACCAGAAATACCAGCATATATTTTTTATTG
TATTTTCTTATCTCATGTCTTACAGTTCTACATTTTACTTAAGAATTCATTGTGATTGCTTGATTAATAT
ACAAGTTATTTTAAAATAACATTTTCTTCAAATATTTGGAGATTTTTCGTAATAAATTTTTTGCCAGTAA
TATTTGTCATAATTGCATTGTGGAAGCTATGACAACTAATTTTTGAAATTAGTTGAGACTTCTCTATGTC
CTAGTACATCATTGATGTTTGTAAGTCTCCCTGATGTACTTAATAAAAATGCATATTCCATATTCTTTCA
ATTGTTGGATGTATAATTTTATATGTGTCTGAGAGGTCAGTCTTGTTAATTGTGTTATTCAGATCTTCTA
TGTCCTTGCTAATATTTTAACTATTTCACTTATCATAATTGAAAGAAAGATGTTGAATTTTTTTCTTACA
AAAGCAGTTGTATTGATTTTTGCTTATATATTTTGCATCTACTAAGTGCATTATTATATATAACCGTTTTAT
CTTTTAGGATGATATAATTCAATATATGGAGGACTTCTCTATCCTTAATGATGTTTCTATGTCTATTTGG

FIG. 5 (continued)

GCTATTATTTATACACCTATAAAATTTTCTCTAAGTGGTTATATTTTCTTATCATTTTACTATCACGAAG
AATTTCTTCGTGATTTAGGAATATCTCTTATAAAAAGCACAGAGGTAAATTTTGAAGAAAAATCCAAACT
AAAAATTATCTATCTTTAAACTAGCAATTTTCTACACTTATGTTTATTGTATCTATTGATATAGTTAGAC
TTGCTTTTACTATCTTACATTATTATGGTGATTTTCCCCTTTTTTAATGCTCCCTTAAAATTCTTTCTTA
TACTTTTTGAATGTATATGCCTATCTCTCTCATAACAAGACAAACATTCTAGCATGATTCTATGATCTGA
ATGTTTGTTTCCCCCCAAATTTGTATGTCGAGTCATAATCACCAAGGTGATTCTATTAGAAGGTGGAGAC
TTTGGAAAGTGATTAGTTCATGAAGGTAGAGTCCTCATGAACAAAATTAGTGTCCTTATGAAAGAGACCC
AATAGAGCTTCCTTGCCTCTTCTAACATGTGAGGTTACAGTGAGAAGATGGTTCTCACCAAATACCAAAT
ATGTTGGTGTCTTGATCTCAGACTTCCCAGGCTCCAGAGCTGCAAAAAGTAAATTTCTATTGTTTATAAA
GTACACAGTTTTCTTATATGCTATATTTTGCTATATTTTCTTACAGCACCCCAAACAGACTGAGACATAT
GTTCACATACTCTTTTATATGCCTCTTTACCCTCTATACAATATGATGCTATCTGGATTTTCAATCTAAA
ATTTTAAATTCTAGACACTATGACTATTTTACCTCCTTTCCTGTTTTTAGTTTTTTTTTAAGACATTGAG
AAAATTTATCAAGTATTTTATTCACTTTGCTTTACAAATCTCATGCAACACCTTCAGAATTGGATTCTTC
TTTTATTTAAGCAATTCTTCCAAAATTGTTTCCAGTACGTGTTTGGTTGCAGTATTTTTTGAGGCCTTATA
TGCTTGAGCATATATCTCTTTATAGCTGAGAGGCTGTTTATCTCAATGTAAAATTATGGGTTCAATGCTC
TTTTACTTCAGTACTTAAAAAATATATTTCTTTGTCTTTTGTGTACCCACTTTTGCTGTTAGAAAGTGAT
ATACTTTCTTTCCTGAAAGGCCTCAATTTTTTTTCTTGTCTTTGATATTCATAAATTTTAATATACTTCT
TCCAAATATGTCTGTGTTCTTACTTATCTCTTGTGTTGAGCATTCAATGGGCACTCTCAACCTGCATTTT
TTGTTTTTTTTAATCTTAGTAAATTATTTGAAAATTTTCATTTATTATTTCTTTAAATATTTCTCCTCTT
CAACTTATTTTTTCTCATTTTAAGGCATTAATAATTAAATTATTCTCAATTTTAGTTAAAAATTATGTAT
ATCTTAACCTTTTACCTATATATGCTTTCAATGTTTTAAATGAAATAACCAATTTTATTTTCCAATTCTT
TCTTGTTTTAAGCCCATATATTATTTTATACTATTTTACATCTTGTACTCCATATTTTCTACTTGTTCTT
TTTTGTTATCTTATTTTGCTTTTATTTCATTTTGCTAATATTCTTTTCTTATATATTTTGTGTATTTGTA
ATGCTTAAACTCCTGTTAAGTGTTTTGTAAAACAATTACTCCTTATGGTGTCTTCAAACCAGTTTACTTT
TTTCTTTCTCTTTTGAAATGTTTTCTCAAAGACATCACTATTTTGCCCTGAAGTCACATTTACTTAGTTA
TGATAGTTTCTTTTTTATAGTAATTGCACAGGGGAAGAGCTAAAGGATAGAACTCTGTCATTGTGAACCC
TGAAAGCTCAGAAAAAGGGGAGGGAAATGAGCCTCAAGGTGATGACCAGTAACCAATAAATCACGTCACT
CTGCCCTTTGACAAACATTTCTTTATCCATGGCTCCCTCAGTCCCCTGAATGCGAAATTGCTTTGAGGAG
ATTGTTAACTAGTACTGCAGAAATACTGAGGGGATTACCTGTAGAAGGGAATGCTCAAGGCTAGTCAGCC
TTTCCTCCTTTGCTCAGCTGCTCTGATTCAGAGCTACTCTGATTTTACTCTGGAGGACACATGCAACCAA
TGTCTGAACAGTCATACTCAATCCCTGCATTGAGGTAGAAAGCACTGATTCCTAGAGGCTGATCTGAATC
ATGCAACTGTATTGAAGGCAACAAAAAATAATAAAATAGCCATGTATTTTAATAGGGAAAGTATATAGTA
ATTGAAAAGAAAAACCAAAATCAATACAAGTAGTATTGTGACCGAGAGACAAAGGTAAATTTGAAGATAG
GTTTGTGATTTCATAATGGAGACCTTTGAATGCTAGAAGCTACCCCCTCCCTTTGTAAAGAACAACATTA
GGTAAATGATTAAAAAATTATGTCAAAGTCTATGATTTTGAAACTCTACCATATTTGAAAATATTATATT
AAAATAATGATACTAAACAAAGAATTTATGACAAATGTTCATCTTTTAAGTAAAAGAACCTTAAAATTTG
TAAGCAGCTAAATCTAATGATATAGGCAACTGCTAGGATATCACAAAAGAATGGGATTTTAATAGTGAAC
TTATACAATTTGCCTGAAATTAATCAAATCAGCACAGAAATGCACAGATGACAAACACTGTAAGATGTAA
GAGGAATTAATCATAAGAGGTTTATTTGGCTAAAGTGACAATTGTTAAAGATAGAATTGCCTAACGTTAG
TTAATAACAGAAAAAATATCAGAAATTTTAAAAAATGCTGTCTTAATCTATTAAAATTATATAAAGATAA
AGCAAAACAATGTAGGTTTATAAACAAGAACCTTTAAAAAAGCATAATACTGATGCTTATTACAAATTTA
TATCTTGAGCTGGGGTACATCATCCAATTTACGCATGAGAAAAGTGTTTTATAATTTTTCACTCTGTAAT
TCATATTTTAAGTTCATCTGAAATGTATTTTACAGAGGTAAGAACAAGCAACTTGGTGCTCAACTCTCTT
CCTGCTCTTCGCCTAGTGCTAAAATAATTTGTGTAAATGAACTGTGAATGAATTTAAGTTTCAGAAATAA
AATTTATATTAATAGAGAGAAAGAAGGATAAATCAATAGTCTTCCAAATATGATACATGTACAATGCAAT
GATATTCACAAACATCTTCATGAACACACGAACATAATTTCTTTTGAATCTTACCATGACCTTCTAAAAT
AAGTAAGCTAAATATTCTATATTATACTACTATTTATGAGGAAACTACATTTCTGTGAATTGTGTAACTT
TTTCATCTTTATAAGGTTAGCAAGCAAAAACAAACAAATAACAAAATAAACAAAAAAACAAAAACTTGGC
CCAGATCTGACTTTAAAGTACCTTCACTTTTATTGTATCACATACGATCTCAGTCCACAGATGGGTTCCT
GATTTAGCCAAGAATATAGTAAAGTGAGTGTAAAGTAGAAGAAAAAAGAAGGAAAATATTAGGTATAGAA
ACCTACATGAAATAAAATGAAATAAAGAGAGCCTACTCTTTCTGAAATGCACCAGTAAAATGTACTCCTA
TCTTGTGTATTAAGTTTATAATCATACATTCAATTCAAAATTTAACTAAAACTATGGAAACTGAGAGCTA
ATAATAAAATGATATACACAGCATTCTAACCAGAAAATCTTCTAAGCAATTGTACAATTCAGATAAGAAG
AAATAATTACAAATGTTCAGAAATTAAGATTAATTAAGACTGTAAAATTTTTTTTTTTTTTTTTTGAGA
CAGGGTCTCACTCTGTCACCCAGGCTGGAGTGCAGTGGCGCGATCTTGGCTCACTGCAAGCTCTGCCTCC
CAGGTTCACGCCATTCTCCTGCCTCAGCCTCCCAAGTAGCTGGGACTACAGGCGCCCACCACCACGCCCA
CTAATTTTTTGTATTTTTAGTAGAGACGGGGTTTCATCATGTTAGCCAGGATGGTCTCGATCTCCTGACC

FIG. 5 (continued)

TCGTGATCTGCCCACCTCGGCCTCCCACAGTGCTGGGATTACAGGCGTGAGCCACCGTGCCCGGCCAAGA
CTGTATAATTTGTTCCTGAAGGGCAGGGAAAATGTAGTGGTAATTTTTCAAGATGAATTGGAAGATAAAG
AAAGAGAGGTCACATTATTTGTGTTATTCAACTGAAATAGTTTTGAATTTCAATAAAACAAGCTAAGAAA
TGCCCTTTGTCATCAAATTGATGTGAAGAGTAAAAAAATTTTAAAAATGAAATTCTCTAAGATAATATGT
GAAAATAAGACTATTTAAATTTCAACAAACATTTAACAAGTGTATACCCATCCTATGTTCGTTTTATCCA
ACTTCTTATCATTCCTAAGTATATTAAGTAAAGTAATAGCTATTAATATGTTGACGTCATTAGCAGAAAA
ATAACTTTGCAAATGATTAAGTGATGACAGTTGTATATCCATGTTATTAGATGTTTAAAATTCAAAAAAT
AATTAATTCAATAAATTTTTGAAACAAATCCATAGAATAAAAACATAGTTTTTCAAAATGTATTTTTCAA
AGGTAAAAATTTCTCACATTAGGCTAGGTGCGTGGCTCATGCCTGTAATCCCAGCACTTTGGGAGGCCAA
GGCGGGCAGATCACGAGCTCAGGAGTTCAAGATGAGCCTGGCCAACATAGTGAAACCCCATCTCTACTAA
AAATACAAAAATTAGCCAGGTGTGGTGGTGCCTGCCTTTAGTCCCAGCTACTCAGGAGGCTGAGGTGAGA
GAATCGCTTGAACCCAGGAGGCAGAGGTTGCAGTGAGCCAAGACCACGCCATTGCACTCCAGCCTTGGGG
GAAGAGTAAGAGTCTGTCTCAAGAAAAAAAAAATTCTCACATTATTGTAAATACTATTACAATAGCTAAC
ATAAATTCAAGATTTATAATTATTTTTTTCTGATGCTCATACAAATACACATTTTACTGGATCTTGGGTG
TTGTAGTAAAAAACAATTTACTAAAACAAAAAAAAAGAATGTATACCTTAAATACATAGAATTTTATTTG
TCAATCATACCTTAATATGAGAAAATAATGTTCTTCTTTTCCAAAGTAAAAAGAAATTAATAGAGCAAAG
CTATATTTTACAACAATGTACATATAATCCATAATTCTGTCTAATACTTGATATTCTACTAACTGAATTG
AAGCAGTACTTGCCAACATTTACATATATATGAATAATTGAATTATAAAAGTTATGAGATGCTGATCTGA
ATTACAAAAGTCCCTCTGTGATAGTAAACACATGCATAAATTAATTCTATAAAGTGTTATTGCATTTTCT
CAAAATACATTGAAGTTCTGTAGTCAAAGTAATCAATAGAGAGCCAAAACTGTTTTTGAACAGTTTAGCA
TATTTTCATTATTAAAAACAAAACTTGCCAATAGATATAAGAAAAAGAGCTGACCAAATTAGAGTTTAAA
TAGCATAAAATAATAATTTTGAAATTCTAAAATTGTATTTTAGAAAATCATGACACGTAGAAAAATTATT
TTAATACAGGTCTCATTTGAATTAGATAAACTTATATTCTATACCTGAATAAAAAGTAATTGAAAATACC
TATGACTTTGCAGCAATAAAAAATGGCAAATGATAAAAAATTCAAATTTTTCTTACATAAATATTTGTGA
AAAGGGGAAACTGAAGAGAGAAAATATGATAGTTTATTTAAAGTGAAACATTTACATAGTTTGATGTAGA
TAAAAGTAAATTGAGAAAATTCCTATTTGGCATTATTTGCTGTGAGTTTACCAAGATAATGTTTTTCTCC
ATTTTAAAAACAATGGTCTATGGTCAAAAAGTAAGTCAAACTATCCCTGTTTGCAGGTGACATGATTCTA
TATCTAGAAAACCCCAAAAGCTCCTTCAGCTGATAAACAACTTCAGCAAAGTTACAGGACACAAAATCAA
TGTACAAAAATCAGTAGCATTCCTATACACCAACAACAGCCAAACCGAGAGCCAAATCAGGAAGGCAATC
CCATTCACAATTGACACAAAAAGAATAAAATACTTTGAAATATAGCTAACTAGGGAGGTGAAAAATCTCT
ACAATGAGACTTATGAAACACTGCTCAAAGAAATTAGAGATGAAACAAACAAAGAGAAAAACATGCTTAT
AGATAGGAAGAATCAATATAATTAAAATGGTCATACTGCCCAAAGCAATTTATAGGTTCAGTGCTATTCC
TATTAAACTACCAGCAATATTCTTCACAGAACTAAAAAAAAAAAAAAAAAAAAACTATTTTGAAATTCATA
CAGAACCAAAATGGCCAAATAGCGAAGACAATCTAAGCAAAAAGAATAAAGCTAGAGACATCATGCCGTC
TGATTTCAAACTATACTACAGGACTATAGTAACCAAAACAGCATGGTACTAGTAGAAAAACAGACACATA
AACCAATGGAACAAAATAGAGAGCCCAGAAATTAGGCCGCATGCCTATGAACATTTGATCTTCAACAAAG
CTCACAAAAACAAGCAATGGGGAAAAAAAACCCTGTTCAATAAGTGATTCTGGGATAACTAGCTGGTCAT
ACACAGAAAATTGAAATTGGACCCCTTCCTTACACCATACATAAAAATTCTAAAAATTCAAATTATAAAA
AAGGAAAAAAAAAAATCAACTCCAGGCAGACTAAAGACTTAAATCTAAAACCTCAAACTACAAAAACCCTG
GAAGACAACCTAGGCAATATCATCCTGGACATAGGAATGGCAAAGATTTCATGACAAATGACACCGAAAG
CAATCAAAACAAAAGCAAATATTGACAAATGAGATATAATTAAACTTAAGAGCTTCTGCACAGAAAAAGA
AACTGTCAACAGCATAAACAGACATCCTACAGAATGGGAGAAAATATTTACAAATATGCATCTAACAAAG
GTCTAATATCCAGCATCTATAAGAAACTTAAATTTACAAGAGAAAAACAAACGGCCTCATTAAAATGTAG
GCAAAGGGTATGAACAGACACTTTTCAAAAGAAGACATACACATGGCCAACAAGCACTTGAAAAAAAGGC
CAATATTACTGATCATTAGAGAAATTCAAATCAAAACCACAATGAGACATTATCTCACGCTAGTCAGATT
ATTATTATTAAAAAATAAAAAACTAACAGATGCCTGGCAAGGTTGTGGAGAAAAGTGAACACTTATACAC
TGTTGGTGGGAGTGTAAATTAGTTCAACCATGTGCAAAGCAGTGTGGCAATTCCTCAAAGAGCTAAAACC
AGAACTACCATTCAACCCAGCAACCTCATCACTGTGTATATACACCCAGAGGAATATAAATCATTCTACT
ATAAAGACACAGGCATGTGAATGTTCATTGCAACATTATTCACAATAGCAAAGAAAGACATGGAATTAAC
CTATATGCCCATCAATGACAGATTGGATAAAGAAAATGTGGTACATACTATGGAATACTATGCAGCCATA
AAAGAACAAGATCATGTCTTTTGTGGAAACATGGATGGAGCTGGAAGCTATCATCTTTAGCAAACTAACA
CAGGAAGAGAAAACCAAATACTTCATGTTCTCACTTATAAGTGGGAGCTAAATGATGAGAACTCATAAAG
ACAAAAAAGGGAATGACAAACACTGGGGTCTAGCTGAGGTTGGAGGGTGGAGGGTGGGAAGAGAGAGAGA
AGCAGAAGAAATAACTATTGAGTACTAGGCTTAATACCTGAGTGATGAAATAATCTGTACCACAAACCCC
CGTGACACGTGTTTACCTGTACAATAAACCTTCACATGTACCTCTGAACATAAAAGTTAGAAAGAAAATA
TTAACAACTTTAAATTTAGTAATCATAAATGTCAAATTAAAAAAAAAAGATTTTAGACTCACACTTATAA
TCATAGCACTTTGGGATGCCGAGGTGGGCGAATCACTTGAGGTCGGGGGTTTGAGATCAGCCTGGCCAAC

FIG. 5 (continued)

ATGGTGAAACCCTGTCTCTACTGAAAATATAAAAATTAGCCAGGTGTGATGGCATGTGCCCATAGTCCTA
GCTATTCAGGAGGCCGAGGCAGGAAAATCTCTGGAACCTGGGAGGCAGAGGTTGCAGTGAGCCGAGATCA
CAACAGTGCACTTTAGCCTGGGTGACAAAGTGAGACTCTGCCTCAAAAAATACATATAAAATAAAAAAGA
TTTTAAATAATATTATAAATAAACTAAAATTTCTAGGAACAATTTTTTAAAATCAGAAAAATAAGTCATA
TGATAATACAGATACTCTTAAGAAATGCATAAAATATATGAATATACATGTGTACTTATTGATGTGCATG
AAGATACACTAATATATCCAACAAGAATAAGCACATCCATTATTTTATAATATTAAAGTAAGCAATAAAA
GGAACACTTAAAAATATTTTCTTCAATTTAATTGACTATATTTTTTTATTTGGAAAACAATTTTAACACA
TATTTTAAATAGTTTAAATAGAGAAAAATGTAAATAAAGCTGTATTACAAAGATATTCATTGATAAACAC
TTCAAAAAATTTTTCAACTTCCTTATTTTTATCACGTATTTTGCTCTAGAAAATTTCCATTCCACATGAT
ACATTTGTTGTATAAGAGATACAAAACAAATTCCTACTAGGGGAAATAAAGCTTCAGTAAGGAGGTGGCA
TTAAGCTGGGCTTTAAAATTCATGCAGAATTCCCGTTGCTTCAAATGGAGAGAAGCAGCAGTGTACCACA
GATAAATGAAGTGAGACGTAATAAGGGTTTGGCTCAAGATAATAAGGAGATGTATAATACTTTTTTATGT
ATAATACTTTTGTTCCAATTCCCTTTATGCTTTACTTCAGTTTTGTTTCTCTAGTTAAATAACTTTGCAT
CTCTAAACTTTATTATTCTTATTTGTATAATGAAGAGAGTAACTTATGCCAGGCAAAGATTTTACAGACA
CTAGAAATAATATATACAAAATAGTTGGAATAGTTCCTGAAAAATAGTAGGTTCCACATGATAACAAGAT
TTATGCTTGTGCTCTTTCTGTATTATTTGGAAAGAAATATGTGAAGTGCAGGAAAGTGGTGTGAAGTTAT
TTTTGTGGGATATCTGGTGTAATCTTTCTCTTTTATCTATGTTATCAAATATTTTTCAAAAGCTGTATTT
CTCATTAGTGCTTTTTGTGAATAAATTAACTAGGAAAATTAGAAGAATGGCAACAATATACATCATAGAA
AGGCATAGATTACAAAGAGAGTATATACACAATACCTGTCCAGAAGATGTGGTATAAGCCAATATTTTAA
TTATACTTATTTACTTCAGATATTGCAAATTTTTCTTATTTTTATACCTTCTTTCTTTTAATGACATTTC
CTATATTTTCATTCACTATGACATTGTTTTCTTTATATCAATACTTATGAAGAGAACTAACTATTCTAAC
TAGGGAGTAGTTAGACTAGTTATTTTAAAATACTTCATTAAAGGACTACAACGTGTGTACCATCTATGAC
TTAGTATTGATTGATTGTCATCTTTCATGTTCTTCATAAGTGGGTAATTTTGAACACTGTTATATTATTT
CAAAGGGTGTTATTTGTTTGTTCAGATGTTTTACAAAGTAATTAACTTTGTTGGCTTGAAATTGCAAACT
CTGTCTTCTTGGTGTCTTAGTCAATTCAGGCTGCTATGACAAAAATACCACAGACTGGGTAGCTTAAACA
ACAAACATTTATTTCTCACAGTTCAGTAGGCTGGGAGACCAAGATCAGGGTGCCAGTATGGTTAGCTTCT
GGTGACAGTTCTCTTCTTGCTTTCCTGACATGGCTAAAAGAGAAAGAGAATGGAAGTGAGTTCTCTTCTT
AAAAGGGTACAAATCTCATTCATGAGGGTTCCACAGCCATTATCTAATCACCCCCCAAAAGCTTCACCTC
CTGATACCATCACATTGGGTTAGGATTTGACATGCGCATTTGAGAGGGACACAAACATTCATTCTATGAC
AGATGGTAATCGAAGCAAAGACAATGAATGGGTTTGCCCAGCAAGAGTATGTAGAGTAAAAAGAGAAGAC
GGTATGAAACAAATCACTGAAAAAAAAAAAAATGTAACAGCCAGAATAACATGATCTAAGGATACTTGGGA
GGAATTATGCAAAAAATAGGATTTGAGTCATGCAGGCAAACTCTTTAAATTTTTACTGGAAAAGACATGA
GAGACAGAGTTATGGAAAAGAAAGCATTTGGTGGAGGCAGATCCATTTTTTCTAATAAAATAAATTAATA
TGGATGAATTGTACAATCATTCCTTAGTAAATTTCAAAACTGCATCCAGGCAAATCTCTTATGCAACAGG
CCTGCCTTAGTTGTGTCTACTGGGTACTTGTTTATTTTTAGGCATGTCAAATTCGACTTGTGAAAAGATG
ATTATATTGTCTTTAATGCTGTCTTCTTTTTCCCACCAAATGACAGTTATTCAAACCAGAAACTATAAAA
CAAACATACAGTTATCCGAACTAGAAAACAAAATCAGAATTTACATTTTCTATTTTCCCCACCTCCTGTT
GGTTCTCCTCTTAAACTTCTCCTTGTGTGTCTGTAAGCTTGTTATACACTTTTCATCTCTACTCTTTTTT
ATTTTCTGAAGTCAGCTTTCTAACAGATCTCTTTTTCCTAAGTTCTTCTTCTTCATGGCTGCCAGAATTA
ACCATCTAAAATTTAATTTTGTTATGTAACATTTTAAAGTGCATATTGACTCCTCAATGTTGAACATATT
TCTATCCTTACACTTCACCTACACAAATAATATTTCTGTTTTTCAAATAATCCGTGTTATTTCACTTCTT
AGGGGCTTTTCATGTGCTTCCTATTTTGTTTTAAGTATTTTGTGTCTTCAATATCTAAGCTTCTATAATC
AACTGAAGACTTAGCCCCAATGTCAACACATCTTTAAGAACTTTAACCTGTAAGGTCAGAATAGTCCCTT
TTTCCTATCTGCACATAACATTACAAACTTATGGCAATTATAAAACTCAATACATATTATACTGTCATTA
TTGGTTTATTGCTGCTGAAGATTATAATTTTCAGTGCATTGATTATGTCTTATTTGTTTTTACTGCCCTT
GTTCCTGTTCCTCTGTACCTGCCTCAACTACATAGCTTAGCAGACTAACTGCTATATTACAGTTGCTCAA
TGAATGTTTCTTGAGTAAATCAGTTGAGTTCCAAAGCTAATCCAAGTTGTGCGTTTGACAAATTAGAAGC
TTGGAACTGTCTTCTGACTTTAAGTTTAGAACTATTGCCATAATAAATTAATGACCGATCTGCCATGATT
GCAGGCAAGTAGAGACTTTATTTCTTATCTCAATGTCAGTTGTCTCTTTCTGCCAATGCACATTTTATTT
GATGATTGTGCACATTTATATCTCTGGTTTTTATTTAAATAAATTTAGAACATATAGCTGGAGACGGTAG
CTCAAACTGAGGATGAAAATAGACATTTATCAAGGTTATTATGTAGCTAGCACTGCATGTACACAGAGGT
ATTTAGGGAGCCACACATATGTCCAAGGCAAGACATATGCTCATAAAACGTCTGAGAAGATTGTATCCTT
TTACCTAATGCTAATCCCCAAGCTTAGAACAAGGCAAGTGAAAGGTCAAAGGGATAAAAAAATACAATAA
ACAAAATAAAAATTTACAAGAAGTTGTTATGGACTAAATATTTGTTCCCCTCTCCCCAAAATTGTGTATT
GAATTTCAAAATCCAATGTGATAGTATTTGGGAGTCTTTGGGAGCTAAAGAGATCATGAGAAATTTGCTC
TTATAATGTGAGTAGTGCCTTACAAGAAAATGCTGGAGAGCTCACTAGATTTTTTTCCTCCATGTGAGAA
TACAAAGAGAAGTTAGCTGTTTGCAGCCTAGGAGAGGGCCCTCACCAGAAATTGACCATGCTGGCACCCT

FIG. 5 (continued)

TATCTCAGACTTCTCACCCTTCAGAACTGTGAGAAATAAATGTTTGTTGTTTAAGCCATCCGTTCCATCA
TAATTTGTGATAGCAGTCTGAACTGACTTAGACAAAAGTTCAACAGCAAATTTGAGCAGTTAGAACACAG
AATCCGCAAACTTGAAGATAAGACAATTGAAATGATTAGTCTGAGAAGCAGAAAGAAAAAAAAAACGAAG
AAAAATTAACAAAACATACGGAACTGTGGACACTATCAGGTGAACCAGCATAACAATTACAGTAGTTCT
AGAAAGAGAAGAGACAGAGAAAAGGGAAGAAATAATATTTGAAAAAAAAGTGGCCGAGAACGTCCCAAAT
TTGATAAAATATATGATCTCAATATCGTAGAAGCATAAGAAAATCCAAATAAACTCAGAGATCCACTTTG
AGGCACATTATGATCAAACTGTCAAAGGCCAAAAAAATAAAAATAAATTCAGAATCTTGACAGCAACAAG
AGTAGGAAATAATCATGGGCAAGAGTTCCTTAATAAGATTAACAACTGATTTCTCATCAGAGACCAGAAG
ACATTGAAATGATATATCCAATAAAGAACTGATATTCAAAAGTATGCAAAGAACATCTAAAACTCAATAA
TTAGAAAAATAACCCAATGATAAAATGAGGATGATATCTGAACAGATGCCTCACTGAAGAAGATATAGAG
ACAACAAATGAGCATGTGGAAAAATGCTCCACATCCCGTCATTAGGGAATTGTAAATTAAACAATAAGCT
ATGTCACTGTATACTTGTTAAAAGGACTAAAATTCCAAACACAAAAATATACCAAATACTGGCAAGAATG
TGGAGCGACAAGAACTCTTATTTACTGCCAGTGAGAATGCAAAATAGTGCAGCCACTTTGGAAAATATTC
TAATAGTTTCTTACAAATTTAAAGATAGGCTTACCATACAATCAAGCATTTGTAGTCCTTGGTATTTACT
GAAATAAGTATCAAGTGGAAAGCATGTCTACACAACAGCCTACAAAGAGGTGTTTATAGCAGCCTTATTG
ATAATTGCCATAAGTTAGAAGCAACCAAGGTGTCCTTCAATATGAGAATAGGTAAAGCGACCTTGGTACA
TTCATGCAATAGAATAAGAATATTTTTAGTGATTAACAAGAAATGAGACATAACCAATGAAAAGACATGA
AACATTAAAAGTATATTTATAAGTAAAAGAACGCAATATTAAAATGTTACCTACTATATGATTCCAACTA
TATGACAAATTTTATTTTATAAATGCTTTACCACAAAAGTTAATTCTAAAAATGTTTGCCACCAAAAAAC
AAACAAAAAACATGGTAGAGATCATCTTTATAGTTTTTTATAATAATCCTCTTGATAAAGATTATATCAT
AAGAAATCTTGACAGTTTACATTCAAGGATATGACATTTTATTTACAAATTAATGAAATCTAATAAAATG
TGACAATGAAAATTTAGCTGAGTATAAAAGAACCTAAATTAGTAGACAGTGAGAGAGGAATGGGGGAGGG
GATGTTTACAAGAAGTTCTACATCAGTACAGAACTTCATAAATTAGTGGATAAGAGCATGGTGAAGAGCA
ATTGTAAATCAAATGAAAATGTTGTGGAACTCTTATTAGTATCTGCAGCCACTCTGGCACTTTAAACATA
TCCAGTAGGAGAGGTTAATTCTCTCAGCAGGAGACCACTCACATTACTTTTTTCTCCCTATAAAATAATG
CATCGTTTTGTCATGCTGGTAAAAAACACATAACATTAAATGTACCTTTTCAACCAATTTTTAAGTGTAC
AATTAAAAAGTGTAAAGTACACTCACATTGATGAACAACAGATCTCTTGAACTTTTTCATTTTCCATTGC
TGAAACTTTGTATCCACTAAACTATCTTCTCCTCAGTTCTAAGTAAGTACCTTTCCACTTTCTGTTTCTA
ATTTTTTGACTACTTTAAATATTTCTTTCTTTTTTCTTTCTTTTCTTTTTTTTTTTTTTTTAAGATGGAG
TCTCGCACTGTCACCCAGGTTGGAGTGCAGTGGTGTGATCTCGTCTCACTGCAACCGCCGCCTCCTGGGT
TCAAGCGATTCTCCTGCCTCAGCCTCCCAAGTAGCTGGGATTACAGGTGACTACCACCATGCGCAGGTAA
TTTTTTTTTTTGTATTTTTAGTAGAGATGGGGTTTCACTATGTTGGCTAGGCTGGTCTCAAACTCCTGAC
CTCGTGATCCGCCCACCTTGGCCTCCAAAAGTGCTGGGATTACAAGTGTGAGCCACTATGCTTGGACTAC
TTTAAATATTTCATATGATAGAATCATACAGTATCTCTCCTTTCGTGACTGGCTTATTTAGCTTAGCATA
ATGTCCTTGAGGTTCATCCATATTGTAGCACATGATGTAATTTACTTATTTTTTAAGTCTGCATAATATT
CCATTGTGTATGTATACCACATTTTCTTTATTCATTCATCAGTAGACATTTGGGTTGCTTCTACATCTTG
GCCGTTGTTAATAATGCTGCATGAATATGCATGTACAAATATCTCTGCTAGATCCTGTTTTGAATTACTT
TGACTATATACCCAGAAGAATAATTAATGGCTTGTATGGTGATTCTATTGTTTAGTATTTGTGGAACCTC
CAAACTCTTTTTCATGAAAGCTGAACCATTTTATATTTCCATCAACAAACATGAAGTTCCTAACTTCTCT
TACTCGTTATTTTCTATTCTTGAAATAGTGGCTTTTCTGATGGTTGTGGGGTGATATCTCATTGTGGTTT
TAATTTGCATTTCCCTGATAAGTAGAAAGTTGAGCATCTTTTAATGTGCTTATTGGCTCTTTGTATATCT
TCTTTGCAGAAATGTCTATGTAAGTCCTTGACCCATTTTTAAATTGGGTTGTTCTTTGTTGTTGTTTCCT
TGGAAAAGTCCATATATTCTAGATATTAACTCCTCATCACTTATATTATTTGCATTTATTCTGTGCCATT
CCATAGGTTATCTTTTCACCTGTTGTTTTCTTTTATGTGCAGATGATTTAAGTTTGATATAGTCTGATTT
GTGTATTTTTAATTTTGTTGCCTGTGCTTTTTGTATCACATTTTAAAAATTGCCAAATTGAATGTCCTGA
AGCTTTTCTTTTATTTTTTTCTGGAAGTTTAAGGTCTTACATTTAGGTATTTAGTTCATTTTGAGTTAAT
TTTTGCATATAGTATAGGGTAAGGGCCCAATTTCATTTCATTGCATGTGGGTATCCAGTTTCCCAAACAT
CATTTGAAGAGGCTGTCCGCTTCCTTGTACTAAATGAATGGTGTTTTGCTGCTTCTTTTAAGAGTCTCTG
TTTGTGTGTAACTTTTGACAGTTTGATTATACTGTGTCTTGGTATAGAGTTTTTTAGATTTATCTTATTT
GGAATTACTTGAGCTTCTTAAATGTTTAGGTTCCTTTATCTCTTAAGATTTAAAAAAATGGGGTCCATAA
TTTACAAGTTTTCAGACCTTTCTCATTTACTTCTCTTCTGGTATTCCCATAATGCATATGTTGCCCTGCT
GGATGGAGTCCCATAATTTCTTTAGGCTCTTCTTTTCTTTTTGCTCCTGTGACTCTAATTTTAGAAGTTC
TGTCTTTGATTTTCCTGATTTTTTCTTCTGCCTAGCCAAGTTACCTGTTGAGTCTTTCTAGTGAATTTTT
CAGTTCAGTTACTTTATAATTCAACTCCAGAATTTCTGTTTGGTTCTTCATAGTTTATAATCTGTTAATA
TTGCTATTTTGTTTATTTGTTATGTTCCTCATTTCATTTAATTGTCTGTTCATATTCTCTTTTAATTCAT
TGCACTACTTGACTAATTTCAAGTTCTATGTCTGGCAATTCCTATATCTTCATTTGTTTTTGGTCAGTTT
CTGGAGATGTAATTTTTTTTTCCTTTTAATGTGTGAGAATCCTTTCTTTCTTTTTATACTTTGTATTATT

FIG. 5 (continued)

TTGTTGTTGAGATTTTAACATTTAAAAAATCAGTCAACTCTCCCAGATTTTGTGAGATGATTTTCCATAA
GGAGAACTCTCCTCACTAATTCTGAATAGAGATTCTGTGGCCTACTCATGCTTTTTTTCTAGTATGTTTT
CCTTTCTTTCTCCTTTAGGCTTGTGTGTGTGATCTGTTTGAAAAGGTTTGTTGGTTTCTATAGAAGACCC
TCCCCTGGGGCTTGAGGTACAGTGGCCTTTCTGGGGCTGCATTAAATTGTTGTACTGGTGCTCCACCTCG
TGTCTCTGTCTGGAACTGCAGTTTTTGGTGTACCTTTGCTTGCAAAGACCGCATTTTTATTAGTACTTGA
ATATAGGCAAGTCAGAAGCCTGTCCTTGGGCAACCTCCCTAAAAGTCAAAATATTGAACATAGGAGATTT
AAATGTTTCCTTCCAATTGCATTGCACAGGGTGGAGTGAGAAAGACTCTAGTGAGAGAGACTGGAAACAA
TCATGATTTTTCTTGCCAGGTTGTTTTCACGATAGCCTGGAGGTACAGAAACCTTGTAATTGGTTCTGAA
GTTCTCACAGAGGCATTTAGTACATATGTTGTTAATATTGTGTCTTGCTGTTGAGGTTCCAGGGCTGTTC
TGCTCTCTTGCTGATGTCACTCTCTTCCACATTTCTTAGTCCTTTTTAATAAAATGATTTTTTAATGATT
AGGACCTGAACAATTTTCATCACTATTCTATGGCACAAAGACTGCATACATTTTTACAAGATGTTAGAAT
TGACTATCTTTGAAGAAAATCTTCATAATTTTTGTCTAACTCTGTTGCCCCTTTCTCCTGTTTTATTATT
CCCATCATCAACTTAATACAACTAGTTTTGATACTCTTCTACATTTTATGCTGTTTCTTAGATAACTTTT
TACATTTTATTTTAAAACTTTTAGTTATCTCTATAAGTTGTATCATTTAATAAATCTTTTGAATTCCTTT
TATCTTCATTGATAGCATATATCATTTGATAGTTTCTTATGCAGAAAGGAACACACCCACATTTTGTCGG
CTATCAAAGAGTTTTGTTGGGCCTTTTATCTCTGTCCCCCAAACATGGCCTAGGGCCAGACACAGAGTAG
GTTTTGGTTATATAAATGTTCACTCATTATTTCTTAAGCATCTTTGTGACAGACACTGTCCTAATCACTG
GGGACGGAGCAATGAACAAAACAGACAAAAACCTATGACTTGATGGGGCTAATATTCTGCTGTGGCAATA
TAAAATAAACTCATAAAGGAATAAATGTATTGTGAGCAGAAAGGGGTGCAATTTTAAAGAGATTGATCAA
GGAAAACCTCACTGTGAAAGTTCCACTGAGCAAAACTCTTAAGGGTGTGAAGGAATGAATGATAGAAATA
CGACTATGGGGAAGAGCCTTTCATGTCAAGTGAAAAGCAAGAACAAAAAGCCTGGAGCAATATAATGAAT
CTGGAATGCTCAATATACAGCAACAAGGTCTAATGTAGCTGGAGAGGAATGACCAAGGACAAGAGTAACA
AAGTATAAGATTAGAAAGATAAAGAGGAATATTTGTGGGGAGGTGGGTGTAAAAAAGAGGATAGGTTGTT
TATGGTCTCATAGGTTATTGGAAAAACTTGATATGACTATAAGTTACATAGGAAAACAGAGGGGCAGCAT
GATCTATTTCTGATTTGTAAAGGACTTCTTTAGCTACTTTGTTGAGAAGAGACTGTTAGGCAGATGTGCA
CAGAAGTAGAAACATGGCTCAGGAGGCTCTTGCAATAATTGAAGCTAGGCATGGTGGTGGAAACCACTGG
GAAATATAGGAGGTAATTAGAAGAGGTCGTTTAGTCAGTTCAGGCTGACAGAATAGAATAGACTTGGTGA
CTTAAACAACAAATATTTGTCTCTCACATTTCCGGAGGCTGAGAATTCTGATATCAGGGTTCTGGCATAA
TTGAGTTCTGATAAGGGCCCTATTCCTGGTTTCCAGAAGGCCATATCCTCATTGTGTCATCACTTGGGGG
TAGGGGAGAGAGAGAGAGAGAAAGAGAGAAATAGAGGGAATCCCTAATTTCTTGTCTTATAAGGGCACTGAT
CTTATCAAGAGGGCTCCATTCTCATGACCTAATTTCCTCAAAAAGACCCTATCACCAAACATCAACACAC
TGGAAATTAGAGTTTCAACATATAAATTTGAGGTAGGGGATATAAAGATGTAATACATAACAGGGTAAAT
ATTAATAGTAGAGAGCCCAAAGAAATTTGTTTATGGATATAAATGTGAGCTGTAATAGAAATGATTAATC
GATACATTTTATTAACATGAAATTGACAAATAAAACATCTATAACCACTGCATCTTACACTGGATGTCAG
TCACTTGTGTTGGTCATAGAATTTTTCTTTGCCTCTGCAAAGTTCTGTTTTTCAGCTGGCTTCCTGGAAA
TGCTGCCTTTGAGAATGTACTGCCACTCCCCTCCCAGTTAGCCAATGCTATTCATATGGAAATAAAGAAT
AGCTCACCATCATGGCCATCTGAGAACATGATGTAGCTTTCTATAAATCAGTTAATGAGATTAATTTAAA
AATAACAACCTTAACTGTAGTGCTCTAATATTTTGATATTATAACCAAATTAGAAATGATGCTTTATCAG
TGTAGTGATAATAACATTTAAATGGCTGAGTAGTAGTACCTGGTAAAAGGGAAAACTAAGTATGGTTTTT
AAGATACAAATAATGTTTTTAAGTAAAGAAGAAAGCTATTATAATTCCATGTGCCTATTGACATTATATA
GTCCTTCGATTAACCATTTTCCCCCTTTCCTTCTGATTTTTCTTAGATGTTCTTGGCAGCTCTGTCACTC
AGCTTTATTGCTAAGACACTAGGTGCAATTATTATGAAAAGTTCCATCATTCATATAGAACGGAGATTTG
AGATATCCTCTTCTCTTGTTGGTTTTATTGACGGAAGCTTTGAAATTGGTAACATTTATTTTCTATTTTA
ATAACCAAACTTGCAAAGTTAAAAAATATATATGCTTTACACCACTGGTTATCAACTGGGGTAAATTTAT
CTCTCACAGGCAATTTGGCAATAACTAAAAACATTTGTGGTTGTCATAACTGCACAGGGGTTGGGGGCAA
TGGAAGTGCTACTGGTATCTAAAGGTAGAGGTCAGGGGTACTGCTAAATATTCTATAATGCACAAAGAAT
GATGTAACTGAAAATGTTGATAGTGAGGATGTTCAGAAACCCTGATTCTACACAAATTCATTTTTTGCAA
ACTAACGCCATGTCATACTTTACCTCCCCTCTCTCAAGATGAAGAAACTTTGGGAGAGGACTGTTATTCT
TAAGGAGAAAGGAATCTTTTCAGAGCAACCTACGTTAGACCTCTATTGTTTCACTGAGCACACAAAAATC
TTTCCTTTGAAATACTGAAGATATTTTGTTGTCTTCATTTTATGTTGGATTTCTCCAATAACAGCTCAGG
GAAAACATTTTCTGGTTCATATTTGTGTTTTTCCCTATTAGTAATTTTTTTCTAGATAATTTATAAGATG
AATATTAAATTTTCTGGGAATTTTTCTCTTTAAATTTTTTTCTTCTAAATTTCCATTGTTTTTCTTTATG
TTTCATTAATCTTTGATGCCATCATCCATCTTACCATATTAAGTTCTAATTTGTATATTTAATCTGTATT
TTATATTTACAACAGCACTTTATTATTCCCTTATTATTTTTAGGCTGCCAGTTCTGATTTCATGGATGCA
ATGTGCCCTTGTACCCGTAAAGGTACTAAATTTTTTATAAAGTAAAAAAAAAATTTACTCATTCATTTTG
GTGCTTTTATTCCAAATTATTTTTATGCTATTTTTTTTCAGAAGTGCTCAGTTATCCTTAACTGCTATTT
GTTTATTGTTATGCCTGAGGCTCCAGATGGATTAGAAGTGGTCATGACTTTTTTTTTTTTTTTTTTTGAG

FIG. 5 (continued)

ACGGAGTCTCGCTCTGTCGCCCAGGCTGTAGTGCAGTGGTGCGATCTCCCCTCACTGCAAGCTCTGCCTT
TCTCCTGCTTCATCCTCCCGAGTAGCTGGGACTACAGGCACCCGCCACTATGCCCGGCTAATTTTTTGTA
TTTTTAGTAGAGACGGGATTTCACTGTGTTAGCCAAGATGGTCTCGATTTCCTGACCTCGTGATCCACCC
ACCTCAGCCTCCTAAAGTGCTGGGATTACAGGTGTGAGCCACCATGCCTGGCCTCTGGAAGTTCTTAATT
AAGTTCCGCCTTTCTGTGGTTTAATAGCACCTCTGTCCATCTATTTTTATCGTTAGTATGAAACTTCTTG
AAGACAGATGCCATGGTTTATTCTTTTTCAAGTAACTTTCTTATTTCTGGCTCTGAGCTTCATGTCAGGT
TCATGTTAGAAATTTAAATAATATTAAGAATAAATAAAGAAACGCATGAAGGAGCACCTTACCCTCATCA
GGAAGATTCATCTCCATTTTTCTTCATTCCAGTATAATCCAGTCAACTCCAAATTTTTCAATAAAATTTT
ACTTCACTAATATTGCCAAGTAATTCAAGTGCTTTTTTTTTGTATTTAAAACAACTTTTCAATGAGTGGT
CTAATGTAGGTGAATTCACCTTCTCAATTAAATCACATTGTCTTTGAGGGAAGGCACTATGTCTTGGACT
CTATTTGCATCCATTCTGGGGTTTTCAATTCTAGACGCAAAATTGAACTAAGCTGTATCAACATAATTTT
GTTCCCTTTCTAGGAAATTTGCTTGTGATTGTATTTGTGAGTTACTTTGGATCCAAACTACATAGACCAA
AGTTAATTGGAATCGGTTGTTTCATTATGGGAATTGGAGGTGTTTTGACTGCTTTGCCACATTTCTTCAT
GGGATAGTAAGTGTTAAAAAAAAAAAAAACCTCTGTGCCACTATCAGTACCTTGTAAATTAGGAGTAGAA
TTTTATTATTATCCCTTTAAATAGGCAGTTACCTTTTGAGAAGATACCCACTAAGTGTGTACAGAAATGA
AATAGTGTCTATTTGTCTACATAATCATTTTATTTATCGTAGCTTTCATATACTTTGAAATAACAAAAAG
ACTAAACTGTAGAGTTTCAAATGAAATAAATAGGCTTTTTATGAATTTTTAGTATAACGTATATACTGTA
CGTCTTTGCCTATAAGATTTTGATTATTTTTTATAAGACCTCAACACTTACACCTATACCCACTGAAGTA
TAGTTGTTCCCATCATTTCACTGAAGCTGTTATTCCTAAGGTCACTGTGTAGTTATAATTACAGTCAGAT
GCTCCTGAGAGAAAAGTTAAAATGGCACATGGGGGAGAAACTTATTTTTCACATTACAGTTAATGTAGCC
AGTTCAAGGATGATATGATTCTACCTCTTTCCATCATAGTGCTATGCCTTGCATGGTCTTGGCTTCATGA
TCCAAATTGTGGCAACGTATTTCCAGGCAACAAGATAGAAGAAGAAAAGAATAAGAAGCAACAAACAGTC
CACACAGGCTGAGGCTTAAGAAGCATTTTCAGAAGCAAAATATCTCTACTGACTTTACATTTACCAGATG
TTAGTTACATTTCACACATAGATATATAAATGCTGAAAAAAATAGACATTATTCCAAGTTACCAAGTTCC
CGGTTAAAAATCCCAAGTATAATTACTGTGGAAGGAAAGAAGAGAGGATATTAGGAGACAATGAGCAGTT
TCTGTTAGAGACACCAATTACTTACTCATTGCCAAATCCAGCAATGACATCATTTGCTCACCATATTAAA
TCCATTCACCCACCATATTTGGCCCTTATAGGAAGTTTCTTCTTAGTGGTACTGCTCTAGCTTGTTTTCA
TCATACTGCACTCTCTTGATTCATTTTCTATCTTTGTGTCTTCTTCATCATGTCCATTTTTTTTCATCTG
CTTTTGGCACCATACCGTCAGAGTCCTCTAATTTCCTTTTTAATCTTTATTTATGATTCTTCATGAGTTG
TATGGAAAATAAACCTTAAAGGCAAGTATCACAGCTTCATCTTCCATTCTACCCTAAAATTAAGGACCAC
AATCTAGATCAGCATTGCTCTAAATATGCCATAATATGTGACACTTTTGCACCTGGTATTTCTACAGCCT
TGAATACCTTTGTTTCTTTGTCTACCCTTCTATTCATCTTCCAGATTCGTTTTACCTGTCATTCTCATGT
TGATGTCTTCTCTGATCTATTCCCGCAACCTCCAAGCAAAGTTGATCATATCCTTTGTCTTTGTGACAAC
TCAGGACCTTATATATTAAACTTATAACTTTTATCATCTATGTTTATACTAGTGTGAAATTCCCTAAGTA
CAAAAACTGTGTGTTTTATTTCTAGCTCTTTGAAGCTTAGCATAATGCCTGGAATACAGTAGGCTGCCTT
TAGAGCTCACGTGGTACCTAATTATTTATGGATATTAACATCTCTGTTATTCCTATCAAGTTTTCTCTCA
TCTAGTTGAAATGGATTAGATTTTATTTTTACTACATTTTGAAGAGTCATACATTAGAGCGTGTGTGTGA
ATATGTGTCCATGAAAGAAAATCTGACAGACTGATCATCTTTGAAGATAATTCAAAAGGATGAATGGTTA
CACACAATTAATAATTACTTTTTAAAAAGGTGAAACTAGGATATTTCATATCTTGACCAAGATATAACCA
CTCCTAGGATAATAGCAAGGTGATAACCCACTTAGCCTGGGGTGTATTGAATTATCTTTCTTGCTGGACA
CTTCCATTTCACTTTTACCCATCACATCTCTTAAAACACATGCTGGGAAATTGACAGAAAGTACTCTGGT
AATTTGGGGAAGATAATGGTGCAAATAAAGGGGAATATTTCTCTGTATTTCTAGGAAAAGTGAAAATATT
CAGTAGATAAGCAAAATGTTTAATTCAGTGATGTTCTTACAGTTACAGGTATTCTAAAGAAACTAATATC
AATTCATCAGAAAATTCAACATCGACCTTATCCACTTGTTTAATTAATCAAATTTTATCACTCAATAGAG
CATCACCTGAGATAGTGGGAAAAGGTAAGAATTAATATTGACAGTAAAAAGTCTTCTAAAATGTATACAT
TTAATTACATCTCTAAAAATTGTTGTGATATTCATTAGCAAAATTTAATTAAGAATGAATAGGAAAAACA
TTTGACTCTTACAGACATAATTATAGTGTTAATATACACAGTTCGCCCATTAACAACACAGGTTTAAACT
ACGCGTTTTCACTTCTATGCAAATTTTGTCCATCTGAACTGGATGATAAACCTGCCGGTAAGAATATCTG
ACATTTTCTATATTTGGATTGAACAGGGCCAACTGCAGAACTTAAGTGTGCATGAATTTGAGAACACACA
GGCAGCCCTGTAACAAATTCCTTAATATACCAAGGGATGACTGTATTATATGTAAAAGCATTTAGAAGTA
GATCAGAAAAGAGAATATTTTCAATAGGAAATTGACAAAGAATATATGCATTAAAGTAAAACAGAAGGAA
ATGGTATAAATATGTAAATAATATAACTTTGCTTTCATTGCAAAAGGCAAACTATTATATCATTTAAAGA
CTTTTTGCCTATTATAACACAAATTATAAATTATAATTGCAAATTGTACTGCTAAAGATTTTTTTAACCT
ATTAAATAGAAAAAGACTAAAAATACATAGAGACGAGGTAGAGGCAAAAAAGGATTTCACATTGTATATA
TTGCTGGAAGTGTATACGTTTGTAAATCTTTCTGGAGATTCATTATCAATATATGTTAAGAACAAAAATA
TACTTACCTACTTAGTCTGAAATTCTGCTATTATTGATTAATCTTAAGGAAATAACCAGGAAACTGCAAA
AGGACTTATTTACAGTTATAGTCATGATAAACCTAATAGAATAAAACAACAAAAAAGAAATTAAAACATA

FIG. 5 (continued)

AGATACTGAATAAACACATTTGGAAACTTATTCAGCACATTACTGTCCAGTCATTAAAGTTTTGATATTA
AAGAAATCTTAACAACATGGAACAATTGTTATAATATGGTGTTAACTGTGTATACCATTTAACAATATGA
ACTAGATTTTTAAATATATAATGGATATAATGAATATAATGTATATGTTTTGTGCAAATCTAGAAGATAT
ATAAAAAAGCTTGAGGTGATCTTCTGTGTGTAATGTGATTACAGATAATTTTTACTTGTTTGTGCTTTTC
TGTATGATATGGCTTGACTGTGTCCCCACTCAAATATCACCTTGATTGTAATAATCTCCACATGCCAAGA
GTGGGGCCAGGTAGAGATAATTGAATTTTGGGGGCGGTTTCCCCCATACTGTTCTCGTGGTAATGAAGAA
GTCTCACAAGATCTGATGATTTTATAAATGAGAGTTCCCCTGCAAAAGCTCTCTTGCCTGCCACCATGTA
AGACATGGCTTTGCTCTTCCTTCATCTTCCGCCATGATTGTGAGGCCCCCCAGCCATGAGGAACTATGAG
TCCATTAGACCCTTTTCCTTTATAAATTACCCAGTCTCAGGTATGTATTTATTAGCAGCATAAGAATGGA
CTAATACACCATATTGTCAAAGTTTGCAAAGTGAATATAAATTACTTGTACTTGTAAATTAAAAAAAAAT
AAGTAGAATAATTAAGAGTTTACAAGTAGTTAAATTTGTAATAGAAATGCTAAAATTAATGTTTAAAATG
AAACACTCTCTTATCTACATAGGTTGTTTAAAGGAATCTGGGTCATACATGTGGATATATGTGTTCATGG
GTAATATGCTTCGTGGAATAGGGGAGACTCCCATAGTACCATTGGGGCTTTCTTACATTGATGATTTCGC
TAAAGAAGGACATTCTTCTTTGTATTTAGGTAATGTACACAAAATATTAAATTGTATGATCACTTTCCCT
TTGTCTACTTTTGAAATAGTAGAGTTACTAAACTTATTATTTTACCTATTAGAACATATATTTGGGTATA
TGTATTGTATCATATTTCTTTTAAAAACATGGTGAATAAGAACCATGCATTCTTGGCATCTAGTAAAATT
GCTTTATAATATTTTCAGGTATATTGAATGCAATAGCAATGATTGGTCCAATCATTGGCTTTACCCTGGG
ATCTCTGTTTTCTAAAATGTACGTGGATATTGGATATGTAGATCTAAGTAAGTACAACCAGAACAAGGTA
CCATGATAACGTCTTTCTAAGCACACATGCGAAAAACATTTTTTCAAATAACTGAATTCACTCTTTCAAT
AGTCCTTTGCTTAATATAATTAGAAAGTTACAAGTAGGAAATAAATGTATTACTAATCAGAATAAATATA
AAATCCAGCTCCTATTTATACTATCTTTATAACTAAGTGTAAAATGAGAGAATGTAAACAAATTTATTTT
CATGAGCTTGGTCCAAAATAACCAAATGTAAAATGTCTCCCTCCCAAACTGACTGTCCAGTCAAGTAAAT
TTTATTTTTCAGTTGATGGTGGCTTGGATGTTGATGTGTACAACTTAAAGTTTGCTTTGCTAAAGTCTTC
TTGTGGCTGCTGCATTGATTTATGGCTGGAGTCATTTGAGAGACTTCACTGTGTATTTTATGGTCATTTT
CCCTGGTCCTAGCAGAGGGCTTGGCGTATGGCAATGTTCAGTAAGTACTTGTTGAACAAAGGAATAAAGC
AGAGGACACATAAATAAAATCTATGATTTTCTTCTTCATTCTCAGAGCATACTTTCCTTCTTATCTCATA
GATGAAAGAGATGCCATGTTATAAAAACTGTCTCAACTTCAGGCCCTTTTCCCTAAAAATATTCTTGCAC
CATATCTATCTTTATCTTCTTTTTCTTTTTTGCAGCTCAGTGGAAAATATATACATCTGTATCCAATGTT
GATAGATCTAGCTGGAGCTTAGATTCTCCCTTCCCGCTTCTTTATCTCCATCTTCTCTTTTATTCAGCAA
ACACACCCAAGTATTTCCCATCTTTATATGTAGATACAGTTTTTTATACCCCCACACAACTTTCCAGCTG
AATCCTTTTTTTATTCCTCTTTAGAACCAAGCACCTAGGAAAATATCAGCTAAATTAGCTAAGATATCTC
ACCTTCTCACCTCCCATCCACTTCTAAATCCAGTATAATCTGCTTCTGTTATTAGTGAAACACAATCAAT
TTCTACCTACTTTACTATAGATTTGTAAATGGGTATATTTCTATCATTTGCGTTAATTGATATTTCCAGT
GCTTCTTCATCCATTTTCCCTCCTTAGATATCTTATTAGTACCTAAAGCACAATATGTCAAAATCTGATC
TCATCACCTTACCTCCAACCCCACTGTATTCCCTATATTCCTCCTTTTGATGAATATCCATACCTTATTC
AATTATTGACTGAGTTACTGTGCCCTGTAATCTCACATTTCTCTGCATTTACACTTGGTAAAACTTTTCC
CTCTTTTTCATTTGCATAGTTCTTGAAGCCTCTTCCAAAATGTGGATCCTCTTAGAGAAGCCTTACTTCA
CCACTTTCCATTAGTCTCAAATTAATAGCCAAGAGCATGCCTTTATTGTAACCCTTCTCACAATGAGCTA
TTAATATTTGTGTGCTTACTTGCCATCTCTTTACCACATGACAGAATGGCATGTTCTTAGCAAATAATAA
TTAGTTAAGTTTGTGAATAAATAAATATGATTTTCCACCTCATTAGGCCTTCAATAGATCATTCCAAAGA
GATCAAAGGATTCATTTCCAAGATGGGATAGACATCACAGTGGGCCAGCAACAGCCAAAAACTTGAAAGT
GTTTGCTAATCTAAAACTATAAAGAAAATACTTGATAAAATGTTTTACATGTTCAATTTTAGACATATGC
CTTAGAGTAGCTACACATTATGTACATTATTTCTACTCATTCAACTCCAGTTTCATCACTGCTTTATCAC
GAAGAGTACAGAAATACGTGGTAAATGTCCTTAGGTTAATTATTTTATAAGCTCTCTAAATAAGAAATTA
TTACATTATTTGAGAATTCATCACCATACAATTTCTAACATTGAATGTTCAGATATCATTATATCTTCTC
TTATTCAGTGATGAGTATGAGCTTCACTTACAAAGTATACTTTGGCAAACTCCAATGCCTAAAGGAGCTG
AAGACATAAAAATAAATGAGTAAAGAGTGCCAGGAACAGGAATTTAGGGTGTGATGGTTAGAATAGGAGA
ATTCTTTTGGTTGTGAACTGCTCTCCCCATGCATCCAAAAGCACTTGTGTTCCTCAGCTCTGGCCTATTC
TTTTAATGCACAAATTTAGGCCCTGCATTGGCAAGGACTTCTGATTGGTTTCCAAGAAAATCCAAACACC
AAAATTTTTGTGTAGAATTTTTCAATTTTTAAGACTGTGAGTGAGCCAAGAAAAACTTTTTCTCACGTCC
TATCTAGCGCGATTATGACCCTTAGTTACTATGTGTAGAACAGTGAAAGAACAGAAAAAAAAAGTCATCAA
AATTACATTTGTCACAGGTGATGAATAAATACTTTGCATGTAGATGGAGTCACTGATTTAACCAATCATT
TCCTGAAGTCTGAGTTGTTGATTATGACATGGTATGATCATATAAATCAAATTTAAACCCAGATCTGTGC
ATACTTGAAAATAATTATTTCTAGGTAGTTTGTTATCAAGTCAATGTTATCTTATATTAGTGAGTTTTCT
TATAGATTAGAGTAATGGCACCATTTAATCGTGCCACAAACTTCTGTGGTGTGTGTTTCTGTATGCATAT
GCTTTTTTATTCTTATTATTTTTCTTTTATTATGGTAAGAACAATTAAAATGACATCTACCTTCTTAAC
AGGTTTTGAAACATACAGTGGACCCATGAACAATAGGTTTAAATTATGCTCGTCCACTTATGCACAGACT

FIG. 5 (continued)

TTTTTCAATAAATATATTGAAAAAATTTGGGGAGATTTGTGAAAATTTGAGAAAATTTATAGATGAATTG
CATAGTGTAGAAGTAAAGGAAACCCTAAGAAAAAGGTATATCATGAGTGCATAAAGTATGTTTAGATACT
CCACTATTTTATCATTTACTACCATAAAATATACACAAATCTATTATAAGAAATTAAACTTATTAGAGGG
TACAAGATGGCCAACTAGACACACTCAGGAAGCACCACTTCCACTGAGGAAGCCCAAAATATTGAATAAA
CTAACATACTTCGAGCATATCTTTTGAGAGAAAACACTGAAAGTCAATAGAGAGGTGACACAGACACTGA
GGCTGAAGAGAGAGAAAGCTGGAAACCCAGTGCAGGGTTGTTGAACACCAGAGATAGTTTCCAGCCCTGA
GTGGCTCCTAGCTAAGGGGTGAGTAAAGTGGCAGTGGGACAGCCTACTCTCACTGTTGACATCTGGGATC
CTACCTACAAGAGAACCCACGACCCCCAGAGACATTGGAACAGGCAGGGGCATCTGCCCAGAGAGTAGGC
AGAAATAGAACTACAGCCAGCCTTGAACCCAGGGGGTTTTGCATGTTGGGTAGCTGCAGCAGAACGCAGC
CATAGGCGCCCAACATCCAAGGCTCTCTTTCTTCCACCAAGTAGCTCTCAACTCACCTGACTTCTGAGCG
AAGAGACAGCGGGGCCAACTTTCCTGTGAGCTGGGACACATCTGTATTGTAGGCCCTTCTGCCCGCCAGT
CCCTCCCAGTACTCCTGCCTGGCCACACCTGCAAGAATATGTGCACAGCACAGCCTCCACTGCTCAGCCT
GAGGGTTTTTTCAAGGACCCCCACCTGAGTACTTCCTCAGTATCCTTGGAGCACTTCAGATCCCCCAGTG
TAGCTACTGCCTGAACCAGAGGGGCCAGACAGTGGAGACACAGGCTAGTCCCAAAACCCCAGGGCTGCAG
TGCATAGCTTGGGAGTGTGAGCTGAGATTGGTGCCCAGCACTCAAGCAGAGGAAGAATTCTGAATCTCAG
AACACTGAGAGGGGTGAGATGCACGGGTTCATGGCCAGTGCAGAATGAGACATGCCTCATTTCATAGGC
CCAGTCCAGGAAGGCTGTGTCCTGTCTGCCAGCTGCTGCCTCTGCCTAAGGGAGCTCCATGGCTCAGAAC
AGTTTCCTAACAAAAGAAATGCAAGTGTGGCACCAGTGACCAGAGCGGGAGATTGGGGGGGTGTCCCCTA
TGGCCCAGGCACAGGCCTGTTAAGGGGGTCATCTCTCTTGCCCGCTGCCACAAGCACTGTTGTAAACACA
CTGAAAAACAAAAGAGTTATGTCCCCGAGTAACAGCTTATCTGCCAGCCATTACTCTTAAGCACCATTTA
CTGGATCACAGCTCAATTTAAAACATCTGCCTATATATTTGAGACTGTACCTCACTCTGTTACCCAGGCT
AGAGCGCAGAGAAGCAATCGTAGCTCACTGCAGCCTCAAGCTCCTAGGCTCAAGCCATTCTCCCACCTCA
GCCTTCTGAGTAGCTGGGACTACAGGCACACACCACTACACTTGGCTAATATGTGTTATTTTCTGTAAAG
ACAGGGTTTTCCATGTTGCCCAGGCTGATCTCAAACTTCTGGCCTCAAGTGATCCTCCCACCTTAGCCTG
GCAAAGTGCTGGAATTACAGGCTTGAGCCACTGTGCCTGACTTCAAAAATAGTTTGTCAGTATACATTGC
ATATGAAACTGAGAGCAAGAATCTAGCTATAAATAAAAATATTGTGCAGAGTCTTATCCCAGAAATTAAA
CCAACTGACCATACTCAACTTATACCACAGTTAAAGGAACACCATTCCTTCAAGATGAAAAAGAATCAAC
AAGAAATCTGGCAATTCAAAAAGTAAGAATGTACCTTAACCTTCAAATGGGTGCATTTGAGCTCTCCAGC
GATGGTTCTTAACCACATTGGAATGACTAAAATGACAGACAGGCAATTCGGAATCTGGATGGCAAGAAAG
CTCATTGAGATTCAGGAAAGTGCTGAAACACAATTTAAGGAATTCAATAATTCCAGTAGAATGATCCAAA
AGCTGAAAGACATAATAGCCATTAAAAAAACACTACTTCTGGAATTAAAAAAAATACTACATGGATTTGA
TAATACATCCAGACCTTTAGCAACAGAACATACCAAAGAGAGAAAAGAATCTCAGAGCTTAAAAACCAGT
TTTTATAATCCACTCCATCAGACAAAAAGAAAGAAAGAAAAAAAAACATAAAAATGAAGAAAACTTCTAG
GAATTTGGTTTCCTTCTGTAAAGAAACCAAGCCTATGATTCATTGGAATTCCTGAGAGAGAAAAAGAGAG
AGTAAACAACTTGTAAAACGTATTTGCAGATATAGTCCATGAAAATATCCTCAAACTTGCTAGAGAGATT
GATATGCAAATTCCTAAATTACAGAGAACCCCTTTGAGATGCTATAAAGATGACAATCCCCAAGGCATCT
ACTCATTAGATTCCCCAAAGTCCACATGAAAGAAATAAATATTTTAAGATTTTTTTGGGGGGCAGCTAGA
GAGATGGATCAAGTCACTGTCAAGGGGAACCCCATCAATCTTGCAGAACACCTTTGAGCAAAAACCATAC
AAGCCAGAAGAGATTGGGGACCTATTTTCAGCACCCTTAAAGAAAAGAAATTTCAACCAAAAATTTAATA
TCCCACCAAATTAATTTTGTAAGTGAAAGAGAACTAAACTCCTTCTCATACAAGCAAACATTGAGGAAAT
TTCTTATCACTAAACCAGCCTTATAACAGGTCTCTAGAAGAGTGCTAAACATGGAAACAAAAGATTAATA
CTTGCCACAACAAATACTCACTTAAATAGGTAGCCCAGACACATAAAGCAACTATACAACCAAGTCTATG
AAACAACCAGCTAACAACATGATGCCATGATCAAAATCTCACGTATCAATAATAACCCTGAATGTAAACA
GGCTAAATGCCCCAAGTAAAAGACACTGAGTGACAAGCTTCATAAGTAGACAAAACTTAGCCTTCTGTTG
TCTTTAAAAGACACATCTTACATGTACAATACCCACAGGATCAAAGTAAAGGAACGGAAAGAGATCTATC
CATGCAAACAGAAAACAAAACAGGGCAGTAATCACTATTCTTATATCAGATAAAACAGACATTAAACCAA
AAACCATCAAGAAGGACAAAGAAGGGTATTACATAAGGATAAAGTGTTCCATTAAACGAGAAGACTTAAC
TATTCTAAATATATATGCAGTCAAAAGTGGAGGACCCAGATTTACAAAAAAGATTCTTAGAGACCTAAGG
AAACTAAAAACAGACAGCCACACCATGATAGTGGAAGACTTCAACAACTCACTGACAGTGTTAGATATCG
AAGCAGAAAATTAAAATGTAAATTTTGGACTTAAACTCAACTCTCAACCAACTGGATCCAAAAACATCCT
ACAGAATACTCCACCCAGCACTATCAGAATATGCTTTCTTCTCATCTGCATATAGATTGTATTCTAAAAT
CAATCATATGCTCAGTCATAAAGTCTCAATACATTCAAAAAATTAAAAGATTTTGAGTACATTCTTGAAC
AAAAGTGCAATAAAAATAGAAATCAATACCAAAAAGATTTCTTAAAACCACCCAAAAGTATGGTAATTCA
ACAACTTTTCCTGAATAATTCTTGGTTTAAGAATGAAAGTAAAACCGTTTTTGACATTAAATAAAATAGA
GACACACCTCACTAAAATCTTTGGGATCTATCTAAAGCAGTGTTAAGAGGAAGTTTACAATGCTAAAGGC
CTTCATCAAGAAGGCAGAGAGATTTCAAATTAACAATTTAACATTGCACTTACACTAACTAGAAAAAAA
AGGACAACCCCAAAGCAAACTGAAAATAAATAACGAAAATCAGAATGAAATTGTGATGCAAAATGTATAC

FIG. 5 (continued)

AAAAGATAAATAAAACCAAGAGTTTGTTATTCAAAAGAATACAAAAAGATTAATAGACTGTTAACTAGAT
TAACAAGGAAAAAAAGGAGACCCAATTAAGCACAATCGGAAATGACAAAGATCACATTACAACTCCCATA
GAAATGCATTACAAATGCCCCTCTGCACACAAATTAGAAAATCTAGAGGAAGTAGAGTCATTCTTGGAAA
CAACCTCCAAAGATTAAACCAGAAAAAAAGTGAAAACCTGAACAGACCGATAACAAGTTATCAAATTGAA
TTAGTAATAAAAAACCTACTGACCAAAAAAAAAGCCCTGGACCAGATGGATTCTCAGCCAAATTCTACTA
ATTCTAATTTTATTCTAACATAAAAGTTCGCTTTTTTAAAGTTAAACTTCAAATTTAAGCACAGAAACAC
ATATGTACCTCATATTATCTCATCTACAGTCAAGAGAAGTGAAAACAAATGTGAAGATGTACTATTAAAG
CATAACTTTATACAATTGACTGTAATATATACGTTACTGCTGTAATAATTTCATAGCACCTCCTGTAATT
GTAGTAATAAGGTTGTGTTGAAAGCACCTGCTTAAAACACCATGTGACACTAATTATCTCCACATGAACA
GTTCCTCTCTCCAATAAATTGCGGATTGCAGCAAAATCTGATTGTGATTCTTGTGCGTTTTTATACTGTT
TAGTGCAATACTGTCAACTTTGAATAACACCGTTGGAGCCATATGAATTGCCACTAGTGATGCTGAAACT
GCTCCTAAGAAACTGAGAAAAGTCACGACATTACAAGAAAAAGTTGTATTGCTTGATATATAATGCAGAT
TGAGGTCTTCAGCTGCCCATTGTTTCAATACAAATGAATCCAGCATAAAGATCATTGTAAAAAACAAAAA
AAGGGAAAAAAAAAGGAAATTCATGATGGCATTGCTGAGTCTATGCCAGCAGGCACAAAATCTTGCACTT
TTAGTAATATACCGTCTTATCTCATATTGAAAATGAAATTGTTATATGGCTGCAAACTTTTATAAGAAAG
GCATAACCACAGACTTTAATGTGATTTGAGAAAAAGTGAAGTTATTATATGACCATTTAAAGCAAAGGAA
GGTGAGGGATCTAAAACTGGAGAAACTAATGCAAGCAAAGGATGGTTTGATAATTTTAGAAAATGATTTG
GGTTTAAAAATTTTCAAAATAACAGAAGCAGCAGCTTCTGCCAAATGAGAGAAAGTGAACAAGTTTTCAG
ATTCCACTAAGAAAATCATTGAGAAAGCATATCTGCATGAGCAGGTTTTTAATGCAGATGAAAGTGTCCT
ATCCTGGGGAAAAGAAAGCCACGAAGGACGTTTATTAATAAAGAAGAGAAGTGAGCACCAGGATTTAAGG
CAGGAAGGGATGAGGTAAGTCTACTATTCTGTACAAATAAGGTCAGGCTTATTATCAAAACTGCTAGTAT
CTACAAAGTTGATAAGTCCCAAACCTTGAAGGCAAAAGATAAAAATCAACTGCTAGTCTTCCAGTCATAC
AAAAGGAAGGTCTGAACAATTAGTACTCTTTTTCAGAATTGTTTCCATCAATGCCTTGTTCCTGAAGACA
GGAAGTAGCTTGACAGTAAGGGACTGCCTTTACAGTTCTTTTCATATCAGTCGATGCCCCTGGTCACCTA
GAAAGCCCATAAGTTCAACATCAAAGGCATTGTAGTGATCTATTTCTTCCACCACAACATCTCTAATTCA
GCCTCTAGATCATGGAGTCATAAGAAACTTTAAAGGATCATTACAGATGATACTCTAACGAAAGGATTAT
CAGTGCTATCAAAGAAAATCCTGATAGGCAGAACATCATAAAAGACTAGAAGAATTACACCATTTAAGAT
GCTATTGTTATAGGGAAAAAAAAAAGTGAAAGTCATTAAGTGCAAAACAATACATTTCTACCAGAGAAAA
TTTTGTTCAGATGTTGTGCATAAATTCATAGGATTAACAACATGGCCAATCAAGAAAATTATGAAAGAGA
TTATGGATATGGAAGAAAAAGTGAGGAGTAAAGAATTTCAAGATATCGGTATTGGAGAAATTCAAGAGCT
AATTCATACCTCATCAGGGAAGTTAACAGAAGATGACCTGATGGAGATGAGTGCCTGCGAACTAGTGTCA
GATGATGGGGAAGGAGACATAGAAGCAGCAGTGCCAGAAACAAATTGTTATTAGGCAATCTAGCAGAAGG
ATTCTGATAATTCAAGACTGTTTTTGGCTTCTTTTATAACAGGGACTCTTGTCTAATGTGGGCACTGAAA
CTAAAGCATGTGTTGGAAGAAGGATTAGTTCCATTTAGAAAAATTTTTAGAGAAATGACAAAACCACAAA
GTCAAATAGAAATTATGGCGTATTTATGAAATAGTTACTGAATGTACTTGCCTCTTTTGCCTTCCCTCTA
CCTCCTCCACCTCTTCCACCTCTTCTACCCTAGTGAAAGCAAGACCAGTGCCTCCCATTCCTTCTCCTCC
TCAGCCTACTCAATGTGAAGAGATGAGAAAGATCTTATGATGGTCCACTTCAACTTAATAGTAAATATGT
TTTATCTTCCCTGTGATTTTCTTTATAACATTTTTTCTCTAGCTTACTTTATATTAAGAATACTATATAT
AATACATATAACATACAAAACATGTGTTAATCAACTGTTTATGTTATTGGTAAGGATTCTGATCAACAGT
AGCTGGTATGATTTGGATCTGTGTTCCCGCCAAAGTCATGTAGAATTGTAATCCCCAATGACGGAGGTGG
GGCCTGGTGGGAGGTGATTGGGTGATAAAGGTAGTTTCTCATGAATAGTTTAACACCATCCCCCTTGATG
CTGATCTCATGATACTGAGTGAATTCTCATGAGATTTATTTGCTCAAAAGTGTGTAATACCTCCCCCCTC
TCTTCTTCCTGTAGAGACTGCAGAACTGCATAACTGAAACTTTATACCCATTGACTAACAACTCCCTGCT
TCCCCTTCCCCTTAATCACTGGCAATAACCATTCTACTCTTTGCTTCTGTGAGTGTTACTGTTTTATGTT
CCTCACATGAATGTAATCATGTAGTATATGTCCTTCTGTAACTGGTTCATTTTGCCTAATGTCCTCAAAG
TTCATCCAAGTTATCACATATTGCAGAATATCCTTCTTTTTAAAGACTGAATAATATTCCATTGTATGTC
TATACAATATTTTCTTTATCCATTTATCCCTCAGCAGACATGAGGTTGTTTTTACAGCTAGCTATTATGA
ATAGTGCTGCAATGAACGTGCAAATGCAAATGGTCTCTTCAAGATAATGATTTCAATTCTTTTATATATG
TACCCAGAAGTGGGATTGCTGGGTCATATGAGAGTTCTGTATTTAATTTTTGAGGAATCTTTATAATACC
TTTTATACTGGCTGTACCTTTTTGTATTCTACCAGCAGTGTACCGTGTTCAAATATCTCCACATTCTTGC
AAACACTTTCTTTCTTAAATGATAGCCATTCTACAGGTGTAAGGTGTAGGAAAAGAGTGGAGTTGTGCTT
TTGATTTGCATTTCCCTGATATGCAATGTTGAAAATCTTTTTATTGACCTGTTGTTCATTTGTGTGTCTT
CTTTGGAGAAATTTCTATTCAGGTATGTAGCCTAATTGTTTTTTCAAATTAATTTTTTTTTTTTTGAGTCA
CTCTCACTCTGTCACCCAGGCTGGAGTGCAGTTGTGTGATCTCAGCTCACTGCAATCTCTGCCTGCCAGG
TTCCAGTGATTATCCAGCCTCAGCCTCCAGAGTATCTGGGATTACAGGTGCCTCCACCACACCTGGCTAA
TTTTTGTATTTTTAGTAGAGATGGGATTTCACCATGTTGGCCTGGCTGGTCTCAAACTCCTGACCTCAGG
TGATCCAATTTGTCTTGGCCTCCCAAAGTGCTGGGATTACAGGTTATCAGCCACTGACTGACATATATAA

FIG. 5 (continued)

AATTGTATTTTTATCATGTACACTCTAATGTTTTGAAATACATATATAAGTGGAATAGTTAAATTTAGCT
AATTAACAAATGCATTATCTTACATAGTTACTTTTGTAGTGGAAACACTTAACATCTACTCTCTCAGCAT
ATTTCAAAAATACAACATATTGTGGTTAAGAATAGTCACCCTGCTGCATAATAAATCTCTGCAATTTTTT
CCTCCTAATTGTAATTATGTATGCTTTGACCAGTATCTCCTCATGTGGGAGATCAGTCAGAGTGGTGGAA
GAAGCTATAGGGAAGGAAGCAGGCCTTTAGAAAGGTCAGAAGGCTCTGCAAAACTTCAGGGGAGACTAAG
CTGAAGATAGCTGTTCTCTTACCCTGAGGCAGAGCACAAGAAATAGGTATAAGGAAGTATAGGGGAATTT
ATCTAAATAGGCTTGTCTACCCATGTTGTCCAGAAACTGACCTTTGACCATCCGTACACGTGACTGTTCC
CAGTAAGGGGGAACAATAATGTTAATTACACACAGATTGTGTTGGCTCCAGCCTTTCGGCATTATGTCTG
TACTAAATAAAAGTGAGCAGCTCCAGCTTGTTGGGACTGCTACTCACTCTTTGGCAGTCCCCTAGCCACT
CTTTCACCACATACCTGTGTCTGAGTACTCCTTTCATCTGTTGGTAGGCCAGGGTCTACCAGGATGGACC
AGGCATCCTCAACTCCACTGTTCTCCCAACCACCTGGCTTCTGGTAGCCACCATTCTACTCACTAATAAC
TAATTAATTTTTATTTCAATAGCTTTTGGGGTAGATGTTGTTTTTCGTTACATGGGTGAATTCTATAATG
ATAAATTTTGATATTTTACATACCTGAGTAATGTACATTGTACCCAATATGTAGTTTTTTTATCCCTCAG
TCCCCTTCCATCTTTCCCCTTCTGAGCCTCCTAAATCCACCACATCAATCTGTATGTCTTTGTATCTTCA
TGGCTTAGCTCCCAATGATAAGTGAGAACATACAGTATTTGGTTTTCCATTCCTGAGTTACTTCACTTAG
AATAATGTCCTCCAGTTCCATCCAAGTTCCTGCAAAATTTTTCATCGTTATTATTTTTTTGCTATTGAGT
TGTAGGATTTCCCCGTGTGCTTTAGAAATTAACCCCTTTTCATATATAAATGATTTATAATATTTTATTT
TATTCTGCATATTTCTTTTTTACCCCATTTATTGTCTCTGTTCTGTTCCATTGGTCTATATTTCTGTCTT
TATGCTGGTACCATATTATATTAATTACTATAGCTTTAAAATACATTTTGTAATTAGGAAATATGAGGCA
GCTTTATTCTTTCTCAATGCTTTTTTGGCTATTTGATGTCCTTCTTGGTTCCATATGTATTTTAGAATTG
TTTGTTATATTTTTGTAAAAATACTATTGGGCTTTTGATAGGTATTGTATTGAATCTTTACATATATTTG
GGTAGTATGGACATTTACTATTAATAAGTCCTTCAATTATTAACACAGAATGTCTTTCTAATTATTTATG
GCTTCTTTATTTCCTCAGTGTCTTGAAGTATTTCATGCACAAGTCTTTCACCTTCTTAAATTTATTTTTG
TGTTTTATTCTTTATGATTTTAGTGTAAATGGAATTGCTTTCCTAATGTCTTTTCAAATAGTACTTGGTT
AATTCATAGAAATATAAGTAATATCTTATAATTATTTTGTATCCTGCAACTTTACAGAATGTGTTTATTC
AATTCTAACAGGTGTGTGTGTGTGTGCATGTGTCATCTTTAGGGTTTTCTATATACAAAATCATGCCATC
TGCAAGTAGAGGCAATTTTACTTCTTTCTTTCAAGTTTGAATGTCTTTTATTTCTTTTTCTTGGTTAATT
GCTCTGGCATAAAATGGCAGGACTGTGTTGAATAGAAGTGATGAGAATGGCCATTCTTCCTTTGTTCCTG
AAAGCTTTCTGTTTTTCACTCTTGAATTTAATGCTAGCTGTGAGCTTTTTAAATATGCACTTCATTTTGT
TGAGGCAATTTTTATCTATTCCTAGCTTGTTGAAAGTTTTTATCACAAAACATTGTTGGATTTTATCAAA
TGCTGTTTAACATCTGCATATTTGATCATGTAGATTTTGTCCTTTTTTTGTTAATGTGTTACATTACGCT
TGGTGATATTTGTTAAACTTAGCATTTCAGGTATAAATCCCCCTTGAATATAGTGTAGTATCCTTTTTAT
ATGCTATTAAATTTGGTTTACTAGTATTGTTTGAGGATTTTCTCCTCTGTCTTCATCAGATATATTGGTT
TGTAGTTTTCTTCCTTTTGGTGTCTTTGTCTGGCTTTGGTATCAGAATAATGCTGGCCTTATAAAATTAG
TTTGAAGATGTTCTCTTCTCTTCAATTTTTGGCAAGAGATTGGAATGGATTGCCATTAATATTTTCTTTA
GCTATTTAGTAACACGCACCAGTAAAGCCATCTGGTCCTAAGTTTTTTGTTGAGAAGTATTTGATTATTA
ATTCAATATTTTTACTGGTTGTAAATCTCTTTATATTTTCTATATTTTCTGTGTTTTATGTCTCCAGGAA
TTTATTTTTTCTTTCTTATCTAATTTTTGATGTATAATTTCTCATAGTAATCTCTTATGATTGTTTTATT
TTTCTAGCATCAATTAAATGTCTCTACTTTCAGCTCTTATTTTGTTTGTTTGAGTCTTTTCTCTTTTGCT
TAGTCTAGTTTAAAGTTTGTCAATTTTGCCTCTCTTTCAAAAAGATCAACACTTAGTTGTGTTGATATTT
TTTCTAATGTTTTTTTTTCCATATTCTTTATTGTATTTATTTCTTCTCTAATCTTTTTTTCTCCTGCTAA
CTTTGGCCTTAGTTTGTTTTTCTTTTTATAATTTTGTGAGGTGTAAAATAGGTTGTTAGTTTAAGATAAT
TCTTTACTTTTTACTAGCATAATTATGTGATATTTATCAGTGTGTACTGAGAGCAAACAATGCCAGATGC
TACTAGTGACCATAAATTAGAGAAATAACCTATGTTTTTTGGATATGGAAATGAAATTTACCCTACAAAT
GTAGATATTTTTTACTGAACACTTCCTCTTACTACTGTTCTTGCTGCATCTCACATTTTAGAATGTTTTG
TTTTTGATTCTCTTCGTATCTAAATATTTTCTAATTTCCCTTTTGATTTCTTTGACAATTTAATTATTGA
AAAGTTTGTTAGTATCCATATTTTTAAAATTTTCTACTTTTCTTTTTGATACTAATTTCCAGTTTTATTC
CATTGTAGTTAGAAAAGATAATTGGTATGATTTTAATTTTAAATTTATCAAGACCTGTTGCATGATGTAA
CATGTGGTCTATCTTAGAAAATATTCCATTTCTATTTGAAAAGAATATACATTCTGTTTTTATTGAGTGA
AGTATTCTCTATGTGTCTGTTACGTTCAATTGGTCTATAATGTTGTTGAAGTCCTCTGTTTCCTCATTGA
TTTTCTCTCTAGTCATTCTATTTATAATTGAAAGTGAGATATTATGAAGTCAGCCTACTATGGAGGGCTA
ACTGTAATACACTATTTTATATAAGAGACTGGAGCATCCTTGGATTTTGGTATCCATAGGGAGTCCTAGA
ACCATTGTTCACAGATACCAAGAGATGATTTTATTGTATTTCTCTATATTTCTCTTTTCAGTTCTGTCCA
TGTTTGCTTTATAGCTTTTGGGTCTTTGAGATTGGGTGAATATATTGGGTTGTATATTCTTGGTGAATTA
ACTTAAAAAATCATTTTATAATGTCCTTTTTGCAACTTGAGACAGTTTTTTACTTAAACTCTTTTTCTTT
CTTTGACAAATAGTTAGGTTGCAAATTTTCCAAACTTGTATGCTCTGCTTCCCCTTTAAATATAACTTTC
AACTTTAGGTCATTTCTTTGCTCTCATATCTGAGCATTGCATGTTAGAAGCAGCCAACCTATATCCTTAA

FIG. 5 (continued)

TGCTTTACTGCTTAGAAATTTCTTCCATCAGATGTTCTAAGTCATTGCTCTTTTTTTTATTTTGGAGAC
AGAGTCTCACTCTGTGGCCCAGGCTGGAGTGCAGTGGTGCGATCTCGGCTCACTACAAGCTCCACCTCCC
AGGTTCACACTATTCTCCTGTTTCTGCCTCCCAAGTAGCTGGGACTACAGGTGCCCACCACGATGCCTGG
CTAATTTTTTTGTATTTTTAGTAGAGATGGGGTTTCACCGTGTTAGCCAGGTTGGTCTCGATCTCCTGAC
CTTGTGATCCACCCACCTTGGCCTCCCAAAGTGCTGGGATTACAGGCGTGAGCCACCGTGCCCGGCCAAG
TCATCACCCTTTATTTCAGACTTCCACAGATCCCCTAGGGTATGAACAAAATGCAGCCAAGTACTTTGCC
CGACACCATGCCCGGCTTATTTTGTACTTTATTAGTGGAGACGGGGTTTCTCCATGTTGGTCAGGCTGGT
CTCAAACTCCCGACCTCAGATGATCCACCCGTCTCAGCCTCCCAAAGTGCTGGGATGACAGGCGTGAGCC
ACCGCGCCTGGCCTATTTTATTTTCTATAGCCTCATAACAGAGGTGAGACTAGTGATTTTAGAGCCACAC
TTCCTGGCTTCTGTTTTTATTATTTTAATTATTTATTATTATTATTATTAATTTTGTTTTTTTGGGGGG
TTGTTTTGTTTTGCTAAGGCATAACAAGAGTGACTTTTGCTCTAGCTCCCAATAACTGTCATTTCTATTT
GAGACCTTTTCAGCATGAACTTCATTGTCCATGTCACGATCTGCATTTTGGTCATAATCATTTATCAGTT
TCCAAGAAGTTTCAAACTTTCCTTCATTTTCTTATCTTCTTCTGAGTCCTCCAAGCTCTTGTAAGCTCTG
CTCATTACCTAGTTCCAAAGTCAAGTCCACATTTTCAGGTATCCTTATAGCAATGTCCCACTTCTTGGTA
ACAATTTTCTGTGTTAGGCCATTCTGGCATTCTTACACAAGAATGCATGAGACTGGCTAATTTATCAAGT
AAAGAGGTTTAATTGGCTTATGATTCTGCAAGCTGTACAGGCATGGCACTGGCATTATCTCAGATTCTGA
GGAGACCCCAAGGAGCTTTTACTCCTGGCAGAAGTTAAAGCAGGAGCAGGCACATCACATGTTGAGAGAA
AGAGCAAGGGGGAGGCAAGGTGCCACACACTTTTTAAGCAATCAGATCTTCTCCTGAGAACTCATACACT
ATTGCAAGGACAGCACCAAGCAATGAAGGATCAACCCCCATGACCCAAACACCTCCCACCAGGCCCTACC
TCCAACATTGGATATTACATTTCAGCAGGAGATTTGAACAAGACAAATACCCAAACCATATCAGCCTCCA
AGTCTTCATGGACTGGTATTGTATAGGAGAAAACTTTCTTCATTCAACCCCAGCAGAGCGTCTGTGGGCC
TCTCAAATTTTGATTCTTTTTTAAACTGCTATCTTTTTGTTAGGAACTTTCAGAATCTAGAGTATGTAGG
GTCTCATGAGCACTTTTAGACAGTGGACAGAGAAGCCCGTCACTTGGTCAACTCCCAGAAAATTTTGAAT
ATTTCACATGCTATCCAATTTTTTCCTTCCCAAGGAGAATTTGAAAACTGAGGTGTTTTCTTTGTTTTTT
GTTTGTTTGTTTGTTTTTCTTTTCTTTTTTACCTCCTCACTCTGCATAGATCTGGGAGCAGGGAGGAGCT
GTAGCAAGTGCTCATGTGCTAATTTAAGCCACCATTTTTGTGCTCTTTGTAGCCCATTGGAAGCAAGCAT
ATGCCTAGCCCCAAGATAGGCAAGACAATGACCAGCTGCTGGAGTTGGACACAGAAAAGATGAAATGTTA
GGTTTGTGGTCGAAATATTTCCCTCCCCATAGAGAAGCTGGAGTTAAGTTTTTGTTTCTAATTTTTTTA
ACTTGGTCATTCTGCCCTAAGCTATGGGCCAGGAGCTATGGGAATGCTTACATACTAGTTCAAGCTGCCT
TCTTTATTTTCCGTAGCCTCCAAAGGTCTGGTATATGCTGAGTCCTGTCAACACTTCAAGATAGGTGATA
TAGAAGACAGTCGCAAGGGTAGTACCTGAAAAGTTACAGTTTTGGATGTGCAGTCTCACTCTGTCTCTCC
ACAGGGATAAGCTGGAGATGCAGTTTTCTTACATTCAGTCTATGTTGAGCCAGGGAATAGAGCTATTGCA
AGTGTTCATAGGCACTTGCAAATTTCTAGTTCCTCTTGAATGCATGGTATTATAATGAGGAGAGGAACAG
CAAAGAGGTGTCTCCAATTTTCTTAAAAGTGTCAATGTAGCTAATATTGCACTTCCCTGGGGTACAATGG
CCTGTCAACTAGCTTCTGGATTTTCCACTAATGGAATTGATCGCTGTATAATTGTTGAATAAAATATTGT
TGAAAGAAAAAAGGGTCCAGTCCTTCCTATTAGGCTATCTTGCTGATAACTCATATTGGCTTTTTTTATT
ACTTAGATTGTTTATTTTATACCTGTTAAAAGAGTGCATTTACACTTGAGATATAGCATTTACATAATAC
TCTTATTCATGATTTAAAGAAAAATATGACTGAAATAAAATGGTTAAATTATCCTTAACTTTTAGAGTCT
AACTCTTCAGGGTTACTTTTAAACTCATATTTTCACTGTATTTTCTTATCCTCTGTGCTGTCAGGAGAGT
TGGAAATGCTTATTTCAGGCATGGTGGGAAGCCCCTTTATTGACTCAGTAGATTTCTTGCAAACTGCTAA
AATTTCATTGCTGACCCTTTCTTGATTTTATTAGCTTGTGCCAATAGACATTTTCAGACAACAATGAGAC
GTCATAGTTCTTCCACAGGTAGTAATTAAACAGTCTGCAAGCTTAAATGTCCAGTGATAGAAACTGTCCA
GTCATGTAATCAGAAAAGCCATCAAGTGCACACAAGCTCAGGCAATGACAACAATATCATGACTGATTCC
TAGACAGTATCTGTTGCATTATGTCATCAAATGTTAGACTGATCCTAGTCTCAGAGATGACAAAAAATTA
AAAGAAAAAAATCGTGTCTTGGAATTGAGGAAATGTAGTTTACTTTCTTCATACCATTATTTCCCTGAAC
CTATTGTATTTCAAAATGATTTTTGACTGGCTTCTATAATTATTTATTCTAGGCACTATCAGGATAACTC
CTACTGATTCTCGATGGGTTGGAGCTTGGTGGCTTAATTTCCTTGTGTCTGGACTATTCTCCATTATTTC
TTCCATACCATTCTTTTTCTTGCCCCAAACTCCAAATAAACCACAAAAAGAAAGAAAAGCTTCACTGTCT
TTGCATGTGCTGGAAACAAATGATGAAAAGGATCAAACAGCTAATTTGACCAATCAAGGAAAAAATATTA
CCAAAAATGTGACTGGTAAGTATTTAACATTCATTGTCAATTTGGAGTTGTTAATCTCAATGAAAAGGAA
GAATGAGTATTCCAAAATAATAAAGCATACCCAACTCATCTGGAGTTGGCTTTCTTTTGCACTAAATTTA
GATAAATTATTTTTCTAAAACTCCTATTAAAGTTAACATATATGTCTTGAGCACATAACAAGTGGAAGAG
AATTAGGTTTGTACTTTTTAGCAGGGAGAAACCAACAAAAGTTTACAAACATCCATTTTTTATGAGCCAA
ATAGTAAATATTAATTTTAGTATTATATGGTCTAAACTGGGAGAGTTCAAAGAATTATAATATTTCATTC
CTTCATTTATTCAACAAGTAGTACCAGGAACTGTACTATGCCCTGGTAATAAAACATTACCTCTATTTTT
CAAGAACCTAGTGGGTGATGCTGAGAAATATATAGACAATAGCAATATAGTGCCTTAAGTATTATGGTGA
AATTAAACTTAACTATTATCAGGTGTAGAGATGGATTAAGGAGAAGGAAGTCGGGAGAAGTTTCTCCCTA

FIG. 5 (continued)

TGTAATTAGAGTAATATTTATTTTGGTAATTATCTATCTATCTATCTTATCTAAATATTCAAAATAAAGT
GGAAGCAAAGGTGGTAGTTAAGATAATTAGACTAAGTAATGTAAATTAGGATGCATCAGCATTTGACAGT
GCCTCCTCTTTTGAATATAAACCCTGGGACTAATGGAGAACCATTGAGAGTCAATAAACAAAGAGAATGA
CTTGGCAGTAGCCAGAGCAAGATATGTGAATCAGTGAGGTGTTGACAGCAGTTTTCAGATTTGGGAGAAA
TGGTGAAATAGCCAAAGCAATGCAACACTTAAACCCTCAGCATCTTTTTCAAGTTTTCTTTAAAGTAAGA
TGACAAATTCTCCAGTGTAGCCTAGGTTCTTCCTTTCATCAGGTCTTTTACTTATTACTTTATTGCTATT
TTCTCCTTTCTATCACACTAACCCAAGAGCAGTGGTGTTCTGGTACTCTTTATATTGGCTCATAGCAGAG
GACTGTTAAGTTTCAGCTACATTGGTAGGTTGAAATTGTTCATGGCAAGAGAATTACCATGATTTATTAC
CATGGAAATTGGGATATACTACAAGTAGAAGTTTGTTTTCCTAAGAATCAGATGTTAAACATTTATGTTT
TTAAAATTTAACATTCACACTAAAAGTACTATACCAATAATTTTCATTTTGTATATGATGTTTCTACTGT
ACCAAATCAAATCTTTAAAAAATAGTAGATTGTCTAAACCTATAAGGAGCGGGGTTGACTGTGATCCAAA
CAGAACAGAGAGGATAATGAAGTTGTAAAAATAGGACAATTGTAGACATAATCTCTATTATGAACAGTTT
TTGTAGGTGTGACCCTAAGAAAGAGGATCTTAAGTATGTATCTATTAGGAATGGATAAAATAAGAATATA
TAGTCAGAAAAAAATATTGAATTTATTCCATATGCTCTTGAATAGAACTAAAACTGATTAGAATGAAAAGA
TGATTTCAGTTCATTACAAAAACAGTGTGTAAACAATGAGAACTTTTCAAAAGTGGAGGAAATTGCTTCC
TAAGGTACTTAGTTTAATGCCACTTAAGTTGTTTATTGATCCACTTATTAATGATATATAGTAGATCATG
ACTATACAGAAGTTTACACTGGATGACATTGAATTTCTCATCCTCAAAAATGCAACGCTTGTGTGAATGT
ATATACTCCATTTCTGTTGAAGAAAGGCCACAACTCACTTATAATACTTACAAATCAGGGATGGTTTTTC
ATGACTGGGGAGACCTGTGGAGAGAAATGTGGCACTTTTGCCCAAGAATTTTAAATGTTGTTTATTCCCA
CTATACATTTTCTTATCTCTTCTTTTTTTCTTTTCTGTTTCTTTTCTCTAACTCCTTCTACTCCTTATTT
CAAGCAGATGCAACTGTTTCGTAGCTGACATTAAATGGATGTCTTAGTTCTGACCATATCTAATGAAAAT
CTTTAGAGATTTAAATAGAGAAAAATATTTCAAAGTCCGTATCATCCAACTCTCAGTAACCATATCTTGG
CTCTGTCTTGATGAACTCTGATACTTCCTACTGTTTTTCTAAGTAGTTCCTTCTACTTTTAAGTCCTATT
ACAGCTAGTTGACCTGGTGATCACAGATCCAAATGACATAATTTCTACCATGAACAGAAGTTAGAAGTTT
GTTACCACAGCTGTTTGTAGGGATAGGTGGTTGTATTATTACTATTATAATACTACTTGGGACACAATAT
TATCCCCTGGCTGCTTTCCTTGTATCTTAAGACAGAGGGTTAATAATATTGCCAAATTTACTGAGAAAGT
ATGTTATGGTAGAAGAGCTGTATACTAGAGAAACAGGAGGTCTGAGTCCTCATACTAAATTAATCTTTAA
GAATTTTGAACCTCAATGGTCTTATTTCTGTGAGTTTTGAATTATGCTGTCTTTACATTTCCATTTAATA
GTTATATTTTTAATATAATACTTATATCATTAAGTACTAATAAATAAGAAACATCATATGTCTTATTCAC
TTTTTGTTTGTTTGTTTTTGGGTTTTTTTGTTTGTTTGTTTGTTTGTTTGTTTGAGATGGAGTCTTGTTG
CTCTATTGCCTAGGCTGGAGTGCAGTGTCACCATCTCAGCTCACTGCAACCTTCGCCTCCCTAATTCAAG
CAATTCTCCTGCCTCAGCCTCCCAAGTAGCTAAGATTACAGGTGTGTGCCATCGTGCTGGCCAATGTTTG
TATTTTTAGTAGAGTTGGGGTTTCACCATGTTGGCCAGGCTGGTCTCGAATTCCTGACCCCAGGTGATCC
ATCTGCCTCGGCCTCCCAAAGTGCTAGGATTACAGGAGTGAGCCACTGTGCCCGGCCTTCACTTTTGTTT
TTTGAACAATTAGCATATTGTCTGGTACCCAGTTGAAAACCTAACATTTGCTGAATGAATGAATAAGTGA
ATTAATATGTTTGCAATAGTATTGTAAAGTACCCAGGATAACCAAATATTAAGTGAAGAAAGCAAGTTAC
AAAACAGCACTTACGTATGACCCTATTTGAGGGTAAAATAAACTAAACTAATAAATATTAATATTCGTAT
GGAAAATATTGAAAGAATATATTTAAAAGCTGTGAACAGCCTGTGGTATTGCAGGCTATTCTCACTCTTT
GTGTTATGTGTTTATAGAATTTTAAATCTTACATGACTTACGTTCACAAATTTTAGATATAAATGTATAT
TTAAGTTGCATTCAAATATTTTCTTTATTTTTACAATTTTACAGGTTTTTTCCAGTCTTTTAAAAGCATC
CTTACTAATCCCCTGTATGTTATGTTTGTGCTTTTGACGTTGTTACAAGTAAGCAGCTATATTGGTGCTT
TTACTTATGTCTTCAAATACGTAGAGCAACAGTATGGTCAGCCTTCATCTAAGGCTAACATCTTATTGGG
TAAGACATATTTTTTACTTGTGTGCTTAATAAGTGAAATAATACTAAATACTGTATTCCAAGTGGTATTT
TATTGTGAAAGTGATTTTGTATTTTAGTAATACAGGATAAGTATAATTTTCTTGTATTCTTTCTCAAATG
TTATTAAACATATAAAACTTGTGATGTCACTATTGCTCTGCATTTGAAGTTGCATCTTATTTTAGATGAG
TTCCTGAAAAAAAATGTTGCAAATAAATGGACAATTTAGAGGTAGTATCTGTATAATTGGATCTTATAATT
TAGTGCTAAGATCTGAGACAAACCCTTTTGTAATTATAATCATTATAATTCTATAATTTATGGACTTTGA
AATCAAGACTCAGTTACTTACAAAAATATGACACTAATAGTTCCAAAAAGAGTATCGATTTAAATACATC
AAAATATGCATAATTCAAAACAAATATATTTACAGAGTATTTTTTGCTACAATATCTATTTTCAATGGC
ACATTTAGATGTGCTTATTAAGGAAAGTTTCCTTGTATTATTCTTCCCACAACTCTAGTATTGTAGACAC
ATTATAGAAATTCAATATAAATATATGATGAATTAAACAACTTATCATGTGGTATGTAACTAGGTCATAA
GTAAACAAGAAAATGAATGTACTGAAGCAGGAGACCAAGCTTCCAGATAATCTCTTTGTTGATCTTAAGA
TAAAAGTTTAAAATCGAAAAATAATGTTTTGACTCCCAGTAACCTAGCCTGAGCTTTTTCCTAGAGAAGA
CTTCATCTTTGTTAACTCTTATTAGACAAAGATATGGAAAAGTTATAGGAGGGATTAAACATTATTAATC
CTGTATGTAGAGCGATTTGTCAGTTCAGGTTCTGTATGTTTTTTAATAAATGACAAAGATATATTAATTT
TTATGTTGTTAAGCTCTGGGCAGATTTAGTGTGAGTTACTGAGGGTTAGAACTCTATCTGAGAGAGGCAA
AAGGCTTTAGATGAAGTTCCATAGGCAGAAAGATGGTGTTTGTTGTTGTTTATTCCAGAAAAACAAAA

FIG. 5 (continued)

TTGCCTCATAGAAATTATCTGCTCCAACAAATATCCTCAGCCACACTGCCTTTTGCTATTGAGGAAACCA
AACTGTCATCATTGGCAGGAACAAATTACACAGATCCCCTACCACCATACTGCTATATCATTCTTCTTTT
TAAAAAGTAATAAGATTGGCATTCTACTATAAAGATACATGCACACATATGTTTATTGCAGCACTATTTG
CAATAGCAAAGACTTGGAACCAACCCAAATGACCACCAATCATAGACTGGATAAAGAAAATGTGGCACAT
GTGTACCATGGAATACTATGCAGCCATAAAAAAGAATGAGTTTATGTCCTTTGCAGGGACATGGATGAAG
CTGGAAACCATCATTCTCAGCAAACTAACACAGGAACAGAAAACCAAACACTGCATGTTCCCACTCATAA
GTGGGAGTTGAACAATGAGAACACATGGACACAGGGAGGGGAACATCACACACCGGGGACTGTTGAGGGG
TGGGAAGCAAGGGGAGGAAGAACATTAGGACAAATACCTAATGCATTCAGGGGTTAAAACCTAGATGACA
GTTTGATAGGTGCAGCAAACCACCATGGCACATGTATATGTATGTAACAAACATGCACATTCTGCACATG
TATCCCAGAACTTAAAGTAAAATTTTAAAAAGAAGCAATAATATTGAATAAATTTGATTGACATACATTG
TGTTTCATCTATAAAGACATATCAGAAAACTCATATATGATTACAACTTTTTTTCTTTTTTTTCTAGGAG
TCATAACCATACCTATTTTTGCAAGTGGAATGTTTTTAGGAGGATATATCATTAAAAAATTCAAACTGAA
CACCGTTGGAATTGCCAAATTCTCATGTTTTACTGCTGTGATGTCATTGTCCTTTTACCTATTATATTTT
TTCATACTCTGTGAAAACAAATCAGTTGCCGGACTAACCATGACCTATGATGGGTTTGTATATATCACTA
TATCAATTGCATAATATGTTAACCATCAAATTAAGAGTCTCTGTATAAGTAATATAAGGCAGAAAACAAT
TTTAACTAAACTTTCTTTAAGTTAAGAGAAATTTCAATTTTAAAATTTTTAAAATATCTGTTTCTTAAGA
CCTCAAACACATTCTTTTATTCCTCCACTAAAGAGAAGCAACATAGGTTGTAATAATAATAACTATTATT
TATGTGGTACTTACAATTAGTAGTGGGTACTTTTATCATTATTTTATGAATGGGAAAAGTAAGGCTTAGA
GAAATACATGGATTACACAGCTAGCATTATTAAGATTCTAACTCAAATTTGAGTTTTTTAAGTCCAAAAC
TCTTAGTCTTAACCACCACTGTAATCTTGGATGGATCATAAGAGTTACATAAATGGCATTAGCCAAAAGT
GACTAAACAACTTTTATCTACAGTTCATATCGATGTTCAACAACTATCTTAACAAAAGAACACTTTTAAT
GTTGTACTGAATTTTCTTTTTTGCAAGCTAATATTGTTTTTTTCTGATATTATCTACATTGGAAGTAGCA
TTAAGAAATATTCTATATATAATTGCATATTAGACATTGAAGAATCTTTACTTTTCCATGATTACCATGT
ATAGCAAAGTATTTTTAGTGCAACAGTCTCCACCTCAAATCAAGGGCAAGAATCCTATGCAGTTTTCTGA
TAATTTCCTGAATATAGCCAACAATTTAAGCTTAGGAAGGTTCACATTCAAGCAACAAGCAGAGATGCTC
AGATCACAATTCAGTAACCATGTTCTTTAGTGCTGCTTACTACTGGTGCTGAGCTTTCAAAGTCTGGATC
CCATGAGGTGTTGGTTTTAACTTGTCAAATATTCCCACATTTTCTTCTATAAACATTGTGCTATTCTTGG
AGGCTTGCCAAGGTTATCTGAAATTGTTTCCCTGCACACTGCTAATTCTGAACTGTTATTGGTATCTCCT
ATCCACCATCAACTACTGTAGTAAATTAAAATACATTGTCCTAGAATACTGAATTTTAGAGGTAAAAGAA
CCTTAGAGATGATGCAATCCAACCCTTGTATTATACTTTCCTTTATTATTGAAGAGTCAGAAAAAATGTA
ACATGTTGAAGTCACACAATGTCTTTAGACTCTAGACTGATCCTATGTCACACCCTTAGTTCAAAAGCCT
TCTTGGTTGTAAGGACAGGCCAGTTTCTTGACAACAAGGTTAGTCACTGTACAAAGTATACAAAAGATGG
CAGCAGAGTTAAACAGAATTTGTTTCATTTAATAAAATTTTATTAAGCCTTTCCTTAAAGGTAAATATTA
AGGATATTTGTAGGATACATCAGTTCCCTCATGGGACTCATAATCTAATGATAAATAATATAATTAATGG
ATTCAACATTCATAAAATCCTGCGACTGGGATAAGTTTTTTTTAAGTATGAATTATTGCAGAGGTCTCG
GAATGTGTTCTGAATATCTCTAAGGATCCCTGAGACTTTATCAAGGGGTGCACAACTTCAAAACTATTTT
TATAATAATACTAAGACATTATTTGCCTTTTTATTCTCATGCTATCCTGACAGTATAGTGATATTTTCTA
ATGCTCCAAGGTATGTTATTAATTCATTAATCTGACTGCTAAAATATGTGTGCTTATGTACTTTTGTGTA
TTAAAATTTTCTTAGTATTACTTTCTAATATAGTACATGTCAAGAGGTACAACTTAATTTAACAAAATCC
CTTTGGAACAAGCCCTCAATCTTTTATAAGAGTGTGAAGGACTTCTGAGAACCAATTTTTTTTCCAAAAA
AAAAAAAAACCCTGTGAGGTTGGCATTATTATCTATGACTTACAAATGGCAAAACTGATTTTAGAAAGAA
GTGCCAGAATTAATATAAACACAGATGTGACTGATTGCAATATCTGGACTGGGTCATTGTCTTAGTCCAT
TCAGGCTGCAAAGTTCTAGGTAGCTTATTAATACACAGAAATTAATTTTCAAGATTCTAAAGGCTGGAA
CATGTAAGACCAAGGTGATGGCACTTTTGGTGTCTAGGAAGGGCCCATTTCTTAATTTATAGACGGTACC
TTCTCATTGTGTCCAGGCATGGTGGATGGGGCAGGCAAAGGGTCAGTAATTCCATTCATGAGTACTCATC
CTCATGACCTTATCACTTTCTAGAGGCCTGACTTCATAAAGTCTTCATATACGAGATTAGTTTTCAATCT
ATGAATTTGGGGGCCACAAACATTCTGACTATAGTAGTCATAAACCATTCTACTTAACCACTCCAAGTAG
TATTTCCTCAAGCAGAATATGCTTTTTAATAAAATTATTGATAATGTAGTTTCTGAAGTATGAATCTTAG
TTTTTCATTTAAATTATGTGCTCATTCAAAGATAACACATCAATCCTCAATTATTATCAAATTAAACATT
TGAAAGAAAATAATTTTTTAAATGTTTAAGCAGAAATGAATTATACAAAAAATATATTTTATAATTTTAG
CTATGTTATAATCATATTTTATAATTTATAACCATTTCATAAAGGAAATCAGTATAAAGTATACTATAGT
TTTATTTCAAAAATATACTGAGCTTTTCTAGCCTTTTTCAACTGATTCTATTCTTGATTTTTCATTTTGT
AGAGGTTCTGCTTTAAGCATGTCTGTTTTTTTCTTACATATTAAAATAGAGATTTTTAAATTCAACCTAG
TTAAATAGCATTCGTAGACTCACAAGACTTTACAGTGAGCTGAAAGGAATGTCAGTCTAATGTCATCACC
TTACTGAAGAGAAACTCAGTCTCAGAAAAAAGATGTAACTTATCTAATGTGAAGTTTCTTCATAGAATTA
TAACAACTTCTTGTCTAAGTCCTACTTAACATCTTTGGTTTATTTTTACATTTTGCTTTTTCTAGGTCAC
AAGTCATGTATTGGCAAAGATGGAGAGCGTAAAATAAATAAGCATTAAAAAAAACTTTGCCATTTCGTCA

FIG. 5 (continued)

TCATCAAAGCAAATTTCTTCATATAAAGAAAAATTCTTTATCTACTTTTTTTCCCTCTTTCTCTGCTTTC
ACTTTACTTCTTCCTTCTCCTCCCCTTCTTTGTCTTTTTCTTCTCTCTCTCTCTTTTTGATATATGTCTA
TCATATATTTCCAGAAATAATCCAGTGACATCTCATAGAGATGTACCACTTTCTTATTGCAACTCAGACT
GCAATTGTGATGAAAGTCAATGGGAACCAGTCTGTGGAAACAATGGAATAACTTACATCTCACCCTGTCT
AGCAGGTTGCAAATCTTCAAGTGGCAATAAAAAGCCTATAGTGAGTATTAGTTTTTACTTTCCTCTCCTT
ATTCAAAAGCACAGATTAGATTGAACAATTTTTTACCAAATATTTCTGTAACTAAGGACTCCATTAAAAA
GATAAAAGAGAAAGTTTCCAGTATTATCTGTTATTGTGATGGGTGTGATGTATAAACAAAGTTTTATATA
AAAGTCTGCTTAGGGCACAATCAGGTTTTTCTGTTACTTGAATTCTAATTGGAGATCACCCCACTTTTTT
CCTTTGAGATTGTAAGACTATGACCTTTTAGAATTTGAATGCATTTAGAATATCTAAGAAGCACCTCATT
TGACTAAAGCCTATAATTTTCATTAAGTTGGAATTACTTTATCCCTCAGAATTCAGGAAAATGAGTTAAC
CCATTGTCAGCACTTCCTATCTTACTAAGACAACAGTCAATATGCAATGTTATATACAGATTCTGATCTG
TTTAGCTCTGGGATCACTACCCTTTTTACTTTTTAAGAAATTAATCAAGGCTTCATGCTCACTTGACTGC
CCTATTCTTGATTTTCTATTTTGATTTTTCCAAAGCTGGCACTTCTACCCAAGATAATGTAGTATCCTGC
TCACCTAATGTCAATATGTCCCATAGAAATGTCATTTATTCCGTCCTGCAAAACCTTTCTTTCCATGTGA
ACTACAGTTTTTCTCTAATCTCCTGGGTAGCTACCTGTCACTGGGAATGGGTTATGGTGTTTCCCATACC
TACAATCCACTCAACATCTCACAAAGTTGTGTAATGTTTTCCTAGGAACTTTTACTATTACCAACATTAC
TAAAACAGTCAACTATAATTATTGCTCTCTGCCACACCCTTCTGTGTTTGATTTTTAAACATTCTCCATC
TACTCTTGCCCATGGATCTACCTACCAATTATAATAAGGAATGGCATGTAGAATTTTAAAGAATAAAGCA
TCCTGGACTTTTTGAAGAAAGGCCACAACTTTAATAAACTTGCACAAATATGGCCCAAAGACTACTTAAA
AGCCCACATCTTAGTCATGGCAACAATGAATCTTTTGTGCAGTTGTTTCCTTTTCCTTTGCTGTTTATTT
TTATTTTGCTGTTTTTTAAAAAAATAATTTAACTCTTATTTTAGGTAAAGGGGATACAAATGAATTTGTG
TTAGATGGGTATATTGTGATAAGCTAAAGTTTAGGTACAATCATTCCCATCCCCCAGGTAGTGAGCATA
ATACCCAATAAGTGGCTTTTTAGTACTTGCTGTTTTTTATCTCTCCACTCTAGTAGTCTGTAATATGTAT
TTTTCCTGTCCTTATATTCGTGTGGACCCAGTGATTAGCTTCCACTTATAAGTGAGAACATGTGGCATCT
GGTTTTCTGTTCCTATGTTAATTCACTTAAGATAATGACCTCCAGCTGCATCCAGGTTGCTGCAAGGGAC
ATTATTTCATCCTTCTTTTGGCCATGTAGTATTCCATTGTCTATATGTACCACATTTCTTTATCTAATTC
ACTGTTGACGGGCACCCAGGTTGAGACCGTGTCTTTGCTATTGTGAATAGAGCTGTGATGACCATAGAAG
TATATAAGTAGATGTGTTTTTGGTAGAAGAATTTATTTTCCTTTGGGTATATACCCGGTAGTGGGATTGC
TGAGTTGAATGGTAGTTCTGTTTAAGTTCTTTGGGAAATCTCGAAACTACTTTACACAGTGACTGAACTA
ATTTACATTCCTACCAACATAGGATAAGCATTCCCTTTCTTCTGCAGCCTTGCCAGCGTCTGTTTTTTTA
ATGTTTTGAACCAGTCAGCCCTTCTGACTGGTGTGAGATGGTATCTCCTTGGGATTTTGATTTGCATTTT
TTTGATGATTAGTGATGTTAAACATTTTTATGTGTTTGTTAGCTGCTTGTATGTCTTCTTTTGAGAAGTG
TCTGTTCATGTCCTTTGTCTACTTTTTAATATTGTTTTTGTTTTTTGCTTGTTGAATTGTTCAAGTTTCT
TATAGATTCTGGATATTAGTCCTGTGTTAGATGCATGGTTTGCAAAGGTTTTCTCCCATTCCATAGATTG
TCTTTTCACTCTGTTGATTATTTTTGTTGTGCAGAAGCTCATTAGTTTAATTATATCCCACTTGTCCATT
TTTTTTGTTGCAATTGCTTTTGAGAACTTAGTCACAAATTTTTTGCCAAGGCCAATATCCAGAATCTTTT
CTTGGTTTTCTTCAGTGGTTTTTATAGTTTTAGGTTTTACATTTCAGTCTGTAATACATTTTGATTAAAT
TTTTTATATGAAAAGAAGGGGTCCAGTTTCATTTCTCTGCATAGTTAGCCAGTTATTCCAGCACCATTTA
CTGAATAATGAGTACTTTCCCCATTGCATTCTTTTTGCTAACTTCATTGAAGATCAGATGGTTTTAGGTG
TGTGGCTTTGCTTCTGGGTTCTCTATTCTGTTCCTTTAGTCTAGGTGTCTGTTTTTGAACCAGTACTATG
CTGTTTGGTTACTGTGGCCTTGCAGTATAGTTTGATATCAGGTAATGGGATGCCTCTCACTTTGTTCTTT
ATGCTTAGGATTGCTTTGACTATTCAGTCTCTTTTTTCCTATGGAATTTTACAATAGTTTTATTCTAATT
CAGTGAAAAATCATGCCGGTTGTTTGATAAGAATACCATTGAATCTGTAGATTGCTTTGGGCAGTATAGA
CAGTTTAATGATAATTTTTCTACCAATCCATGAGAGTAGAATGTTTTTCCACTTGTTTGTGTCACCTATA
ATTTCTTTCATCAGGGTTTGTATTTATCCTAGTAGAGATCTTTCACTTCCTTGGTTTAAATGTATTCCTA
GGTATTTAATTTATTGTAGTTATTCTAAATGGAATTGCATTATTGATTTGGGTATCAGTTTAACTGTTAT
CGGTGTATAGAAATGCTACTAATTTTTTTCCATTGATTTTGTATTCTGAAACTTTATTAGAGTATGTTGT
CAGTTCTAGGAGGCTTTTGGCAGAGTATTTAGGGTTTTTTTTTAATTAATTAATTTATTTATTTTTAATT
ATACTTTAAGTTTTAGGGTACATGTGCACATTGTGCAGGTTAGTTACATATGTATACATGTGCCATGCTG
GTGCACTGAACCCACTAACTCGTCATCTAGCATTAGGTATATCTCCCAATGCTATCCCTCCCCCCTCCTC
CCACCCCACAACAGTCCCCAGAGTGTGATATTCCCCTTCCTGTGTCCATGTGATCTCATTGTTCAATTCC
CACCTATGAGTGAGAATATGCGGTGTTTGGTTTTTTGTTCTTGCAACAGTTTACTGAGAATGATGTTTTC
CAGTTTCATCCATGTCCCTACAAAGGACATGAACTCATCATTTTTTATGGCTGCATAGTATTCCATGGTG
TATATGTGCCACATTTTCTTAATCCAGTCTATCACTGTTGGACATTTGGGTGGGTTCCAAGTCTTTGCTA
TTGTGAATAATGCCACAATAAACATACGTGTGCATGTGTCTTTATAGCAGCATGATTTACAGTCATTTGG
GTATATACCCAGTAATGGGATGGCTGGGTCAAATGGTATTTCCAGTTCTAGATCTCTGAGGAATCGCCAC
ACTGACTTCCACAATGGTTAAACTAGTTTACAGTCCCACCAACAGTGTAAAAGTGTTCCTATTTCTCCAC

FIG. 5 (continued)

ATCCTCTCCAGCACCTGTTGTTTCCTGACTTTTTAATGATTGCCATTCTAACTGGTGTGAGATGGTATCT
CATTGTGGTTTTGATTTGCATTTCTCTGATGGCCAGTGATGATGAGCATTTTTTCATGTGTTTTTTGGCT
GCATAAGTGTCTTCTTTTGAGAAGTGTCTGTTCATGTCCTTCGCCCACTTTTTGATGGGGTTTTTTGTTT
TTTTCTTGTAAATCTGTTGGAGTTAATTGTAGATTCTGGATATTAGCCCTTTGTCAGATGAGTAGGTTGT
GAAAATTTTCTCCCATTTTGTAGGTTGCCTGTTCACTCTGATGGTAGTTTTTTTTGCTGTGCAGAAGCTC
TTTAGTTTAATTAGATCCCATTTGTCAATTTTGTCTTTTGTTGCCATTGCTTTTGGTGTTTTAGACATGA
ATTCCTTGCCCATGCCTATGTCCTGAATGGTAATGCCTAGGTTTTCTTCTAGGGTTTTTATGGTTTTAGG
TCTAACGTTTAAGTCTTTAATCCATCTTGAATTGATTTTTGTATAAGGTGTAAGGAAGGGATCCAGTTTC
AGCTTTCTACATATGGCTAGCCAGTTTTCCCAGCACCATTTATTAAATAGGGAATCCTTTCCCCATTGCT
TGTTTTTCTCAGGTTTGTCAAAGATCAGATAGTTGTAGATATGCGGCATTATTTCTGAGGGCTCTGTTCT
GTTCCATTGATCTATATCTCTGTTTTGGTACCAGTACCATGCTGTTTTGGTTACTGTAGCCTTGTAGTAT
AGTTTGAAGTCAGGTAGTGTGATGATGCCTCCAGCTTTGTTCTTTTGGCTTAGGATTGACTTGGCGATGT
GGGCTCTTTTTTGGTTCCATATGAACTTTAAAGTATTTTCCAATTCTGTGAAGAAAGTCATTGGTAGCTT
GATGGGGATGACATTGAATCTGTAAATTACCTTGGGCAGTATGGCCATTTTCACGATATTGATTCTTCCT
ACCCATGAGCATGGAATGTTCTTCCATTTGTTTGTATCCTCTTTTATTTCCTTGAGCAGTGGTTTGTAGT
TCTCCTTGAAGAGGTCCTTCACATCGCTTGTAAGTTGGATTCCTAGGTATTTTATTCTCTTTAAAGCAAT
TGTGAATGGGAGTTCACTCATGATTTGGCTCTCTGTTTGTCTGTTGTTGGTGTATAGGAATGCTTGTGAT
TTTTGTACATTGATTTTGTATCCTGAGACTTTGCTGAAGTTGCTTATCAGTTTAAGGAGATTTTGGGCTG
AGACAATGGGGTTTTCTAGATATACAATCATGTCATCTGCAAACAGGGACAATTTGACTTCCTCTTTTCC
TAATTGAATACCATTTATTTCCTTCTCCTGCCTAATTGCCCTGGCCAGAACTTCCAACACTCTGTTGAAT
AGGAGTGGTGAGAGAGGGCATCCCTGTTTTGTGCCAGTTTTCAAACGGAATGCTTCCAGTTTTTGCCCAT
TCAGTATGATATTGGCTGTGGGTTTGTCATAGATAGCTCTTATTATTTTGAAATACGTCCCATCAATACC
TAATTTATTGAGAGTTTTTAGCATGAAGTGTTGTTGCATTTTGTÇAAAGGCTTTTTCTGCATCTATTGAG
ATAATCATGTGGTTTTTGTCTTTGGCTCTGTTTATATGCTGGATTACATTTATTGATTTGTGTATATTGA
ACCAGCCTTGCATCCCAGGGATGAAGCCCACTTGATCATGGTGGATAAGCTTTTGGATGTGCTGCTGGAT
TCATTTTGCCAGTATTTTATTGAGGATTTTTGCATCAATGTTCATCAAGGATATTGGTCTAAGATTCTCT
TTTTTTGTTGTGTCTCTGCCTGGCTTTGGTATCAGAATGATGCTGGCCTCATAAAATGAGTTAGGGAGGA
TTCCCTCTTTTTCTATTGACTGGAATAGTTTCAGAAGGAATGGTACCAGTTCCTCCTTGTACCTCTGGTA
GAATTCAGCTGTGAATCCATCTGGTCCTGGACTCTTTTTGGTTGGTAAGCTACTGATTATTGCCACAATT
TCAGATCCTGTTATTGGTCTATTCAGAGATTCAACATCTTCCTGATTTAGTCTTCGGAGAGTGTATATGT
CAAGGAATTTATCCATTTCTTCTAGATTTTCTAGTTTATTTGCGTAGAGGTGTTTGTAGTATTCTCTGAT
GGTAGTTTGTATTTCTGTGGGATCGGTGGTGATATCCCCTTTATCGTTTTTTATTGTGTCTATTAGATTC
TTCTCTCTTTTTTTCTTTATTAGTCTTGCTAGCGGTCTATCAATTTTGTTGATCCTTTCAAAAAACCAGC
TCCTGGATTCACTAATTTTTTGAAGGTTTTTTTTGTGTCTCTATTTCCTTCAGTTCTGCTCTGATTTTA
GTTATTTCTTGCCTTCTGCTAGCTTTTGAATGTGTTTGCTCTTGCTTTTCTAGTTCTTTTAATTGTGATG
TTAGGGTGTCAATTTTGGATCTTTCCTGCTTTCTCTTGTGGGCATTTAGTGCTATAAATTTCCCTCTACA
CACTGCTTTGAATGCGTCCCAGAGATTCTGGTATGTCGTGTCTTTGTTCTCGTTGGTTTCAAAGAACATC
TTTATTTCTGCCTTCATTTCGTTATGTACCCAGTAGTCATTCAGGAGCAGGTTGTTCAGTTTCCATGTAG
TTGAGCGGTTTTGAGTGAGATTCTTAATCCTGAGTTCTAGTTTGATTGCACTGTGGTCTGAGAGATAGTT
TGTTATAATTTCTGTTCTTTTCCATTTGCTGAGGAGAGCTTTACTTCCCAGTATGTGGTCAGTTTTGGAA
TAGGTGTGGTGTGGTGCTGAAAAAAATGTATATTCTGTTGATTTGGGGTGGAGAGTTCTGTAGATGTCTA
TTAGGTCCGCTTGGTGCAGAGCTGAGTTCAATTCCTGGGTATCCTTGTTGACTTTCTGTCTCATTGATCT
GTCTAATGTTGACAGTGGGGTGTTAAAGTCTCCCATTATTAATGTGTGGGAGTCTAAGTCTCTTTGTAGG
TCACTCAGGACTTGCTTTATGAATCTTGGTGCTCCTGTATTGGGTGCATATATATTTAGGATAGTTAGCT
CTTCTTGTTGAATTGATCCCTTTACCATTATGTAATGGCCTTCTTTGTCTCTTTTGATCTTTGTTGTTTT
AAAGTCTGTTTTATCAGAGACTAGGATTGCAACCCCTAACTTTTTTTGTTTTCCATTTGCTTGGTAGATC
TTCCTCCATCCTTTTATTTTGAGCCTATGTGTGTCTCTGCACGTGAGATGGGTCTCCTGAATACAGCACA
CTGATGGGTCTTGACTCTTTATCCAATTTGCCAGTCTGTGTCTTTTAATTGGAGCATTTAGTCCATTTAC
ATTTAAAGTTAATATTGTTATGTGTGAATTTGATCCTGTCTTTATGATGTTAGCTGGTTATTTTGCTCTT
TAGTTGACGCAGTTTCTTCCTAGTCTTGATGGTCTTTACATTTTGCCATGATTTTGCAGTGGCTGGTACC
AGTTGTTCCTTTCCATGTTTAGCGCTTCCTTCAGGAGCTCTTGTAGGGCAGGCCTGGTGGTGACAGAATC
TCTCAGCATTTGCTTGTCTGTAAAGTATTTTATTTCTCCTTCGCTTATGAAGCTTAGTTTGGCTGGATAT
GAAATTCTGGGTTGAAAATTCTTGTCTTTAAGAATGTTGAATATTGGCCCCCACTCTCTTCTGGCTTATA
GGGTTTCTGCCGAGAGATCCGCTGTTAGTCTGATGGGCTTCCCTTTGAGGGTAACCCGACCTTTCTCTCT
GGCTGCCCTTAACATTTTTTCCTTCATTTCAACTTTGGTGAATCTGACAATTATGTGTCTTGGAGTTGCT
CTTCTCAAGGAGTATCTTTGTGGCATTCTCTGTATTTCCTGAATCTGAACGTTGGCCTGCCTTGCTAGAT
TGGGGAAGTTCTCCTGGATAATATCCTGCAGAGTGTTTTCCAACTTGGTTCCATTCTCCCCATCACTTTC

FIG. 5 (continued)

AGGTACACCAATCAGACGTAGATTTGGTCTTTTCACATAGTCCCATATTTCTTGGAGGCTTTGCTCGTTT
CTTTTTATTCTTTTTTCTCTAAACTTCCCTTCTCACTTCATTTCATTCATTTCATCTTCCATTGCTGATA
CCCTTTCTTCCAGTTGATCGCATCGGCTCCTGAGGCTTCTGCATTCTCCACGTAGTTCTCGAGCCTTGGT
TTTCAGCTCCATCAGCTCCTTTAAGCACTTCTCTGTATTGGTTATTCTAGTTATACATTCTTCTAAATTT
TTTTCAAAGTTTTCAACTTCTTTGCCTTTGGTTTGAATGTCCTCCTGTAGCTCAGAGTAATTTGATCGTC
TGAAGCCTTCTCTCAGCTCGTCAAAGTCATTCTCCATCCAGCTTTGTTCCATTGCTGGTGAGGAACTGCA
TTCCTTTGGAGGAGGAGAGGTGCTCTGCTTTCTATAGTTTCCAGTTTTTCTGTTCTGTTTTTTCCCCATC
TTTGTGGTTTTATGTACTTTTGGTCTTTGATGATGGTGATGTACAGATGGGTTTTCGGTGTGGATGTCGT
TTCTGTTTGTTAGTTTTCCTTCTAACAGACAGGACCCTCAGCTGCAGGTCTGTTGGAATACCCTGCCGTG
TGAGGTGTCAGTGTGCCCCTGCTGGGGCGTGCCTCCCAGTTAGGCTGCTCAGGGGTCAGGGGTCAGGGAC
CCACTTGAGGAGGCAGTGTGCCCGTTCTCAGATCTCCAGCTGCGTGCCGGGAGAACCACTGCTCTCTTCA
AAGCTGTCAGACAGGGACATTTAAGTCTGCAGAGGTTACTGCTGTCTTTTTGTTTGTCTGTGCCCTGCCC
CCAGAGGTGGAGCCTACAGAGGCAGGCAGGCCTCCTTGAGCTGTGGTGGGCTCCGCCCACTTCGAGCTTC
CAGGCCGCTTTGTTTTTCCTAATCAAGCCTGGGCAATGGCGGGCGCCCCTCCCCCAGCCTCGCTGCCGCC
TTGCAGTTTGATCTCAGACTGCTGTGCTAGCAATCAGCGAGACTCCATGGGCGTAGGACCCTCCAAGACA
GGTGCGGGATGTAATCTCGTGGTGCGCCGTTTTTTAAGCCCCTCGGAAAAGCGCAGTATTCGGGTGGGAG
TGACCCGATTTTCCAGGTGCTGTCCGTCACCCCTTTCTTTGACTGGGAAAGGGAACTCCCTGACCCCTTG
CGCTTCCCAAGCCAGGCAATGCCTCGCCCTGCTTCGGCTCACGCACGGTGCGCGCACCCACTGACCTGCG
CCCACTGTCTGGCACTCCCTAGTGAGATGAACCCGGTACCTCAGATGGAAATGCAGAAATCACCCGTCTT
CTGCGTCGCTCACGCTGGGAGCTGTAGACCGGAGCTGTTCCTATTCGGCCATCTTGGCTCCTCCAACCAG
GGTTTTTGAGATATAGAATCATATCATAGTGCAGAGAGATAATGTGAGTTCATTTCCTATTTGTCAGTGT
TTTATTTCTGTCTCTTTCCTGATTGATCTGTCTAGGATTTCCAGTACTATGTTGAATAGGAGTGGTGAGA
GTGGGCATTCATGCTTTGCTCCTGTTCTTAAGAAGAATGCTTCCAGCTTTTGCACATTATATATGAAGTT
GGCTGTGGTTTTATCATAGATGGCTCTTATTATTTTGAGCTATGTTCCTTCAATGCCCAGTTTGTTGAAG
AACTTTATCATAAAAGGATGGTGGATTTTATTGAAAGCTTTTTCTGCATCTGGTGAAATGCTCATATACT
GTTTATCCTAAATTCCATTTATGTAGTGAATCACATTTATTGATTGTGTATACTGGACCATCCTTACATC
TCAAAAATAAAGCCTACTTGGTCATGATGAATTCACTTTTTGATGTGCTGCTGGATTCAGTTTGCTAGTG
TTTTGTTGAGGAATTTTGCACCTATATGCATCTATATTCATCTATATTCACCAGGGATATTGGCCTGTTG
GTTTGTTTTTTGATGTTGTTGTTGTTTTTGTGTCTTGCTATATTTTGGTACCAGGATGATTCTGGCTTCAA
AAAAATCAGTTAAGAAAGAGTCCTTCTTTCTCAATTTTTCAGAATAATTTAGTACAGTGGGTACTCACTC
TTTTTTGTATTTCCAGTAGAATTTGGCTATGAATGCATTTGGTCTAGGGCTTTTATTGATAGGCAGGTTT
TTTCAGTACTGATTCAAATTTGGAACTCTATATTAGTGTTCAGGGTTTCAATTACTCTTTGTTCGTCTTG
GATGGTTGTTGGATGGTTCATTTTGGATGGTTGGATAAGAATGACCCAGTTAATACATGCTCCCTCTTTG
CACACTAGCGAAGGCCTGAAAGTGATAGAATATTAGAACCCTAAAAAGAATTGTGTCTACCACAAGACAT
AATCTTCATTATACTGGCAATGACTATGCCATTTGGGGACTATTGCAAAGTTTTTATTATTTATTTATTT
GTGTATTTATTTATTTATTACTAAATCCTCAATAATGAACCATCACTTCTTAAAATAGTGTTCTTTGTAC
CAAAGCTTAGTTTTATTGACCAATACACTTGTTCCATAAAAAATTCCTCTATATTATTCCTAGTGAAAAA
AAATAGTAAGAACTGTAAGTTTGGCAGAACTGTAGATGTATAGATTTAAATTCTTCTACAATTCTTCCTT
CAATAATTGATCTTTAGCATTAATAGATTCAACGTGAGGTTCCCTTAAACTTTAGCCTAGATTTAGAACA
GAATTTATTAAAGCCACCTGTCTATATAAACTGTTCAACTGATTAAAAATCTGAAATCACTTGTTTCTAC
ATTTTCCACTTCTGTGCTCTAAACACTAGTGGGCATTCTGTTGTGTTTAACCTCTCTGGTAATAATATC
ATCTGTCATTGTATCCTTGGATTTTGTTTATGCCTGCTAAATTAAAATTTTAGCATCTCTACCTGTCTCT
ATTTTTCCTGGACTCAGTGCCATTTTCATGGGTGACTCCAGTTAAATTTTGATTACTCCCAAACTGCTAA
ATTATCTGAATTCTTTGGATAATTCCTCCTCAGGGCATGTCTCTGAAACTTAGAGATTGTCCAAAAGAGT
ATGTGCTCTGCAGAGGGTAAAAGGGAATGGAAAATAATTATTAAAGAGAATCTATAGTGATGAGAAAATT
GTATACAGAGTTCTAGGCACTAATTTCTTTGTTTCTTAGTTTTAAAATTAAGAATGAACTAAATGTCAAT
CATGAATTACATTGTCTTATATAGAAAGAAATCCACAAAACTATTTTACCTTTTATCTCTTAAGCAACTG
TATTTTTAGAATCTTCTTAAACTGTAAATATATTAGTTTGAACAAGTGAGACTTCACTAAATATAATGCA
ATGTATTTGCAGCACTGTTAGGTCTTGCAAATTTCTTATGTCATATTTTATACACAACGCTTAAGGTGTT
TTACAACTGCAGTTGTTTGGAAGTAACTGGTCTCCAGAACAGAAATTACTCAGCCCATTTGGGTGAATGC
CCAAGAGATGATGCTTGTACAAGGAAATTTTACTTTTTTGTTGCAATACAAGTCTTGAATTTATTTTTCT
CTGCACTTGGAGGCACCTCACATGTCATGCTGATTGTTAAGTAAGTATGACTTTTAAAAACATTTTCATA
TGCATGAGACTATAAACACACCTAATGATATGCATATTTTTACATAATATACTGGGAATTCAAATTCATA
TTTCATCAAATTTTAATTTTCTGAGAATTCATTTTATTAAAATTACTATGAACTCTCAAGGCTGTAATTA
ATAATTTTGCCTCTAATTCTTCCATTAAAAGTCCAGATTCCATACGTTTCTTCTCTTACTAAGAATCTGA
AGACACAGACTGACAATTCTCTCAGTTGTAAAAGAATCGCCCTAGGATCCTAAAAGAACTTGTTGAATTT
TGAGTTGCCTTACATCCTAATGAGAGATGCCTTGCATCTCTCAGGGTAAATCTATTGATTTCACTAAAAT

FIG. 5 (continued)

AAAGCATTTGAAAACTAGATATAAAATATGCTCCATTTGATAACATTCCAAAACTTTTAATCGACTCACA
GCATGACTTTTATAATACCCTTGTAGAAAAATAAAAAAATACACAGGAAGAATTAGTTCCTTTCTTGGCT
CATTAGAAAAGATACAATGCTTGGTGAATATTACATGGTAAATGAAACCAATAAGATACTTGTTGTCATA
CAGCTTTCAAAATTACAGGAAAGACTGGTGTGAGATAAATAATCTTAAAATCAAAGCACATATTTATAAA
TTGTTCTGAGTCCTCATCAGGAAAAAGATTTCCCTAAAAAGAAAGATTCAAAAGGAAAGTTAATTTAGGA
TTGAGGTGGGGGGCTGTGAAGAAGAGGATTCAGAGTACATCTCAAAATAAGTAACATTTATTCTAAAGGT
CTAAAGAAAAAGCCAAATGAAAGGGTTTCCAGGAGAGGGTCTTGGTGCTGACGCCTTAATACAGGAAAGA
GCTGGTGTGTTTGAGAAATGAAAAGAAGCTGGCAGATTGAAACATACTGAATGAGAGGTTGTGACACATG
ATAAGATTGGAGAGTTAGGAAGGGTGCAGGTAATGCATGCCCTACTGGCCAAGTTGATTCAATCACCTAA
AACTTGTAACATGTAAATAATTGCTTTTAGATCTTAAAAATATACATGTGTAAGTATAGTGACCTGGGTT
AACATTCAATTGTACTTTTAAAACTTACATTGTTGATCATAAGTTCACTGTCAGCCAACAGCATGACATG
GTAGAGATGAAAAAAAAAAAGCATTTTTAACATTTGTTAACATTAGTATCAACCTGTAAATTGAATTTACA
GTTGTTTAATTTTGACCCTGACTGCAAATCTTATCAAATTATTTATACTAAATATGCCACAGATATAGCT
CCATCTTAATATAAAATGTTGTCTACTCAAAAGGAGAAGTCTTTCATATTTGCCAAATTAAATTCATTAA
CATATTAAAAATAACCTTAAAATTAAATAATAGTCTGCATATCAACAGGTTTTAGCTTTTTATTTTAAAC
TCATGAGTTTGAAAAAACACTGTTCCATCATCGATGATAACAATATCATATCTGTTTCAGAAATTGATTA
AATCAGCATTACAACTTGTCAAAAATATTTAACTCTTGCTAGCCTTTGATTTTATTGAAATAAGCATTTT
GTGAATATGACTACAGAATAAAAATATAAATTTCAGTTTGTTAATAGTTTTCTAATGCTTAACACTATGA
AGCTATTTTTTAAACTTGATTAAGTAGGCAGAAGGACATCCATTTATTCAATATGTATTCATTTTTTATG
TCAGGCATAGTTGTATGCACTGAGGATGCAACTGTGAACAAAAGTGATAGAACTTTATAAGCTTTTAGTA
TGGGTGGGGAATGAAGGAATGAATGTGTGTAGCAGAAAACACAGTAAACAAATAAGTGAGTAAACATCTA
AAATAGAGTAAGTGTGAAGCACTAGAAAGATAAATAAATCACAGTTAAGAAAATAGAAAAAAATGAGAAA
ATAGGCAAGAGATACTAGTTCAGATATGGTGCTTTGGAAGTCCTTTGAGTAAAGACCTGAATGAAGAGAT
AGAAAATAAAGGTACAAGCCATGCTAAATGGAGACATAGGAGGAACAATCCAGGCAAGGTAGAAGAAAGG
TCAGCGTCCTGGTGTGAAGTATAGTTGACATGTACAAGGTCCAAAAACGTGTGTAAGGAGGAGAGAGGTG
ACAAGTGCAGCAAGAGAGCTAGCCTAGTTCAGATCCTATGGGTCACAGGAAAGACTTTGAAATATATTCT
AAATGTGTTGAAAGCCCAAGGGGATTTAAGCATTAGTATTTGCAAAGATGCCTTACATAACTAGAAGATC
ACTCTGGCTGTGGGTAGAAAGTGTGTTTTGTGAAAACAATAGTGAAGTCAGGGAAAACAGAAGGCTTGAA
TTGTTCTTCTCAAGATGGAAGCTTGATTGAGAATGCTGATAATAGGAAAATATGAAGTAAATGAAATGAG
TAAATGAAACAAATATGAGTCTCAGTTGTTTTGCTTTATTTTATTATATTTATTTATTTATTTTTGAGAG
ACAGTCTTGCTCTGTCACCCAGGCTGGAGTGCAGTAGCACAACCTTGGATTGCTGCAACCCTCCGCCTCC
CAGGTTCAAACGATGCTCCTGCCTCAACCTCCTAAGTAGCTGGAATTACAGGTGCACGCCACCGTGCCTG
ACTAATTTTTGTATTTTTAGTAGGACCTGGTTTTACCACGTTGGCCAGGCTGGTCTCAAACTCCTGACCT
CAAGTGATCTGCTAGCCTCTGCCTCTCAAAGTGCTGGGATTACAGGCCTGAGCCACAGCACCTGGCCTTT
GTTTTATTTTTTAATGCAAAGCCAGTAGGGTTTGCTGAGACATTGAATGTGGCATGTGAGAAAGATAATT
TAAGGATAATCCCAAAGTTCTGGCTTGAGTTCTGGAAGGATGGTGGTACTATTGAACAAAATGGGAAAGA
CTAAGAAAGGGTAGATTGGGAAAGTGAAAAAGCAAGAATTTGTTCTATCTCTATAAAGCTGAGCAGCCTG
TTCAATATCTAGCAATGTCATATATGCAATCCAACAGGAGAAACCTTGATGCCAGAGCCATAAATTTTAG
AGTCAGCAACGTACAGATGGTATTTATTTTTATTTTTACTTATTTATTTATTTAGAGACAAGGTCTCATT
TTGTTGTCCAGGCTGAAGTATAATGGCATGATTATAGCTCACTGTAACCTTGAATGCCTGTATTCAAGCA
ATCCCCCAAGGCGGTATTAAAATCCATGGAACTAATGAGATCTTCTAGGGACTGAGTACAGATAGAAACA
AGATCCTAGGATCAGTTCTCAATCACTCTAATTTAAAGATCACTAATAGGAGAAACCAATAAAGAAAACT
GAGGAGGTTTCATGAGAAAAACTAGGAAAGAGCGTTGTCCTCAAACTAATAAAGCATATGTCAAAAAGAG
CATAAGTAACTGTGTCAAGGGCTGCTGAGAGTTCACAGGAGTTGAACCTGGGAGGCGGAGGCTGCAGTGA
GCCAAGATCGCTCCACTGCACTCCAGCCTGGGAGACAGAGCAAGACTGGTCTAAAAAAAAAAAAAAAGAA
AAGAAAACCACAAACCAATATCCCTGATGAACATATGAAAAAATTATCAATAAAACACTAGCAAATCAAA
TCCGATGGCACATAAGAAAAATTTTATAACATGATCAAGTTGTTTTTATTCTAGGGATGAAGGGTTGGTT
CAACATATATAAATCAATAAATGTGATTTGCCACATAGAATAAACTAAAAACCAAAACCATTTGATAAGA
CAAAATTAAAAACAAAAACCATATGATCATCTCAATAGATGCAGAAAAATTATTTGATAAAATTTAACAT
CTTTCATGACAAAAATCCTCAACAATCTGGGCATCAAAGGAACATACCTCAAAATAATAAAAGCTATGTA
TGACAAACCCACTGCCAACTTCATACTGAAAGGAAAAAAGTTGAAAGCATTCTCCTGAGACCTGAAACAA
GACAAGTGTGTCTATTTTCACTACTCTTACTGCACATAGTATGGGAAGTCCTAGCTAGAGCAATCAGGCA
ATAGAAAGAAAGAAAAGGTATCCAAATTAGAAAAGAGGAACTCAAATAAACTCTGTTCACTGATGATATG
CAACAATAACAACAAAAAATAGACTAATGGGACTTAAACTAAAAATTTCCTGCACAGCAATGGAAATAATC
AACAGAGTAAACAGACAACCTACAGGAAGGGAAAAAATATTTACAAACAATACATCTGACAAAGGGCTAA
TATCCTTAATCTATAAGAAATACAAAAAAACTCATCAAGAAAAAAATTATTAAAAATAGGGTAAATGATA
CGACCAGCATGTTTCAAAAGACAAACAGTCAACAAACAACAAACATATGACAAAATGCTCAATATCACTA

FIG. 5 (continued)

ATCATCAGAGAAATGAAAATTAAAGCTACAGTGAGATTCCATTTTATACCAGTCAGAACGGCCATTACTA
AAAAGTCAAAAAGCAAGATACTGGTAAGAATGTTGAGGAAAAGGAATGCTTATATACTGTTGAGAATATA
AATTAGTACAACCTTTATGAAAAACAATGTGGAGATTTTTCAAGTATCTGAAAATAGAAGTACCATTTGA
CCCAGCAATCCAACTATTGGATATCTACCAAAAGGAAAGTAAATCATTTTATGAAAAAGACTCATGCTCT
TTCACACTTATTATAACACTGACTAGACCACAAAAAATCAGTATCTTCAGAGGCATAATAAAGTCTGTTC
TAACCACTTCCTCATAGGATTTTCATAAGTACCATATGAGAAAATATTTTAAGCCATCTTGAAATCATGA
TGCATTGAATAAATAAGGGAATAATTATTATTATTGCTCAAGTGTTTGCCTTTTAAAACAATTAAAATAT
AATTTTATATAATGGGGCCATTCAACTGTGAGCTTAATTCTATCATGGAGAAAAACAACACAGGAGAAGG
TTTAATGTTGTTTCGTTTTGATATTTTAATGATATTTAATGTTTCTTTGCCTTTGTCTTGTTTCAGAATT
GTTCAACCTGAATTGAAATCACTTGCACTGGGTTTCCACTCAATGGTTATACGAGCACTAGGTATGATGA
AAAAAAAAAAAAAAAAAAAAAAAAATATATATATATATATATATATATATATATATACACACACACATACAT
ATATTAAATTTAAGTTATAAATATTAATGTCAAGGATTAAAGACTGTAATGAATCTTTAATTATGATAGT
AAATAAAATTAGTATCCTTTCTATTTCTGTGATAAATAAAAACAATAAGAGACAGAGTAAAATTGAGTGA
TGGACCTAAAGGAGAATTCGATTGTTAATTATACATAAAGTCAATCTGTTAAGACTAAGGAATTATTGTA
TTTGTATTACACTCTTTCAAACACAAAGATAGATGGTCCTCCAAATTTTTCTTTTTTTTCAGAAAAATAA
GAATATTTCCTCCCAGTAGGCAGAGTGAAGGGCCTAACTTCTAAACTGTGGCATGATTTAGGCAAGGCCT
AAAGCTAGCTTGGGAAGCGTGGGAATCTGGTCAGAGAATCTGGCCAGGCTATGGCCAAATTACAATGAAG
AAATTGTCTAAGAAGCGTATTTGATGATAAAGTCACAAATCCTCAAAGTTAAAAAAGAAGAAATATAAAG
GGAATAGAAGAGAGGAAATGAGATGCTATAGTATTCTGTTGGTTTTCTTCCCTCCGTTCCGTTTTGTGTG
TCTCTAATCTCCCAGACTCTGTACATTCTGGCAGGTTTCTACCTTCAGTTTCAATGGAGATACCTCTCTG
CTAGAACCTGGGTGACAAAAGCTTAAAGTAACATCTGGGTTGTTAGTACTCCTTCTCATATGTAGAAATG
AGACTATGAGAATGGAGTAAAATTTTTTTTAGCAATAGAAAATAGGAAAAAAAATGAGTTTCACCATTCT
AATTCTGAGTATCCTATTTCGATGTATCCAATCTGTGGCACGATGGAACCTAAATGCACCTATGGAAAAA
ATACACATTTAGTACAAAACTTTCAATTCATAAACAATTGTCTTGAATACAATAAACGTGTAAATTGTGG
AAGGCCTATATATTTACCTGAAAAAGTCATTTAGAAAATAGGTTATGAGTTTTAAAATTGTAGTGATTAG
GACAAAGTTTATTACTTAAAACAATCCATTACGTTTGTTCAAATCAGTGGCATTATGTGGGAAAATAAA
CTGTTAGCATATATTTTTCATTTTTCAAAGGGTGGCTGTGATTTTTGAAACCTGAAAATTTCTCACTCAT
TTCCTCAGTACCGGGTTTTCTCAGATACATTGGCCTCAGTCCCTTGTCATTTTAATATTTCTCACTCTCA
AAAAATTGAGACTGAGGAAAACTAAATGGAATTAGTAAAATTGTGATATATCAATCACTATCATTTTATC
CATGGCAAAATAAATTCTGAAAATTATTCACCACAATACAAAAAAAAACAAAGTAAAGTTATGAACACTT
TAGTTGCACCATCTTAAGGACAGTTCTCTACTGGCGTGTCCCTAAAATTCTTCATCAAATTACCTTTGCC
TAGAACCAGGAGTGAATCTCAGAGTTCATTAAAACAGCAGTGGAAGCAGATGGACACTTATTATATAAAC
AACATATCTGTCTGTGAAAAGCCTTGCATTCTGCTAAATCATGAGCTACAAATAAAAATTAACTAAGAAA
AAGACCACTGAAAACTTATCATTGTGATCAGAACACTAACACAAACAAAATTCAGTACCACAAGCCCTAA
CTTAGCCTAAGCTGCTTCAGGAGGTATTTACAAATGCACAAAATCAATTGTAGAAAATCACTGGACTGTG
AGCTCTAATGACATCAATAAGTGGGAAGTAGATGTCTGAGCCCAGAAAAAAGTACAACCTGCCAAAAGCT
AAGCACTCTCTGAAGCTCAGCCTATACTTATCTGGGGAGGGAGTTCTGATGAAGCACTCACTTTTAAATT
CTCTTAAAATAATGTTAAAAAAAAAAAAAGTCTGCTTTTACAGCAATTGAGCCAAGATCTTTTTCCTTTC
CCCATAAAATTGTAATTCTACTCCATTTCAGGTTTCTTTGCCTAAGAAAAATCCCATATTAACCAACATA
ACTTCCAAGTTTTACTAACAACATTCTCCTTTTTACCATTCAGGCTTAAGTTAATTGTTATCATAAGAAG
AACAGAGTATATATGCATGTATGTAGGGAGGGTACGAGTAGGTAAAAGGTGTCAATGACATTACTACATG
ATTTGGGTCTTTGAGATTTCTAATAATCTTTATTATTGGGTAGATGCAGAACAAAATAATAAACGAATCC
TCCAAATTTTTGAACTTTTATTTAATCAAAATATATCAATGTGGAATATCATGCAGTTACATTTAAAATA
TGTTCCCTAAACTGACATCTTCTCTTCTCCTATTACAGGAGGAATTCTAGCTCCAATATATTTTGGGCT
CTGATTGATACAACGTGTATAAAGTGGTCCACCAACAACTGTGGCACACGTGGGTCATGTAGGACATATA
ATTCCACATCATTTTCGTAAGTTGTCATAAATATATTTCATTATTTTTTCTTTGACTATATTAATTCCTA
AAAAATATCATTTTCATTATATAATAATATTAATAATGATAGCCACCATTTAATGAAAACTGACTTTGCA
TGCAGTATGGTATCAAGCAATCTCGTATCTCATTTTAGTACTCATAGAAACTATAGGAAATGGATATTTT
CTTCTATTCTGTTATATACGAAGAAACTGTGATTCAAGGATAATAACCAACTTGTCAAAAATCAGAGATA
ATAGAAAATGGCTAGGATTTGTATGTGAATCTTTTTTGTTTCCAAAACTCTCCTCATGTCAGTATATATA
AGGATAAATATACACATGTAAATATAGACACAGACATATATATATGCATGTGTGTGTATTCGATTGCCTC
TGACTTCTCTAGAAAGAAACAGAATGACTAGCTGGGGCTCTGGTCATATGTCAATTAAGAAAAAACGGGA
AAATATGTTTCTATATTACTCTATTCGTGGGGAGAGATATTCCGTAAGTGACATGAAGATAACTGCATGG
GCATCTGGAAAAACAAAAAGCTACAATTATACTTTACCTCTTTAAAAAAAAACTAATTTCAAATTCATAT
ATTGACAAATTATACACTTTGAAATGTGAAACTACATGTATTAAAACTCATAGTATAATTTCTTTCAATT
ATCTACGAAGCAGAAACTAAGTATGACCCAAATGCCCAAAACCATAATAGAAAAAAAGACAAAATATTTA
TAAAATCTGCATCATTAAACTTTGAAAAGGAAATTTCAAAGTGAAAGTATAAATTAGGAGAATAATTTGC

FIG. 5 (continued)

AACTTGTAACACAGACACAGGCAAATATCCCGAATATATACGGAACTCTTAAACATCAGCAAAAAAACCA
TCCAATGCTGGCAAGGATGCAAAACAACAGGAATTTCCTTTAATTTTTCTTTCATTGCTGGTGGATATGT
AAAAAATAGTACAGCCATGGTAGAAGACAGTCTGGAAGTTTCTTACAAAGAAAAACACAGGCTTATGATA
CTGTTAAGTAATCATGCACCTAGGTATTTACCTAAGTTAGATGAAAACATGACCCCACAAAAACCTGCAC
TTGCATATGAAAAAATGGAAGCAAACAAGATGTCTTTCAATAGGTGAATGGATAGCCAAACTGGGGTATA
TTCATACAATAGAAAATTATTCAGCAATAAAAAGAAGTGACCTATCAACTCACAAAAAGACAAGAAAGAA
ATTAAATGCATGTAGCTAAGTGAAAGAAGGCAGTCTAAAGAAGCTTCTGGGCCTGGTGCAGTGGCCCATG
CCTGTAATCTAGGCACTTTGGGAGGCCAAGGTGGGAGGATTCATGAGGCCAGGATTTCAAGACCAGCCTG
GACAACATGACAAAACCCTGTCTCTACTAAAAATACAAAAATTAGCCAGTCACGGTGGTGCACATCTGTA
ATTTCAGCTACTTGGGAGGCTAAAGCACAAGAATCCCTTGAACCCAGGAGGCGGAGGTTGCAGTAAGCCA
AGCTCATGGCACTGCTCTCCGGCCTGGCTGACAGAGCGAGACTCTGTCTCAAAAAAAGAAAAAAAAAGAA
CATTAAAAAAAATTAAAGAAGCTTCTGACTGTATTATTCTAACTGTATGACCTTTTGTAAAAGGGCCAAA
CTATGAAGACAATGAAACATCAGTGGTTGCTAGGAGCTCAGTGGGGAGAAGATAAGGATGAGTAGGTGGA
GCACAGGGCATTTTAAGGGTGGTGAAATGATTTTATATGATATTATCATGTTGGATACATGATGTTATGT
ATTTGTCAAACCTATGGACCCATACCCATACAACATACAAACCACATAAAAAGCAAACTCTAATCTAAAA
TATGAATTTAATAATAATGCATTCATATTGGTTCATCAATTGTAACAAAGTTACACACTAATACAAACTG
TTAATGATAGGGGAAACTGTATGTGTGGGGCGGGGAGTATATGGGACTTCATACTTTCTGTACAGTTTTT
CTGTAAATCTAAAATTTCTGTAAAAAGTATGTTCTATTAAAAAAAATCAAGTATCTCCCAAAGAAAAAAT
CACGAATGGCTATTAAATATATAAAAAGATGCTCAAATTAATTGATAATGACAGGATTGCAATTAAAACT
CACCCAAATTGTCAACCATCAAAAATGTTAAGTAGACATTGTCTTGGCAAAAGTACAGAACTTTGAGCCA
GCAGCAAACTTCTAGAAATTTATCCTACAGATAACTATACTCCCAAATAGATAAAATGGCACATATATAA
GATTACATACATGTGTATGGCAACATTGTTTATGATGGCAAAATATTGGAAGCAACTTAAATATCTCTTG
ATAAGGGAGTAATTAGATAAATAGTTCTACCTGCAGGAAAATGAATAGTCTGATGTCTTGAAAAAAGAAG
AAAAAATTATTTGTTTACTAATATGGAACCTTCTTCAAGACATATTTTTATATGAAAAAAAAGAACCATG
AAGAATGTGTATGGAGCATGCTATCATTTATATGAAAGTGGAGGTTTATTAGTTCAGGATACATCTCTGG
AGTAAAGACCTAGGATCAAATTTACCAAACAGACTCTCTTCCATTTAATGTGTAAATTCACTATCTAAAA
TCCCCAGCAGATAAAATGATCCAACTTTTTCCAGAATTGTACCCCACAGACATTCTCACAAATTTATTTA
AATATTAATGACAGAAAATGTCTCACAAAATGGGAGAAAGAAATGAAAAGAAATTACAAATGAAAACTTC
ATAAATTTATCTTAATGACTTTATTTAAGAATGTGTTCATTTTTTATTGAAATCATCATGTATTTCCAGG
ACACCTGGCAAGATGCTCCTCAGAATTTCCCCAAAGCAATGACCACAACTTCAAGTATTAATGTAACATT
TTGAGATGGCTTTATAATGGTTTGAGTATAAAAAGACCCTAAAACTATTTTTTAAGCCATACTAGTTCCT
TTTTGTTCAGTGAAGGTTTAGTTAGAACTAAAATGGAATTTAAAAATATTTTATGTTAATTGATTTATTA
ATGCATTCTTCTTGTTGAACAACTGGTATAGTATCCAAATTTTTAATATACTGCAAAGACCATTGTGATA
ACATTATATAGTGTATATGTGTACTATATATATTTAATATGCATATATATGCATATATAAGACAGACATA
TTATATATATGTTATTCTTGTGTACTTTAATTTATGCTCATCCCAAGACTTTAAGATTTAAAGGGTCGGT
CTTTGTACATCCCCACATATTTATCATTTTCTTTTCTCTGATTTCTTCTTGCATGTCAGATTCTATCTAG
GGTCATTTTCCTTCTGATTAAAGTCGATTTTTAAAAATGTCTTTCAGTGAGCTCTTTAGTGGCAAATTGC
CAATTTAAATTTCTCTGGAAGGAACTTTAGTTCAACTGTATACTTAAAAGAAATGTACAAGGTATAGAAT
TCTAAATTGACAACTATTTTCTCTTGTCAGATTGAAGATATTACTCTATTGTCTTCTAAGTTCCATTTTA
CTCTTGATAAGTAAGCTGTTGTCTGTTTTCTTGTTCCTTTAAGGTAACCTCACTCCTCTGTGGATTCTTT
AAATATCTTGTCTTAATCCCTGGAATCTGTAATTACACTATGTTCAGGTTGCAGATGGAATAAGTTTGCT
AATTAGCTGAACTCAAGATAAGAAAATTATTTGGTTGGGCCCAATATAACCACAAATATCCTAAAAAATA
AAAAGAGGAGGTCAGAAGGATGTGATGTGAGAAAGACTCAGTCTATTGTTGCTGGGTTTGAAGATGGAAG
AAAGGGGCCAGGAGCCGAGGAATGTAGGTGGCCTCTAGAAGTGAGAAAAAGCGAAGGAACAGCTTATTTC
CTGGAGGTCCCAGAAAGGAATACAGCCCTGCTGATACCTTGATTTTAGCCAACTAAGACAAGTATTAGGC
TTCTAACTGCCAGGAAATGCTCCGGGCTTAGCTCACACACCCTTTTCTTTCATAAAGTTCACACCATTCC
AACCAGCTGGAAATGACCAACCCTCTTTGGGACTTACCACATTGTAGCTAACTCATGGCCCTTATCACTT
TCCTTTTGGTCACTTGTGTTCTTTGCTTGATTGTGTAAAGTGGAATTTAAAAAAAAAAAAAGAGCAGTGC
ATTTACCAATGAATACATAAAAAGTTAAATTGTTACCTTAAGAATTTTTTAAATAAACTCAATTTTAGAG
AGTTTTAGGATCACAGTAAAATTGAGGAGAAATTACAGAGATTTCCCACATACCACCTGCCCCACACATG
CATAGCCTATCCTACCATCAATGTCTCCCAACAAAGGGTGATACAGTTGTTACAAATGATGAAACAACAT
TAACACATCTTTATCTCCCAGAGTCCACAGTTTACATTAGGTTTCACTCTTGACATTGTACTTTTATGGG
TTTGGACAAATGCATAATGACATATATCCACCATTACAGTATTATACAAAGTAGTTTCTCTACCCTAAAA
ATCCTCTGCTCTGCCTATTCATTCCTTCCTCCTCTAAAACCCCTGGAGACCACTGTGCTTTTTACTGTTT
TCATAGTTTTGCGTTTTCCAGAATCATACAGTATGTAGCATTTTTAGACTAGCTTATTTAACTTAATCAC
ATGCATTTAAATTTCCTCCAGGTGTTTCAATTGCTTGATAGCTCATTTCTTTTTATTGCTGAATAATATT
CCATTGTCTAGATGTATAACAGATTATTTATATATTCACCTACTGAGGGCATCTTGATGGCTTCCAAGTT

FIG. 5 (continued)

TCATGTTTCTTTGATGATATATATGAAGATGTTTGATTCTGTTATATTAACCCTGGATCCTGTGTCCTGA
AACCTTGCAATAATTGCTTATTAGTTCCAAGTGTGTTTTTGTCTGTTATTTTAAACTTTCTACTTAGACA
ATTATGTCATATTGCAAACAAAGACAATTTCTTTCTTTTCAATCTATATACATTTCATTTTCTTTTCTTT
TTAAAAATTACATTAATTACGACTCCCAGTACCATGTTGAAAAACAGTGGTGAGAGGGGACGTTTTTGAC
TTGTTCCTGACCTTAGTGGGAAGACTTTGAGTTTCTCACTATTAAGTATGAAGTTAGATGTAGGGTTTTG
GCAGATATTTTTGATCAAGTTGAGGAGGTTCTCCCCTATTCCAAGTTTAATGGGAGTTTTTATTATAAAT
GAGTGTTTGATTTTGCAAATTCACTTTTCTAGATCTATTGATGTGATCATGTCATTTTATTATTCTTCTT
TAGCCTGTTAATGTAATGAACTGTAAGAATTCATTTTGAATGTTGAACCAGTCTTGGAAACCTGAGGGAA
ATCCCACTTAGTCATGATGTATACTATATTTATACATTGTTGGATTCAATCTGATATTTTTTGAGAATTT
TTGCGTCTATGTTCATGAGAGAAGTTGCTCTGTAGTATTCTTTTTTTTTTTTTTTTTTTTTTTGGAGACA
TAGTTTTGCTCTTGTTACCCAGGCTGGAGGGCAATGGTGCGATCATGGCTCACCGCAACCTCCGCTTCCC
AGGTTCAAGCGATTCTCCTGCCTCAGCCTCCCGAGTAGCTGGGATTACAGGCATGCACCACCATACCCGG
CTAATTTTGTACTTTTAGTAGAGACAAGGTTTCTCCACGTTGGTCAGGCTGGTCTCGAACTCCTGACCTC
AGGTGATCCGCCCACCTCGGCCTCTCAAAGTGCTGGCATTGCAGGTGTGAGTCACCATGCCCAGCCCTCT
GTAGTATTCTTTTCTTGTAATGTCTTTGTCTGATTTTGTTATTAGGATAATGCTAGCCTCACAGAATGAA
ATAGGAAGTACTTCTGCTGCTGCTATCATCTGAAGAAGATTGTAATGATTTGGTATAATTTCTTACTTAA
GTGTTTGATAGAATTCACCAATGAACCTATCTTAATTTGATGCTTTCTTTTTTATTATTATTATTATACT
TTAAGTTCTAGGGTACATGTGCACAATGTGCTGGTTTGTTACATAGGTATACATGTGCCATGTTGGTGTA
CTGCACCCATTAACTACTCATTTACATTAGGTATATCTCTCAGTGCTATCCCTCCCCCCTCCCCCCACCC
CACGACAGGCCCCAGTGTGTGATGTTCCCCTTCCTGTGTCCAAGTGTTCTCACTGTTCAATTCCCACCTA
TGAGTGAAAACATGTGGCATTTGGTTTTTTTGTCCTTGTGATAGTTTGCTGAGAATGATGGTTTCCAGCT
TCATCCATGTCCCTACAAAGGACATGAACTCATCCTTTTTTATGGCTGCATAGTATTCCATGGTTTATAT
GTGCTACATTTTCTTAATCCAGTCTATCACTGATGGACATTTGGGTTGGTTCCAAGTCTTTGCTATTGTG
AATAGTGCAGCAATAAACAAACTTGGCTTTTTGGCTAATATCAAGTATAGTATCTGTTCTTTTCAGTTTA
GTTTGATGCTTTCTGTTTTAGAAGGTTATTAAATATGGATTCATTTTTAGAGAGTTCTATCCTCCTTCAA
TGCCTGGGGTTCCATGAGGAAATCAGAGCTTTTTCCCAAAAATGGTACCTCCTATTTTTCCCAAGGACTC
CTCGTCTGTTAGAAATGAACTTAGTTCCTTTCATGTGGTCATCAAGAGGGGCAAAAAGACAGACTGAGGA
AATAATTCACTCAAGTGAGAAAAATAAATAAATAAAAACTTCTCAAAAAAACAAGATCCAAGAAGAGAAA
AAGCACAAAGGTCTTGTATATAGATATATACACACACAGACACACACACATATATATACATATATGTATA
TATGTGTGTATATATGTATATGCTATATATACATGTATATATGTGTATGTATATATACACACAAACGTAT
ATGTGTGTCTGTAAAGAGAGAGGGAGAGCGAGAGAGAGTATGGGAGAGCACTTGGATATCCATTTTTAAT
TAAGCTGACTTTTAGCTATAGTGCCCTTTAAAAAAAATCCTTTATATCTCTTATTATCTGACTTTAGCAA
GGCCAAACAGCCAGTATTTCTGGCTTTTGAACTTCTTTAGAAATAGTAATCTCCTAGGTGAAATAAATAA
GCCTTAACTGAGGTTGTAACTTAACCATGAGTGTATGAGGTATTTTCAAATAGGTGGTAAGCAGTTTTTA
CAAGATCTAGAATCTTCAAAGGTAACTCACAGAAACGAAAATTCAAGAAGGGAAGCCAGAAGTTGGTCAT
GGAGGAGCAGAGAATCAACAAATGGAAAAAGCCACAAGAATATCAAATCAGAAAGCATTCATTCCCTGGG
CCAAGAATTGAGTCCCAGGCCACCATTGTGAAAAGACAAACTCTTAGCTTCTGAGCTATAGCATTGGATA
GTCTTCATTACCTTTCCCAGAAGGATTCCAGTGCAACCGATTTCAAGCTTGCAAAGGCTTTTAACTGCTC
GAGATAATTTTTAGAGCTAACTATGACATTAACTACAAAATTCCTGTCCTCTAGATGGCAGAGACCAAGA
GTAAGTACTGCCACATAGTTACAAGATCAAGCTCCCACGGACATAAAACAAGATGAGAGGGAAACCTCAT
CCAGTATAGGTTTCAGGAACACACAGCAAAGTTTGTAACCGACCAGCCCAAGAGGCTGGCTTAAAAAGTA
GGCTTATAGGAATCCTAAGCCTACTTTCTACATTCTTTCCTATGACACCCCTCTCCATTACAGAACAACA
CTAAAAGACAAATTCTTAGCACAAAGTACACCAGATTTGCTAAAGCCTAAGACTAGTCTCAAAAATTCAT
TTTTCTATTAATCAGACCACACACACACAGAGAGAGAGAGAGAGAGACAGAAAGACAGAGAGACAGAGAG
ACAGAGAAAGACAGAGACAGAGACAGAGAGACAGAGACCAGAAGCTTGGCTGGTAACAAATTCTTACCCC
TTTTGCCAGCATACCACGTTTCTGGGTTCCCTTTCTCTGCAGCTTCCAGAAGAATGAAGTGGCTTTTGAT
GACCCTGCTCATTGCACCATAGCTTTGGGGGCCAAGCCACTTTACAAAAGAAAATTATCCTTTTCTGTTT
TATAAAACTATAGGCAAAAGCTTCTCATTTTTGCAAGATGCTGCCCAATGGGCTGCATGAGGAACCAAAT
TAACATTTTCCACCCCAGCCTAGCAAAATACACATAACAAAACAGACATTTGTCACCTCATTCAGCACCC
AATATTGACCTGGCGAGGCTCAAACTTTCTTTCATTGGTCCCTATCATCTCTGATCCACTCAAGATGTGG
AGGGCTAAACTCCAACTGAGAATTCAGGTCTCTGGGCAAGATGAAGAAGTGGACAGTCACCCCGACTCAG
GCCTTTTTGAGCTTCCTTCAGGACTCACTGAATGTGACCAGACAAATAATGAGGGTTTTCTGAGTTAGGT
GTCCTAGACTTCCATCAGTAGTTCCTTTAGAGGTCTCCTCCACATATACAAATACACACAACAAAGACAA
GACAGACAGAAGGCCTTCCAAACCACGACTTCTAACCAAGAATTCCGAGTCTTCCTCCCAAACGAACCTT
CTATTCTCCACCTGAGAATTCTCCCTAAAATCTTCTTGATTGAAGAGAAATCTCCTGAACCAAGACTTCC
TACTAATTAGAGCTAACCAACACCTCCAAAGGAGCTGAACTGAGACCTCAAAAAAAAAACAAACAAACAA
AAAAAAAAAAACAAGAGCCCCAAAGGAGCCAAACCAAGGCCCCTAAAGAAGCCAAATCATGATCCCCAAA

FIG. 5 (continued)

GGAGCCAAACCAACTGGGAGAAGAAAGGAGGAGTTGGCAGTGCCTAGAATACTCACCAAATTAGTTTGGA
GACAGACATCATTTCCAGGAACTATTTCTCCATTGCAATTAAATCCATGCACATTGGGTCAGCAGCACCC
TGCCAGTAGAGACAGTGCCAGAGTCAGCCCACAGTCCAAGAGAACTAGGCAGCCACTTGGGCTGGCCTCT
GGATCCATCACCAGAGCAGGGCTACTGAACCATGGGCAGGTAGGCACAAAGGCAATCCCAGATGAGACCC
CTAGTGTGTAACCACCTAACGGGTTCACCTTGCCCACTGCCTAGACAGAGCTTATTTATCAAGAAAGATC
TTACTTATCAAAACAGAGAAATTGCAATAAAGAGTAATTCATGCAGAGCCAGCTGTGCAGTACACCAGAG
TTTTGTTATTATTCAAATCAGTCTCTCTGAGAATTTGAGGACTGGAGTTTTTAAAGATAATTTGGTGGGT
AGGGGGGCCAGTGAGTCAAGAGTTCTGATTGGTCAGGTGAGAGATGAAATCATAGGGAGTTGATACTGTC
CTCTCGTGCTGAGTCACTTCCTGGGAGGGGGCCACAGGATGAGATAGGCCAGTTTATCAATCTGGGTGGT
GTGAGCTCATCTGTGAAGTTCAGGATCTGCAAAATATATCAAGTATTGATCTTAGGTTTTACAATAGTGC
TGTTATCCTCAGGAGCAATTTGGTTAGAGTCAGAATCTTGTAGCCTCCAGATGCATTACTCCTAAATCAT
AATTTCTAATCTTTTGGCTAATTCGTTAGTCCTACAAAGGTAGTCTGTTTCCCAGGCAAGAAGCTGGTTT
GTTTTGGGAAAGGACTGTTACTGTCTTGGTTTTAAACTCGAAGCTATAAACTAAATTTCTCCCAGAATTA
GTTCGGCTTACACCCAGAAATCAACAAGAACAGCTTGGAGGATAGAAGCAAGATGGAGTTGGTTAGGTCA
GCTCTCTTTCAGTCTCGGTTATAGTTTTGCAGTGAAAATTTCATAAGCATTTAGTGCAATAAACTTTCCA
CTTTATGCTGTTGAAGCTATATCCTAGAGGTTTTAAAATACTTTGTCTCGATTTTCATTTGTTTAAAACA
AAAAAATTGTGTTCTGCTCTAATTTTGTTATTTACCCAAAAGTAATTCAGGACCAAGTTATACAGATTTC
TTGTAATTGTGTAGTTTCAAGAGTTGCTCTTGATACTGATTTCTATTTTTATTCTGCTGTGGTTCATGAA
GATGTTTGTTATAACTCTGATTTTTTAAAAAATTTATTGTGACTTATGACTTAGAATGTGGTTAGTTTTA
GAGAATGTTTTATGAACAGATAAAAAATGCATTTTCTCTGATTTTTGGGTGAAGTATTCTCTAGATATCT
ATTAGATCCACTTGGTAAAGAGTCTACTTCAAGTCGAATTTTTTTTTTTTTTTTTAGCTTTTGGCCTTG
ATGATGTGCCTGCCTAGTGCTGTCAGTCTGGTGTCGAAGCTTATTACTCATTGTATTACTTTCTATCTCT
TTGCTTAGGTCTGGTAGTATTTATTTTATAAATATGATTGCTTCAGTATTGAGTGTGTATATATTTAGAT
TAGTTAAATCTTGTTGAATTAAATGCTTTATCATTATGTAATGCACTTACTTGGTTTTTTTTAAACTGTT
GTTTGTTTAAGGTCTGTTTTATTTGATACAAAGAGAGGAATTTCAGCTTATTTTTGCTTTCCATTTGAAA
GATAGATCTTTCTTCATTCTTTTACTTTAAGTCTATGGGTGTCCTTACATACGAGATGGATTCCTTAAGG
GCAGCAGAAGGTTGCCTTTTTTTTTTTAATCCACTTTGCTACTCTATGTCTTTTATATGAAGCATTTAGG
CAATTTACATTCAAAGTTAATATTGATATGTGAGATTTTGTACCTCTCATACTGTTGTTAGCTAGTTGCT
TTATAGTTGCAATTGTGTAGTTACTTAATAGGATCTGTAGGCTTTGTAATTATGGGTGCTTTTATAGTAG
CAAGTATTGGTCTGTTTTTTCCTGTTTTGAACTCCTTTGAGCATTTTTTCTAAAACTGATCTGGTGGTGA
CATATTTCCTTAGTGTTTACTGGTCTGGGAAATATTTTATTTCTACTTTATTCACAAATCTTCATTTGGG
AAGTTATGAAGTTCTTGGCTGTCATTATTATTTTTCTTTTGTAAGTCTAACAATAGGCCCCCAGTCTCTT
CTAGCTTGTAATGTATCTGCTGGGAAGTTCACCTTTAGTCTAATGGTATTTCCTTCATAAATAATTTGGC
CCTTTTCTCTAGCTGCCGTTAGGATTTGTTTTTTCATGTTGAACTTAGGCAATCTGATGACTATATTCAT
ATAGTATCTGAATGGTTGTTTTGTATAGTATCTCATACTATAGTATGTTTTGTATAGTATCTCATACACT
GTTGCACCCACAACAGTGTACAGTGGAGAGAGTGGGAAATTACCCTCTATCCAGATTCATTCCTGAGTGT
TGGTACTGCCTCCTTCAGTAATTGGTGCTGTGCCCATGTTCTCTTTGTCCCAGGGGAAGCTATAGTGGGC
TACAGTCCCCACTCTTTTAGGGGAAGAACACATTGAGGGTTAGATCTCCAGAGGTCCTGCTGTCTCCCCA
AAGTCCACTGACCCCTGTGCCTACCAAAGTCAGAGCAGTTTGTTGGACATGTTTGCCAGGAATTGGGTGG
CATGGTGACTCAAAGATGGAGAATCCTCAGGCAGGGCGGTGGCATACCATAGATGCACCAACAGTATGGC
ACATCTTTCCTTTAGATAGAAAGGTGGTGCAGCTGTACCTGTGCAGGCTGGCCACCTAGTTGTCTATCCC
TGGGGAGTTCCCAAATTGCCACCAATAGCATTACCCTGCATCAAGAGGGCAGAGGAAATTCCTAACAATT
TGGTGGTCAGCAGATTATCAGAGATGTGAGGGGAGCAGAGAAGCACTTTCAGCTAAATTTTCACAGGGTT
CTCTGGGGGTTGATTATTACCAGGCTTTTACCGCTTTTCTTTACTACACCACAGCTGCTTCTTATGGGCA
CTATAACAGTTCCTGGCTCTCTTTCTCAGTTTTTTATTTGGTACTTCTTTATTCACCAGTAACTTTGATC
TTCTTTCTGAGGAGAACTGTAATTTGATGTCCCTGGTCAGCCATCTTGAAAAGAACTTGACTTATTTTTT
TATCAGTGGCAGCATGATATATCTTCCTCCATCTAATTACTTTTAATCTATACATCTATAAGTAGATCTC
TTAGAGACTACATATAGTTTGTTTCTTCTTTTTAATCCTTTAACAAACTCAGTCTTTTAATTGGTGGATT
TAGATCATTGACATTAAAAGTGACTACTGATGTTGTGAGACCAATGTTGATTATAATTTTACTATTGTCT
ATTTGTTATACTTGTTCTTTGATCCTATTTTTGTCTTCTATTCTTTTTTCTTCTGTTGTGTTCTTAACTA
AATAGTCTATATGACTCTGATTTTATATGACTATATAATCATAACTTTTTATGTTACCTTTCTTTATGTA
TATCAAGTTTCTGACCTATATGAGTCTCTCTAAAAAGCTTCTCTTAACATTTCTTACAAGGAAGATGTAC
TGGAAAAACATTTCTTCAATTGTTGTTTGTCTGAGAATGTGTTTATTTCTACTTTACTTTTAAAAGAATT
TCACAGAGTACAGAATTTTAAGTTGGTGATTTTTTTCTCTTAAGACTTTAAATATTTCACTCCACTCTCT
TCTTGCTTGCATGGTTTCTGAAGAGAAGTCTATTTTCTCCCCTATAGATAAAATTTGTTTTTCCTTCTGG
TTAGTTTCAGGATAAAGTTTTCTTTATCTTTGACTTTCTGTAATTTGAAAATAACACACCTACACGTAGT
TTTTCTGGTCAATAATAACTTATTTGTATATTTAAAAATAACTTAGGAAGTGTAGTTGAATTGTTTGTAA

FIG. 5 (continued)

CTCAAAGGACAAATCCTTAGCATTTTCTGAGTTTCCTGAATCTGTGATATAGTGTCTGACATTAATTTAA
GAGAAATTCTTAGTAATTTTTTTTTTTTTGAGATGGAGTCTCACTCTGTTGCCCAGGCTGGAGTGCAATG
GCATGATCTTGGCTCACTGCAACCCCCGCCTCCCGAGTTCAAGTGATTCTCCTGCCTCAGCCTCCTGAGT
AGCTGGGATAACAGGCACCCGCCACCACGCCCAGCTAGTTTTTGTATTTTTGGTATAGACGGGGTTTCAC
CATGTTGGTCAGGCTGGTCTCTAACTCCTGACCTCGTGATCTGCCTGCCTCAGTCTCCCAAAGTGCTGGG
ATTACAGGCATGATCCACTGCACCTGGCCAGTAATTATTTTTTAAAAATGTTTCTTTTGCTCCTTTTCTC
TTTGTTTTCCTTCTAACCTTTCCATTACACCCACTTATATAATTGTCTCAAAATTTTTATATGATTTCAA
TTGATTTACTTTTTAGTCTTGTTTCTCTTTGCTTTTCAGTTTTGGAGGTTTTCATTGATATATCCTCAAA
TTAGAGAGTCTTCATCAGTTGTGTTCTATCTACTAATAAGCCCATCAAAGGCATTCTTTATTTCTGCTAC
AGAATTTTTTATTTTTAGCATTTTCTTGGGTTCTTAAAATTTTTATTTTTATACTTACATTGTCCATCTG
TTATTGAATGCTGTCTACCTTATTGATTAGAACACTTAACATATTAATCATAGTTGTTTTAAATTCCATT
TTGAAAATTTCCACGTCCCGGACATATCTAGGTCTGGTTTAAAGCTTACTTATTCCTTTCAATCTATGTT
TTTTTTTTCACTTTTGGTATGACTGGCAATTTTTTTCATTACAGTTAAGCATAATGCATTAGGTAAAAGG
AACTGCTTTGATAAGCCTTTATTAATATGGTGTAAGGTGCTGGAGAAGGGGTAGCATTCTACAGGCCTAC
ATTTAGGTTTTATTATTTTAGTTATAATCCAGTAACCTCTGGATTATAAATTTCAAACATACTTCTCAGT
TTCTCCTCCCAGCTGTAGGTGGGGCAGGATGGCTTAACAGGGCTTGAGTTGTATATTTTTCTCGTTTTAT
GAAGAAGGCCAGAGGCAACTAGAGTATAGTTTCTATGGCTTCATAACCCTATTACAATAATAAAATATCT
ATCGTTATGCCCCAATAAAAAGAATTATTAGAATTATTGTCTTAATATTTTATTTATAATTTTTTTTCTT
TAGGATCTGGATACTGGAGAAAATGTTTTAAGTTATTACACACAATTTAAACTGATTTATTGTTTTATTT
TCTCTATTTCTACAGAAGGGTCTACTTGGGCTTGTCTTCAATGTTAAGAGTCTCATCACTTGTTTTATAT
ATTATATTAATTTATGCCATGAAGAAAAAATATCAAGAGAAAGATATCAATGCATCAGAAAATGGAAGTG
TCATGGATGAAGCAAACTTAGAATCCTTAAATAAAAATAAACATTTTGTCCCTTCTGCTGGGGCAGATAG
TGAAACACATTGTTAAGGGGAGAAAAAAAGCCACTTCTGCTTCTGTGTTTCCAAACAGCATTGCATTGAT
TCAGTAAGATGTTATTTTTGAGGAGTTCCTGGTCCTTTCACTAAGAATTTCCACATCTTTTATGGTGGAA
GTATAAATAAGCCTATGAACTTATAATAAAACAAACTGTAGGTAGAAAAAAATGAGAGTACTCATTGTTAC
ATTATAGCTACATATTTGTGGTTAAGGTTAGACTATATGATCCATACAAATTAAAGTGAGAGACATGGTT
ACTGTGTAATAAAAGAAAAAATACTTGTTCAGGTAATTCTAATTCTTAATAAAACAAATGAGTATCATAC
AGGTAGAGGTTAAAAAGGAGGAGCTAGATTCATATCCTAAGTAAAGAGAAATGCCTAGTGTCTATTTTAT
TAAACAAACAAACACAGAGTTTGAACTATAATACTAAGGCCTGAAGTCTAGCTTGGATATATGCTACAAT
AATATCTGTTACTCACATAAAATTATATATTTCACAGACTTTATCAATGTATAATTAACAATTATCTTGT
TTAAGTAAATTTAGAATACATTTAAGTATTGTGGAAGAAATAAAGACATTCCAATATTTGCAAGCTGTGA
TTGTCAAACAACATATTACATTATGTGTTAAGTTTCCAGTGGGCCCACGGTAATGTATTAGGAAAAATTG
ACTTTGACTAATGTAGCCACTCTCATACTTATCTTAGCTAGATTTCCTAGATCATTTGCCGCACCTTCTA
CGTCAGCACTTGCTTCTTCACTTTGTACTTAGATAATGAAACCAGCTTCTTTTTTTAAACCCCGTGAAAC
AAATTCTACAGCTTTTTTTCTTTTGCAGCTTTCCCACGTCTCTTAGTCATCATAGAATGACAGAGAGTTA
TGTCCTTGCTCTAGATTAGATTTGGCCTAAGGGAACATTGTGGCTGCTTTGTTCTTCAATCCAGGCTACT
GAAGTTTTCTCCATGTTAGCCATAAGTCTGTTTCACTTTGTTATTATTTGTGTGTTCACTGAAGTAGGAC
TCTTAATTATCTTCAAGTACTTTATTTTTGCATTCACAACTTGGCTAACTGCTGAATGCAAGATGCTTAG
TTTTGACTTACCTTGGCTCTTGATATGCCTTCCTCACTAAACTTAATCATTTCTAAAATTTGACTTAAAA
TGAGAGATATGTGACTCTTTCTTTCACTCAAACACCTAGAGGTCATTGTAAGGTTATTATTTGGCTTAAT
TTCTATGTTGTTCTGTCTCAGGACATAGGAAGGCCCAAGGGGATGGAGAGAGATGTAGCAATAGCTGGTT
GGTGGAGCATTCAGAACACACACAACTTTATTGATTAAGTTCCACGTATTATATGGGTATGGATAGTGGC
AAGTCAAATCAATTACAATAGTAACATCAAAGATCACTAACCACAGGTCACTATCACAGATACAATAACA
ATGAATAAGTCTGAAATATTGTGAGAATTAGTAAAATGTGACACAGAGACATAAAGTGAGCACATATTTT
TGAAAAAATGATGTCAATAGACTTGTTTGATGCAGGATTGCCACAAACTTCCAATTTGAAAACAAAAAAC
AAACAAAAAAAAACACCAAAATATGTGAAGTGCAATAAAGTGAAGTTCAATAAAATGAAGTATGCCAGGAA
TAAAAACTAGCAGGATCACAGGATCAACCTCTACTTAAAAGTATTAGAAATATGGAGGTAAATAGAAGAA
ATAGCTAAAAAGAGTTGTAAATGCTTGCCTCTGGAAAGCAGTAATAATAAGCAGAGAAAAACTCATTTTC
AATATGAGATTTTTGATATAATCTTATTTTTACAACTTTGTGCATAAATGGCTTTGGTAAAAATTAAAAA
TCAATCATCAGACTGGTATGTCTCTTATTAATCAACAATAAACAATAATATTGATACCCAGGTACTACAC
TGAGAGCCTTGGGTGAGCCTCCAAGTCTTGCTGGCTTCAGATACCAGAAAGATCACAGGGGTTAATGCAC
TAAGCAGACTCTTGAGGTCCCTGATTCCAGGACTTGACTCTGGGATAGCATTTCTGAACCTGCCCTCGGC
CAGAGGGGAGCCCATTGTTCTGAAGTTTGAATCCCACCTCAGGCAGAATTCAATAGAAGCTGATTAAAGT
GCCCTTGGGCCTTAAGGAAACATTGGCAGTAGTCTAGCAGTACTCCCTGTGGGCCTGAAGTGTTGTGGCT
ATGGGTTGAGGCTCCTTTGTATTTGGAAATGCGAGGGAAGAGTGGGAAAGACGGTCTTGTGGTTTGCGTG
CCACCTCAGCCACAATATGATAGAACACCAGGTAGACTTTACGAGTTTTGGCTCTAGTCTCTGACTCCTG
GATGGCATCTCTGGACCCACATGGACCTGGGGGACCTCGCCACCCTGAAAGGAAGGACACAGGCCTTGC

FIG. 5 (continued)

TGGCTTTTCTGCCTGCTGATTGTAGAGCCCCATGGCCTTGAGCAAACATTGGCAGTAGTCAGGGAGTAAT
TACAGCAGACCTTGGGCAAGACTCATAAATGTGCTGGCTTCAGGTGTAACCCAATGTAGTCATAGTTCTG
GATGCCACAGAGGTGCTTACGCCACTCCAAACC

FIG. 6 Wildtype SLCO1B1 polypeptide sequence (NCBI Accession No. NP_006437.3) (SEQ ID No. 73)

MDQNQHLNKTAEAQPSENKKTRYCNGLKMFLAALSLSFIAKTLGAIIMKSSIIHIERRFEISSSLVGFID
GSFEIGNLLVIVFVSYFGSKLHRPKLIGIGCFIMGIGGVLTALPHFFMGYYRYSKETNINSSENSTSTLS
TCLINQILSLNRASPEIVGKGCLKESGSYMWIYVFMGNMLRGIGETPIVPLGLSYIDDFAKEGHSSLYLG
ILNAIAMIGPIIGFTLGSLFSKMYVDIGYVDLSTIRITPTDSRWVGAWWLNFLVSGLFSIISSIPFFFLP
QTPNKPQKERKASLSLHVLETNDEKDQTANLTNQGKNITKNVTGFFQSFKSILTNPLYVMFVLLTLLQVS
SYIGAFTYVFKYVEQQYGQPSSKANILLGVITIPIFASGMFLGGYIIKKFKLNTVGIAKFSCFTAVMSLS
FYLLYFFILCENKSVAGLTMTYDGNNPVTSHRDVPLSYCNSDCNCDESQWEPVCGNNGITYISPCLAGCK
SSSGNKKPIVFYNCSCLEVTGLQNRNYSAHLGECPRDDACTRKFYFFVAIQVLNLFFSALGGTSHVMLIV
KIVQPELKSLALGFHSMVIRALGGILAPIYFGALIDTTCIKWSTNNCGTRGSCRTYNSTSFSRVYLGLSS
MLRVSSLVLYIILIYAMKKKYQEKDINASENGSVMDEANLESLNKNKHFVPSAGADSETHC

COMPOSITIONS AND METHODS FOR TREATING AND PREVENTING CORONARY HEART DISEASE

RELATED APPLICATION

The present application claims the benefit of and priority to U.S. provisional patent application Ser. No. 61/546,802, filed Oct. 13, 2011, the content of which is incorporated by reference herein in its entirety.

STATEMENT OF RIGHTS TO INVENTIONS MADE UNDER FEDERALLY SPONSORED RESEARCH

This work was supported by the following grant from the National Institutes of Health, Grant Number HL74753. The government has certain rights in the invention.

TECHNICAL FIELD

The present invention relates generally to compositions and methods for assessing the treatment of coronary heart disease (CHD) in individuals based on their individual genetic makeup. Specifically, the present invention pertains to methods for identifying genetic polymorphisms that affect uptake and metabolism of CHD specific therapeutics and assessing treatment/prophylactic protocols to maximize efficiency of CHD treatment.

BACKGROUND OF THE INVENTION

Coronary heart disease (CHD), the leading cause of morbidity and mortality worldwide, is caused by atherosclerotic plaque deposition in the coronary arteries (i.e. atherosclerosis). CHD is a multi-factorial disease, and independent risk factors include: age, gender, hypertension, smoking, diabetes, family history of premature CHD, elevated levels of low density lipoprotein cholesterol (LDL-C) (>160 mg/dl), and decreased levels of high density lipoprotein cholesterol (HDL-C) (<40 mg/dl for males and <50 mg/dl for females). However, these established CHD-risk factors account for only about half of the variability in CHD events in the U.S. population. Accumulating data indicate that emerging risk factors, including lipoprotein sub-fractions, are better markers of CHD than many of the established CHD risk factors. Additionally, other factors such as the genetic background of an individual may influence how much the major risk factors affect absolute risk.

A simple paradigm of atherosclerosis is that there is an antagonistic relationship between apolipoprotein-B (apo-B)-containing particles, such as low density lipoprotein (LDL) particles, and apoA-I-containing particles, such as high density lipoprotein (HDL) particles. For example, apo-B-containing particles promote atherosclerosis (i.e. they are atherogenic) because they are deposited on the arterial wall; however, apoA-I-containing particles counteract this effect (i.e. they are atheroprotective) because they remove excess cholesterol from the arterial wall.

The various HDL subpopulations differ in size and composition, which impart each of the varying HDL subpopulations with different functions and pathophysiological relevance. The many different functions of HDL are not distributed evenly among the various HDL subpopulations. The best illustration of this is the fact that cells have several different ways by which to remove excess cholesterol. Different HDL particles interact with the different pathways specifically depending on the cell type, the expressed receptor protein type on the surface of the cell, and the cellular cholesterol content. Moreover, the different HDL subpopulations participate differently in the anti-oxidation, anti-inflammation, and cell-signaling processes based on the particles' lipid and protein composition.

Most importantly, the HDL subpopulation profile can differentiate subjects with increased risk for CVD from subjects without such risk independently of HDL-C level. This is very important, as some subjects (or even an entire ethnic group) may have low HDL-C levels but present no history of elevated CVD risk. This is due to the fact that these subjects may have not only hyperactive HDL catabolism, but also hyperactive HDL function. However, some subjects with high HDL-C may experience a CVD event due to low HDL metabolism/catabolism or dysfunctional HDL.

Statins have emerged as an important class of therapeutic compounds for the treatment of CHD. Statins are drugs that inhibit HMG CoA reductase, the rate limiting enzyme in cholesterol biosynthesis, and thereby lower LDL cholesterol. By lowering cellular cholesterol synthesis, statins up-regulate the LDL receptor on the liver cell surface, resulting in enhanced LDL apolipoprotein B clearance. Lowering LDL cholesterol with statin therapy reduces the risk of CHD morbidity and mortality. It has been documented that the absolute reduction in statin induced LDL cholesterol lowering clearly predicts reduction in CHD events. Moreover the absolute reduction in LDL cholesterol levels is greatest in subjects with elevated LDL cholesterol levels at baseline. Additionally, lathosterol is a direct precursor of cholesterol in the bloodstream, and serves as an excellent marker of cholesterol biosynthesis. Individuals with elevated plasma lathosterol/cholesterol ratios generally have significantly greater LDL cholesterol lowering in response to statin therapy than individuals with low plasma lathosterol/cholesterol ratios.

The SLCO1B1 gene encodes a liver-specific polypeptide member of the organic anion transporter family. The SLCO1B1 transporter is primarily responsible for the ability of statins to inhibit cholesterol synthesis. About 20% of the population is heterozygous for the rs4149056 allele, while about 3% is homozygous for the rs4149056 allele. The rs4149056 allele (625T>C)) results in an amino acid substitution (V174A) in the SLCO1B1 protein that decreases the function of this transporter, thereby decreasing the efficacy of statin treatment in terms of LDL cholesterol lowering (Niemi M et al. (2006) "SLCO1B 1 polymorphism and sex effect the pharmacokinetics of pravastatin but not fluvastatin." Clin Pharmacol Ther 80:356-66).

Niemi et al. (2006) reported that following a single oral dose of 40 mg of pravastatin in 32 subjects the areas under the curve of pravastatin blood levels were significantly greater for those subjects carrying the uncommon CC phenotype versus the wildtype TT SLCO1B1 genotype. In a study of 28 subjects, the SLCO1B1 haplotype significantly affected the degree of lathosterol (a marker of cholesterol synthesis) lowering induced by pravastatin (Gerloff T et al. (2006) "Influence of the SLCO1B1*1b and *5 haplotypes on pravastatin's cholesterol lowering capabilities and basal sterol serum levels." Naunyn Smiedebergs Arch Pharmacol 373:45-50). In another study of 16 healthy volunteers, Igel and colleagues reported that SLCO1B1 haplotype was associated with a doubling of plasma pravastatin levels as compared to other haplotypes (Igel M et al. (2006) "Impact of the SLCO1B1 polymorphism on the pharmacokinetics and lipid-lowering efficacy of multiple-dose pravastatin." Clin Pharmacol Ther 79:419-26). In addition, it was also found that the SLCO1B1 genotype affected pravastatin metabolism and LDL-C lowering response in 20 children with familial hypercholesterolemia and 12 cardiac transplant recipients (Hedman M et al. (2006) "Pharmacokinetics and response to pravastatin in pediatric patients with familial hypercholesterolemia and in pediatric cardiac transplant recipients in relation to polymorphisms of the SLCO1B1 and ABCB1 genes". Br J Clin Pharmacol 61:706-15).

The Apolipoprotein E (ApoE) genotype predicts LDL cholesterol lowering response to statins, including atorvastatin and pravastatin. The ApoE gene makes a protein that becomes a lipoprotein when combined with fat. The lipoprotein ApoE is a very low-density lipoprotein, which is responsible in part for removing cholesterol from the bloodstream. Genetic variations in ApoE affect cholesterol metabolism, and may alter an individual's chances of having heart disease, and in particular a heart attack or a stroke.

There are three relatively common variants of ApoE, known as ApoE2, ApoE3, and ApoE4. About 15% of the population carry the ApoE2 allele and are more responsive to statins in terms of LDL cholesterol lowering, while about 20% of the population carry the ApoE4 allele and are less responsive in terms of statin induced LDL cholesterol lowering.

Combinatorial analysis of an individual's genotype at multiple loci and their blood chemistry profile can be used to assess treatment and/or prophylaxis of the individual with respect to coronary heart disease (CHD).

SUMMARY OF THE INVENTION

The present invention provides compositions and methods for assessing and treating coronary heart disease; and in particular for managing elevated cholesterol. According to the invention, baseline cholesterol, and especially LDL cholesterol, in combination with certain genetic factors (as provided herein) are useful in combination for determining the amount and type of cholesterol-lowering treatment for patients on an individualized basis. For example, the identification of particular genetic polymorphisms in combination with baseline cholesterol determines whether a statin is indicated and, if so, at what dose. The invention recognizes the synergistic combination of baseline cholesterol levels and genetic polymorphisms in the diagnosis and treatment of coronary heart disease on a personalized basis.

In a particular application, the SLCO1B1 locus and the apolipoprotein E (ApoE) locus are analyzed to determine which polymorphisms are present. That information is then used in combination with baseline LDL cholesterol in order to determine whether a cholesterol synthesis inhibitor (e.g., a statin) is indicated and at what dose; or whether a statin is contraindicated and, instead, a cholesterol absorption inhibitor (e.g., ezetimibe) should be prescribed. In certain embodiments, the inventive diagnostic algorithm indicates that both a statin and ezetimibe should be prescribed.

The invention is implemented in any manner consistent with the teachings herein. Provided below are algorithms to guide the analysis of the synergistic effects described herein and their relation to treatment and dosage. In a preferred embodiment, an algorithm according to the invention weights cholesterol baseline and genetic polymorphisms in order to determine treatment and/or dose. An example of weighted approach is provided below. The baseline cholesterol component of the diagnostic algorithm can be total cholesterol, LDL cholesterol, HDL cholesterol, or some combination thereof. In addition cholesterol baseline can be expressed as a balance of different types of sterols; for example a ratio of plasma lathosterol to cholesterol in umol/mmol.

The invention utilizes biomarkers that correlate with the efficacy of a cholesterol-reducing drug in view of baseline cholesterol in order to provide a proper treatment regimen and proper dose. Methods of the invention allow one to characterize the likelihood that a patient will respond to a drug treatment based on the patient's cholesterol levels and an array of polymorphisms associated with response to cholesterol-lowering drugs. The invention allows a patient to be characterized as hypo-responsive, hyper-responsive, or normally-responsive to statin treatment, which then allows proper prescribing and dosing.

In one aspect, the invention generally provides a method of determining a statin dosage for an individual in need of treatment with a statin. The method involves determining the genotype of the individual at the SLCO1B1 locus and the ApoE locus, and determining the presence or absence of the rs4149056 polymorphism at the SLCO1B1 locus, and the presence or absence of the ApoE2, ApoE3, and/or ApoE4 polymorphisms at the ApoE locus. According to the method, identifying the presence of the SLCO1B1 rs4149056 C polymorphism and the ApoE genotype or phenotype corresponding to either the ApoE3/ApoE4 or ApoE4/ApoE4 genotypes determines the statin dosage. In one embodiment, the method further involves identifying the plasma LDL cholesterol concentration (mg/dl) and/or the plasma lathosterol/cholesterol (LSC) ratio (umol/mmol) for the individual, where a LDL concentration below about 100 mg/dl and a LSC ratio less than about 70 umol/mmol in men and less than about 85 umol/mmol in women indicates that statin treatment is contraindicated, or at least will not be effective, in lowering LDL-C unless the individual has an ApoE genotype or phenotype corresponding to ApoE2/ApoE2 or ApoE2/ApoE3. Alternatively, LDL concentration below about 100 mg/dl and a LSC ratio less than about 90 irrespective of gender indicates that statin treatment will not be effective in lowering LDL-C unless the individual has an ApoE genotype or phenotype corresponding to ApoE2/ApoE2 or ApoE2/ApoE3.

In another aspect, the invention provides a method of assessing statin dosage for an individual in need of treatment with a statin, the method involves determining the genotype of the individual at the SLCO1B1 locus and the ApoE locus, and determining the presence or absence of the rs4149056 polymorphism at the SLCO1B1 locus, and the presence or absence of the ApoE3 and/or ApoE4 polymorphisms at the ApoE locus. According to the method, determining that the SLCO1B1 genotype is homozygous rs4149056 C/C polymorphism and the ApoE genotype or phenotype is ApoE3/ApoE4 or ApoE4/ApoE4, indicates that the statin dosage needs to be is in the range of about 40 mg to about 80 mg/day or the patient should receive ezetimibe therapy.

In another aspect, the invention provides a method of assessing statin dosage for an individual in need of treatment with a statin, the method involves determining the genotype of the individual at the SLCO1B1 locus and the ApoE locus, and determining the presence or absence of the rs4149056 polymorphism at the SLCO1B1 locus, and the presence or absence of the ApoE2, ApoE3, and/or ApoE4 polymorphisms at the ApoE locus. According to the method, determining that the SLCO1B1 genotype is heterozygous rs4149056 C/T or homozygous rs4149056 T/T and the ApoE genotype or phenotype is ApoE2/ApoE2, ApoE2/ApoE3, or ApoE3/ApoE3, indicates a statin dosage in the range of about t 20 mg to about 40 mg/day. In one embodiment, the method further involves identifying a plasma LDL cholesterol concentration (mg/dl) and a plasma lathosterol/cholesterol (LSC) ratio (umol/mmol) for the individual, where an LDL cholesterol concentration of about 100 mg/dL or greater and a LSC ratio about 90 umol/mmol or greater in both men and women indicates that statin treatment is indicated unless the individual has a SLCO1B1 rs4149056 genotype of C/C and an ApoE genotype or phenotype comprising ApoE4/ApoE4. When the latter variants are present the combination of low dose statin and ezetimibe should be used.

In another aspect, the invention involves a method of treating a patient to reduce serum LDL cholesterol by assessing the patient's ability to respond to statin treatment by obtaining a plasma LDL cholesterol level and a plasma lathosterol/cholesterol ratio, determining a SLCO1B1 genotype from a nucleic acid sample of the patient by identifying the presence or absence of a SLCO1B1 rs4149056 polymorphism, and determining the patient's ApoE phenotype or genotype as either ApoE3/ApoE3 or ApoE4/ApoE4, where the combined characteristics of SCLO1B1 rs4149056 T/C or C/C genotype, ApoE3/ApoE4 or ApoE4/ApoE4, a plasma LDL cholesterol concentration of about 100 mg/dl and a LSC ratio of less than about 90 umol/mmol contraindicates statin treatment in the patient; and instead indicates treating the patient with ezetimibe and/or dietary modification to reduce the patient's cholesterol. In one embodiment, the combined characteristics include a plasma LDL cholesterol below about 160 mg/dl and a LSC ratio between about 90-160 umol/mmol in irrespective of gender indicate statin treatment in the patient. In another embodiment, the ApoE3/ApoE3 or ApoE4/ApoE4 status is determined by analyzing the nucleic acid of the patient. In another embodiment, the ApoE3/ApoE3 or ApoE4/ApoE4 status is determined by analyzing the protein of the patient.

In another aspect, the invention involves a method of treating a patient to reduce serum LDL cholesterol by assessing the patient's responsiveness to statin treatment by obtaining a plasma LDL cholesterol level and a plasma lathosterol/cholesterol ratio (LCR) and assigning weighted values (A) and (B), respectively, determining the patient's ApoE phenotype or genotype as one of ApoE3/ApoE3 or ApoE4/ApoE4 and assigning weighted value (C), and determining a SLCO1B1 genotype from a nucleic acid sample of the patient by identifying the presence or absence of a SLCO1B1 rs4149056 polymorphism and assigning weighted value (D). The weighted value is assigned to the plasma LDL cholesterol level (A) as follows: an LDL cholesterol concentration greater than about 160 mg/dl is assigned a weighted value of +2, an LDL cholesterol concentration between and including about 100 to about 160 mg/dl is assigned a weighted value of +1, and an LDL cholesterol concentration less than about 100 is assigned a weighted value of 0. The weighted value is assigned to the plasma LCR ratio (B) as follows: a plasma lathosterol/cholesterol ratio greater than about 160 umol/mmol in both men and women is assigned a weighted value of +4, a plasma lathosterol/cholesterol ratio between 90-160 umol/mmol in men and women is assigned a weighted value of 0, and a plasma lathosterol/cholesterol ratio<90 umol/mmol in both men and women is assigned a weighted value of −4. The weighted value is assigned for ApoE type (C) as follows: an ApoE type of ApoE2/ApoE2 is assigned a weighted value of +2, an ApoE type of ApoE2/ApoE3 is assigned a weighted value of +1, an ApoE type of ApoE3/ApoE3 or ApoE2/ApoE4 is assigned a weighted value of 0, an ApoE type of ApoE3/ApoE4 is assigned a weighted value of −1, or an ApoE type of ApoE4/ApoE4 is assigned a weighted value of −2. The weighted value is assigned to the SLCO1B1 genotype (D) as follows: an SLCO1B1 genotype of T/T is assigned a weighted value of 0, an SLCO1B1 genotype of T/C is assigned a weighted value of −1, or an SLCO1B1 genotype of rs4149056/rs4149056 is assigned a weighted value of −2. The weighted values (A), (B), (C), (D) are combined. When the combined weighted value is in the range of +4 to +8, the patient may be characterized as hyper-responsive to statin treatment and requires a statin dosage in the range of about 10-20 mg/day. When the combined weighted value is in the range −3 to +3, the patient may be characterized as a normal responder and requires a statin dosage in the range of about 40 mg/day. When the combined weighted value is in the range −8 to −4, the patient may be characterized as hypo-responsive to statin treatment and requires treatment with maximal doses of statins at 40-80 mg/day and/or ezetimibe treatment. Once the patient is characterized as a particular type of responder, the method involves administering the required statin dosage to the patient, thereby treating the patient so as to reduce serum LDL cholesterol. In one embodiment, the hypo-responsive patient is treated with a non-statin drug. In another embodiment, the non-statin drug is ezetimibe.

In another aspect, the invention includes an in-vitro diagnostic kit for identifying an appropriate therapeutic regiment to enable an individual in need of treatment to obtain a target cholesterol level. The kit includes a first reagent for detecting the presence or absence of a polymorphism in the SLCO1B1 gene, and a second reagent for detecting ApoE3/ApoE3 or ApoE4/ApoE4 in a biological sample from the individual, where the first reagent includes an rs4149056 specific primer set, and the second reagent includes an rs7412 specific primer set and an rs429358 specific primer set, or an anti-ApoE antibody, and packaging therefore.

The present invention pertains to compositions and methods for assessing the treatment of CHD in individuals based on their genetic makeup (i.e. personal genome sequence) by identifying genetic polymorphisms at genetic loci that affect uptake and/or metabolism of CHD specific therapeutics, and assessing treatment/prophylactic protocols to maximize efficacy of CHD treatment. In a preferred embodiment, the invention provides compositions and methods for assessing the treatment of CHD in an individual based on their genotype at both the SLCO1B1 and ApoE loci.

Other and further aspects and features of the invention will be evident from the following detailed description and the accompanying drawings, which are intended to exemplify, not limit, the invention.

BRIEF DESCRIPTION OF THE DRAWINGS

FIG. 1 shows the wildtype ApoE nucleic acid molecule (NCBI Accession No. NM_000041.2) (SEQ ID No. 68).

FIG. 2 shows another exemplary wildtype ApoE nucleic acid molecule (NCBI Accession No. NG_007084.2) (SEQ ID No. 69)

FIG. 3 shows an exemplary ApoE polypeptide wildtype sequence (NCBI Accession No. NP_000032.1) (SEQ ID No. 70).

FIG. 4 shows an exemplary SLCO1B1 nucleic acid molecule (NCBI Accession No. NM_006446.4) (SEQ ID No. 71).

FIG. 5 shows an exemplary wildtype SLCO1B1 nucleic acid molecule (NCBI Accession No. NG_011745.1) (SEQ ID No. 72).

FIG. 6 shows an exemplary wildtype SLCO1B1 polypeptide sequence (NCBI Accession No. NP_006437.3) (SEQ ID No. 73).

DETAILED DESCRIPTION OF THE INVENTION

The invention features compositions and methods that are useful for assessing the treatment and/or prophylaxis of coronary heart disease (CHD) in individuals based on their individual genetic makeup.

The present invention provides methods of assessing the treatment and/or prophylaxis of coronary heart disease (CHD) by determining a subject's genotype and/or plasma LDL cholesterol level and/or plasma lathosterol/cholesterol ratio, and administering a therapeutically effective amount of a compound, such as, for example, a statin, to a subject (e.g., a mammal such as a human). The present invention is based, at least in part, on the inventors' discovery that polymorphisms within genes that encode proteins involved in the uptake and metabolism/catabolism of therapeutic agents used to treat CHD modulate the efficacy of the therapeutic agent, and that this modulation is combinatorial (i.e. polymorphisms at different loci may interact with one another in either antagonistic or synergistic ways). A polymorphism or variant is a polynucleotide or polypeptide sequence that differs from a wild-type or reference sequence by one or more nucleotides or one or more amino acids. A polymorphism may include single or multiple nucleotide insertions, deletions, and/or alterations of the genomic sequence of a specified locus.

Thus, one embodiment is a method of assessing treatment of a subject suffering from or susceptible to CHD, or a symptom thereof that is based, at least in part, on a knowledge of the combination of an individual's genotype at the solute carrier organic anion transporter family member 1B1 (SLCO1B1) locus and the apolipoprotein E (ApoE) locus. The method includes the steps of determining the subject's genotype at least at SLCO1B1 and ApoE, and administering to the subject an assessed therapeutic amount of a statin dosage, or other suitable therapeutic compounds to treat CHD, or symptoms thereof, under conditions such that the disease is treated in a manner that has been assessed for the subject's own genomic sequence at the SLCO1B1 and ApoE loci. In one embodiment, knowledge of a subject's SLCO1B1 and ApoE genotype may be combined with knowledge of the subject's plasma LDL cholesterol level and plasma lathosterol/cholesterol ratio, thereby further assessing treatment.

The therapeutic methods of the invention (which include prophylactic treatment) in general comprise administration of a therapeutically effective amount of the compounds herein, such as a statin to a subject (e.g., animal, human) in need thereof, including a mammal, particularly a human. Such treatment will be suitably administered to subjects, particularly humans, suffering from, having, susceptible to, or at risk for heart disease, disorder, or symptom thereof, for example, CHD. Determination of those subjects "at risk" can be made by any objective or subjective determination by a diagnostic test or opinion of a subject or health care provider (e.g., genetic test, enzyme or protein marker, marker (as defined herein), family history, as well as other medically accepted indicators).

In one embodiment, the invention provides a method of monitoring treatment progress. The method includes the step of determining a level of diagnostic marker (marker) (e.g., any SLCO1B1 and/or ApoE polymorphism delineated herein) or diagnostic measurement (e.g., screen, assay) in a subject suffering from or susceptible to a disorder or symptoms thereof associated with CHD, in which the subject has been administered a therapeutic amount of a compound herein sufficient to treat the disease or symptoms thereof. The level of marker determined in the method can be compared to known levels of marker in either healthy normal controls or in other afflicted patients to establish the subject's disease status. The controls or reference level can be established by determining the levels of markers in a subject that has not been diagnosed with a disease according to the invention, for example heart disease or CHD, and/or does not exhibit any detectable symptoms associated with this disease. In addition, controls or reference levels can be determined by levels of markers in a subject positively diagnosed with a disease according to the invention. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to this invention; this pre-treatment level of marker can then be compared to the level of marker in the subject after the treatment commences, to determine the efficacy of the treatment.

Methods of the invention are used to assess treatment of heart disease. Heart disease includes but is not limited to coronary heart disease (CHD), cardiomyopathy, cardiovascular disease (CVD), ischemic heart disease, heart failure, hypertensive heart disease, inflammatory heart disease, and valvular heart disease. Heart disease is a systemic disease that can affect the heart, brain, most major organs, and the extremities. Coronary heart disease that causes the failure of coronary circulation to supply adequate circulation to the cardiac muscles and surrounding tissues. Cardiovascular disease is meant any of a number of specific diseases that affect the heart itself and/or the blood vessel system, especially the myocardial tissue, as well as veins and arteries leading to and from the heart. For example, CVD may include, but is not limited to, acute coronary syndromes, arrhythmia, atherosclerosis, heart failure, myocardial infarction, neointimal hyperplasia, pulmonary hypertension, stroke, and/or valvular disease. CVD may be diagnosed by any of a variety of methods known in the art. For example, such methods may include assessing a subject for dyspnea, orthopnea, paroxysmal nocturnal dyspnea, claudication, angina, chest pain, which may present as any of a number of symptoms known in the art, such as exercise intolerance, edema, palpitations, faintness, loss of consciousness, and/or cough.

Atherosclerosis is a heart disease in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

In certain embodiments, methods of the invention are used to determine an appropriate treatment to lower low density lipoprotein (LDL) cholesterol (LDL-C), which is associated with increased heart risk. Typically, a low HDL-C blood concentration value is below 40 mg/dl in men and is below 50 mg/dl in women. In contrast to LDL, high density lipoprotein (HDL) cholesterol (HDL-C)," is the cholesterol level of "good particles" measured in plasma, after the removal of apo-B containing lipoproteins (very low density lipoprotein cholesterol and low density lipoprotein particles). High blood concentration values of HDL-C are above 60 mg/dl and protect against heart disease. A HDL-C blood concentration value between 40 and 60 mg/dl is considered borderline.

Methods of the invention can be used to determine a patient's responsiveness to statin treatment to reduce LDL cholesterol and to determine a proper statin dosage for the patient. By Statin is class of drugs used to lower cholesterol levels by inhibiting the enzyme HMG-CoA reductase, which plays a central role in the production of cholesterol in the liver. Statins may include but are not limited to Advicor® (niacin extended-release/lovastatin), Altoprev® (lovastatin extended-release), Caduet® (amlodipine and atorvastatin), Crestor® (rosuvastatin), Lescol® (fluvastatin), Lescol XL (fluvastatin extended-release), Lipitor® (atorvastatin), Livalo® (pitavastatin), Mevacor® (lovastatin), Pravachol® (pravastatin), Simcor® (niacin extended-release/simvastatin), Vytorin® (ezetimibe/simvastatin), Zocor® (simvastatin), or generic atorvastatin, lovastatin, pravastatin, or simvastatin. In certain embodiments, the proper statin dosage is the amount of a statin required to reduce LDL-C to target levels, relative to an untreated patient. The effective amount of statin(s) used to practice the present invention for therapeutic treatment of a disease varies depending upon the manner of administration, the age, body weight, and general health of the subject. Additionally, statin dosage may vary depending upon which statin is being administered. For example, a typical statin dosage range for atorvastatin, pravastatin, lovastatin, and simvastatin is from about 10 mg to about 80 mg. For these three statins, a "normal" statin dosage may range from about 10 mg to about 40 mg, while a "high" statin dosage may range from about 40 mg to about 80 mg.

Diagnostic Methods

The present invention provides a number of diagnostic assays that are useful for characterizing the genotype of a subject. The present invention can be employed to genotype a gene of interest in a subject, where the gene of interest has similar or variant isoform(s). In certain embodiments, genotyping is the characterization of two alleles in one or more genes of interest. Desirably, the methods of the invention discriminate between the genotype of a gene of interest and the genotype of the similar isoform(s). Preferably, both or all alleles corresponding to a gene of interest are identified. Accordingly, the invention provides for genotyping useful in virtually any clinical setting where conventional methods of analysis are used.

The genotype of an individual may be determined as heterozygous or homozygous for one or more variant alleles of interest. Heterozygous generally means that a chromosomal locus has two different alleles. In one embodiment of the invention, heterozygous refers to a genotype in which one allele has a wild-type SLCO1B1 sequence (e.g., encoding a SLCO1B1 protein that has normal transporter activity) and the other allele has a sequence encoding a SLCO1B1 variant such as, for example, rs4149056 that does not have normal transporter activity (e.g., an alteration of Valine 174 to Alanine). Homozygous generally means a chromosomal locus has two identical alleles. In one embodiment, homozygous refers to a genotype in which both alleles have a wild-type SLCO1B1 sequence (e.g., encoding a SLCO1B1 protein that has normal transporter activity). In some embodiments, homozygous can refer to a genotype in which both alleles have a sequence encoding a SLCO1B1 variant that does not have normal transporter activity such as, for example, rs4149056 that does not have normal transporter activity (e.g., an alteration of Valine 174 to Alanine). In particular embodiments, the SLCO1B1 variant alleles with reduced or eliminated transporter activity are identical at one or more SNPs.

In various aspects, the methods of the invention determine or detect the presence of both of SLCO1B1 and APOE genetic variants, whether at the nucleic acid or protein level. The present methods provide a genetic means for the analysis of biomarkers in SLCO1B1 and APOE associated with drug metabolism, for example, statin metabolism. Results obtained from SLCO1B1 and APOE genotyping assays may be used to select an appropriate therapy for a subject, monitor drug therapy in a subject, identify a subject as responsive to drug therapy, or identify a subject as sensitive to a drug. This level of genotyping will better enable individualized pharmacogenetic-based therapy.

An apolipoprotein E (ApoE) nucleic acid molecule is a polynucleotide encoding an ApoE protein that, when combined with fat, becomes a lipoprotein. An exemplary wildtype ApoE nucleic acid molecule is provided at NCBI Accession No. NM_000041.2 (SEQ ID. No. 68) (see FIG. 1). Another exemplary wildtype ApoE nucleic acid molecule is provided at NCBI Accession No. NG_007084.2 (SEQ ID No. 69) (see FIG. 2). In certain embodiments, a ApoE polypeptide is a polypeptide or fragment thereof having at least about 85% amino acid identity to the exemplary wildtype sequence of NCBI Accession No. NP_000032.1 (SEQ ID No. 70) (see FIG. 3). In certain embodiments, an ApoE2 is an ApoE allele that encodes an ApoE protein that has a cysteine residue at amino acid positions 130 and 176 (sometimes listed as amino acid positions 112 and 158 in the early ApoE literature) in the receptor-binding region of ApoE. At the genotypic level, ApoE2 is defined by two SNPs: rs429358 (position 471 of the ApoE cDNA, position 7903 of the ApoE genomic DNA, and position 17680159 of the chromosome) and rs7412 (position 609 of the ApoE cDNA, position 8041 of the ApoE genomic DNA, and position 17680297 chromosome). The ApoE2 genotype is rs429358 (T) and rs7412 (T). In certain embodiments, ApoE3 is meant an ApoE allele that encodes an ApoE protein that has a cysteine at position 130 and an arginine at position 176. At the genotypic level, ApoE3 is defined by two SNPs—rs429358 and rs7412 (see above for nucleotide positions of these two SNPs). The ApoE3 genotype is rs429358 (T) and rs7412 (C). In certain embodiments, ApoE4 is meant an ApoE allele that encodes an ApoE protein that has an arginine at both positions 130 and 176. At the genotypic level, ApoE4 is defined by two SNPs—rs429358 and rs7412 (see above for nucleotide positions of these two SNPs). The ApoE4 genotype is rs429358 (C) and rs7412 (C).

Exemplary ApoE polymorphisms include rs7412, rs429358, rs769452, rs769455, rs11542029, rs11542031, rs11542038, rs28931576, rs28931578, rs28931579, rs111833428, rs121918392, rs121918393, rs121918394, rs121918395, rs121918396, rs121918397, rs121918398, and rs121918399. The most common ApoE polymorphism are commonly referred to as ApoE2, ApoE3, and ApoE4, respectively. These polymorphic forms differ from each other only by amino acid substitutions at positions 130 and 176of the ApoE protein. These amino acid changes are caused by SNPs at nucleotide positions 471 (rs429358) and 609 (rs7412) of the ApoE cDNA, respectively. The ApoE2 allele has a cysteine at amino acid positions 130 and 176 in the receptor-binding region of ApoE. The ApoE3 allele has a cysteine at amino acid position 130 and an arginine at amino acid position 176. The ApoE E4 allele has an arginine at both amino acid positions 130 and 130.

SLCO1B1 is the name for a solute carrier organic anion transporter family, member B1 nucleic acid molecule. In certain embodiments a SLCO1B1 is a polynucleotide encoding an SLCO1B1 polypeptide. SLCO1B1 is a gene that encodes a liver-specific member of the organic anion transporter family. The SLCO1B1 protein is a transmembrane receptor that mediates the sodium-independent uptake of numerous endogenous compounds including bilirubin, 17-beta-glucuronosyl estradiol and leukotriene C4. This protein is also involved in the removal of drug compounds such as statins, bromosulfophthalein and rifampin from the blood into the hepatocytes. An exemplary SLCO1B1 nucleic acid molecule is provided at NCBI Accession No. NM_006446.4

(SEQ ID No. 71) (FIG. 4). Another exemplary wildtype SLCO1B1 nucleic acid molecule is provided at NCBI Accession No. NG_011745.1 (SEQ ID No. 72) (FIG. 5). In certain embodiments, a SLCO1B1 polypeptide is a polypeptide or fragment thereof having transporter activity and at least about 85% amino acid identity to the exemplary wildtype sequence of NCBI Accession No. NP_006437.3 (SEQ ID No. 73) (FIG. 6). In certain embodiments, a SLCO1B1-056 polymorphism is the rs4149056 polymorphism, which results in a T to C nucleotide change at position 625 within the gene (sometimes referred to as position 521 in the early literature) that causes a missense mutation at position 174 in the SLCO1B1 protein from valine to alanine (V174A).

Exemplary SLCO1B1 polymorphisms include rs4149056, rs61176925, rs61760183, rs61760245, rs71581941, rs71581978, rs71581987, rs71581988, rs72559742, rs72559745, rs72559746, rs72559747, rs72559748, rs72661137, rs74064211, rs74064213, rs74700754, rs77468276, rs77871475, rs79109623, rs79135870, rs112560299, rs112909948, rs113495867, and rs113635866.

In particular embodiments, the invention provides for the detection of SLCO1B1 and APOE allelic variants and SNPs listed in Table 1 and Table 2, respectively. In preferred embodiments, the invention provides for the detection of the rs4149056 (corresponding to a T to C change at nucleotide position 625 of the SLCO1B1 cDNA, and a valine to alanine change at position 174 of the SLCO1B1 protein) polymorphism in the SLCO1B1 gene, and the rs429358 (corresponding to a T to C change at nucleotide position 471 of the ApoE cDNA, and an arginine to cysteine change at position 130 of the ApoE protein) and rs7412 (corresponding to a C to T change at position 609 of the ApoE cDNA, and an arginine to cysteine change at position 176 of the ApoE protein) polymorphisms in the ApoE gene. Advantageously, the methods of the invention distinguish between homozygous and heterozygous alleles of SLCO1B1 and/or ApoE.

TABLE 1

SLCO1B1 Polymorphisms That Alter Amino Acid Identity

| Polymorphism ID | Position on Chromosome 19 | SEQ ID NO. | Sequence | Polymorphism: N in Sequence | Amino Acid Change |
|---|---|---|---|---|---|
| rs2291075 | 21331625(+) | 1 | GATTTNGCTAA | C/T | F |
| rs2306282 | 21329802(−) | 2 | CTCTANTGAGT | T/C | N/S |
| rs2306283 | 21329738(−) | 3 | TGAATNGATAT4N | C/T | D |
| rs4149056 | 21331549(+) | 4 | ATATGNGTTCA | T/C | V to A |
| rs4149057 | 21331599(+) | 5 | TACCANTGGGG | T/C | L |
| rs4603354 | 21331636(+) | 6 | AGAAGNACATT | A/G | E, G |
| rs11045818 | 21329761(+) | 7 | ACATCNACCTT | G/A | S |
| rs11045819 | 21329813(+) | 8 | CATCANCTGAG | C/A | T, P |
| rs11045852 | 21349885(+) | 9 | GCACTNTCAGG | A/G | I, V |
| rs11045853 | 21349910(+) | 10 | TTCTCNATGGG | G/A | Q, R |
| rs11045854 | 21350034(+) | 11 | TCACTNTCTTT | G/A | L |
| rs11045859 | 21355537(+) | 12 | GCTGTNATGTC | G/A | V |
| rs11557087 | 21294536(+) | 13 | ATAAANCAGCA | A/G | T, A |
| rs34671512 | 21391976(+) | 14 | ATATTNATTTA | A/C | L, F |
| rs55737008 | 21392047(+) | 15 | GGATGNAGCAA | A/G | E, G |
| rs55901008 | 21353529(+) | 16 | CTATANTGGTG | C/T | T, I |
| rs56061388 | 21327529(+) | 17 | GATTGNATTTG | C/T | A, V |
| rs56101265 | 21325716(+) | 18 | GAAGCNTTGAA | C/T | L, F |
| rs56199088 | 21392011(+) | 19 | GAAAGNTATCA | A/T | D, V |
| rs56387224 | 21355583(+) | 20 | GTGAANACAAA | A/T | N, Y |
| rs57040246 | 21353557(+) | 21 | AAATANGTAGA | C/T | Y |
| rs59113707 | 21355489(+) | 22 | AAATTNAAACT | C/G | F, L |
| rs59502379 | 21358933(+) | 23 | AGCAGNTTGCA | G/C | A/G |
| rs61176925 | 21355561(+) | 24 | CTATTNTATTT | A/C | L, F |
| rs61760183 | 21325669(+) | 25 | CTGGGNTAAAT | A/G | Q, R |
| rs61760245 | 21353483(+) | 26 | AGGGANGGGAA | A/G | I, V, Y |

TABLE 1-continued

SLCO1B1 Polymorphisms That Alter Amino Acid Identity

| Polymorphism ID | Position on Chromosome 19 | SEQ ID NO. | Sequence | Polymorphism: N in Sequence | Amino Acid Change |
|---|---|---|---|---|---|
| rs71581941 | 21375289(+) | 27 | TTATANGAGCA | C/T | RX |
| rs71581978 | 21327539(+) | 28 | GTGAGNTACTT | C/T | S |
| rs71581987 | 21370128(+) | 29 | AATGCNCAAGA | C/T | P, S |
| rs71581988 | 21370177(+) | 30 | AATACNAGTCT | A/T | Q, L |
| rs72559742 | 21349993(+) | 31 | TGCCGNAAAAT | -/A | K, Q |
| rs72559745 | 21329817(+) | 32 | ACCTGNGATAG | A/G | E, G |
| rs72559746 | 21331606(+) | 33 | GGGGCNTTCTT | G/T | R, L |
| rs72559747 | 21353478(+) | 34 | TAATCNCCTGT | C/G | P, R |
| rs72559748 | 21358855(+) | 35 | CTCAGNCTGCA | A/G | D, G |
| rs72661137 | 21370183(+) | 36 | AGTCTNGAATT | G/T | W, L |
| rs74064211 | 21358922(+) | 37 | TCACCNTGTCT | C/T | P |
| rs74064213 | 21358965(+) | 38 | AGCCTNTAGTG | A/G | I, V |
| rs74700754 | 21375275(+) | 39 | TTTCCNCTCAA | A/T | H, L |
| rs77468276 | 21355535(+) | 40 | CTGCTNTGATG | G/C | L, V |
| rs77871475 | 21353471(+) | 41 | TCCTTNCTAAT | A/T | T, S |
| rs79109623 | 21353505(+) | 42 | TTTGANGTTGT | C/T | T, M |
| rs79135870 | 21331891(+) | 43 | CAATCNTTGGC | A/G | I, V |
| rs112560299 | 21391957(+) | 44 | ATCACNTGTTT | A/T | H, L |
| rs112909948 | 21370119(+) | 45 | ATTTGNGTGAA | A/G | S, G |
| rs113495867 | 21353483(+) | 46 | CCTGTNTATGTT | —/G | Y, V |
| rs113635866 | 21294538(+) | 47 | AAAACNGCAGA | A/G | T |

TABLE 2

Polymorphisms That Alter Amino Acid Identity

| SNP ID | CHROMOSOME 19 POSITION | SEQ ID NO. | SEQUENCE | Polymorphism: N in Sequence | Amino Acid Change |
|---|---|---|---|---|---|
| rs7412 (E2) | 45412079(+) | 48 | AGAAGNGCCTG | C/T | R to C |
| rs429358 (E4) | 45411941(+) | 49 | ACGTGNGCGGC | T/C | R to C |
| rs769452 | 45411110(+) | 50 | GGAACNGGCAC | T/C | P to L |
| rs769455 | 45412040(+) | 51 | AGCTGNGTAAG | C/T | R to C |
| rs11542029 | 45411121(+) | 52 | TGGGTNGCTTT | C/T | R to C |
| rs11542031 | 45411123(+) | 53 | GGTCGNTTTTG | C/T | R |
| rs11542038 | 45411153(+) | 54 | CAGACNCTGTC | A/G | T |
| rs28931576 | 45411151(+) | 55 | TGCAGNCACTG | A/G | T to A |
| rs28931578 | 45412008(+) | 56 | GCTGCNGGTGC | A/G | Q to R |
| rs28931579 | 45412493(+) | 57 | TGCCCNGCGAC | A/C | S to R |

TABLE 2-continued

Polymorphisms That Alter Amino Acid Identity

| SNP ID | CHROMOSOME 19 POSITION | SEQ ID NO. | SEQUENCE | Polymorphism: N in Sequence | Amino Acid Change |
|---|---|---|---|---|---|
| rs111833428 | 45411042(+) | 58 | CAAGCNGTGGA | A/G | A |
| rs121918392 | 45411034(+) | 59 | AGGTGNAGCAA | A/G | K to E |
| rs121918393 | 45412013(+) | 60 | GGGTGNGCCTC | A/C | S to R |
| rs121918394 | 45412043(+) | 61 | TGCGTNAGCGG | A/C/G | K to Q |
| rs121918395 | 45412289(+) | 62 | GCGACNGCCTG | C/T | R to C |
| rs121918396 | 45412236(+) | 63 | GGCCTNGGGCG | A/G | X to W |
| rs121918397 | 45412041(+) | 64 | GCTGCNTAAGC | A/C/G | H to R |
| rs121918398 | 45412428(+) | 65 | GCAGCNCCAGT | A/G | H to R |
| rs121918399 | 45411100(+) | 66 | GCCAGNGCTGG | C/T | H to R |
| rs7412 | 45412079(+) | 67 | AGAAGNGCCTG | C/T | R to C |

Types of Biological Samples

The genotyping methods of the invention involve detecting or determining a genetic variant or biomarker of interest in a biological sample. In one embodiment, the biologic sample contains a cell having diploid DNA content. Human cells containing 46 chromosomes (e.g., human somatic cells) are diploid. In one embodiment, the biologic sample is a tissue sample that includes diploid cells of a tissue (epithelial cells) or organ (e.g., skin cells). Such tissue is obtained, for example, from a cheek swab or biopsy of a tissue or organ. In another embodiment, the biologic sample is a biologic fluid sample. Biological fluid samples containing diploid cells include saliva, blood, blood serum, plasma, urine, hair follicle, or any other biological fluid useful in the methods of the invention.

Genotyping of SLCO1B1 and APOE Polymorphisms

A SLCO1B1 and/or ApoE isoform is amplified by long range PCR to determine the genotype of the polymorphism, e.g., the rs4149056 (corresponding to a T to C change at nucleotide position 625 of the SLCO1B1 cDNA, and a valine to alanine change at position 174 of the SLCO1B1 protein) polymorphism in the SLCO1B1 gene, and the rs429358 (corresponding to a T to C change at nucleotide position 471 of the ApoE cDNA, and an arginine to cysteine change at position 130 of the ApoE protein) and rs7412 (corresponding to a C to T change at position 609 of the ApoE cDNA, and an arginine to cysteine change at position 176 of the ApoE protein) polymorphisms in the ApoE gene. The amplified nucleic acid corresponding to the SLCO1B1 and/or ApoE polymorphism may be analyzed using a variety of methods for detecting variant alleles to determine the genotype. For example, the presence or absence of one or more of the rs4149056 (corresponding to a T to C change at nucleotide position 625 of the SLCO1B1 cDNA, and a valine to alanine change at position 174 of the SLCO1B1 protein) polymorphism in the SLCO1B1 gene, and the rs429358 (corresponding to a T to C change at nucleotide position 471 of the ApoE cDNA, and an arginine to cysteine change at position 130 of the ApoE protein) and rs7412 (corresponding to a C to T change at position 609 of the ApoE cDNA, and an arginine to cysteine change at position 176 of the ApoE protein) polymorphisms in the ApoE gene may be evaluated using various techniques. For example, the SLCO1B1 gene is amplified by long range PCR and sequenced to determine the presence or absence of a single nucleotide polymorphism (SNP). In certain embodiments, real-time PCR may be used to detect a single nucleotide polymorphism of the amplified products. In other embodiments, a polymorphism in the amplified products may be detected using a technique including hybridization with a probe specific for a single nucleotide polymorphism, restriction endonuclease digestion, primer extension, microarray or gene chip analysis, mass spectrometry, or a DNAse protection assay.

Long Range Polymerase Chain Reaction (PCR)

Polymerase chain reaction (PCR) is widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

Exemplary methods for performing long range PCR are disclosed, for example, in U.S. Pat. No. 5,436,149; Barnes, Proc. Natl. Acad. Sci. USA 91:2216-2220 (1994); Tellier et al., Methods in Molecular Biology, Vol. 226, PCR Protocols, 2nd Edition, pp. 173-177; and, Cheng et al., Proc. Natl. Acad. Sci. 91:5695-5699 (1994); the contents of which are incorporated herein by reference. In various embodiments, long range PCR involves one DNA polymerase. In some embodiments, long range PCR may involve more than one DNA polymerase. When using a combination of polymerases in long range PCR, it is preferable to include one polymerase having 3'→5' exonuclease activity, which assures high fidelity generation of the PCR product from the DNA template. Typically, a non-proofreading polymerase, which is the main polymerase is also used in conjunction with the proofreading polymerase in long range PCR reactions. Long range PCR can also be performed using commercially available kits, such as LA PCR kit available from Takara Bio Inc. Polymerase enzymes having 3'→5' exonuclease proofreading activity are known to those in the art. Examples of suitable proofreading enzymes include TaKaRa LA Taq (Takara Shuzo Co., Ltd.) and Pfu (Stratagene), Vent, Deep Vent (New England Biolabs).

Sequencing

DNA sequencing may be used to evaluate a polymorphism of the present invention. One DNA sequencing method is the Sanger method, which is also referred to as dideoxy sequencing or chain termination. The Sanger method is based on the use of dideoxynucleotides (ddNTP's) in addition to the normal nucleotides (NTP's) found in DNA.

Pyrosequencing is another method of DNA sequencing that may be used to evaluate a polymorphism of the present invention, for example as described in U.S. Pat. Publ. No. 2006008824; herein incorporated by reference). Pyrosequencing, which is also referred to as sequencing by synthesis, involves taking a single strand of the DNA to be sequenced, synthesizing its complementary strand enzymatically one base pair at a time, and detecting by chemiluminescence the base that is added.

Pyrosequencing, optionally coupled with amplification of the nucleic acid target, can sequence large numbers of target molecules, usually employing automated sequencing apparati, including long sequences (e.g., 400 million bp/10 hr in a single run). Sequencing methods are well known to those of skill in the art.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

Real-Time PCR (rtPCR)

The presence or absence of polymorphisms in SLCO1B1 and/or ApoE isoforms may be detected using real-time PCR. Real-time PCR typically utilizes fluorescent probes for the selective detection of the polymorphisms. Various real-time PCR testing platforms that may be used with the present invention include: 5' nuclease (TaqMan® probes), molecular beacons, and FRET hybridization probes. These detection methods rely on the transfer of light energy between two adjacent dye molecules, a process referred to as fluorescence resonance energy transfer (see, e.g., Espy et al (2006) Clin Microbiol Rev. 2006 January; 19(1): 165-256 for a review of various rtPCR approaches that may be used with the present invention).

5' Nuclease Probes

In certain embodiments, a 5' nuclease probe may be used to detect a polymorphism of the present invention. 5' nuclease probes are often referred to by the proprietary name, TaqMan® probes. A TaqMan® probe is a short oligonucleotide (DNA) that contains a 5' fluorescent dye and 3' quenching dye. Molecular beacons and FRET hybridization probes typically involve the measurement of fluorescence during the hybridization step.

Genotyping for the 12754T>del ("Asp260fs") or Gly143Glu (428G>A, "Gly143Glu") in the carboxylesterase-1 gene may be evaluated using the following (5' endonuclease probe) real-time PCR technique. Genotyping assays can be performed in duplicate and analyzed on a Bio-Rad iCycler Iq® Multicolor Real-time detection system (Bio-Rad Laboratories, Hercules, Calif.). Real-time polymerase chain reaction (PCR) allelic discrimination assays to detect the presence or absence of specific single nucleotide polymorphisms in the SLCO1B1 and/or ApoE gene, may utilize fluorogenic TaqMan® Probes.

Real-time PCR amplifications may be carried out in a 10 μl reaction mix containing 5 ng genomic DNA, 900 Nm of each primer, 200 Nm of each probe and 5 μl of 2× TaqMan® Universal PCR Master Mix (contains PCR buffer, passive reference dye ROX, deoxynucleotides, uridine, uracil-N-glycosylase and AmpliTaq Gold DNA polymerase; Perkin-Elmer, Applied Biosystems, Foster City, Calif.). Cycle parameters may be: 95° C. for 10 min, followed by 50 cycles of 92° C. for 15 sec and 60° C. for 1 min. Real-time fluorescence detection can be performed during the 60° C. annealing/extension step of each cycle. The IQ software may be used to plot and automatically call genotypes based on a two parameter plot using fluorescence intensities of FAM and VIC at 49 cycles.

FRET Hybridization Probes

FRET hybridization probes, also referred to as LightCycler® probes, may also be used to detect a polymorphism of the present invention. FRET hybridization probe technology permits melting curve analysis of the amplification product. Like molecular beacons, FRET hybridization probes have the advantage of being recycled or conserved during PCR temperature cycling, and a fluorescent signal does not accumulate as PCR product accumulates after each PCR cycle.

Primer Extension

Primer extension is another technique which may be used according to the present invention. A primer and no more than three NTPs may be combined with a polymerase and the target sequence, which serves as a template for amplification. By using less than all four NTPs, it is possible to omit one or more of the polymorphic nucleotides needed for incorporation at the polymorphic site. It is important for the practice of the present invention that the amplification be designed such that the omitted nucleotide(s) is(are) not required between the 3' end of the primer and the target polymorphism. The primer is then extended by a nucleic acid polymerase, in a preferred embodiment by Taq polymerase. If the omitted NTP is required at the polymorphic site, the primer is extended up to the polymorphic site, at which point the polymerization ceases. However, if the omitted NTP is not required at the polymorphic site, the primer will be extended beyond the polymorphic site, creating a longer product. Detection of the extension products is based on, for example, separation by size/length which will thereby reveal which polymorphism is present. For example, U.S. Ser. No. 10/407,846, which is which is hereby incorporated by reference, describes a form of primer extension.

RFLP

Restriction Fragment Length Polymorphism (RFLP) is a technique in which different DNA sequences may be differentiated by analysis of patterns derived from cleavage of that DNA. If two sequences differ in the distance between sites of cleavage of a particular restriction endonuclease, the length of the fragments produced will differ when the DNA is digested with a restriction enzyme. The similarity of the patterns generated can be used to differentiate species (and even strains) from one another.

Restriction endonucleases in turn are the enzymes that cleave DNA molecules at specific nucleotide sequences depending on the particular enzyme used. Enzyme recognition sites are usually 4 to 6 base pairs in length. Generally, the shorter the recognition sequence, the greater the number of fragments generated. If molecules differ in nucleotide sequence, fragments of different sizes may be generated. The fragments can be separated by gel electrophoresis. Restriction enzymes are isolated from a wide variety of bacterial genera and are thought to be part of the cell's defenses against invading bacterial viruses. Use of RFLP and restriction endonucleases in SNP analysis requires that the SNP affect cleavage of at least one restriction enzyme site.

Mass Spectrometry

Mass spectrometry may also be used to detect a polymorphism of the present invention. By exploiting the intrinsic properties of mass and charge, mass spectrometry (MS) can resolved and confidently identified a wide variety of complex compounds. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). Methods of mass spectroscopy that may be used with the present invention include: ESI, ESI tandem mass spectroscopy (ESI/MS/MS), Secondary ion mass spectroscopy (SIMS), Laser desorption mass spectroscopy (LD-MS), Laser Desorption Laser Photoionization Mass Spectroscopy (LDLPMS), and MALDI-TOF-MS.

Hybridization

There are a variety of ways by which one can assess genetic profiles, and may of these rely on nucleic acid hybridization. Typically, a probe or primer of between 13 and 100 nucleotides, preferably between 17 and 100 nucleotides in length up to 1-2 kilobases or more in length will allow the formation of a duplex molecule that is both stable and selective. For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Pharmacogenetics: Consequence for Drug Therapy

SLCO1B1 is important for the uptake and metabolism of many known compounds in humans and non-human animals such as, for example, bilirubin, 17-beta-glucuronosyl estradiol and leukotriene C4, statins, bromosulfophthalein and rifampin. Thus, the presence or absence of one or more polymorphisms of the present invention may be used to "individualize" or modify a therapy for a subject or patient based on the sensitivity of the subject to a therapeutic due to the presence or absence of a polymorphism of the present invention.

A number of SLCO1B1 genetic variants alter the coding sequence of the SLCO1B1 protein, including rs4149056, rs61176925, rs61760183, rs61760245, rs71581941, rs71581978, rs71581987, rs71581988, rs72559742, rs72559745, rs72559746, rs72559747, rs72559748, rs72661137, rs74064211, rs74064213, rs74700754, rs77468276, rs77871475, rs79109623, rs79135870, rs112560299, rs112909948, rs113495867, and rs113635866 (see, e.g., Table 1). The SLCO1B1 gene polymorphism rs4149056 (nt 625 T to C) results in Valine at position 174 being replace with Alanine) is termed the SLCO1B1-056 mutation. It is further contemplated within the scope of the invention that any genetic polymorphism that encodes a V174A mutation is equivalent to rs4149056. This genetic variant, especially in the homozygous state, markedly impairs the catabolism of statins, resulting in significantly higher statin blood level relative to statin blood level in an individual after administration an oral dose of statin. High statin blood levels also result in reduced efficacy in suppressing endogenous cholesterol synthesis and LDL-C lowering, and an estimated 50% chance of developing significant adverse effects especially myopathy on statin therapy in homozygotes. The 625T>C SNP due to the rs4149056 allele at SLCO1B1 resulting in the replacement of valine by alanine at residue 174 in the amino acid sequence of the SLCO1B1 protein results in significantly less Pravastatin induced LDL-C lowering in a large elderly population with either established vascular risk or at risk of vascular disease.

In certain embodiments, evaluating the presence or absence of a polymorphism of the present invention may be used to individualize a therapy and/or determine the sensitivity of a subject to a compound. The compound may be a prodrug, an illicit drug, an opioid, a dopaminergic or noradrenergic drug, an ACE Inhibitor, or an HMG-CoA reductase inhibitor or "statin".

Kits

The invention also provides kits for genotyping any one or more of a SLCO1B1 and/or ApoE polymorphism. Such kits are useful for the diagnosis of a sequence alteration in SLCO1B1 and/or ApoE relative to wild-type SLCO1B1 and/or ApoE sequences in a biological sample obtained from a subject. Alternatively, the invention provides for selecting a drug treatment regimen for CHD, or adjusting a dosage of a CHD specific therapeutic, such as, for example, a statin. In various embodiments, the kit includes at least one primer pair that identifies a SLCO1B1 polymorphism and at least one primer pair that identifies a ApoE polymorphism (e.g., the rs4149056 (nt 625 T to C; aa 174 V to A) polymorphism in the SLCO1B1 gene, and the rs429358 (nt 130 T to C; aa 130 R to C) and rs7412 (nt 176 C to T; aa 176 R to C) polymorphisms in the ApoE gene), together with instructions for using the primers to genotype in a biological sample. In additional embodiments, the kit also includes instructions for selecting an appropriate therapy for a subject, monitoring drug therapy in a subject, identifying a subject as responsive to drug therapy, or identifying a subject as sensitive to a drug. Advantageously, such testing is carried out prior to drug administration or after an adverse event associated with drug administration. Preferably, the primers are provided in combination with a thermostable DNA polymerase capable of long-range PCR amplification (e.g., a high density array). In yet another embodiment, the kit further comprises a pair of primers capable of binding to and amplifying a reference sequence. The reference sequences serves as a basis for sequence comparison. By "single nucleotide polymorphism" or "SNP" is meant a DNA sequence variation occurring when a single nucleotide in the genome differs between members of a biological species or paired chromosomes in an individual. SNPs are used as genetic markers for variant alleles.

In various other embodiments, the kit includes reagents or components for genotyping SLCO1B1 and ApoE in combination with reagents or components for the detection of a single nucleotide polymorphism (SNP) or variant of a gene encoding an additional enzyme involved in drug. The kits which contain reagents and components for determining a SLCO1B1 and/or ApoE genotype and for detecting variants in additional enzyme and/or transporters involved in drug metabolism, are useful for guiding disease specific pharmacotherapies. For example, in the treatment of CHD, one or more drugs, including Angiotensin converting enzyme (ACE) inhibitors including Capoten® (captopril), Vasotec® (enalapril), Prinivil®, Zestril® (lisinopril), Lotensin® (benazepril), Monopril® (fosinopril), Altace® (ramipril), Accupril® (quinapril), Aceon® (perindopril), Mavik® (trandolapril), and Univasc® (moexipril)); Angiotensin II receptor blockers (ARBs) including Cozaar® (losartan), Diovan® (valsartan), Avapro® (irbesartan), Atacand® (candesartan), and Micardis® (telmisartan); Antiarrhythmia drugs including Tambocor® (flecainide), Procanbid® (procainamide), Cordarone® (amiodarone), and Betapace® (sotalol); Antiplatelet drugs; Beta Blockers including Sectral® (acebutolol), Zebeta® (bisoprolol), Brevibloc® (esmolol), Inderal® (propranolol), Tenormin® (atenolol), Normodyne®, Trandate® (labetalol), Coreg® (carvedilol), Lopressor®, and Toprol-XL® (metoprolol); and Calcium Channel Blockers including Norvasc® (amlodipine), Plendil® (felodipine), Cardizem®, Cardizem CD®, Cardizem SR®, Dilacor XR®, Diltia XT®, Tiazac® (diltiazem), Calan®, Calan SR®, Covera-HS®, Isoptin®, Isoptin SR®, Verelan®, Verelan PM® (verapamil), Adalat®, Adalat CC®, Procardia®, Procardia XL® (nifedipine), Cardene®, Cardene SR® (nicardipine), Sular® (nisoldipine), Vascor® (bepridil); aspirin; digoxin; diuretic drugs; Heart Failure Drugs including Dobutrex® (dobutamine) and Primacor® (milrinone); Vasodialators such as Dilatrate-SR®, Iso-Bid®, Isonate®, Isorbid®, Isordil®, Isotrate®, Sorbitrate® (isosorbide dinitrate), IMDUR® (isorbide mononitrate), Apresoline® (hydralazine), and BiDil® (hydralazine with isosorbide dinitrate); warfarin; and surgery. In one preferred embodiment, an agent of the invention is administered in combination with a statin, such as Advicor® (niacin extended-release/lovastatin), Altoprev® (lovastatin extended-release), Caduet® (amlodipine and atorvastatin), Crestor® (rosuvastatin), Lescol® (fluvastatin), Lescol XL (fluvastatin extended-release), Lipitor® (atorvastatin), Livalo® (pitavastatin), Mevacor® (lovastatin), Pravachol® (pravastatin), Simcor® (niacin extended-release/simvastatin), Vytorin® (ezetimibe/simvastatin), and Zocor® (simvastatin) may be prescribed depending on their predicted efficacy in a patient. The patient is evaluated for SLCO1B1 and ApoE genotype and/or expression or catalytic activity to predict the responsiveness of the patient to an CHD-specific therapeutic whose metabolism is affected by SLCO1B1 and ApoE genotype. Such kits may contain one or more genomic tests of enzymes or drug transporters documented to have important SNPs. SNPs may be evaluated using a disease targeted panel of tests (e.g., a microarray). Such panels include commercially available microarrays for detecting one or more SNPs (e.g., AmpliChip® CYP450 Test; Roche). In other embodiments, the kit includes instructions for selecting one or more treatments based on the results of genotyping SLCO1B1 and ApoE and detecting one or more genetic variants in an enzyme involved in drug metabolism or drug transporter. Thus, testing performed on a patient using the kits of the invention may guide treatment selection specifically tailored to the individual.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Determination of Sample Population Baselines for Key Risk Factors

As summarized in Table 3, the participating subjects were elderly, with a median age of 75±3 years at baseline. Mean LDL-C levels were in the moderate-risk category (130-160 mg/dl), as defined by the United States National Cholesterol Education Program (Expert Panel. Executive Summary of The Third Report of The National Cholesterol Education Program (NCEP) Expert Panel on Detection, Evaluation, And Treatment of High Blood Cholesterol In Adults (Adult Treatment Panel III). JAMA 2001; 285:2486-97). Also, approximately 50% of the men and about one third of the women reported a history of all types of vascular disease. Data on ApoE phenotype distribution in this population are also shown in Table 3. Genotype frequencies for all SNPs examined conformed to Hardy-Weinberg equilibrium (p>0.05, data not shown).

TABLE 3

| Study Subjects (n = 5,418) | | |
|---|---|---|
| Study Characteristics Mean (SD)a | Men (n = 2,621) | Women (n = 2,797) |
| Age (years) | 74.99 (3.3) | 75.64 (3.4)b |
| BMI (kg/m2) | 26.56 (3.6) | 27.12 (4.7)b |
| History diabetes mellitus, n (%) | 324 (12.4) | 251 (9.0)b |
| History hypertension, n (%) | 1333 (50.9) | 2026 (72.5)b |
| History vascular disease, n (%) | 1371 (52.3) | 1033 (37.0)b |
| History of MI, n (%) | 508 (19.4) | 222 (7.9)b |
| Current smoking, n (%) | 847 (32.3) | 586 (21.0)b |
| Alcohol consumption, n (%) | 1851 (70.6) | 1165 (41.7)b |
| Total cholesterol (mg/dl) | 207.0 (30.7) | 231.9 (34.5)b |
| LDL-cholesterol (mg/dl) | 138.5 (27.8) | 154.9 (35.3)b |
| HDL-cholesterol (mg/dl) | 45.6 (12.2) | 53.0 (13.4)b |
| Triglyceride (mg/dl) | 132.4 (64.3) | 140.6 (59.4)b |
| apoA-I (mg/dl) | 124.4 (22.2) | 139.9 (24.1)b |
| apoB (mg/dl) | 110.6 (21.3) | 119.1 (22.6)b |
| apoE 2/2 + 2/3 (%) | 13.1 | 11.3 |
| apoE 3/3 (%) | 63.1 | 65.7 |
| apoE 3/4 + 4/4 (%) | 23.8 | 23.0 |
| SLCO1B1_625T > C-rs4149056 | MAF C:0.16 | |
| SLCO1B1_388A > G-rs2306283 | MAF G:0.38 | |
| LXRA_-115G > A-rs12221497 | MAF A:0.14 | |

BMI: body mass index. MAF: minor allele frequency.

aMeans (S.D.) unless otherwise specified; differences between men and women were assessed using a t-test for continuous traits and $\chi^2$ test for binary traits.

bp < 0.001, apoE 2/4 carriers were excluded (see Materials and Methods section)

a) Sample Population Baseline TC or LDL-C Levels Are Not Genotype Dependent

Genetic analysis of the sample population revealed no association of baseline TC or LDL-C levels with any SLCO1B1 or LXRA genotype as stratified by gender (see Table 4).

TABLE 4

| Adjusted Baseline Lipid Levels (mean ± SD, mg/dl) by Gender and Genotype | | | | | | | | | | |
|---|---|---|---|---|---|---|---|---|---|---|
| | | | n | TC | LDL-C | | | | | |
| Gene | SNP | Genotype | Men | Women | Men | Women | p[a] | Men | Women | p[a] |
| SLCO1B1 | 625T > C | TT | 1871 | 1997 | 207.2 ± 30.9 | 232.3 ± 34.8 | 0.880 | 138.6 ± 28.0 | 155.2 ± 31.8 | 0.850 |
| | | TC | 674 | 721 | 207.2 ± 30.3 | 231.7 ± 33.4 | | 138.8 ± 27.6 | 154.6 ± 30.3 | |
| | | CC | 73 | 75 | 207.1 ± 29.1 | 232.1 ± 37.6 | | 139.7 ± 26.5 | 153.9 ± 30.7 | |
| SLCO1B1 | 388A > G | AA | 1010 | 1125 | 208.3 ± 29.5 | 232.7 ± 33.9 | 0.161 | 139.3 ± 27.9 | 155.1 ± 31.0 | 0.330 |
| | | AG | 674 | 1280 | 206.6 ± 30.9 | 231.3 ± 34.8 | | 138.2 ± 27.9 | 154.6 ± 31.5 | |
| | | GG | 395 | 388 | 206.4 ± 29.9 | 232.5 ± 35.6 | | 138.3 ± 27.2 | 155.6 ± 32.6 | |
| LXRA | 115$\overline{G}$ > A | GG | 1924 | 2076 | 206.8 ± 30.6 | 232.6 ± 34.9 | 0.936 | 138.2 ± 27.9 | 155.3 ± 32.0 | 0.729 |
| | | GA | 647 | 661 | 208.5 ± 31.0 | 230.5 ± 33.8 | | 140.1 ± 27.9 | 154.3 ± 30.2 | |
| | | AA | 46 | 53 | 206.8 ± 28.3 | 231.6 ± 29.9 | | 135.9 ± 24.7 | 155.3 ± 26.5 | |

[a]p values using the three genotypes, men and women combined; adjusted for gender, body mass index, age, alcohol, smoking, diabetes, ApoE phenotype, and country.

b) SLCO1B1 SNP is Associated with Lowered LDL-C Response to Pravastatin

The effect of SNPs at nucleotide positions 388 (e.g. A>G) and 625 (e.g. T>C) of the SLCO1B1 gene and also at nucleotide position −115 (e.g. G>A) of the LXRA gene on responsiveness to Pravastatin in subjects of various genotypes was assessed by analyzing the correlation of different SNP genotypes with the 6 month and 12 month changes in TC and LDL-C levels in treated subjects, as shown below in Table 5. Neither the presence of the LXRA SNP at nucleotide position −115 nor the SLCO1B1 SNP at nucleotide position 388 were associated with lipid lowering. However, subjects carrying the SLCO1B1 SNP at nucleotide position 625 (e.g. T>C) had significantly less LDL-C lowering in response to Pravastatin. For example, subjects who were wildtype (T/T) for the SNP at position 625 represented about 71.5% of the sample population and displayed −37.0% LDL-C lowering, subjects who where heterozygous (T/C) for the SNP at position 625 represented about 25.8% of the sample population and showed −36.0% LDL-C lowering, and subjects who were homozygous (C/C) for the SNP at position 625 represented about 2.7% of the population and showed −31.8% LDL-C lowering (p=0.003 at 6 months, and p=0.022 at 12 months). The percentage reductions in LDL-C given are for the 6 month time point (Table 5).

TABLE 5

| Percent LDL-C Response to Pravastatin by Genotype | | | | | | | |
|---|---|---|---|---|---|---|---|
| | | Adjusted mean percent LDL-cholesterol reduction[a] | | | | | |
| Gene | SNP | n | 6 months | p[b] | n | 12 months | p[b] |
| SLCO1B1 | 625T > C | | | | | | |
| | TT | 1345 | −37.0 ± 10.8 | | 1331 | −35.9 ± 11.8 | |
| | TC | 509 | −36.0 ± 10.4 | 0.003 | 504 | −34.6 ± 12.5 | 0.022 |
| | CC | 47 | −31.8 ± 12.8 | | 45 | −31.8 ± 11.7 | |
| SLCO1B1 | 388A > G | | | | | | |
| | AA | 772 | −36.7 ± 10.5 | | 758 | −35.9 ± 11.2 | |
| | AG | 859 | −36.6 ± 10.7 | 0.775 | 861 | −35.3 ± 12.3 | 0.157 |
| | GG | 269 | −36.2 ± 11.6 | | 260 | −34.3 ± 12.8 | |
| LXRA | 115$\overline{G}$ > A | | | | | | |
| | GG | 1412 | −36.6 ± 10.7 | | 1403 | −35.5 ± 12.1 | |
| | GA | 463 | −36.4 ± 10.7 | 0.822 | 150 | −35.1 ± 11.6 | 0.871 |
| | AA | 27 | −37.4 ± 10.9 | | 29 | −35.3 ± 11.2 | |

[a]Values are provided as mean ± S.D,

[b]p values for data combining men and women, adjusted for gender, body mass index, age, alcohol, smoking, diabetes, ApoE phenotype, and country.

c) SLCO1B1/LXRA SNPs Are Not Associated with History and Incidence of CVD

Genetic analysis of the sample population revealed no association of any of the SLCO1B1 or LXRA SNPs with either vascular disease at baseline or fatal or non-fatal CHD events on trial in either the placebo or statin groups (see, e.g., Table 6).

TABLE 6

Analysis of Incidence of Coronary Heart Disease (CHD) Death or Nonfatal Myocardial Infarction (MI) on Trial by SNP Carrier Status

| SNP | Genotype | Number of new case/ Total subjects (%) | Adjusted[a] HR[c] | p | Number of new case/ Total subjects (%) | Placebo[b] HR[c] | p | Number of new case/ Total subjects (%) | Pravastatin[b] HR[c] | p |
|---|---|---|---|---|---|---|---|---|---|---|
| 625T > C | TT | 427/3868 (11.0) | 1 | | 232/1956 (11.9) | 1 | | 195/1912 (10.2) | 1 | |
| | TC | 155/1395 (11.1) | 1.01 (0.84-1.21) | 0.996 | 83/693 (12.0) | 1.03 (0.80-1.33) | 0.738 | 72/702 (10.3) | 0.99 (0.76-1.30) | 0.659 |
| | CC | 16/148 (10.6) | 0.99 (0.60-1.64) | | 12/81 (14.8) | 1.24 (0.69-2.22) | | 4/67 (6.0) | 0.64 (0.24-1.73) | |
| 388A > G | AA | 224/2135 (10.5) | 1 | | 122/1051 (11.6) | 1 | | 102/1084 (9.4) | 1 | |
| | AG | 279/2489 (11.2) | 1.08 (0.90-1.29) | 0.426 | 150/1275 (11.8) | 1.04 (0.82-1.32) | 0.577 | 129/1214 (10.6) | 1.13 (1.87-1.47) | 0.629 |
| | GG | 94/783 (12.0) | 1.17 (0.92-1.49) | | 54/404 (11.4) | 1.17 (0.85-1.61) | | 40/379 (10.6) | 1.12 (0.78-1.62) | |

[a]p values for men and women combined; adjusted for gender, body mass index, age, alcohol, smoking, diabetes, hypertension, ApoE phenotype, randomized treatment, and country. No significant differences were noted when men and women were separated.

[b]p values for men and women combined; adjusted for gender, body mass index, age, alcohol, smoking, diabetes, hypertension, ApoE phenotype, and country. No significant differences were noted when men and women were separated.

[c]Hazards ratio (95% confidence intervals).

The SNPs 625T>C and 388A>G are within SLCO1B1 d) SLCO1B1 SNP is not Associated with Myositis and/or Myalgia

In this randomized study with 5,804 subjects, 2,913 subjects received placebo and 2,891 received Pravastatin (three of whom refused medication). Of the 2,888 subjects started on Pravastatin, 724 discontinued their medication (5 withdrew consent, 219 died, 346 refused to participate or did not attend follow up examinations, and 107 had non-fatal adverse events). This adverse event rate was very similar to the placebo group where 116 subjects discontinued medication because of non-fatal adverse events. There were no reported cases of rhabdomyolysis in PROSPER, and there were 36 reported cases of myalgia in the Pravastatin group versus 32 cases of myalgia in the placebo group. At the 3 month visit there no subjects that had creatine kinase levels>10 the upper limits of normal. There was no association of the SLCO1B1 rs4149056 SNP with myalgia in the Pravastatin group.

Example 2

Assessing Statin Dosage Using Combined SLCO1B1 and ApoE Genotyping

Elevated levels of plasma or serum low density lipoprotein (LDL) cholesterol are a major risk factor for coronary heart heard disease, a leading cause of death and disability in our society (1,2). Lowering LDL cholesterol with statin drugs has clearly been shown to inhibit cholesterol biosynthesis, and decrease the risk of CHD. Moreover the degree of risk reduction is dependent on the amount of LDL cholesterol lowering. Four factors that are clearly and significantly related to LDL cholesterol lowering response to statins were identified:

1) the plasma level of LDL cholesterol, 2) the ratio of lathosterol/cholesterol in plasma, 3) apolipoprotein (apo) E genotype, and 4) solute carrier organic anion transporter (SLCO1B1 rs4149056) genotype.

According to the invention, a novel point system was developed to predict statin induced LDL cholesterol lowering response, as shown below. This model provides an excellent fit (p<0.0001) to actual data with regard to LDL cholesterol lowering generated on over 3,000 subjects studied at baseline and then placed on pravastatin 40 mg/day for 6 months. Moreover this model predicts more than 75% of the marked variability in statin response that is observed. Those with +4 to +8 points are hyper-responders to statins, and are ideal candidate for statin treatment. Those with −4 to +4 points are normal responders and are candidates for statin therapy. Those with −8 to −4 points are hypo-responder to statins (emphasize dietary modification and consider use of ezetimibe and/or anion exchange resins).

| Prediction of LDL Cholesterol Lowering Point System | | |
|---|---|---|
| 1. | Plasma LDL Cholesterol (mg/dl): | |
| | >160: | +2 |
| | 100-160: | +1 |
| | <100: | 0 |
| | LDL Cholesterol Points = | — |
| 2. | Plasma Lathosterol/Cholesterol Ratio umol/mmol cholesterol: | |
| | >160: | +4 |
| | 90-160: | 0 |
| | <90: | −4 |
| | Lathosterol Points: | — |
| 3. | ApoE Genotype: | |
| | ApoE2/2: | +2 |
| | ApoE2/3: | +1 |
| | ApoE3/3: | 0 |
| | ApoE3/4: | −1 |
| | ApoE4/4: | −2 |
| | ApoE Genotype Points: | — |
| 4. | Statin Uptake Transporter (SLCO1B1) Genotype: | |
| | T/T: | 0 |
| | T/C: | −1 |
| | C/C: | −2 |
| | Statin Uptake Genotype Points: | — |
| 5. | Total Points: | |

+4 to +8 Points = Hyper-responder (ideal candidate for statins)

−3 to +3 Points = Normal Responder (candidate for statin)

−8 to −4 Points = Hypo-responder to statins (emphasize dietary modification and consider use of ezetimibe and/or anion exchange resins)

According to one embodiment, the determination of whether an individual having high LDL cholesterol and in need of statin treatment to reduce the level of LDL cholesterol is a hyper-responder, a normal-responder, or a hypo-responder with respect to the ability of the individual to metabolize a statin can be made by solving the equation X=A+B+C+D, where A is the number of points associated with the individual's plasma LDL cholesterol level, B is the number of points associated with the individual's plasma lathosterol/cholesterol ratio, C is the number of points associated with the individual's ApoE genotype, and C is the number of points associated with the individual's SLCO1B1 genotype. The resulting value of X is then used to determine the class of responder to which the individual belongs.

Methods and Materials

Study Subjects:

The results and the methodology used in the PROspective Study of Pravastatin in the Elderly at Risk (PROSPER) study have been previously described (see e.g., Shepherd J et al. PROspective Study of Pravastatin in the Elderly at Risk. Pravastatin in elderly individuals at risk of vascular disease (PROSPER): a randomized controlled trial. Lancet (2002) 360:1623-30 and Shepherd J et al. The design of a prospective study of Pravastatin in the Elderly at Risk (PROSPER). PROSPER Study Group. PROspective Study of Pravastatin in the Elderly at Risk. Am J Cardiol (1999) 84:1192-97).

In the present study 2,804 men and 3,000 women between the ages of 70 and 82 with pre-existing vascular disease (n=2,404) or at least one of three major vascular risk factors (diabetes n=575, smoking n=1,433, or hypertension n=3,360) were randomized to Pravastatin 40 mg/day (n=2,891) or placebo (n=2,913) and followed up on for 3.2 years, on average. Over this 3.2 year period of time, the mean LDL-C reduction in the active treatment group was 32%, and the risk of developing CHD was decreased by 19%, which was statistically significant (Shepherd J et al. (2002) Lancet 360:1623-30). This effect translates into an estimated 30% risk reduction in CHD events over 5 years, which is consistent with other statin trials. Additionally, analysis of the treatment group found that HDL-C was increased by 5% and triglycerides were decreased by 12% versus baseline in those subjects placed on Pravastatin. For subjects that were judged to have good compliance (i.e. taking medication more than 75% of the time), these alterations on the lipid levels were even greater: −34% (risk reduction for CHD), +5% (increased HDL-C), and −13% (decreased triglycerides), respectively. No significant lipid changes were noted in the placebo group. Lipid levels were similar at onset of the study in subjects randomized to Pravastatin or placebo.

Biochemical and DNA Analysis:

Total cholesterol (TC), HDL-C, and triglycerides were assessed in subjects after an overnight fast at 6 months, and at 12 months, and LDL-C was calculated by the Friedewald formula, as previously described (Shepherd J et al. (2002) Lancet 360:1623-30). Apolipoprotein B (apoB) was measured only at baseline as described. DNA was isolated from cells from this cohort, and DNA from 5,783 subjects participating in this study was also available. ApoE phenotype was determined on plasma samples by Western blotting, using the method of Havekes et al. in the central laboratory of the Royal Infirmary in Glasgow, Scotland (Havekes L M et al. A rapid micro method for apolipoprotein E phenotyping directly in serum. J Lipid Res (1987) 28:455-63). Subjects were classified according to the presence of apoE2, apoE3, or apoE4 bands on gel blotting (Havekes L M et al. (1987) J Lipid Res 28:455-63). This gel phenotyping method has been shown to have 99% concordance with genotyping (Lahoz C et al. Frequency of phenotype-genotype discrepancies at the apolipoprotein E locus in a large population study. Clin Chem (1996) 42:1817-23).

DNA analysis was conducted by genotyping two single nucleotide polymorphisms (SNPs) of the SLCO1B1 gene—388A>G (rs2306283) and 511T>C (rs4149056)—using standard methods (e.g. Taq Man® SNPs genotyping assays by Applied Biosystems, Foster City, Calif.). The custom assay identification numbers for these analyses were C_1901697_20 and C_30633906_10, respectively. Additionally, DNA analysis was also conducted by genotyping one SNP of the LXRA gene, rs12221497, and the custom assay identification number for this analysis was C_30887860_10. The end points were ascertained after PCR amplification was performed using standard methods (e.g. an Applied Biosystems 7900 HT Sequence Detection System). Genotypes with quality scores below the 95% threshold were repeated and 5% blinded replicates for genotype determinations were performed. In addition, a total of 119 subjects (−2.2% of the sample size) who had the apoE4/2 phenotype were excluded from these analyses, as well as 246 subjects who had missing apoE phenotype. These subjects were excluded because apoE phenotype or genotype can affect statin-induced LDL-C lowering response, as well as CHD risk, in an allele dependent manner. For example, subjects carrying the apoE4 allele having the greatest response in terms of LDL-C lowering and the highest CHD risk, however, apoE2 and apoE4 phenotype have opposite effects in this regard. The subject characteristics for these individuals representing the 5,418 subjects are shown in Table 3.

Statistical Analysis:

Observed genotype frequencies were compared with those expected under Hardy-Weinberg equilibrium using a $\chi 2$ test. For data analysis, multivariable analysis of covariance (ANCOVA) was performed to detect associations between the lipoprotein levels at baseline as well as changes in response to the treatment with Pravastatin at 6 months and with SLCO1B1 genotypes adjusted for gender, body mass index, age, alcohol, smoking, diabetes, apoE phenotype, and country of origin, since subjects participating in PROSPER were either from Scotland, Ireland, or the Netherlands. Prevalence at baseline of myocardial infarction (MI) and all types of vascular disease (history of angina, claudication, MI, stroke, transient ischemic attack, peripheral arterial disease surgery, or amputation for vascular disease more than 6 months before study entry) at baseline, as well as incidence of primary endpoints (CHD death or nonfatal MI or fatal non-fatal stroke), and all cardiovascular events (primary endpoints and coronary artery bypass grafting, coronary angioplasty, and peripheral artery surgery or angioplasty), were compared between carriers of different SLCO1B1 SNP genotypes using multivariable logistic regression analysis in all subjects and stratified by gender and treatment. All analyses were fully adjusted for age, gender, country, history of vascular disease, body mass index, history of diabetes, as well as history of hypertension, alcohol use, current smoking, and apoE phenotype. To evaluate the modifying effects of genotypes and gender on the response to treatment, gene-treatment and gene-gender interaction terms were added to the regression models. Lewontin's D value was calculated to assess the linkage disequilibrium (LD) between the two SNPs of interest (Lewontin R C. The interaction of selection and linkage. II. Optimum models. Genetics 1964; 50:757-82). There was no interaction between these SNPs and also no interaction between these SNPs and apoE genotype. All analyses were performed using SAS/STAT and SAS/Genetics [including proc haplotype procedure] (SAS Version 9.1, SAS Institute Inc., Cary, N.C.). A two-sided $p<0.05$ was considered statistically significant.

Other Embodiments

From the foregoing description, it will be apparent that variations and modifications may be made to the invention described herein to adopt it to various usages and conditions. Such embodiments are also within the scope of the following claims.

INCORPORATION BY REFERENCE

All citations to sequences, patents and publications in this specification are herein incorporated by reference to the same extent as if each independent patent and publication was specifically and individually indicated to be incorporated by reference.

We claim:

1. A method of determining a statin dosage, the method comprising the steps of:

determining a level of cholesterol in a blood and/or plasma sample obtained from a patient;

conducting an assay in the sample to identify the presence or absence of a SLCO1B1 biomarker and an Apolipoprotein E gene (ApoE) biomarker that are associated with statin efficacy; and determining a dosage of statin for said patient based upon said cholesterol level and said presence or absence of said SLCO1B1 and ApoE biomarkers, wherein the statin is selected from the group consisting of pravastatin, atorvastatin, and cerivastatin.

2. The method of claim 1, wherein said cholesterol is LDL-cholesterol.

3. The method of claim 1, wherein the biomarkers are genetic polymorphisms, and the polypmorphisms are an rs4149056 C polymorphism at a SLCO1B1 locus and selected from the group consisting of an ApoE2 polymorphism, an APoE3 polymorphism, and an ApoE4 polymorphism at an ApoE locus.

4. The method of claim 1, wherein said polymorphism is C/T or a T/T genotype at SLCO1B1-056 and an ApoE genotype selected from the group consisting of ApoE2/E2, ApoE2/E3, and ApoE3/E3.

5. The method of claim 4, wherein said statin dosage is between about 20 and about 40 milligrams.

6. The method of claim 1, further comprising the step of measuring an amount of said biomarker.

7. The method of claim 6, wherein said level and said amount are weighted.

8. A method for identifying a patient's likelihood of responding to statin treatment, the method comprising the steps of:

determining a baseline level of cholesterol in a blood and/or plasma sample obtained from a patient;

identifying a SLCO1B1 polymorphism and an ApoE polymorphism in said sample that are indicative of statin efficacy;

characterizing said patient's likelihood of responding to statin treatment based upon said level and the presence or absence of said SLCO1B1 and ApoE polymorphisms identified in said identifying step, wherein the statin treatment comprises a statin selected from the group consisting of pravastatin, atorvastatin, and cerivastatin.

9. The method of claim 8, further comprising categorizing said patient as a normal responder or a hypo-responder.

10. The method of claim 8, further comprising the step of obtaining a plasma lathosterol/cholesterol ratio in said sample and wherein said characterizing step further comprises said ratio.

11. The method of claim 10, wherein said baseline level of cholesterol, said ratio, and said polymorphisms contraindicate statin treatment.

12. The method of claim 11, wherein said cholesterol is LDL cholesterol.

13. The method of claim 12, wherein said baseline level of cholesterol is about 160 mg/dl or less and said ratio is less than about 215.

* * * * *

SEQUENCE LISTING

```
<160> NUMBER OF SEQ ID NOS: 73

<210> SEQ ID NO 1
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 1

gatttngcta a                                                          11


<210> SEQ ID NO 2
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 2

ctctantgag t                                                          11


<210> SEQ ID NO 3
<211> LENGTH: 12
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t
<220> FEATURE:
<221> NAME/KEY: misc_feature
<222> LOCATION: (12)..(12)
<223> OTHER INFORMATION: n is c or t

<400> SEQUENCE: 3

tgaatngata tn                                                         12


<210> SEQ ID NO 4
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 4

atatgngttc a                                                          11


<210> SEQ ID NO 5
<211> LENGTH: 11
<212> TYPE: DNA
<213> ORGANISM: Homo sapiens
<220> FEATURE:
<221> NAME/KEY: misc_feature
```

<222> LOCATION: (6)..(6)
<223> OTHER INFORMATION: n is t or c

<400> SEQUENCE: 5
taccantggg g 11

<210> SEQ ID NO 6
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 6
agaagnacat t 11

<210> SEQ ID NO 7
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 7
acatcnacct t 11

<210> SEQ ID NO 8
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or a

<400> SEQUENCE: 8
catcanctga g 11

<210> SEQ ID NO 9
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 9
gcactntcag g 11

<210> SEQ ID NO 10
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 10
ttctcnatgg g 11

<210> SEQ ID NO 11

<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 11
tcactntctt t 11

<210> SEQ ID NO 12
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or a

<400> SEQUENCE: 12
gctgtnatgt c 11

<210> SEQ ID NO 13
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 13
ataaancagc a 11

<210> SEQ ID NO 14
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 14
atattnattt a 11

<210> SEQ ID NO 15
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 15
ggatgnagca a 11

<210> SEQ ID NO 16
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 16
ctatantggt g 11

<210> SEQ ID NO 17
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 17
gattgnattt g 11

<210> SEQ ID NO 18
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 18
gaagcnttga a 11

<210> SEQ ID NO 19
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 19
gaaagntatc a 11

<210> SEQ ID NO 20
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 20
gtgaanacaa a 11

<210> SEQ ID NO 21
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 21
aaatangtag a 11

<210> SEQ ID NO 22
<211> LENGTH: 11
<212> TYPE: DNA
<213> ORGANISM: Homo sapiens
<220> FEATURE:

<221> NAME/KEY: misc_feature
<222> LOCATION: (6)..(6)
<223> OTHER INFORMATION: n is c or g

<400> SEQUENCE: 22
aaattnaaac t 11

<210> SEQ ID NO 23
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or c

<400> SEQUENCE: 23
agcagnttgc a 11

<210> SEQ ID NO 24
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 24
ctattntatt t 11

<210> SEQ ID NO 25
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 25
ctgggntaaa t 11

<210> SEQ ID NO 26
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 26
aggganggga a 11

<210> SEQ ID NO 27
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 27
ttatangagc a 11

<210> SEQ ID NO 28
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 28
gtgagntact t 11

<210> SEQ ID NO 29
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 29
aatgcncaag a 11

<210> SEQ ID NO 30
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 30
aatacnagtc t 11

<210> SEQ ID NO 31
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is - or a

<400> SEQUENCE: 31
tgccgnaaaa t 11

<210> SEQ ID NO 32
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 32
acctgngata g 11

<210> SEQ ID NO 33
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or t

<400> SEQUENCE: 33
ggggcnttct t 11

<210> SEQ ID NO 34
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or g

<400> SEQUENCE: 34 taatcnccctg t 11

<210> SEQ ID NO 35
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 35
ctcagnctgc a 11

<210> SEQ ID NO 36
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or t

<400> SEQUENCE: 36
agtctngaat t 11

<210> SEQ ID NO 37
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 37
tcaccntgtc t 11

<210> SEQ ID NO 38
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 38
agcctntagt g 11

<210> SEQ ID NO 39
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 39
tttccnctca a 11

<210> SEQ ID NO 40
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is g or c

<400> SEQUENCE: 40
ctgctntgat g 11

<210> SEQ ID NO 41
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 41
tccttnctaa t 11

<210> SEQ ID NO 42
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 42
tttgangttg t 11

<210> SEQ ID NO 43
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 43
caatcnttgg c 11

<210> SEQ ID NO 44
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or t

<400> SEQUENCE: 44
atcacntgtt t 11

<210> SEQ ID NO 45
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 45
atttgngtga a 11

<210> SEQ ID NO 46
<211> LENGTH: 12
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is - or G

<400> SEQUENCE: 46
cctgtntatg tt 12

<210> SEQ ID NO 47
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 47
aaaacngcag a 11

<210> SEQ ID NO 48
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 48
agaagngcct g 11

<210> SEQ ID NO 49
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 49
acgtgngcgg c 11

<210> SEQ ID NO 50
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is t or c

<400> SEQUENCE: 50
ggaacnggca c 11

<210> SEQ ID NO 51
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 51
agctgngtaa g 11

<210> SEQ ID NO 52
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 52
tgggtngctt t 11

<210> SEQ ID NO 53
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 53
ggtcgntttt g 11

<210> SEQ ID NO 54
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 54
cagacnctgt c 11

<210> SEQ ID NO 55
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 55
tgcagncact g 11

<210> SEQ ID NO 56
<211> LENGTH: 11
<212> TYPE: DNA

<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 56
gctgcnggtg c 11

<210> SEQ ID NO 57
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 57
tgcccngcga c 11

<210> SEQ ID NO 58
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 58
caagcngtgg a 11

<210> SEQ ID NO 59
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 59
aggtgnagca a 11

<210> SEQ ID NO 60
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or c

<400> SEQUENCE: 60
gggtgngcct c 11

<210> SEQ ID NO 61
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, or g

<400> SEQUENCE: 61
tgcgtnagcg g 11

<210> SEQ ID NO 62
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 62
gcgacngcct c 11

<210> SEQ ID NO 63
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 63
ggcctngggc g 11

<210> SEQ ID NO 64
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, or g

<400> SEQUENCE: 64
gctgcntaag c 11

<210> SEQ ID NO 65
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a or g

<400> SEQUENCE: 65
gcagcnccag t 11

<210> SEQ ID NO 66
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is c or t

<400> SEQUENCE: 66
gccagngctg g 11

<210> SEQ ID NO 67
<211> LENGTH: 11
<212> TYPE: DNA
<213> ORGANISM: Homo sapiens
<220> FEATURE:
<221> NAME/KEY: misc_feature
<222> LOCATION: (6)..(6)

<223> OTHER INFORMATION: n is c or t

<400> SEQUENCE: 67

```
agaagngcct g                                                            11
```

<210> SEQ ID NO 68
<211> LENGTH: 1223
<212> TYPE: DNA
<213> ORGANISM: Homo sapiens

<400> SEQUENCE: 68

```
gggatccttg agtcctactc agccccagcg gaggtgaagg acgtccttcc ccaggagccg     60
actggccaat cacaggcagg aagatgaagg ttctgtgggc tgcgttgctg gtcacattcc    120
tggcaggatg ccaggccaag gtggagcaag cggtggagac agagccggag cccgagctgc    180
gccagcagac cgagtggcag agcggccagc gctgggaact ggcactgggt cgcttttggg    240
attacctgcg ctgggtgcag acactgtctg agcaggtgca ggaggagctg ctcagctccc    300
aggtcaccca ggaactgagg gcgctgatgg acgagaccat gaaggagttg aaggcctaca    360
aatcggaact ggaggaacaa ctgaccccgg tggcggagga gacgcgggca cggctgtcca    420
aggagctgca ggcggcgcag gcccggctgg gcgcggacat ggaggacgtg tgcggccgcc    480
tggtgcagta ccgcggcgag gtgcaggcca tgctcggcca gagcaccgag gagctgcggg    540
tgcgcctcgc ctcccacctg cgcaagctgc gtaagcggct cctccgcgat gccgatgacc    600
tgcagaagcg cctggcagtg taccaggccg gggcccgcga gggcgccgag cgcggcctca    660
gcgccatccg cgagcgcctg gggcccctgg tggaacaggg ccgcgtgcgg gccgccactg    720
tgggctccct ggccggccag ccgctacagg agcgggccca ggcctggggc gagcggctgc    780
gcgcgcggat ggaggagatg ggcagccgga cccgcgaccg cctggacgag gtgaaggagc    840
aggtggcgga ggtgcgcgcc aagctggagg agcaggccca gcagatacgc ctgcaggccg    900
aggccttcca ggcccgcctc aagagctggt tcgagcccct ggtggaagac atgcagcgcc    960
agtgggccgg gctggtggag aaggtgcagg ctgccgtggg caccagcgcc gcccctgtgc   1020
ccagcgacaa tcactgaacg ccgaagcctg cagccatgcg accccacgcc accccgtgcc   1080
tcctgcctcc gcgcagcctg cagcgggaga ccctgtcccc gccccagccg tcctcctggg   1140
gtggacccta gtttaataaa gattcaccaa gtttcacgca aaaaaaaaaa aaaaaaaaaa   1200
aaaaaaaaaa aaaaaaaaaa aaa                                           1223
```

<210> SEQ ID NO 69
<211> LENGTH: 10612
<212> TYPE: DNA
<213> ORGANISM: Homo sapiens

<400> SEQUENCE: 69

```
tggagagctg gtctaccacc ggcggcctgg agaggagggc actgtcatgt ctctagctgg     60
gaaatacaca tgtgagcctg gcgcctgggt ccgagggtgg aggggctggg cccctggact    120
cctcctgggt ctgagggagg acgggctagg gccctggaca ctcaggtctg agggaggagg    180
cctgggttcc cagatgccca aatccccttg gtaatgagac cccgcctcca ccccactctc    240
tgacagtgaa caactggttg gcaacggtaa cgttgggcca ggcgggcatg cacgcaacat    300
actaccacaa agccagtgac caggtgagtg ggtgcaggga ctagctggtg ctgccagggg    360
ctgctgggcc tggaagtcca ggtggggcca cttgctaatt ctcatgtgtt gctccggccc    420
ctccagctgc aggtgggtgt ggagtttgag gccagcacaa ggatgcagga caccagcgtc    480
```

```
tccttcgggt accagctgga cctgcccaag gccaacctcc tcttcaaagg taaaggtctc    540
ggttccccta cgcgggaaac aggcaggagg tgactcaact ctgagtggat gtgtgggcca    600
ccacaggtgc tggaggacag tgtgctgcca ccctgtgggc ctccacatta ccagggaaca    660
cttgttaaaa ggtaggtggg gccgggtgcg gtggctcacg cctgtaatcc cagcactttg    720
ggaggccaag gcgggccgag gtaaggagat tgagaccatc ctggctaaca cggtgaaact    780
ccgtctctac taaaaataca aaaacaaaat tagccgggtg tggttgcggg tgcctatagt    840
cccaactact gaggctgagg cgggaaaatg gtatgaaccc aggaggcgga gcttgcggtg    900
agccgagatc gtgccaccgc actccagcct gggtgacaga gcaagactcc atctcaaaaa    960
aaaaaaagta ggtggacaac cctctactat gttttatgct tggaaaaaaa aagtaggtag   1020
agcagccagg cgtggtgact cacgcctgta atcccagcat tttgggaggc caagccaggt   1080
agaatacttg aggccaggag ttggagacca gcctggccaa cgtggtgaaa tcccctctct   1140
actaaaagta caaaaattag ccaggtgtgg tagcgtgctg caactgtagt ccccgctact   1200
taggaggctg aggcacaaga atcacttgaa cctgggaggc ggaggttgca gggagttgag   1260
actgcaccac tgcactccag cctgggtgac agagtgagac tccatctcca aaaaaaataa   1320
aatgaaataa ataaataaat gttaaaaaaa atctggtgga gcatctgatg ggtgtttggg   1380
ccaagctgga gctttgtcca tcccctctta tttttctgca cttgactctc ttattttttct   1440
gagactggtc tccctctgtc gcccaggcta gagtgcagca gtgcaactgc ggctcactgc   1500
agcctccacc tcccgggctc aagcagcctt cccacctcag cctcctgagt agctaggacc   1560
acaggtgtat gccaccaggc ccagctaatt tttttgatag ttttgggaga catgggggtt   1620
tcaccatgtt gcccaggctg gtctcgaact cctggactca agccttggcc tcccaaagtg   1680
ctgggattat aggtgtgagc caccacaccc agccagggta gaaggcactt tggaagcctc   1740
gagcctgccc cattcatctt acgttagtgg aaactgaggc ttccagaggt ttcaaggtca   1800
caactaaatc cagaacctca tctcaggcac actggtcgta gtcccaatgt ccagtcttaa   1860
gtcttcttgg atatctgtgg ctcacagatt ttgggtgttt gagcctcctg ctgagcactg   1920
ctggggccac agcggtgacc agccctgtct tcacgggact cagtgagagg aacagattca   1980
tccgcagagt gggcaggact aggttggggg aacccagggg tctagagggc ttttcagagg   2040
gcaggggtca ctgagcggag agcagaggag gagtgagcca tttgctccag cgtgaagttg   2100
ttggtgtgat ggggtttcag ggtggcagga gcagtgtggt taaaggtctg gaagctgtcg   2160
gcatgtggct ggtatccaag gtggccagga actctgcatg gatatggtgg gaagctggca   2220
cgcctctcac ctcagctctt ccctgcaggc tctgtggata gcaactggat cgtgggtgcc   2280
acgctggaga agaagctccc accccctgccc ctgacactgg cccttggggc cttcctgaat   2340
caccgcaaga acaagtttca gtgtggcttt ggcctcacca tcggctgagc cctcctggcc   2400
cccgccttcc acgcccttcc gattccacct ccacctccac ctccccctgc cacagagggg   2460
agacctgagc ccccctccct tccctccccc cttgggggtc gggggggaca ttggaaagga   2520
gggaccccgc caccccagca gctgaggagg ggattctgga actgaatggc gcttcgggat   2580
tctgagtagc aggggcagca tgcccagtgg gcctggggtc ccgggaggga ttccggaatt   2640
gaggggcacg caggattctg agcaccaggg gcagaggcgg ccagacaacc tcagggagga   2700
gtgtcctggc gtccccatcc tccaaagggc ctgggcccgc cccgaggggg cagcgagagg   2760
agcttcccca tccccggtca gtccaccctg ccccgtccac tttcccatct cctcggtata   2820
```

-continued

```
aatcatgttt ataagttatg gaagaaccgg gacattttac agaaaaaaaa caaaaaacaa   2880
caaaaaatat acgtgggaaa aaaaacgatg ggaggcctcc gttttctcaa gtgtgtctgg   2940
cctgttttga gcatttcatc cggagtctgg ccgccctgac cttcccccag ccgcctgcag   3000
ggggcgccag agggccggag cacggaaagc agcggatcct tgatgctgcc ttaagtccgg   3060
ctcagagggg cgcagcgtgg cctggggtcg ctatcttccc atccggaaca tctgccctgc   3120
tgggggacac tacgggcctt cccttgcctg agggtagggt ctcaaggtca cttgccccca   3180
gcttgacctg gccggagtgg ctatagagga ctttgtccct gcagactgca gcagcagaga   3240
tgacactgtc tctgagtgca gagatggggg cagggagctg ggagagggtt caagctactg   3300
gaacagcttc agaacaacta gggtactagg aactgctgtg tcagggagaa ggggctcaag   3360
gactcgcagg cctgggagga ggggcctagg ccagccatgg gagttgggtc acctgtgtct   3420
gaggacttgg tgctgtctgg attttgccaa cctagggctg gggtcagctg atgcccacca   3480
cgactcccga gcctccagga actgaaaccc tgtctgcccc cagggtctgg ggaaggaggc   3540
tgctgagtag aaccaacccc aggttaccaa ccccacctca gccacccctt gccagccaaa   3600
gcaaacaggc ccggcccggc actgggggtt ccttctcgaa ccaggagttc agcctcccct   3660
gacccgcaga atcttctgat cccacccgct ccaggagcca ggaatgagtc ccagtctctc   3720
ccagttctca ctgtgtggtt ttgccattcg tcttgctgct gaaccacggg tttctcctct   3780
gaaacatctg ggatttataa cagggcttag gaaagtgaca gcgtctgagc gttcactgtg   3840
gcctgtccat tgctagccct aacataggac cgctgtgtgc cagggctgtc ctccatgctc   3900
aatacacgtt agcttgtcac caaacatacc cgtgccgctg ctttcccagt ctgatgagca   3960
aaggaacttg atgctcagag aggacaagtc atttgcccaa ggtcacacag ctggcaactg   4020
gcagagccag gattcacgcc ctggcaattt gactccagaa tcctaacctt aacccagaag   4080
cacggcttca agcccctgga aaccacaata cctgtggcag ccagggggag gtgctggaat   4140
ctcatttcac atgtggggag ggggctcccc tgtgctcaag gtcacaacca aagaggaagc   4200
tgtgattaaa acccaggtcc catttgcaaa gcctcgactt ttagcaggtg catcatactg   4260
ttcccacccc tcccatccca cttctgtcca gccgcctagc cccactttct tttttttctt   4320
tttttgagac agtctccctc ttgctgaggc tggagtgcag tggcgagatc tcggctcact   4380
gtaacctccg cctcccgggt tcaagcgatt ctcctgcctc agcctcccaa gtagctagga   4440
ttacaggcgc ccgccaccac gcctggctaa cttttgtatt tttagtagag atggggtttc   4500
accatgttgg ccaggctggt ctcaaactcc tgaccttaag tgattcgccc actgtggcct   4560
cccaaagtgc tgggattaca ggcgtgagct accgccccca gcccctccca tcccacttct   4620
gtccagcccc ctagccctac tttctttctg ggatccagga gtccagatcc ccagcccccct   4680
ctccagatta cattcatcca ggcacaggaa aggacagggt caggaaagga ggactctggg   4740
cggcagcctc cacattcccc ttccacgctt ggcccccaga atggaggagg gtgtctgtat   4800
tactgggcga ggtgtcctcc cttcctgggg actgtggggg gtggtcaaaa gacctctatg   4860
ccccacctcc ttcctccctc tgccctgctg tgcctggggc agggggagaa cagcccacct   4920
cgtgactggg ggctggccca gcccgcccta tccctggggg agggggcggg acagggggag   4980
ccctataatt ggacaagtct gggatccttg agtcctactc agccccagcg gaggtgaagg   5040
acgtccttcc ccaggagccg gtgagaagcg cagtcggggg cacggggatg agctcagggg   5100
cctctagaaa gagctgggac cctgggaacc cctggcctcc aggtagtctc aggagagcta   5160
ctcggggtcg ggcttgggga gaggaggagc gggggtgagg caagcagcag gggactggac   5220
```

```
ctgggaaggg ctgggcagca gagacgaccc gacccgctag aaggtggggt ggggagagca   5280
gctggactgg gatgtaagcc atagcaggac tccacgagtt gtcactatca tttatcgagc   5340
acctactggg tgtccccagt gtcctcagat ctccataact ggggagccag ggcagcgac    5400
acggtagcta gccgtcgatt ggagaacttt aaaatgagga ctgaattagc tcataaatgg   5460
aacacggcgc ttaactgtga ggttggagct tagaatgtga agggagaatg aggaatgcga   5520
gactgggact gagatggaac cggcggtggg gagggggtgg ggggatggaa tttgaacccc   5580
gggagaggaa gatggaattt tctatggagg ccgacctggg gatggggaga taagagaaga   5640
ccaggaggga gttaaatagg gaatgggttg ggggcggctt ggtaaatgtg ctgggattag   5700
gctgttgcag ataatgcaac aaggcttgga aggctaacct ggggtgaggc cgggttgggg   5760
ccgggctggg ggtgggagga gtcctcactg gcggttgatt gacagtttct ccttccccag   5820
actggccaat cacaggcagg aagatgaagg ttctgtgggc tgcgttgctg gtcacattcc   5880
tggcaggtat gggggcgggg cttgctcggt tccccccgct cctccccctc tcatcctcac   5940
ctcaacctcc tggccccatt caggcagacc ctgggccccc tcttctgagg cttctgtgct   6000
gcttcctggc tctgaacagc gatttgacgc tctctgggcc tcggtttccc ccatccttga   6060
gataggagtt agaagttgtt ttgttgttgt tgtttgttgt tgttgttttg tttttttgag   6120
atgaagtctc gctctgtcgc ccaggctgga gtgcagtggc gggatctcgg ctcactgcaa   6180
gctccgcctc ccaggtccac gccattctcc tgcctcagcc tcccaagtag ctgggactac   6240
aggcacatgc caccacaccc gactaacttt tttgtatttt cagtagagac ggggtttcac   6300
catgttggcc aggctggtct ggaactcctg acctcaggtg atctgcccgt ttcgatctcc   6360
caaagtgctg ggattacagg cgtgagccac cgcacctggc tgggagttag aggtttctaa   6420
tgcattgcag gcagatagtg aataccagac acggggcagc tgtgatcttt attctccatc   6480
acccccacac agccctgcct ggggcacaca aggacactca atacatgctt ttccgctggg   6540
cgcggtggct cacccctgta atcccagcac tttgggaggc caaggtggga ggatcacttg   6600
agcccaggag ttcaacacca gcctgggcaa catagtgaga ccctgtctct actaaaaata   6660
caaaaattag ccaggcatgg tgccacacac ctgtgctctc agctactcag gaggctgagg   6720
caggaggatc gcttgagccc agaaggtcaa ggttgcagtg aaccatgttc aggccgctgc   6780
actccagcct gggtgacaga gcaagaccct gtttataaat acataatgct ttccaagtga   6840
ttaaaccgac tccccctca ccctgcccac catggctcca aagaagcatt tgtggagcac   6900
cttctgtgtg cccctaggta ctagatgcct ggacggggtc agaaggaccc tgacccacct   6960
tgaacttgtt ccacacagga tgccaggcca aggtggagca agcggtggag acagagccgg   7020
agcccgagct gcgccagcag accgagtggc agagcggcca gcgctgggaa ctggcactgg   7080
gtcgcttttg ggattacctg cgctgggtgc agacactgtc tgagcaggtg caggaggagc   7140
tgctcagctc ccaggtcacc caggaactga ggtgagtgtc cccatcctgg cccttgaccc   7200
tcctggtggg cggctatacc tccccaggtc caggtttcat tctgcccctg tcgctaagtc   7260
ttggggggcc tgggtctctg ctggttctag cttcctcttc ccatttctga ctcctggctt   7320
tagctctctg gaattctctc tctcagcttt gtctctctct cttcccttct gactcagtct   7380
ctcacactcg tcctggctct gtctctgtcc ttccctagct cttttatata gagacagaga   7440
gatggggtct cactgtgttg cccaggctgg tcttgaactt ctgggctcaa gcgatcctcc   7500
cgcctcggcc tcccaaagtg ctgggattag aggcatgagc caccttgccc ggcctcctag   7560
```

-continued

```
ctccttcttc gtctctgcct ctgccctctg catctgctct ctgcatctgt ctctgtctcc   7620
ttctctcggc ctctgccccg ttccttctct ccctcttggg tctctctggc tcatccccat   7680
ctcgcccgcc ccatcccagc ccttctcccc gcctcccact gtgcgacacc ctcccgccct   7740
ctcggccgca gggcgctgat ggacgagacc atgaaggagt tgaaggccta caaatcggaa   7800
ctggaggaac aactgacccc ggtggcggag gagacgcggg cacggctgtc caaggagctg   7860
caggcggcgc aggcccggct gggcgcggac atggaggacg tgtgcggccg cctggtgcag   7920
taccgcggcg aggtgcaggc catgctcggc cagagcaccg aggagctgcg ggtgcgcctc   7980
gcctcccacc tgcgcaagct gcgtaagcgg ctcctccgcg atgccgatga cctgcagaag   8040
cgcctggcag tgtaccaggc cggggcccgc gagggcgccg agcgcggcct cagcgccatc   8100
cgcgagcgcc tggggcccct ggtggaacag ggccgcgtgc gggccgccac tgtgggctcc   8160
ctggccggcc agccgctaca ggagcgggcc caggcctggg gcgagcggct gcgcgcgcgg   8220
atggaggaga tgggcagccg gacccgcgac cgcctggacg aggtgaagga gcaggtggcg   8280
gaggtgcgcg ccaagctgga ggagcaggcc cagcagatac gcctgcaggc cgaggccttc   8340
caggcccgcc tcaagagctg gttcgagccc ctggtggaag acatgcagcg ccagtgggcc   8400
gggctggtgg agaaggtgca ggctgccgtg ggcaccagcg ccgcccctgt gcccagcgac   8460
aatcactgaa cgccgaagcc tgcagccatg cgaccccacg ccaccccgtg cctcctgcct   8520
ccgcgcagcc tgcagcggga gaccctgtcc ccgccccagc cgtcctcctg gggtggaccc   8580
tagtttaata aagattcacc aagtttcacg catctgctgg cctcccccctg tgatttcctc   8640
taagccccag cctcagtttc tctttctgcc cacatactgg ccacacaatt ctcagccccc   8700
tcctctccat ctgtgtctgt gtgtatcttt ctctctgccc tttttttttt ttttagacgg   8760
agtctggctc tgtcacccag gctagagtgc agtggcacga tcttggctca ctgcaacctc   8820
tgcctcttgg gttcaagcga ttctgctgcc tcagtagctg ggattacagg ctcacaccac   8880
cacacccggc taatttttgt atttttagta gagacgagct ttcaccatgt tggccaggca   8940
ggtctcaaac tcctgaccaa gtgatccacc cgccggcctc ccaaagtgct gagattacag   9000
gcctgagcca ccatgcccgg cctctgcccc tctttctttt ttagggggca gggaaaggtc   9060
tcaccctgtc acccgccatc acagctcact gcagcctcca cctcctggac tcaagtgata   9120
agtgatcctc ccgcctcagc ctttccagta gctgagacta caggcgcata ccactaggat   9180
taatttgggg gggggggtgg tgtgtgtgga gatggggtct ggctttgttg gccaggctga   9240
tgtggaattc ctgggctcaa gcgatactcc caccttggcc tcctgagtag ctgagactac   9300
tggctagcac caccacaccc agctttttat tattatttgt agagacaagg tctcaatatg   9360
ttgcccaggc tagtctcaaa cccctgggct caagagatcc tccgccatcg gcctcccaaa   9420
gtgctgggat tccaggcatg gggctccgag cccggcctgc ccaacttaat aatacttgtt   9480
cctcagagtt gcaactccaa atgacctgag attggtgcct ttattctaag ctattttcat   9540
tttttttctg ctgtcattat tctccccctt ctctcctcca gtcttatctg atatctgcct   9600
ccttcccacc caccctgcac cccatcccac ccctctgtct ctccctgttc tcctcaggag   9660
actctggctt cctgttttcc tccacttcta tcttttatct ctccctccta cggtttcttt   9720
tctttctccc cggcctgctt gtttctcccc caaccccctt catctggatt tcttcttctg   9780
ccattcagtt tggtttgagc tctctgcttc tccggttccc tctgagctag ctgtcccttc   9840
acccactgtg aactgggttt ccctgcccaa ccctcattct ctttctttct ttcttttttt   9900
tttttttttt tttttttttt ttttgagaca gagtcttgct ctgttgccca gcctggagtg   9960
```

```
cagtggtgca atcttggttc actgcaacct ccacttccca gattcaagca attctcctgc  10020

ctcagcctcc agagtagctg ggattacagg cgtgtcccac cacacccgac taatttttgt  10080

atttttggta gagacaaggc ttcggcattg ttggccaggc aggtctcgaa ctcctgacct  10140

caagtaatct gcctgcctca ccctcccaaa gtgctgggat tacaggcatg agccacctca  10200

cccggaccat ccctcattct ccatcctttc ctccagttgt gatgtctacc cctcatgttt  10260

cccaacaagc ctactgggtg ctgaatccag gctgggaaga gaagggagcg gctcttctgt  10320

cggagtctgc accaggccca tgctgagacg agagctggcg ctcagagagg ggaagcttgg  10380

atggaagccc aggagccgcc ggcactctct tctcctccca ccccctcagt tctcagagac  10440

ggggaggagg gttcccacca acgggggaca ggctgagact tgagcttgta tctcctgggc  10500

cagctgcaac atctgcttgt ccctctgccc atcttggctc ctgcacaccc tgaacttggt  10560

gctttccctg gcactgctct gatcacccac gtggaggcag cacccctccc ct          10612
```

```
<210> SEQ ID NO 70
<211> LENGTH: 317
<212> TYPE: PRT
<213> ORGANISM: Homo sapiens

<400> SEQUENCE: 70

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255
```

```
Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315


<210> SEQ ID NO 71
<211> LENGTH: 2800
<212> TYPE: DNA
<213> ORGANISM: Homo sapiens

<400> SEQUENCE: 71

aaagggtgga cttgttgcag ttgctgtagg attctaaatc caggtgattg tttcaaactg      60

agcatcaaca acaaaaacat ttgtatgata tctatatttc aatcatggac caaaatcaac     120

atttgaataa aacagcagag gcacaacctt cagagaataa gaaaacaaga tactgcaatg     180

gattgaagat gttcttggca gctctgtcac tcagctttat tgctaagaca ctaggtgcaa     240

ttattatgaa aagttccatc attcatatag aacggagatt tgagatatcc tcttctcttg     300

ttggttttat tgacggaagc tttgaaattg gaaatttgct tgtgattgta tttgtgagtt     360

actttggatc caaactacat agaccaaagt taattggaat cggttgtttc attatgggaa     420

ttggaggtgt tttgactgct ttgccacatt tcttcatggg atattacagg tattctaaag     480

aaactaatat caattcatca gaaaattcaa catcgacctt atccacttgt ttaattaatc     540

aaattttatc actcaataga gcatcacctg agatagtggg aaaaggttgt ttaaaggaat     600

ctgggtcata catgtggata tatgtgttca tgggtaatat gcttcgtgga ataggggaga     660

ctcccatagt accattgggg ctttcttaca ttgatgattt cgctaaagaa ggacattctt     720

ctttgtattt aggtatattg aatgcaatag caatgattgg tccaatcatt ggctttaccc     780

tgggatctct gttttctaaa atgtacgtgg atattggata tgtagatcta agcactatca     840

ggataactcc tactgattct cgatgggttg gagcttggtg gcttaatttc cttgtgtctg     900

gactattctc cattatttct tccataccat tctttttctt gccccaaact ccaaataaac     960

cacaaaaaga aagaaaagct tcactgtctt tgcatgtgct ggaaacaaat gatgaaaagg    1020

atcaaacagc taatttgacc aatcaaggaa aaaatattac caaaaatgtg actggttttt    1080

tccagtcttt taaaagcatc cttactaatc cctgtatgt tatgtttgtg cttttgacgt    1140

tgttacaagt aagcagctat attggtgctt ttacttatgt cttcaaatac gtagagcaac    1200

agtatggtca gccttcatct aaggctaaca tcttattggg agtcataacc atacctattt    1260

ttgcaagtgg aatgttttta ggaggatata tcattaaaaa attcaaactg aacaccgttg    1320

gaattgccaa attctcatgt tttactgctg tgatgtcatt gtccttttac ctattatatt    1380

ttttcatact ctgtgaaaac aaatcagttg ccggactaac catgacctat gatggaaata    1440

atccagtgac atctcataga gatgtaccac tttcttattg caactcagac tgcaattgtg    1500

atgaaagtca atgggaacca gtctgtggaa acaatggaat aacttacatc tcaccctgtc    1560

tagcaggttg caaatcttca agtggcaata aaaagcctat agtgttttac aactgcagtt    1620

gtttggaagt aactggtctc cagaacagaa attactcagc ccatttgggt gaatgcccaa    1680

gagatgatgc ttgtacaagg aaattttact tttttgttgc aatacaagtc ttgaatttat    1740

ttttctctgc acttggaggc acctcacatg tcatgctgat tgttaaaatt gttcaacctg    1800
```

```
aattgaaatc acttgcactg ggtttccact caatggttat acgagcacta ggaggaattc   1860

tagctccaat atattttggg gctctgattg atacaacgtg tataaagtgg tccaccaaca   1920

actgtggcac acgtgggtca tgtaggacat ataattccac atcattttca agggtctact   1980

tgggcttgtc ttcaatgtta agagtctcat cacttgtttt atatattata ttaatttatg   2040

ccatgaagaa aaaatatcaa gagaaagata tcaatgcatc agaaaatgga agtgtcatgg   2100

atgaagcaaa cttagaatcc ttaaataaaa ataaacattt tgtcccttct gctggggcag   2160

atagtgaaac acattgttaa ggggagaaaa aaagccactt ctgcttctgt gtttccaaac   2220

agcattgcat tgattcagta agatgttatt tttgaggagt tcctggtcct ttcactaaga   2280

atttccacat cttttatggt ggaagtataa ataagcctat gaacttataa taaaacaaac   2340

tgtaggtaga aaaaatgaga gtactcattg ttacattata gctacatatt tgtggttaag   2400

gttagactat atgatccata caaattaaag tgagagacat ggttactgtg taataaaaga   2460

aaaaatactt gttcaggtaa ttctaattct taataaaaca aatgagtatc atacaggtag   2520

aggttaaaaa ggaggagcta gattcatatc ctaagtaaag agaaatgcct agtgtctatt   2580

ttattaaaca aacaaacaca gagtttgaac tataatacta aggcctgaag tctagcttgg   2640

atatatgcta caataatatc tgttactcac ataaaattat atatttcaca gactttatca   2700

atgtataatt aacaattatc ttgtttaagt aaatttagaa tacatttaag tattgtggaa   2760

gaaataaaga cattccaata tttgcaaaaa aaaaaaaaaa                         2800
```

<210> SEQ ID NO 72
<211> LENGTH: 115603
<212> TYPE: DNA
<213> ORGANISM: Homo sapiens

<400> SEQUENCE: 72

```
gattcctctg cagtgtaact tcatggtttt tgaggcaaag gaaggctggc agtaaacaaa     60

atatgtgagt aaaatttata gtatgatggt gagagaataa aaattgagtg tcaaagggag    120

taatattaaa aaattgttag agaagacttc gctgggaaag tgtcatttgt ttgggtacta    180

gaatatggtg agggagtaag ttatgcagct atagggaaag aacattccag acagaaagaa    240

aaataggaac aaagattctc agtagaggat ctataactta taaggcctta aagctgttct    300

ttggattttt gagtgatatg tgaagccaat gggggatttg agcagagcta tgacatggta    360

tgaccctcac ttatatgtta agatttacac aggggaagga ggttggggaa gaggggctgt    420

gagtggtcag gaggaaagct gagatacaag tatgagggta ttgcaataat tcaggaccag    480

cctgaaagtt gtggaggagg taagaaatca tcagattctg ggtatatttg gaaattagag    540

cctaatgtga gtgtgagaaa tagagaagaa tgattctaat attgtatgtg gctgtgcatg    600

tgcacgcatg tgtgcaactg gaatgacaga attacaatgt atggggatta ttgtcttccc    660

tggacaataa tccctggaaa tggggattat tacaagagga gaggttgggg aaggaaagac    720

aaagatacca tgttagaaaa tattaagtgt aagatgccta ttagagatat ataggaagat    780

ggtgagaagt caatggataa atctagagtt catgagtaac ttggctagag aaaaaatttt    840

ggaattatca acgtatggat aagatttaaa gacatgagaa tagatgaggt cacaaacaca    900

cacagtaagg ttattgtctg acatgcttca atttagaaga caaagataaa gaatttagag    960

taaatgaagt gtaaataagt aagtcagtga gttagaaggc aaaccacaaa gggtagtgtc   1020

ctgcaaagtt ttgcttaggg agggaattct cagttctgaa aaatgctgct aatagttcaa   1080
```

-continued

```
gtcagatgag gactattaga tgtagcattt aggtaattta tgacttagga aaagtagttt   1140
cagtggaaat ttgggggcaa aagcctgata agagtgtgct caagagagaa tgtagagaga   1200
gagattgaaa gcaataatta gacaagctat ttctctgtaa aaatagcaca gaaatagggc   1260
aatattagga aaaaatggga tcaaaagaga gatttttgga agatgaaaaa gtgacagcat   1320
tcttacatgc tgatggaaac atttaaaaag aggatagtgc tatccttaaa aacacaaggg   1380
gaggagtcaa tgtcatatgc aagtggagat tggccttagc ttaaacttgg gtagttcact   1440
aaggcagacc atgtggtggt actggggctt tacatagata aatgtggtca agggagcttt   1500
tgaagtttct tctttattta tttatttttt cagtaaaata attcatcagc tgaaggtggg   1560
gaagggatgt attagaattt caaaaaaaaa aaaaaaagat gaaggcacaa aatgctcaga   1620
gtgcaaaatg gcgtgaatga tttcttggca aaatgaaagg tccatttggg cttcctaatc   1680
atacgtttaa agtcagcatg gttgagagat tttcctcagt tacatttagc ttcataaggg   1740
aaatgtgcag agttatttga gagttaaatt taatcaagat tgtggctttg acatgcaatt   1800
aaaataatgc aaaacagtca aaattatatg aagttatata gaagagagtg attaccgtga   1860
ccattaaatt aacccagatg tatagataag gaacaccgaa atctctggca aaatcaaatt   1920
gtaggttata catcctggtc agtggaagca tgtggatcta gggtgttact gagtgtgagc   1980
taggagtgat aaagagtggt gctccaatct ttgatattat ggagagatta cagtggtgtg   2040
aaaagcatag gatatgccca tagcagtagg tagaagccaa gatcattgag gagaaggcta   2100
aaaaataaaa agaaaataaa aagaaaacag agaattaaaa agattctctt catggtcatt   2160
accatcatga ataattaaaa tagtagtagc attttgagag aatggctttg gatcgagagc   2220
taaaattgtc atgaaatgag tgggagtgac tgagcgttga tagatgattt caacaagagg   2280
aataagtgat agagtctttc aatatgagat ccaaaactat ggattatgag tgtaaagggt   2340
ggggaaatgt aaagaaacta gcaaagtgag gcacattgga aaccagccca tctggtttgc   2400
agcaatatgg gggataaggc aacccctatg tatcactgct gcaggagagg gagtgtctca   2460
gggaagacca atttttaagt tcaaggcaga agtgaagcag aataactcag agaagaggta   2520
aaggtaaggg gagtttcagt catgactagt gatgggttcc agaaaactca agagaagaat   2580
ttcagtccag gattgggaga aagagagaag atgggggcaa acataggaat gtgcagagcc   2640
ctgtggggat tagagaagag gtgatgagtc atcagggaat ccctaccttc ttatggtggt   2700
cactaccata agagcgataa ttgccatggt aatattagtc ttgatgatgc cagagctttg   2760
atcattggtg ggtatagaaa catgtttgga gaataatatg tagaatagga gttctttcca   2820
ggagagtgta gctttctgga gctgtctctt aatcagcacc aacagaagtg aaatgttcgg   2880
gtaagggcgg atctgcttgg agcctgacgg ttccctcttg aggtgtgcct gtggtacaca   2940
cctgagaact ctggggctaa aacctattgg acataggttt tacagatcta caggatacag   3000
atctcagaga ttttatttgt attcatttaa tataaattaa ctgctctaaa atttataata   3060
tgcaaatatc atacaattaa tctaattagg tgttgaatct ataatgtgcc aggcattatg   3120
taaggcactt tacatacact aaatctttat tccaaatata gacttcttac tttatagatg   3180
agtgcactga tgctcagaaa tggtaaataa cctactgatg tttatactgc tggcaggtag   3240
cagagacata tcggcattta agtctttcag acttcaaagg ccatgatatt tcatcagagc   3300
tgtgatagcc gttcctgaaa aaaatatcag ctgattcttt aaatcaattt ttgtcatcta   3360
actgatgcgt ggctgttagc ataatattga tcttgaaaga tgttttgcaa catctttccc   3420
ctggtgtact cttgtttttc catgatccca caaaatgagc agtctaatta tttacacaat   3480
```

```
taggaagaga aaaggggcac agagaatgct ctttgacctc tgaaaatatt ggagaatttt   3540
acaactggca cctttagctc aggattataa aggttgttag ttagtttgta ctgttttatc   3600
ttcattgtat ataatatata tattagtctc caaacatgtt gatgtgtttt caatgaaatg   3660
gatgtctgag gagaaaacca ttagcctgag aaaacccaaa ctgtattccc attgtgaata   3720
aaaggaagtc cataaaaatg atggaaaatg ttctgcattc ctgttatgat atcaaaatct   3780
ggcagtacat gaaaattttt caaagtgctt atttaacagg cataatcttt ggtctcctga   3840
gccagaatct gctgggtatg ggactggatt gctattttga caactcgcca gtagattctt   3900
actcagcaga gtatttggaa gccttactct aatattttgg ccttgggtct acatttctca   3960
gttctgcaca gtcattcttc ccctctacac tactctttag tttgtctcat gattccaata   4020
ctctcaataa ttaaccaaga atagaactaa tcaatcagat aactgtggca cagacatcaa   4080
atacattttg ctgcaaccat atcaacaaat gtcccatgaa tgataagggg taaccatatt   4140
ctcatatatg catcctcaca ttaccacata tatatatgtg catatgtgta tacaggtaaa   4200
agtgtgtata tatgtataca tgtatgtttg tgtgtatata catacatata tcttcacact   4260
tttctgaaat atatatattt atgtgagaga agggtctgta ctttatttca gaagagagct   4320
taatgtccaa ggtataattg agagtctaaa atgtttgagt tattgaatta attaaacttc   4380
atctctactc aagaaaactt ttaactgagt taagctcttc ctttctccac aagtcaagtc   4440
aataaaagga aactgtgata ttaataattc tttcctgttt tgatgtaaag aatctatcgc   4500
ataaagcagt cttaattttc atcattcaga aaaatggtct tgcagttaat tgggactctc   4560
ttattccagg tggtatctcc agtctccata cataccacgt tagaaccata cttatgtacc   4620
aagcaaagag ggtatatttt aatttttaaa tgccaatgta acctgtaggc atattttta    4680
tttgtcttaa attatttcct atttggaagt tttaaatacc tggaataatt tattgtactc   4740
atatttttaa agaaaaaaat cttatgccac caacttaatt gaataaacaa gtaaaagcca   4800
ttcccaaaag taaggtttac ttgttaagat taacaaaaaa taatgtgaga attctgagaa   4860
atataatctt taaatattgg caactggagt gaactcttaa aactaactag gttttatatg   4920
tttgactaga gcaatgacat aataaggtgg ttaatcatca ctggacttgt tttcaaaaag   4980
ccaactactt taagaggaat aaagggtgga cttgttgcag ttgctgtagg attctaaatc   5040
caggtaagaa ccattgagat tctctaattt ttacatatat tttatgtaag aaattttcac   5100
ggaagaagat tttgatggtc ttgaaaaata ttacgaattt tatgctctgt gtcttccaca   5160
cgcttacatt ctgagccctt aaaacatagt aaatattcct tctgggagta gaagagcctc   5220
aggtttatat actgttaaaa ataaagtaga gaaaataata cctttatata tttaaatata   5280
aagtttcaaa tcttggtctt attaatttcc aaacaaataa aaatcaagtc tcaaaaatga   5340
agctctagtt accttcttaa aatatgctac aggataatta tttttgtcaa ctacattgac   5400
tgatcacact agactcctta tttctttgat gtcttcttaa ctggatgaag gcagccaagg   5460
gtgggagtag agggaagagt taattggcaa acataaaaaa caggtgtctc aaagtcacat   5520
aaccacctca gtttccttgt ttcaactcaa gtttgataca gggtgaaggg aaatatattt   5580
tctagataat ttatctccaa ttaaataagc aaaaagtctt ctcagtacag tttttttctt   5640
tttttatttc attattatta tactttaagt tttagggtac atgtgcacaa catgcaggtt   5700
tgttacatat gtatacatgt gccatgttgg tgtgctgcac ccattaactc atcatttaac   5760
attgggcata tctcctaatg ctatccctcc cctctccccc accccacaac agtccccggt   5820
```

gtgtgatgtt ccctttcctg tgtccatgtg ttctcattgt tcagttccca cctatgagtg 5880
agaacatgcg gtgtttggtt ttttgtcctt gcgatagttt gttgagaatg atggtttcca 5940
gtttcatcca tgtccctaca aaggacataa actcatcatt tttatggctg catagtattc 6000
catggtgtat gtgtgccaca ttttcttaat ccactctatc gttgttggac atttaggttg 6060
gttccaagtc tttgctactg tgaatagtgc cgctataaac atacgtgtgc atgtgtcttt 6120
atagcagcat gatttataat cccttgggta tatatccact tatgggatgg ctgggtcaaa 6180
tggtatttcc agttctagat ccctgaggaa tcgccacact gtcttccaca atggttgaac 6240
tagtttacag tcccaccaac agtgtaaaag tgttcctatt tctccacatc ctctccagca 6300
cctgttgttt cctgactttt taatgatcgc tattctaact ggtgtgagat agtatctcat 6360
tgtggttttg atttgcattt ctctgatggc cagtgatgat gagcattttt tcacgtgttt 6420
tttggctgca taaatgtctt ctgttgagaa gtgtctgttc atgtccttca cccacttctt 6480
gatggggtcg tttgtctttt gtaaatttgt ttgagttcat tgtagatttt gggtattagc 6540
cttttgtcag atgagtaggt tgcaaaaatt ttctcccatt ctgtaggttg cctgttcact 6600
ctgatggtag tttcttttgc tgtgcagaag ctctttagtt taattatatc tcatttgtca 6660
tttttggctt ttgttgccat tgcttttggt gttttagaca tgaagtcctt gcccatgcct 6720
atgtcctgaa tggtattgcc taggttttct tctagggttt ttatggtttt aggtctaaca 6780
tttaagtctt taatccatct tgaattaatt tttgtgtaag gtgtaaggaa gggatccagt 6840
ttcagctttc tacatatggc ttgccagttt tcccagcatc atttattaaa tagggaatcc 6900
tttccccatt gcttgttttt ctcaggtttg tcaaagatca gatagttgta gatatgcggc 6960
actatttctg agggctctgt tctgttccat tggtctatat ctctgttttg gtaccagtac 7020
catgctgttt tggttactgt agccttgtag tatagtttga agtcaggtag ggtgatgcct 7080
ccagctttgt tcttttcgct taggattgac ttggtatgcg ggctcttttt tggttccata 7140
tgaactttaa agtagttttt tccaattctg tgaagaaagt cattggtagc ttgatgggga 7200
tggcattgaa tctataaatt accttggaca gtatggccat tttcatgata ttgattcttc 7260
ctgcccatga gcatggaatg ttcttctatt tgttcgtatc ctcttttatt tcattgagca 7320
gtggtttgta gttctccttg aagaggtcct tcacatccct tgtaagttgg attcctaggt 7380
attttattct ctttgaagca attgtgaatg ggagttcact catgatttgg ctctctgttt 7440
gtctgttatt ggtgtataag aatgcttgtg atttttatac attgattttg tattctgaga 7500
ctttgctgaa gttgcttatc aacttgagga aattttgggc tgagatgatg ggtttttcta 7560
gatatacaat catgtgatct gcaaacaggg acaatttgac ttcctctttt cctaattgaa 7620
taccctttat tttcttctcc tgcctgattg ccctggccag aacttccaac attatgttga 7680
ataggagcag tgagagaggg catccctgtc ttgtgcccgt tttcaaaggg aatgcttcca 7740
gtttttgccc attcagtatc atattggctg caggtttgtc atagatagct cttattattt 7800
tgagatacat cccatcaata cctaatttat tgagagtttt tagcatgaag ggttgttgaa 7860
ttttgtcaaa ggcctttttct gcatctattg agatgatcat gtagtttttg tctttggttc 7920
tgtttatatg ctggattaca tttattgatt tgcgtatgtt gaaccagcct tgcatcccag 7980
ggatgaatcc cacttggtca tgttggataa gctttttgat gtgctgttgg atttggtttg 8040
ccagtatttt attgaggatt tttgcatcaa tgttcatcaa ggatattggt ctaaaattct 8100
cttttttgt tgtttctctg ccaggctttg gtatcaggat gatgctggcc tcataaaatg 8160
agttagggag gattccctct ttttctattg attggaatag tttcagaagt attggtacca 8220

```
gttcctcctt gtacctctgg tagaattcgg ctgtgaatcc atctggtcct ggactttttt   8280
ttgttggtaa gctattgagt attgcctcaa tttcagagcc tgttattggt ctattcagag   8340
atgcaacttc ttcctggttt agtcttggga ggatgtatgt gtcaaggaat ttatccattt   8400
ctgctagatt ttctagttta tttgcctaga ggtgtttata gtattctctg atggtagttt   8460
gtatttctgt gggatcggtg gttatatcct ctttatcatt ttttattgca tctatttgat   8520
tcttctctgt ttttcttctttt attagtcttg ctagtggtct atcaattttg ttgatgcttt   8580
caaaaaacca gctcctggat tcattaattt tttgaagggt tttttgtgtc tctatttcct   8640
tcagttctgc tctgatggta gttatttctt gccttctgct agcttttgaa tgtgtttgct   8700
cttgcttttc tagttctttt aattgtgatg ttggggtgtc aattttggat ctttcctgct   8760
ttctcttgtg ggcatttagt gctataaatt tccctctaca cactgcttta aatgtgtccc   8820
agagattctc gtatgttgtg tgtttgttct cattggtttc aaagaacatc tttatttatg   8880
ccttcatttc attatgtacc cagtagtcat tcagtagcag attgttcagt ttccatgcag   8940
ttgagcagtt ttgagtgagt ttcttaatcc tgagttctag tttgattgcg ctgtggtctg   9000
agaaacagtt tgttataatt tctgttcttt tccatttgct gaggagagct ttacttccaa   9060
ctatgtggtc aatttcagag taggtgtggt gtggtgctga aaagaatgta tattctgttg   9120
atttggggtg gagagttctg tagatgtcta ttaggtccgc ttggtgcaga gctgagttca   9180
attcctgggt atccttgtta actttctgtc tcattgatct gtctaatgtt gacagtgggg   9240
tgttaaagtc tcccattatt attgagtgga attctaagtc tctttgtagg tcactaagga   9300
cttgctttat gaatctgggt gctcctgtat tgggtgcata tatatttagg atagttagcg   9360
cttcttgttg aattgatccc tttaccatta ggtaatggcc ttctttgtct cttttgatct   9420
ttgttggtat aaagtctgtt ttatcagaga ctaggattgc aacccctgcc tttttttgtt   9480
ttccatttgc ttggtagatc ttcctccatc cctttatttt gagcctatgt gtgtctctgc   9540
atgtgagatg gatttcctga ctacagtgca ctgattggtc ttgactcttt atccaatttg   9600
ccagtctgtg tcttttaatt gcagcattta gcccatttac atttaaagtt aatattgtta   9660
tgtgtgaatt tgatcctgtc attgtgatgt tagctggtta ttttgctcat tagttgatgc   9720
agtttcttcc tagccttgat ggtctttaca atttggcatg tttttgcagt ggctggtacc   9780
agttgttcct ttccatgttt agtgcttcct tcaggagctc ttttagggca ggcctggtgg   9840
tgacaaaatc agcatttgct tgtctgtgaa ggattttgtt tctccttcac ttatgaagct   9900
tcgtttggct ggatatgaaa ttctgggttg aaaattcttt tctttaagaa tgttgaatat   9960
tggtccccac tctcttctgg cttgtagagt ttctgccgag agatcagctg ttagtctgat  10020
gggcttccct ttgtgggtaa cccaaccttt ctctctggct gcccttaata ttttttcctt  10080
catttcaact ttggtgaatc tgacaattat gtgtcttgga gttgctcttc tcgaggagta  10140
tctttgtggc gtactctgta tttcctgaat ctgaacgttg gcctgccttg ctagattggg  10200
gaagttctcc tggataatat cctgcagagt gttttccaac ttggttccct tctccccatc  10260
actttcaggt acaccaatca gacgtagatt tggtcttttc acatagtccc atatttcttg  10320
gaggctttgt tcgtttcttt ttattctttt ttctctaaac ttctcttctc acttcatttc  10380
attcatttcg tcttccatca ctgataacct ttcttccagt tgatcctatc agctactgag  10440
gcttctgcat ttgtcatgtg gctctcttgc cttggttttc agctccatca agtcctttaa  10500
gaacttctct gcattggtta ttctagttat ccatttgtct gatttttttt caaagctttt  10560
```

```
aacttctttg ccattggttt gaatttccac ctgtagctca gagtagtttg atcatctgaa  10620
gccttcttct ctcaacttgt caaagtcatt ctccatccag ctttgttccg ttgctggtga  10680
ggagctgcat tcctttggag gaggagaggc gctctgatct ttagagtttc cagtttttct  10740
gctctgtttt tttctcatct ttgtggtttc atctatcttt ggtctttgat gatggtgacg  10800
tacagatggg tttttggtgc ggatgtcctt tctgtttgtt agttttcctt ctaacagaca  10860
ggaccctcag ctgcaggtct gttagagttt gctagaggtc cactgcagac cctgtttgcc  10920
tgggtttcag cctcagtggc tgtagaagag cggatattgg tgaaccacaa atgctgctgc  10980
ctgatcgttc ctctggaagt tttgtctcag aggagtaccc gaccgtgtga ggtgtcagtc  11040
cgcccctact ggggggtgcc tcccagttag gctactcggg ggtcagggac ccacttgagg  11100
aggcagtctg cctgttctca gatctcaagc tgcgtgctgg gagaaccact gctctcttca  11160
aagctgtcag agagggacat ttaagtctgc agaggttact gctgtctttt tgtttgtctg  11220
tgccctgccc ccagagatgg agcctacaga ggcaggcagg tgtccttgag ctgtggtggg  11280
ctccacccag ttcgagcttc ccagccgctt tgtttaccta atcaaacaac taactcagca  11340
atggtggccg cccctccccc agcctcgctg ccaccttgca gtttgatctt ggatggctgt  11400
gcttgcaatg agcgagactc tgtgggcata ggaccctcca agccaggtgc aggatataat  11460
ctcctggtgt gctgtttttt aagccggttg gaaaagcaca gtattagggt gggagtgacc  11520
caattttcca ggtgccgtct gtcacccctt tctctgacta ggaaagggaa ttccctgacc  11580
ccttgtgctt cccgggtgag gcaatgcctc gccctgcttt ggcttgcgca cggtgcgctt  11640
cacccactgt cctgcaccta ctgtctggca ctccccagtg agatgaaccc ggtacctcag  11700
ttggaaatgc agaaatcacc agtcttctgt gttgctcatg ctgggagctg tagaccagag  11760
ctgttcctat ttggccatct tggctcctcc cctcagcaca gtttttagca tgaactaagg  11820
cctcaataaa tattagttcc cttctccaat tcagaaagtt gtctgccttg ataagacaat  11880
tgtttttatt gtgaaagtga ggtggagatg ggggattgtc tctcctataa aaggtctaag  11940
aagttagcaa atgctgtttt tcctttttgc tcctcagttg cataagtaca tggtagaaat  12000
tgggtcactt tgcctaaacc ggttttctat aacctattaa gtattaaaag cttgacacag  12060
ataagtagag gctgataaga ttctgtcctg caccccactc ctatcaaatt tggaagaact  12120
gacctcttcc gggaagaatt gcaatgctaa atccaaatgc ctatggttct atcttataaa  12180
caaatggtgt cctcaaaatt catttatgta aatcatttga aatttaagaa aaaaatatgt  12240
tcagagaaaa atatgttaaa tgtcaaggtg aattagaaag tgtggcattt agtcaagcat  12300
aaattaatat tccaactttc tagttacttt gtagtaactt atttaacatt ttggtgaaat  12360
gaggaacaaa gtgtccacct ttttttcctg aatattttat ctgaagatct aggagagaga  12420
tgtgaaatag tatttttctg gggaagtagg ggaaatacaa agaaaagtaa tgacttcagg  12480
tatattctcc actggtacag caggatggga gatattatca acaggtggta agtataaaaa  12540
tattgaagag gtacaatttg gatcagcatt acaaccaaga atggagaatg acattcagga  12600
ttgaaagaaa catacaagag ggcagaaagc tttcttcttg ggactgtggt ttcatgtgtc  12660
tgcaggtgct atgggtatat tgagaatggt tctaaaaaca ggggcttggt ttaggttgtg  12720
aagaccatca aatagaaact gtgaatttta ttttgtgtcg ttaaagggat ctttgaaaga  12780
ttcttaggat aaatatgata tgcataggat agaaagaaag gtgggagaca ggacaaacag  12840
aagttaatca attgaaataa accaggtttg gagtggtggg acaatagcct tcaagacatc  12900
aagaatattt gttagtagaa agaaaatcga agcctaaaac taaaggaaga ctatccacct  12960
```

```
tgcaagtcat acagagatat ttgctattat ataatttttt taaaaaaaga tttcctaata  13020
tttaaattat gaagaaagag atagaaacag atattcatgg aaaaaatggg gtgaaattaa  13080
tcaaagggca gcttattacc ttgagactaa acagccattg actttttttct tacctcactg  13140
aacccagaaa cccgacatat ctaggtacag gcatgcataa aacatgtaca cacacaaaat  13200
gtaataattg gagttcactt agaggtacac atgtatgggt ttctgtattc aaccatatgt  13260
tgatatatac tcacatatat gtaagtgata atatcctgtt tgttacttcc acatttatgc  13320
actatccctt aaatatgtat tatatatatt tatattattc agaatccatc agcccttgtt  13380
gaataaatta gtgaataaaa tatagagtcg agtctcatta ttcacagatt ctatataaga  13440
aaatttgtct attcactaaa attcctttgt aacaccaaaa tcaatactgc tggactttca  13500
tgggcattca catgcatgtg caaagtggtg aaaaatttga gctgccatgt tcccaactaa  13560
ggttgaacaa aatgaagctc tgtcttcttg tttctgctca catatgataa agaaatatcc  13620
ttttcacact gtatttattg ccacattttt ggcatttttg tgttttgtgt ttctgagttg  13680
aatgtttcga atgggcccca aagatagtgc tgaagtgctc tccggtgcac aagagtatct  13740
gagggaaaag atacatatgc tgtataagct tcctccaggc ctgaactaca gtgttgttga  13800
caactaattc aatgttaatg aatcaatagt atgtattaaa taaagtgtct ttaaacaaaa  13860
catacataaa acacagttct atattgaaca atttaccaaa atattgtgac cagaggcaga  13920
caggcatata actaacccca catctctcca aggaacaatg gttcaatatt tgctaattca  13980
gtgttcccag caactttata aaacataact actgcaacaa gtatcaactg tacatataat  14040
atatattaga catattgtat aattactgcc ctattaaaaa tcatgtatct atgctgtgtc  14100
tgcttatata gatatcttag atacataaat atgtattgtt tacatacata ggagcaagaa  14160
tgtatttcta aaactccatg aagaacacat tatattctat ataaaagagt cagttgaagt  14220
aaaaagttaa ctcattttac tagtctttaa agtaggactt taatgactct caaaataaca  14280
atttctctca tacattgact ccaaaacttt agttgttgaa tttattctgc agatatggcc  14340
acataaaacc aaaatggcat atgatatatt aagaacatct ttaatatgaa atgattagat  14400
acaacctaaa agctgatgaa tatagaacca gttgcatata ttatggacaa cttaataccc  14460
tgctaccata agaaaaatga gaaagactta ttaagattaa gtatatagag aagataaaaa  14520
ggtagagaat gatgtttaag gtatgctacc atttgcattg aaaaggaaaa tattatgtac  14580
ttaatgaaaa atccatatta tatttctgga taatgggaca agagttagag gaagaatctt  14640
tgttttattt ttttaatttg cattttcaac tatatgcatt ttctcttgga aaagaaatga  14700
acaaaatcaa aataaagtaa catcatgatg gtggtaaggt caagcaatac cagagttgct  14760
ctgagaagta cttggagtac actttgctct ttttaacaaa tccaaattct gtttgctttt  14820
tgagcctgat tccagtggtg tctcctttat aaaactgagg ccattctaat ttaattcttt  14880
atattatttt tgtatctgtt ttgaatatct actctgtgca aggggctaat aggcacattt  14940
taaaactaga aggataaaga aaacatatat ttgcttttat aaattttaca atataggtgt  15000
gtagaaaaga taataattta aatttctata atttaaaatg ttcatgtaat ctggtgtgtg  15060
attctatatt acttacttgt ttcaaatttc tctccacaaa tttatttttc tattaaattg  15120
taatctcctt aggctagaat ttgtgtctgt ctttcctact tttgtttcca gcattgacct  15180
agcagagtgg taacgacata gtagaccctg agtgaatgtt agtgaatggt tgattgattg  15240
atgatgatct tgtggctttt cttatttcta aattatatat tgtaaaaata aaataaacta  15300
```

```
tactttttct tccttaatag gtgattgttt caaactgagc atcaacaaca aaaacatttg  15360
tatgatatct atatttcaat catggaccaa aatcaacatt tgaataaaac agcagaggca  15420
caaccttcag agaataagaa aacaagatac tgcaatggat tgaaggtaga ataagtttta  15480
tgtttttgag ctaaaataag taaataggga actttaatgt atagaaaagc aagttgttaa  15540
aaagaacatt atgtttcaaa ttataatttt caattgaagc atatattgaa atattaacat  15600
aatgattcat accttgattt aaaccagtct tttaatctga ttaagtattt ctttggcgaa  15660
atttttgatg cttaatagtt tatcaatgta gaaaatttag aaatattttg atagcttctc  15720
tttggttttg gattgatcac gacatattta ggaatgtgat taaaataaaa aatgcataat  15780
gaataatatt ttaaaattct tagaattgac ttataaactt agaatattaa tgtcttgaga  15840
ctcactttgt gatactgact tatttaaaaa ttcttttaaa aaaaaaaaca aaaaacagga  15900
tttaaaaaag ttctgataag taatttaggc tcatggaacg gaggtctatg atagtcaaaa  15960
acttggccaa aagacctgtt tgacgattta gaaaagccat ttaatgtttt catttgccag  16020
ctggtaaaag taataattct gctttttgct tttggcacaa actgtattaa atgatacagt  16080
tgaggtatta agtgatgctg gcatttttat aaacaggaat gagtactcct aagcacaatg  16140
ctaaatgaga agccaagact cagaaaagtt aagaaatttt cctgaagtca tctacattgt  16200
gaattgaaaa ccctggaacc caagacaaag cctttaaatc cccatatgga agtcttgagg  16260
aaatcaagaa ataagggtca ccttttatca atgttttaac tttttattt agtcaaattt  16320
gtagtcttat acagctgaat aaaggccacc aagattggag tcaattacaa taatgttata  16380
aaaggttcct tttagctcct tccagggaac ataaaatttg tttgttttct gagattactg  16440
ataaagcctt ctctgatgaa atatttgagt aacatttagg ccaagtggca gtcataagga  16500
aaaagtattg gttaatgcaa gtgaattatg ttctatattc taaggataat ataatgtact  16560
gaattgtttt tatttttaaa tactgagtgt tacagtaatt tcactgacat gtgcatagca  16620
aaatggcagc aaactgcctg aagcaataaa atttccagag tgatccctta tagcatatct  16680
ggagaagctg ggagttaggg aattagcagt gtgtggaaag gacattaact gcagcccaat  16740
aaagaagact agagctagag gaagatactg ggataagact ggcatcccta atgctggtat  16800
ttcagaaaca tcgctaaatt ggttaatcat gtctacaagt gatatttaaa ataatatttt  16860
cactcactta aattgttaac attgatatgt tgttgataaa gaatattaaa ctcaacaatc  16920
attttacaat aattctgtaa agacttgcgt gcctgtagtt gaggtttgtt gcatttctga  16980
gcttactttt tattcatgag aaatgaaaac ataatgggag aaaattttt aaataaaggg  17040
tattttaatt ttttatgaag tttgggactt caaagtatta acaaaagttg ctgaaaatat  17100
attgactttt actttcatta aattacattt tatcatctaa tttcttaatt ttctgtattt  17160
gaaatattat gatttagaga tatctctgta gatagaaaga taatgaaaac aatagtaaaa  17220
caaatgtaat tcaggagcat aaaaaaagat gagagaaacc ttaataatag tagctaacat  17280
ttatcaagca tttactatat gccagacatt gatttagtgt tttacttttg ctaacagatt  17340
ttttccttac cataattcta tcaactggat ggtattatct ccccttttca gatgaaaaaa  17400
cctagatata gacagggcaa atgtcttctc ctaggtctca aagttggtaa ttggtacact  17460
gaaggtctga actcaggcaa tctgattcca aatcctatgc tctcaactgt attccatatt  17520
gctaaaataa atgtggattt ttgtaatatt agtaccctca agatgttatg gcaagcaggc  17580
ttttataagt ggtgtcttta ataactttcc tcattcccata cttctaaaaa attatcttaa  17640
ggttaaatta ttgagtgtca agcaactgtg gattctaaca cttgctaaca tgcatgcaca  17700
```

```
cacccaaata tacatgttgt tactgactta catatacaga cacagcaggt ggcaatatat  17760

aagtgcaaat tgataatata tccgtggaaa tacaaacaaa actttgagaa atcaaatact  17820

tgaattcttt tctacccctt ctcctcaatt tttgtactga actaactaca ttacatagaa  17880

cctgctagta tatgtttcat cattacactt gtcatttctt ctcttcaaat ttaaacccaa  17940

caagatacag gggaagattt aaatgcaatc caaagaaaac aggaaaacaa ttcaagagtt  18000

taaagatgac atagtcattt taagaaagaa ccaaaattaa cttctgaaat taaatatttt  18060

actacaggaa tttcataata caattatagt aattaacaac aaaatagacc aagcttaaga  18120

aagaatctca gagtttgaag attacccctt tgaatcaaca caagcagaca aaattaaagg  18180

aaaaatatta atgaaaaaaa cctctgagaa atatgggatt atgtaaagag accaagcctg  18240

tgactcattg gcattcctga aagaggagaa agagtaagca acttggaaaa tgtctttgag  18300

gataaagtcc atgaaaaatt tcccagtctt gctagagagg tggatatgca agttcaaaaa  18360

attcaaagaa tcccttcaag atactataca agatggtcat ccacaagaca cataatcatc  18420

agattctcca aggtaaacaa gaaagaaaaa aaccttaaag gcagctagag agaaggggca  18480

ggtcacttac aaaaggagcc ccatcagtct aacaatagat ctttcagcag aaagcttaca  18540

agctagaaga gattggggac ctattttcac catccttaaa gaaaagaaat tgcaactaag  18600

aattttatat tctgccaaac taagcttcat aagtaaagaa aaaatattat tttcggtcaa  18660

gcaaatgcta acagaatttg ttaccattag acctgcctta ccagagatgc ttaagggagt  18720

cctaaacatg gaaatgaaag aatgatacct gtcaccacaa aaatagactt aactacagag  18780

cccacagaca ttataaagca attatgcaat caagccaaca taataaccag ctaacaacac  18840

tatgacagaa tcaaatcctc acatatcagt attaatcttg aatgtaaatg ggttaaatgc  18900

ctacacttaa aaggcataga atagcaagtt ggataaagaa gcaagaccca accgttttgt  18960

tgtcttcatg actcatgtat catgacatcc ataagataga aaatgaataa attgaaataa  19020

tatttatctc agagttgtca ggatatttat aaggtgctta gcacagtgtt acatagaaac  19080

tcaataaatt ggaaagttcc aacatagtag cattatagtt gctgcacttt ttttgagaca  19140

gggcctctgt cacccaggct ggagtgcagt ggcataatct tggctcactg caaactccac  19200

ctcccaggct caagtgattc tcccacctcc tgagtagctg gaactacagg cacatgccac  19260

ttcacccagc attttttca ttttttttt ttttttttt ttttttagta gagatgaggt  19320

cttaccttgt tgccaggctg gtcttaaatt cctaggctca agcaatcagc ccgccttggc  19380

ctcctaaagt gctggaatta caggtatgag ccatcacatc tggaagctgt ttctttttaa  19440

agtgactaca ttaatttact tgatcacgag taatacataa atgaaaattt gagaatacat  19500

tcactccaat atttggaatt atgtgacttc tagattttg caatttaagt aggcataaaa  19560

tggtactttg ttttagtatt tgtctgtgct ccttgattct tataaatatt atattttgtg  19620

aaatccattg ctgaatgcaa gtggtgctgg ttacatttgc ctatttccaa gttttagtac  19680

atttattttt gaaatatatt ttatcagttt aaggacttac ttgtaatatc tttgtgtggt  19740

cttggtatta ggttaatgtt ggcctcaata aatgagatag gaagtatttt tttctgcttc  19800

taacctctga aaaaaactgt agagaattga tataaattaa ttcttaggta tttggtagaa  19860

ttcaacagtg aaaccatgta ggcctgtttc tttctgtttt ggaaagttat taaaatcagt  19920

tcaatttctt aaacagaaat agtcctttta atattgtcta tttattcttg tacaaaattg  19980

ggtagatcgt gtctttcaat atattggtct attttatata ggttatcata gttgtaggca  20040
```

```
gagtgttgct tatagtattt ctttattatc cttttcatgt atattggatc tgtagttatg  20100
tccccgcctt tatttctgtt attagtaatt tgtgccttcc ctcatcttct taggtaacct  20160
ggctgggtca attttattaa tctttctaaa gaattaactt gtggttttgt caatttcctc  20220
tattgatttc ctgtttatga tttaattgat ttcaggtcca atttttattc tatttttttct  20280
tgtgcttact taaaatttaa tttgcttttc tttttgattt tcccaaggtg gaaacttaga  20340
tattgatttt agcattttct tgttttctaa catatgcatt cagtgcaata aatctctaag  20400
tcttgatttt gctacctttc acaaattttg atcacttgta tgtttaattt tatttttttc  20460
aagatgtttt aaaattttttc ttcagatttc ttttgactca taagttactt aaaagtgtgg  20520
tagttaatct ccacatattt tggtattttt ccagttatct ttctgttata ttctagctta  20580
atttcattgt catctaagag aagacattat tagtttaaat gtgttaaggt gtgttttatg  20640
gcttaggctg tggtatatat tggtgaatat tccatgtaag cttaagaaga atgtgtattc  20700
tgttgttgtt ggatgaaata acatatagat gtttattata tccagttaat tgatgatgtt  20760
gttaaggtca atcatgttct tcctgttttt acctgctgga tctttccatt tctagagaga  20820
tgtagagtct ccaaatacca tagtgtattc atttatttct ccttgtattt ctactggctt  20880
ttacttcaga tagtttgcag ctctgttgtt tggtgcctct atgttaagaa gtgttatgtt  20940
ttcttaagaa ttgacccctt taacattttg taatgccccg tttttacctc tgttaatttc  21000
cttgctttag agtctgctgt gtccaaaatt aatttagatt gtcttgcttt gttttggtta  21060
ttgttaccat ggaatgtttt tctccacttc tttacttttt taaaaaatta cactttaagt  21120
tctgggatac atgtgcagaa tgtgcacatt tgttacatag gtaaacacat gccatggtgg  21180
tttgctgcac ccatcaaccc gtcatctaca ttaggaattt ctcctaatgc tactccctag  21240
ccccccaacc cccaacaggt gctggtgtgt aatgttcccc tccctgtgtc catgtgttct  21300
cattgttcaa ctcccactta tgagtgggaa catgcagtgt ttggatttct gctcctatgt  21360
tagtttactg agaatgatgg tttccagctt catccatgtc cctgcaaagg acataaactc  21420
attctttctt ttggctgcat agtattccat ggtgtatatg tgccacattt tatttatcca  21480
ttcaattatt gatgggcatt tgggttggtt ccaagtcttt gctattgtga atagtgctgc  21540
aataaacata catgtgcatg tgtctttata gtagaatgat ttataatcct atggatacat  21600
tcaacaatgg ttgaattaat ttacactccc accaacaggg taaaagcatt cctatttctc  21660
cacatcctct ccagcatctg ttgtttcctg actttttaat gatcgcttcc aactggcgtg  21720
agatagtatc tcattgcagt tttgatttgc attctctaat gaccagtgat gatgagcttt  21780
tttaatatgt ttgttggcca cataaatgtc ttattttgag aagtgtctgt tcatatcctt  21840
ggcccacttt ttgatggcat tgtttgtttc tttcttgtaa atttgtttaa gttccttgta  21900
gattctggat attagctctt tgtcagatgg atagattgta aaaattttct cccattctgt  21960
aggttgcctg ttcactctga tgatagtttc ttttgctatg caggagcttt ttagtttaat  22020
tagatcccat ttgtcaatct gggtttttgt tgccattgct tttgtgtttt tagtcatgaa  22080
gtatttgtcc atgcctatgt cctgaatggt attgcctagg ttttgttcta gggtttttat  22140
ggtgttaggt cttacattta agtctttaat ccatcttgag ttaatttttg aataaggtgt  22200
aagaaagggg tccagtttca attttctgca tatggctagc cagttttccc aacatcatat  22260
atattaagaa gggaatcctt tttccattgc ttttttttggt cagacttgtc aaagatcgga  22320
tggttgtaga tatgtggcat tatttctgag gtctctgttc tgttccattg gtctatatat  22380
ctgttttggt aaaagtacca tgctgtgttg gttactggag gcttgtagta tcatttaaag  22440
```

```
tcaggaagca tgatgcctcc agctttgttc tttttgctta ggattgtctt ggctatatgg  22500
gctttttttt tttttttttt ttggttccat atgaaattta aagtagtttt ttccaattct  22560
gtgatgaaag tcaatggtag cttgatgggg atagcattga atctataaat tactttgggc  22620
agtatggcca tttttacaat attgattctt cctatccatg agcatagaat gtttttccat  22680
ttatttgtgt cctctcttat ttcattgagc agtggtttgt agttctcgtt gaagaggtcc  22740
ctcacacccc ttgtaagttg tattcctagg tattttattc tcattgtagc aattgtgaat  22800
ggaagttcac tcatgatttg gctctctgtt tgtctattat tggtgtatag gaatgcttgt  22860
gatttttaca cattgatttt gtatcctgag actttgctga agttgcttat cagcttaagg  22920
agattttggg ctgagacaat ggggttttct aaatatacaa tcatatcatc tgcaaacaaa  22980
gacaatttga cttcctctct tcttatttga gtatctttta tttatttctc ttgcctgatt  23040
gccctggcca gaacttccaa tactatgttg aataggagtg gtgagagagg gcatccttgt  23100
cttgtgccgg ttttcaaagg gaatgcttcc agctttcacc cattcagtat gatattggct  23160
gtgggtttgt tatagatagc tcttattatt ttgagatata ttccatcaat acctagttta  23220
ttgagagatt ttagcacagc tccagtgtgc agctcccaaa aagatcaacg cagaaggtgg  23280
gtgatttctg catttccaac tgaggtaccc agctcatctc tttgagactg gttagacagt  23340
gggtgcagcc aacagggggc aagccgaagc agggtagggt gtcacctaac ctgggaagtg  23400
caagttgtca ggaaacttcc tcccctagcc aagggaagcc acgagggact gtgccctgag  23460
gaaaagtgca ttctggtcca gatactatgc ttttcccagt ctttgccact ggcagaccag  23520
gagattccct cgggtgccta caccaccagg gccctgggtt gcaagcacaa aactgggtgg  23580
ctgtttgggc agacactgag atagctgcag gattttcttt ttaaacccca gtggtgcctg  23640
ggacaccagc aagacagaac ccttcactcc cctggaaaag gggctgaagc tagggaacca  23700
agtggtctag ctcagtggat cccaccccca tagagcccag caagctgaga tccactggct  23760
tgaaattctc cttgccagcc gagcagtctg aagtcaaccc gggatgctcg agcttggtag  23820
ggggaggggt gtctgccatt actgaggctt gagtaggtgc ttttccctca caatgcaaac  23880
aaagccacta ggaactgggt ggagcccacc gcagctccac aaagcccctg tagccagact  23940
gcctctctag attcctcctc tctgggcagg gcatctctta aagaaaggca gcagccccag  24000
tcacgggctt atatataaaa ttccctctat ctgggacaga gcacctggga gaaggggcag  24060
ctgtgggcgc agcttcagca gacttaaact atcctgcctg ctggctctga agagggcagt  24120
ggatctccta gcaccattct caagctctgc taagggacag actgcctcct taagtgggtc  24180
cctgactccc gtgcctcctg actgggagac acctcacagc agggttcaac agacacctca  24240
tgcaggagag ttctggctgg catctggtgg gtgcccctct ggaatgaagc ttccagagga  24300
aggaacaggc cgcaatctct gctgttctgc agccactgct ggtgatacct aggcaaacag  24360
ggtctggagt ggacctccag caaactccag cagacctgca gctgaggggc ctgactgtta  24420
gaagaaaaac ctacaaacag aaaggaatag catcaacatc aacaaaaagg atgtccacac  24480
aaaaacccca tctgaaaggc accaacatca aagaccaaag gtagataaat ccacgaagat  24540
gaggaaaaac aagtgcaaaa aggctgaaaa ttccaaaacc cagaatgcct catctcctcc  24600
aaaggatcat gtttactttt aatctatatg tgtttatata tttaaagtgg gtttcatgta  24660
gacaacatat agttggttct tgttacttga tctactgtgt caatttcaat cttttaatta  24720
atacatttag atcatttgcg ttaaaagtga ttactgatat atagtcatgt gtcatttaac  24780
```

```
aacaggaatg cattatgaga aatgcattgt tagataattt tgtcattgtg caaacatctt  24840
agcgtgtaca tacataaacc tagatattat agcctactac acacctaagc ttatggtata  24900
ggctattact ttgatgctac caaaacctgt acattattgt agtttactaa atactaatta  24960
caacacagtg atattggtgt atctaaacat atctgagcac agaaaagata aagtaaaaat  25020
atggtattat aatcttatgg gaccatcatt gtatatgctc tccaacattg acttaaatgt  25080
cattatgaca tgtgtgactg tagttagatt agtatctacc atagcggttg ggttgcctgg  25140
gtgtttgcaa gataaattta caaataattc aagtccactt tcacgtgacg tcataccact  25200
tcatgggtag tatgagtacc tgataatagc aaattattta taatactttc cttccatttc  25260
ttgtatcatt attgtcattc atttcaattt tgtgtcagca tacataatca aatacattat  25320
agatattatt ttaaaaacag ttatgtctta gattaagaat aagaaaagta ataatttata  25380
ttttatgctc acttatttct cctccaatgt tttccttgct ttaagtagat ctgagtttct  25440
gatttatatt attttatctt tctgtaaaga actcctttta acaccttgca aggctgatct  25500
aaaggcaaaa catttctttc agtttcattt ctcagaggaa gttttatttc tccttcatgt  25560
tagatggata aatacacagg gtatggggaa ggtatttttt cctctgtatt cttttgggat  25620
ttttttcctt tgtctgtgat tttctatagt tttaaaatga catgactagg tgtaactttt  25680
tgggcattta tacaacttgt tattctatgg acttccagga tctgtggttt gttgtctgat  25740
actaatttgg ggaaattctc ggttgttatt gtttcaaata tttctttagt ctctatttct  25800
ccttctagtg attccattat gtatatgcta tacctttttt agttggccca cagtttttttg  25860
atactttgtt ctgatttttt tgtctttgtt atttttattt gctttttagt tttgcagatt  25920
ttaattcata tatcctgaat ctcagatatc ctgttttcag tcttgtgcag tatactgatg  25980
tgtttaccaa aggcattctt catttctgct acgatgttgt gacattataa tttttttaat  26040
gaaattttta tctgtctgct tacattgctc tgttcttgtg tgcttcttta ttttaccact  26100
agaacactta gcatattaat cacagttgtt ttaaattctc agtccaataa atccaacatc  26160
ctttctgtat ctgagtttgg ttctgattct tgctctgtct cttcaaaatt atatatattt  26220
tttttctttt agatgactgg taatatattc tggatatcca gacataatgt attgagtttt  26280
gtaaaacctg ctatacatag gccttcaata attgttgcta aggtgtggga gaggagaggc  26340
ttttttttt tttttttgc ctctggactg taaccttcac aagtgttttt ttagtatttt  26400
ttttccttct tggtcagaat gggtttggta gagtgagatg gattttggta ttttccttct  26460
gtcacatgga agactagaat tggctggagc tgggtatttc ctttcccttc ggtcagttag  26520
gctctaataa cacaccatct tatgaggctc tgataaacta gttctgccta agggcaagca  26580
ctaaaagtcc tattaaaaac agagggctct agtctatttc aaaaatgagt cttgtctcct  26640
catgctactg aaagaacaag ataatttttc tccaacattt actataagaa cctggtcaag  26700
ctcctggagg gaaaactcaa aatgtggagg tcaccgactg ggttcccttg gagtgtttag  26760
tgctcagact taaccacact gagtgagact ctagcagttt atcaattata gtgaaggtat  26820
ttctaccttg tcactggttc ctgtgcagtt tctgttcatg agtctctact gctataagct  26880
gtgacacttt gtaatcacct atttgtctct ccaatcttga aggcagtcga ttgccattgg  26940
tcctcacctc ttttacagat ccagaaagag ttgctgcatt ttaaattggt tcagtgtttt  27000
tcttgttgtt actataaaat ggcaagctcc aagctccttg aaggtttcca gagcctagaa  27060
accagaaata ccagcatata tttttattg tattttctta tctcatgtct tacagttcta  27120
cattttactt aagaattcat tgtgattgct tgattaatat acaagttatt ttaaaataac  27180
```

```
attttcttca aatatttgga gatttttcgt aataaatttt ttgccagtaa tatttgtcat  27240
aattgcattg tggaagctat gacaactaat ttttgaaatt agttgagact tctctatgtc  27300
ctagtacatc attgatgttt gtaagtctcc ctgatgtact taataaaaat gcatattcca  27360
tattctttca attgttggat gtataatttt atatgtgtct gagaggtcag tcttgttaat  27420
tgtgttattc agatcttcta tgtccttgct aatattttaa ctatttcact tatcataatt  27480
gaaagaaaga tgttgaattt ttttcttaca aaagcagttg tattgatttt tgcttatata  27540
ttttgcatct actaagtgca ttattatata accgttttat cttttaggat gatataattc  27600
aatatatgga ggacttctct atccttaatg atgtttctat gtctatttgg gctattattt  27660
atacacctat aaaattttct ctaagtggtt atattttctt atcattttac tatcacgaag  27720
aatttcttcg tgatttagga atatctctta taaaaagcac agaggtaaat tttgaagaaa  27780
aatccaaact aaaaattatc tatctttaaa ctagcaattt tctacactta tgtttattgt  27840
atctattgat atagttagac ttgcttttac tatcttacat tattatggtg attttcccct  27900
tttttaatgc tcccttaaaa ttctttctta tactttttga atgtatatgc ctatctctct  27960
cataacaaga caaacattct agcatgattc tatgatctga atgtttgttt ccccccaaat  28020
ttgtatgtcg agtcataatc accaaggtga ttctattaga aggtggagac tttggaaagt  28080
gattagttca tgaaggtaga gtcctcatga acaaaattag tgtccttatg aaagagaccc  28140
aatagagctt ccttgcctct tctaacatgt gaggttacag tgagaagatg gttctcacca  28200
aataccaaat atgttggtgt cttgatctca gacttcccag gctccagagc tgcaaaaagt  28260
aaatttctat tgtttataaa gtacacagtt ttcttatatg ctatattttg ctatattttc  28320
ttacagcacc ccaaacagac tgagacatat gttcacatac tcttttatat gcctctttac  28380
cctctataca atatgatgct atctggattt tcaatctaaa attttaaatt ctagacacta  28440
tgactatttt acctcctttc ctgtttttag ttttttttta agacattgag aaaatttatc  28500
aagtatttta ttcactttgc tttacaaatc tcatgcaaca ccttcagaat tggattcttc  28560
ttttatttaa gcaattcttc caaaattgtt tccagtacgt gtttggttgc agtatttttg  28620
aggccttata tgcttgagca tatatctctt tatagctgag aggctgttta tctcaatgta  28680
aaattatggg ttcaatgctc ttttacttca gtacttaaaa aatatatttc tttgtctttt  28740
gtgtacccac ttttgctgtt agaaagtgat atactttctt tcctgaaagg cctcaatttt  28800
ttttcttgtc tttgatattc ataaatttta atatacttct tccaaatatg tctgtgttct  28860
tacttatctc ttgtgttgag cattcaatgg gcactctcaa cctgcatttt ttgttttttt  28920
taatcttagt aaattatttg aaaattttca tttattattt ctttaaatat ttctcctctt  28980
caacttattt tttctcattt taaggcatta ataattaaat tattctcaat tttagttaaa  29040
aattatgtat atcttaacct tttacctata tatgctttca atgttttaaa tgaaataacc  29100
aattttattt tccaattctt tcttgtttta agcccatata ttattttata ctattttaca  29160
tcttgtactc catattttct acttgttctt ttttgttatc ttattttgct tttatttcat  29220
tttgctaata ttcttttctt atatattttg tgtatttgta atgcttaaac tcctgttaag  29280
tgttttgtaa aacaattact ccttatggtg tcttcaaacc agtttacttt tttctttctc  29340
ttttgaaatg ttttctcaaa gacatcacta ttttgccctg aagtcacatt tacttagtta  29400
tgatagtttc ttttttatag taattgcaca ggggaagagc taaaggatag aactctgtca  29460
ttgtgaaccc tgaaagctca gaaaaagggg agggaaatga gcctcaaggt gatgaccagt  29520
```

```
aaccaataaa tcacgtcact ctgccctttg acaaacattt ctttatccat ggctccctca  29580
gtcccctgaa tgcgaaattg ctttgaggag attgttaact agtactgcag aaatactgag  29640
gggattacct gtagaaggga atgctcaagg ctagtcagcc tttcctcctt tgctcagctg  29700
ctctgattca gagctactct gattttactc tggaggacac atgcaaccaa tgtctgaaca  29760
gtcatactca atccctgcat tgaggtagaa agcactgatt cctagaggct gatctgaatc  29820
atgcaactgt attgaaggca acaaaaaata ataaaatagc catgtatttt aatagggaaa  29880
gtatatagta attgaaaaga aaaaccaaaa tcaatacaag tagtattgtg accgagagac  29940
aaaggtaaat ttgaagatag gtttgtgatt tcataatgga gacctttgaa tgctagaagc  30000
taccccctcc ctttgtaaag aacaacatta ggtaaatgat taaaaaatta tgtcaaagtc  30060
tatgattttg aaactctacc atatttgaaa atattatatt aaaataatga tactaaacaa  30120
agaatttatg acaaatgttc atcttttaag taaaagaacc ttaaaatttg taagcagcta  30180
aatctaatga tataggcaac tgctaggata tcacaaaaga atgggatttt aatagtgaac  30240
ttatacaatt tgcctgaaat taatcaaatc agcacagaaa tgcacagatg acaaacactg  30300
taagatgtaa gaggaattaa tcataagagg tttatttggc taaagtgaca attgttaaag  30360
atagaattgc ctaacgttag ttaataacag aaaaaatatc agaaatttta aaaaatgctg  30420
tcttaatcta ttaaaattat ataaagataa agcaaaacaa tgtaggttta taaacaagaa  30480
cctttaaaaa agcataatac tgatgcttat tacaaattta tatcttgagc tggggtacat  30540
catccaattt acgcatgaga aaagtgtttt ataatttttc actctgtaat tcatatttta  30600
agttcatctg aaatgtattt tacagaggta agaacaagca acttggtgct caactctctt  30660
cctgctcttc gcctagtgct aaaataattt gtgtaaatga actgtgaatg aatttaagtt  30720
tcagaaataa aatttatatt aatagagaga aagaaggata aatcaatagt cttccaaata  30780
tgatacatgt acaatgcaat gatattcaca aacatcttca tgaacacacg aacataattt  30840
cttttgaatc ttaccatgac cttctaaaat aagtaagcta aatattctat attatactac  30900
tatttatgag gaaactacat ttctgtgaat tgtgtaactt tttcatcttt ataaggttag  30960
caagcaaaaa caaacaaata acaaaataaa caaaaaaaca aaaacttggc ccagatctga  31020
ctttaaagta ccttcacttt tattgtatca catacgatct cagtccacag atgggttcct  31080
gatttagcca agaatatagt aaagtgagtg taaagtagaa gaaaaaagaa ggaaaatatt  31140
aggtatagaa acctacatga aataaaatga aataaagaga gcctactctt tctgaaatgc  31200
accagtaaaa tgtactccta tcttgtgtat taagtttata atcatacatt caattcaaaa  31260
tttaactaaa actatggaaa ctgagagcta ataataaaat gatatacaca gcattctaac  31320
cagaaaatct tctaagcaat tgtacaattc agataagaag aaataattac aaatgttcag  31380
aaattaagat taattaagac tgtaaaattt tttttttttt ttttttgaga cagggtctca  31440
ctctgtcacc caggctggag tgcagtggcg cgatcttggc tcactgcaag ctctgcctcc  31500
caggttcacg ccattctcct gcctcagcct cccaagtagc tgggactaca ggcgcccacc  31560
accacgccca ctaatttttt gtatttttag tagagacggg gtttcatcat gttagccagg  31620
atggtctcga tctcctgacc tcgtgatctg cccacctcgg cctcccacag tgctgggatt  31680
acaggcgtga gccaccgtgc ccggccaaga ctgtataatt tgttcctgaa gggcagggaa  31740
aatgtagtgg taatttttca agatgaattg gaagataaag aaagagaggt cacattattt  31800
gtgttattca actgaaatag ttttgaattt caataaaaca agctaagaaa tgccctttgt  31860
catcaaattg atgtgaagag taaaaaaatt ttaaaaatga aattctctaa gataatatgt  31920
```

```
gaaaataaga ctatttaaat ttcaacaaac atttaacaag tgtataccca tcctatgttc  31980
gttttatcca acttcttatc attcctaagt atattaagta aagtaatagc tattaatatg  32040
ttgacgtcat tagcagaaaa ataactttgc aaatgattaa gtgatgacag ttgtatatcc  32100
atgttattag atgtttaaaa ttcaaaaaat aattaattca ataaattttt gaaacaaatc  32160
catagaataa aaacatagtt tttcaaaatg tatttttcaa aggtaaaaat ttctcacatt  32220
aggctaggtg cgtggctcat gcctgtaatc ccagcacttt gggaggccaa ggcgggcaga  32280
tcacgagctc aggagttcaa gatgagcctg gccaacatag tgaaacccca tctctactaa  32340
aaatacaaaa attagccagg tgtggtggtg cctgccttta gtcccagcta ctcaggaggc  32400
tgaggtgaga gaatcgcttg aacccaggag gcagaggttg cagtgagcca agaccacgcc  32460
attgcactcc agccttgggg gaagagtaag agtctgtctc aagaaaaaaa aaattctcac  32520
attattgtaa atactattac aatagctaac ataaattcaa gatttataat tatttttttc  32580
tgatgctcat acaaatacac attttactgg atcttgggtg ttgtagtaaa aaacaattta  32640
ctaaaacaaa aaaaaagaat gtatacctta aatacataga attttatttg tcaatcatac  32700
cttaatatga gaaaataatg ttcttctttt ccaaagtaaa aagaaattaa tagagcaaag  32760
ctatatttta caacaatgta catataatcc ataattctgt ctaatacttg atattctact  32820
aactgaattg aagcagtact tgccaacatt tacatatata tgaataattg aattataaaa  32880
gttatgagat gctgatctga attacaaaag tccctctgtg atagtaaaca catgcataaa  32940
ttaattctat aaagtgttat tgcattttct caaaatacat tgaagttctg tagtcaaagt  33000
aatcaataga gagccaaaac tgtttttgaa cagtttagca tattttcatt attaaaaaca  33060
aaacttgcca atagatataa gaaaaagagc tgaccaaatt agagtttaaa tagcataaaa  33120
taataatttt gaaattctaa aattgtattt tagaaaatca tgacacgtag aaaaattatt  33180
ttaatacagg tctcatttga attagataaa cttatattct atacctgaat aaaaagtaat  33240
tgaaaatacc tatgactttg cagcaataaa aaatggcaaa tgataaaaaa ttcaaatttt  33300
tcttacataa atatttgtga aaaggggaaa ctgaagagag aaaatatgat agtttattta  33360
aagtgaaaca tttacatagt ttgatgtaga taaaagtaaa ttgagaaaat tcctatttgg  33420
cattatttgc tgtgagttta ccaagataat gtttttctcc attttaaaaa caatggtcta  33480
tggtcaaaaa gtaagtcaaa ctatccctgt ttgcaggtga catgattcta tatctagaaa  33540
accccaaaag ctccttcagc tgataaacaa cttcagcaaa gttacaggac acaaaatcaa  33600
tgtacaaaaa tcagtagcat tcctatacac caacaacagc caaaccgaga gccaaatcag  33660
gaaggcaatc ccattcacaa ttgacacaaa aagaataaaa tactttgaaa tatagctaac  33720
tagggaggtg aaaaatctct acaatgagac ttatgaaaca ctgctcaaag aaattagaga  33780
tgaaacaaac aaagagaaaa acatgcttat agataggaag aatcaatata attaaaatgg  33840
tcatactgcc caaagcaatt tataggttca gtgctattcc tattaaacta ccagcaatat  33900
tcttcacaga actaaaaaaa aaaaaaaaaa aaactatttt gaaattcata cagaaccaaa  33960
atggccaaat agcgaagaca atctaagcaa aaagaataaa gctagagaca tcatgccgtc  34020
tgatttcaaa ctatactaca ggactatagt aaccaaaaca gcatggtact agtagaaaaa  34080
cagacacata aaccaatgga acaaaataga gagcccagaa attaggccgc atgcctatga  34140
acatttgatc ttcaacaaag ctcacaaaaa caagcaatgg ggaaaaaaaa ccctgttcaa  34200
taagtgattc tgggataact agctggtcat acacagaaaa ttgaaattgg accccttcct  34260
```

```
tacaccatac ataaaaattc taaaaattca aattataaaa aaggaaaaaa aaaatcaact  34320
ccaggcagac taaagactta aatctaaaac ctcaaactac aaaaaccctg gaagacaacc  34380
taggcaatat catcctggac ataggaatgg caaagatttc atgacaaatg acaccgaaag  34440
caatcaaaac aaaagcaaat attgacaaat gagatataat taaacttaag agcttctgca  34500
cagaaaaaga aactgtcaac agcataaaca gacatcctac agaatgggag aaaatattta  34560
caaatatgca tctaacaaag gtctaatatc cagcatctat aagaaactta aatttacaag  34620
agaaaaacaa acggcctcat taaaatgtag gcaaagggta tgaacagaca cttttcaaaa  34680
gaagacatac acatggccaa caagcacttg aaaaaaaggc caatattact gatcattaga  34740
gaaattcaaa tcaaaaccac aatgagacat tatctcacgc tagtcagatt attattatta  34800
aaaaataaaa aactaacaga tgcctggcaa ggttgtggag aaaagtgaac acttatacac  34860
tgttggtggg agtgtaaatt agttcaacca tgtgcaaagc agtgtggcaa ttcctcaaag  34920
agctaaaacc agaactacca ttcaacccag caacctcatc actgtgtata tacacccaga  34980
ggaatataaa tcattctact ataaagacac aggcatgtga atgttcattg caacattatt  35040
cacaatagca aagaaagaca tggaattaac ctatatgccc atcaatgaca gattggataa  35100
agaaaatgtg gtacatacta tggaatacta tgcagccata aaagaacaag atcatgtctt  35160
ttgtggaaac atggatggag ctggaagcta tcatctttag caaactaaca caggaagaga  35220
aaaccaaata cttcatgttc tcacttataa gtgggagcta aatgatgaga actcataaag  35280
acaaaaaagg gaatgacaaa cactggggtc tagctgaggt tggagggtgg agggtgggaa  35340
gagagagaga agcagaagaa ataactattg agtactaggc ttaatacctg agtgatgaaa  35400
taatctgtac cacaaacccc cgtgacacgt gtttacctgt acaataaacc ttcacatgta  35460
cctctgaaca taaaagttag aaagaaaata ttaacaactt taaatttagt aatcataaat  35520
gtcaaattaa aaaaaaaaga ttttagactc acacttataa tcatagcact ttgggatgcc  35580
gaggtgggcg aatcacttga ggtcgggggt ttgagatcag cctggccaac atggtgaaac  35640
cctgtctcta ctgaaaatat aaaaattagc caggtgtgat ggcatgtgcc catagtccta  35700
gctattcagg aggccgaggc aggaaaatct ctggaacctg ggaggcagag gttgcagtga  35760
gccgagatca caacagtgca ctttagcctg ggtgacaaag tgagactctg cctcaaaaaa  35820
tacatataaa ataaaaaaga ttttaaataa tattataaat aaactaaaat ttctaggaac  35880
aattttttaa aatcagaaaa ataagtcata tgataataca gatactctta agaaatgcat  35940
aaaatatatg aatatacatg tgtacttatt gatgtgcatg aagatacact aatatatcca  36000
acaagaataa gcacatccat tattttataa tattaaagta agcaataaaa ggaacactta  36060
aaaatatttt cttcaattta attgactata ttttttttatt tggaaaacaa ttttaacaca  36120
tattttaaat agtttaaata gagaaaaatg taaataaagc tgtattacaa agatattcat  36180
tgataaacac ttcaaaaaat ttttcaactt ccttattttt atcacgtatt ttgctctaga  36240
aaatttccat tccacatgat acatttgttg tataagagat acaaaacaaa ttcctactag  36300
gggaaataaa gcttcagtaa ggaggtggca ttaagctggg ctttaaaatt catgcagaat  36360
tcccgttgct tcaaatggag agaagcagca gtgtaccaca gataaatgaa gtgagacgta  36420
ataagggttt ggctcaagat aataaggaga tgtataatac ttttttatgt ataatacttt  36480
tgttccaatt ccctttatgc tttacttcag ttttgtttct ctagttaaat aactttgcat  36540
ctctaaactt tattattctt atttgtataa tgaagagagt aacttatgcc aggcaaagat  36600
tttacagaca ctagaaataa tatatacaaa atagttggaa tagttcctga aaaatagtag  36660
```

```
gttccacatg ataacaagat ttatgcttgt gctctttctg tattatttgg aaagaaatat  36720
gtgaagtgca ggaaagtggt gtgaagttat ttttgtggga tatctggtgt aatctttctc  36780
ttttatctat gttatcaaat atttttcaaa agctgtattt ctcattagtg ctttttgtga  36840
ataaattaac taggaaaatt agaagaatgg caacaatata catcatagaa aggcatagat  36900
tacaaagaga gtatatacac aatacctgtc cagaagatgt ggtataagcc aatattttaa  36960
ttatacttat ttacttcaga tattgcaaat ttttcttatt tttatacctt ctttctttta  37020
atgacatttc ctatattttc attcactatg acattgtttt ctttatatca atacttatga  37080
agagaactaa ctattctaac tagggagtag ttagactagt tattttaaaa tacttcatta  37140
aaggactaca acgtgtgtac catctatgac ttagtattga ttgattgtca tctttcatgt  37200
tcttcataag tgggtaattt tgaacactgt tatattattt caaagggtgt tatttgtttg  37260
ttcagatgtt ttacaaagta attaactttg ttggcttgaa attgcaaact ctgtcttctt  37320
ggtgtcttag tcaattcagg ctgctatgac aaaaatacca cagactgggt agcttaaaca  37380
acaaacattt atttctcaca gttcagtagg ctgggagacc aagatcaggg tgccagtatg  37440
gttagcttct ggtgacagtt ctcttcttgc tttcctgaca tggctaaaag agaaagagaa  37500
tggaagtgag ttctcttctt aaaagggtac aaatctcatt catgagggtt ccacagccat  37560
tatctaatca ccccccaaaa gcttcacctc ctgataccat cacattgggt taggatttga  37620
catgcgcatt tgagagggac acaaacattc attctatgac agatggtaat cgaagcaaag  37680
acaatgaatg ggtttgccca gcaagagtat gtagagtaaa aagagaagac ggtatgaaac  37740
aaatcactga aaaaaaaaaa atgtaacagc cagaataaca tgatctaagg atacttggga  37800
ggaattatgc aaaaaatagg atttgagtca tgcaggcaaa ctctttaaat ttttactgga  37860
aaagacatga gagacagagt tatggaaaag aaagcatttg gtggaggcag atccattttt  37920
tctaataaaa taaattaata tggatgaatt gtacaatcat tccttagtaa atttcaaaac  37980
tgcatccagg caaatctctt atgcaacagg cctgccttag ttgtgtctac tgggtacttg  38040
tttattttta ggcatgtcaa attcgacttg tgaaaagatg attatattgt ctttaatgct  38100
gtcttctttt tcccaccaaa tgacagttat tcaaaccaga aactataaaa caaacataca  38160
gttatccgaa ctagaaaaca aaatcagaat ttacattttc tattttcccc acctcctgtt  38220
ggttctcctc ttaaacttct ccttgtgtgt ctgtaagctt gttatacact tttcatctct  38280
actctttttt attttctgaa gtcagctttc taacagatct ctttttccta agttcttctt  38340
cttcatggct gccagaatta accatctaaa atttaatttt gttatgtaac attttaaagt  38400
gcatattgac tcctcaatgt tgaacatatt tctatcctta cacttcacct acacaaataa  38460
tatttctgtt tttcaaataa tccgtgttat ttcacttctt aggggctttt catgtgcttc  38520
ctattttgtt ttaagtattt tgtgtcttca atatctaagc ttctataatc aactgaagac  38580
ttagccccaa tgtcaacaca tctttaagaa ctttaacctg taaggtcaga atagtccctt  38640
tttcctatct gcacataaca ttacaaactt atggcaatta taaaactcaa tacatattat  38700
actgtcatta ttggtttatt gctgctgaag attataattt tcagtgcatt gattatgtct  38760
tatttgtttt tactgccctt gttcctgttc ctctgtacct gcctcaacta catagcttag  38820
cagactaact gctatattac agttgctcaa tgaatgtttc ttgagtaaat cagttgagtt  38880
ccaaagctaa tccaagttgt gcgtttgaca aattagaagc ttggaactgt cttctgactt  38940
taagtttaga actattgcca taataaatta atgaccgatc tgccatgatt gcaggcaagt  39000
```

agagacttta tttcttatct caatgtcagt tgtctctttc tgccaatgca cattttattt 39060
gatgattgtg cacatttata tctctggttt ttatttaaat aaatttagaa catatagctg 39120
gagacggtag ctcaaactga ggatgaaaat agacatttat caaggttatt atgtagctag 39180
cactgcatgt acacagaggt atttagggag ccacacatat gtccaaggca agacatatgc 39240
tcataaaacg tctgagaaga ttgtatcctt ttacctaatg ctaatcccca agcttagaac 39300
aaggcaagtg aaaggtcaaa gggataaaaa aatacaataa acaaaataaa aatttacaag 39360
aagttgttat ggactaaata tttgttcccc tctccccaaa attgtgtatt gaatttcaaa 39420
atccaatgtg atagtatttg ggagtctttg ggagctaaag agatcatgag aaatttgctc 39480
ttataatgtg agtagtgcct tacaagaaaa tgctggagag ctcactagat ttttttcctc 39540
catgtgagaa tacaaagaga agttagctgt ttgcagccta ggagagggcc ctcaccagaa 39600
attgaccatg ctggcaccct tatctcagac ttctcaccct tcagaactgt gagaaataaa 39660
tgtttgttgt ttaagccatc cgttccatca taatttgtga tagcagtctg aactgactta 39720
gacaaaagtt caacagcaaa tttgagcagt tagaacacag aatccgcaaa cttgaagata 39780
agacaattga aatgattagt ctgagaagca gaaagaaaaa aaaaacgaag aaaaattaac 39840
aaaacatacg gaactgtggg acactatcag gtgaaccagc ataacaatta cagtagttct 39900
agaaagagaa gagacagaga aaagggaaga aataatattt gaaaaaaaag tggccgagaa 39960
cgtcccaaat ttgataaaat atatgatctc aatatcgtag aagcataaga aaatccaaat 40020
aaactcagag atccactttg aggcacatta tgatcaaact gtcaaaggcc aaaaaaataa 40080
aaataaattc agaatcttga cagcaacaag agtaggaaat aatcatgggc aagagttcct 40140
taataagatt aacaactgat ttctcatcag agaccagaag acattgaaat gatatatcca 40200
ataaagaact gatattcaaa agtatgcaaa gaacatctaa aactcaataa ttagaaaaat 40260
aacccaatga taaaatgagg atgatatctg aacagatgcc tcactgaaga agatatagag 40320
acaacaaatg agcatgtgga aaaatgctcc acatcccgtc attagggaat tgtaaattaa 40380
acaataagct atgtcactgt atacttgtta aaaggactaa aattccaaac acaaaaatat 40440
accaaatact ggcaagaatg tggagcgaca agaactctta tttactgcca gtgagaatgc 40500
aaaatagtgc agccactttg gaaaatattc taatagtttc ttacaaattt aaagataggc 40560
ttaccataca atcaagcatt tgtagtcctt ggtatttact gaaataagta tcaagtggaa 40620
agcatgtcta cacaacagcc tacaaagagg tgtttatagc agccttattg ataattgcca 40680
taagttagaa gcaaccaagg tgtccttcaa tatgagaata ggtaaagcga ccttggtaca 40740
ttcatgcaat agaataagaa tatttttagt gattaacaag aaatgagaca taaccaatga 40800
aaagacatga aacattaaaa gtatatttat aagtaaaaga acgcaatatt aaaatgttac 40860
ctactatatg attccaacta tatgacaaat tttattttat aaatgcttta ccacaaaagt 40920
taattctaaa aatgtttgcc accaaaaaac aaacaaaaaa catggtagag atcatcttta 40980
tagtttttta taataatcct cttgataaag attatatcat aagaaatctt gacagtttac 41040
attcaaggat atgacatttt atttacaaat taatgaaatc taataaaatg tgacaatgaa 41100
aatttagctg agtataaaag aacctaaatt agtagacagt gagagaggaa tgggggaggg 41160
gatgtttaca agaagttcta catcagtaca gaacttcata aattagtgga taagagcatg 41220
gtgaagagca attgtaaatc aaatgaaaat gttgtggaac tcttattagt atctgcagcc 41280
actctggcac tttaaacata tccagtagga gaggttaatt ctctcagcag gagaccactc 41340
acattacttt tttctcccta taaaataatg catcgttttg tcatgctggt aaaaaacaca 41400

```
taacattaaa tgtacctttt caaccaattt ttaagtgtac aattaaaaag tgtaaagtac  41460
actcacattg atgaacaaca gatctcttga actttttcat tttccattgc tgaaactttg  41520
tatccactaa actatcttct cctcagttct aagtaagtac ctttccactt tctgtttcta  41580
attttttgac tactttaaat atttctttct tttttctttc ttttcttttt tttttttttt  41640
taagatggag tctcgcactg tcacccaggt tggagtgcag tggtgtgatc tcgtctcact  41700
gcaaccgccg cctcctgggt tcaagcgatt ctcctgcctc agcctcccaa gtagctggga  41760
ttacaggtga ctaccaccat gcgcaggtaa tttttttttt tgtattttta gtagagatgg  41820
ggtttcacta tgttggctag gctggtctca aactcctgac ctcgtgatcc gcccaccttg  41880
gcctccaaaa gtgctgggat tacaagtgtg agccactatg cttggactac tttaaatatt  41940
tcatatgata gaatcataca gtatctctcc tttcgtgact ggcttattta gcttagcata  42000
atgtccttga ggttcatcca tattgtagca catgatgtaa tttacttatt ttttaagtct  42060
gcataatatt ccattgtgta tgtataccac attttcttta ttcattcatc agtagacatt  42120
tgggttgctt ctacatcttg gccgttgtta ataatgctgc atgaatatgc atgtacaaat  42180
atctctgcta gatcctgttt tgaattactt tgactatata cccagaagaa taattaatgg  42240
cttgtatggt gattctattg tttagtattt gtggaacctc caaactcttt ttcatgaaag  42300
ctgaaccatt ttatatttcc atcaacaaac atgaagttcc taacttctct tactcgttat  42360
tttctattct tgaaatagtg gcttttctga tggttgtggg gtgatatctc attgtggttt  42420
taatttgcat ttccctgata agtagaaagt tgagcatctt ttaatgtgct tattggctct  42480
ttgtatatct tctttgcaga aatgtctatg taagtccttg acccattttt aaattgggtt  42540
gttctttgtt gttgtttcct tggaaaagtc catatattct agatattaac tcctcatcac  42600
ttatattatt tgcatttatt ctgtgccatt ccataggtta tcttttcacc tgttgttttc  42660
ttttatgtgc agatgattta agtttgatat agtctgattt gtgtattttt aatttttgttg  42720
cctgtgcttt ttgtatcaca ttttaaaaat tgccaaattg aatgtcctga agcttttctt  42780
ttattttttt ctggaagttt aaggtcttac atttaggtat ttagttcatt ttgagttaat  42840
ttttgcatat agtatagggt aagggcccaa tttcatttca ttgcatgtgg gtatccagtt  42900
tcccaaacat catttgaaga ggctgtccgc ttccttgtac taaatgaatg gtgttttgct  42960
gcttctttta agagtctctg tttgtgtgta acttttgaca gtttgattat actgtgtctt  43020
ggtatagagt tttttagatt tatcttattt ggaattactt gagcttctta aatgtttagg  43080
ttcctttatc tcttaagatt taaaaaaatg gggtccataa tttacaagtt ttcagacctt  43140
tctcatttac ttctcttctg gtattcccat aatgcatatg ttgccctgct ggatggagtc  43200
ccataatttc tttaggctct tcttttcttt ttgctcctgt gactctaatt tttagaagttc  43260
tgtctttgat tttcctgatt ttttcttctg cctagccaag ttacctgttg agtctttcta  43320
gtgaattttt cagttcagtt actttataat tcaactccag aatttctgtt tggttcttca  43380
tagtttataa tctgttaata ttgctatttt gtttatttgt tatgttcctc atttcattta  43440
attgtctgtt catattctct tttaattcat tgcactactt gactaatttc aagttctatg  43500
tctggcaatt cctatatctt catttgtttt tggtcagttt ctggagatgt aatttttttt  43560
tccttttaat gtgtgagaat cctttctttc tttttatact ttgtattatt ttgttgttga  43620
gattttaaca tttaaaaaat cagtcaactc tcccagattt tgtgagatga ttttccataa  43680
ggagaactct cctcactaat tctgaataga gattctgtgg cctactcatg cttttttttct  43740
```

```
agtatgtttt cctttctttc tcctttaggc ttgtgtgtgt gatctgtttg aaaaggtttg  43800
ttggtttcta tagaagaccc tcccctgggg cttgaggtac agtggccttt ctggggctgc  43860
attaaattgt tgtactggtg ctccacctcg tgtctctgtc tggaactgca gtttttggtg  43920
tacctttgct tgcaaagacc gcatttttat tagtacttga atataggcaa gtcagaagcc  43980
tgtccttggg caacctccct aaaagtcaaa atattgaaca taggagattt aaatgtttcc  44040
ttccaattgc attgcacagg gtggagtgag aaagactcta gtgagagaga ctggaaacaa  44100
tcatgatttt tcttgccagg ttgttttcac gatagcctgg aggtacagaa accttgtaat  44160
tggttctgaa gttctcacag aggcatttag tacatatgtt gttaatattg tgtcttgctg  44220
ttgaggttcc agggctgttc tgctctcttg ctgatgtcac tctcttccac atttcttagt  44280
ccttttttaat aaaatgattt tttaatgatt aggacctgaa caattttcat cactattcta  44340
tggcacaaag actgcataca tttttacaag atgttagaat tgactatctt tgaagaaaat  44400
cttcataatt tttgtctaac tctgttgccc ctttctcctg ttttattatt cccatcatca  44460
acttaataca actagttttg atactcttct acattttatg ctgtttctta gataactttt  44520
tacattttat tttaaaactt ttagttatct ctataagttg tatcatttaa taaatctttt  44580
gaattccttt tatcttcatt gatagcatat atcatttgat agtttcttat gcagaaagga  44640
acacacccac attttgtcgg ctatcaaaga gttttgttgg gccttttatc tctgtccccc  44700
aaacatggcc tagggccaga cacagagtag gttttggtta tataaatgtt cactcattat  44760
ttcttaagca tctttgtgac agacactgtc ctaatcactg gggacggagc aatgaacaaa  44820
acagacaaaa acctatgact tgatggggct aatattctgc tgtggcaata taaaataaac  44880
tcataaagga ataaatgtat tgtgagcaga aaggggtgca attttaaaga gattgatcaa  44940
ggaaaacctc actgtgaaag ttccactgag caaaactctt aagggtgtga aggaatgaat  45000
gatagaaata cgactatggg gaagagcctt tcatgtcaag tgaaaagcaa gaacaaaaag  45060
cctggagcaa tataatgaat ctggaatgct caatatacag caacaaggtc taatgtagct  45120
ggagaggaat gaccaaggac aagagtaaca aagtataaga ttagaaagat aaagaggaat  45180
atttgtgggg aggtgggtgt aaaaaagagg ataggttgtt tatggtctca taggttattg  45240
gaaaaacttg atatgactat aagttacata ggaaaacaga ggggcagcat gatctatttc  45300
tgatttgtaa aggacttctt tagctacttt gttgagaaga gactgttagg cagatgtgca  45360
cagaagtaga aacatggctc aggaggctct tgcaataatt gaagctaggc atggtggtgg  45420
aaaccactgg gaaatatagg aggtaattag aagaggtcgt ttagtcagtt caggctgaca  45480
gaatagaata gacttggtga cttaaacaac aaatatttgt ctctcacatt tccggaggct  45540
gagaattctg atatcagggt tctggcataa ttgagttctg ataagggccc tattcctggt  45600
ttccagaagg ccatatcctc attgtgtcat cacttggggg taggggagag agagagagaa  45660
agagagaaat agagggaatc cctaatttct tgtcttataa gggcactgat cttatcaaga  45720
gggctccatt ctcatgacct aatttcctca aaaagaccct atcaccaaac atcaacacac  45780
tggaaattag agtttcaaca tataaatttg aggtagggga tataaagatg taatacataa  45840
cagggtaaat attaatagta gagagcccaa agaaatttgt ttatggatat aaatgtgagc  45900
tgtaatagaa atgattaatc gatacatttt attaacatga aattgacaaa taaaacatct  45960
ataaccactg catcttacac tggatgtcag tcacttgtgt tggtcataga atttttcttt  46020
gcctctgcaa agttctgttt ttcagctggc ttcctggaaa tgctgccttt gagaatgtac  46080
tgccactccc ctcccagtta gccaatgcta ttcatatgga aataaagaat agctcaccat  46140
```

```
catggccatc tgagaacatg atgtagcttt ctataaatca gttaatgaga ttaatttaaa  46200
aataacaacc ttaactgtag tgctctaata ttttgatatt ataaccaaat tagaaatgat  46260
gctttatcag tgtagtgata ataacattta aatggctgag tagtagtacc tggtaaaagg  46320
gaaaactaag tatggttttt aagatacaaa taatgttttt aagtaaagaa gaaagctatt  46380
ataattccat gtgcctattg acattatata gtccttcgat taaccatttt ccccctttcc  46440
ttctgatttt tcttagatgt tcttggcagc tctgtcactc agctttattg ctaagacact  46500
aggtgcaatt attatgaaaa gttccatcat tcatatagaa cggagatttg agatatcctc  46560
ttctcttgtt ggttttattg acggaagctt tgaaattggt aacatttatt ttctatttta  46620
ataaccaaac ttgcaaagtt aaaaaatata tatgctttac accactggtt atcaactggg  46680
gtaaatttat ctctcacagg caatttggca ataactaaaa acatttgtgg ttgtcataac  46740
tgcacagggg ttgggggcaa tggaagtgct actggtatct aaaggtagag gtcaggggta  46800
ctgctaaata ttctataatg cacaaagaat gatgtaactg aaaatgttga tagtgaggat  46860
gttcagaaac cctgattcta cacaaattca ttttttgcaa actaacgcca tgtcatactt  46920
tacctcccct ctctcaagat gaagaaactt tgggagagga ctgttattct taaggagaaa  46980
ggaatctttt cagagcaacc tacgttagac ctctattgtt tcactgagca cacaaaaatc  47040
tttcctttga aatactgaag atattttgtt gtcttcattt tatgttggat ttctccaata  47100
acagctcagg gaaaacattt tctggttcat atttgtgttt ttccctatta gtaatttttt  47160
tctagataat ttataagatg aatattaaat tttctgggaa tttttctctt taaatttttt  47220
tcttctaaat ttccattgtt tttctttatg tttcattaat ctttgatgcc atcatccatc  47280
ttaccatatt aagttctaat ttgtatattt aatctgtatt ttatatttac aacagcactt  47340
tattattccc ttattatttt taggctgcca gttctgattt catggatgca atgtgccctt  47400
gtacccgtaa aggtactaaa ttttttataa agtaaaaaaa aaatttactc attcattttg  47460
gtgcttttat tccaaattat ttttatgcta tttttttttca gaagtgctca gttatcctta  47520
actgctattt gtttattgtt atgcctgagg ctccagatgg attagaagtg gtcatgactt  47580
ttttttttt tttttttgag acggagtctc gctctgtcgc ccaggctgta gtgcagtggt  47640
gcgatctccc ctcactgcaa gctctgcctt tctcctgctt catcctcccg agtagctggg  47700
actacaggca cccgccacta tgcccggcta attttttgta tttttagtag agacgggatt  47760
tcactgtgtt agccaagatg gtctcgattt cctgacctcg tgatccaccc acctcagcct  47820
cctaaagtgc tgggattaca ggtgtgagcc accatgcctg gcctctggaa gttcttaatt  47880
aagttccgcc tttctgtggt ttaatagcac ctctgtccat ctatttttat cgttagtatg  47940
aaacttcttg aagacagatg ccatggttta ttctttttca agtaactttc ttatttctgg  48000
ctctgagctt catgtcaggt tcatgttaga aatttaaata atattaagaa taaataaaga  48060
aacgcatgaa ggagcacctt accctcatca ggaagattca tctccatttt tcttcattcc  48120
agtataatcc agtcaactcc aaatttttca ataaaatttt acttcactaa tattgccaag  48180
taattcaagt gctttttttt tgtatttaaa acaacttttc aatgagtggt ctaatgtagg  48240
tgaattcacc ttctcaatta aatcacattg tctttgaggg aaggcactat gtcttggact  48300
ctatttgcat ccattctggg gttttcaatt ctagacgcaa aattgaacta agctgtatca  48360
acataatttt gttccctttc taggaaattt gcttgtgatt gtatttgtga gttactttgg  48420
atccaaacta catagaccaa agttaattgg aatcggttgt ttcattatgg gaattggagg  48480
```

```
tgttttgact gctttgccac atttcttcat gggatagtaa gtgttaaaaa aaaaaaaaac  48540
ctctgtgcca ctatcagtac cttgtaaatt aggagtagaa ttttattatt atccctttaa  48600
ataggcagtt accttttgag aagataccca ctaagtgtgt acagaaatga aatagtgtct  48660
atttgtctac ataatcattt tatttatcgt agctttcata tactttgaaa taacaaaaag  48720
actaaactgt agagtttcaa atgaaataaa taggcttttt atgaattttt agtataacgt  48780
atatactgta cgtctttgcc tataagattt tgattatttt ttataagacc tcaacactta  48840
cacctatacc cactgaagta tagttgttcc catcatttca ctgaagctgt tattcctaag  48900
gtcactgtgt agttataatt acagtcagat gctcctgaga gaaaagttaa aatggcacat  48960
gggggagaaa cttatttttc acattacagt taatgtagcc agttcaagga tgatatgatt  49020
ctacctcttt ccatcatagt gctatgcctt gcatggtctt ggcttcatga tccaaattgt  49080
ggcaacgtat ttccaggcaa caagatagaa gaagaaaaga ataagaagca acaaacagtc  49140
cacacaggct gaggcttaag aagcattttc agaagcaaaa tatctctact gactttacat  49200
ttaccagatg ttagttacat ttcacacata gatatataaa tgctgaaaaa aatagacatt  49260
attccaagtt accaagttcc cggttaaaaa tcccaagtat aattactgtg gaaggaaaga  49320
agagaggata ttaggagaca atgagcagtt tctgttagag acaccaatta cttactcatt  49380
gccaaatcca gcaatgacat catttgctca ccatattaaa tccattcacc caccatattt  49440
ggcccttata ggaagtttct tcttagtggt actgctctag cttgttttca tcatactgca  49500
ctctcttgat tcattttcta tctttgtgtc ttcttcatca tgtccatttt ttttcatctg  49560
cttttggcac cataccgtca gagtcctcta atttcctttt taatctttat ttatgattct  49620
tcatgagttg tatggaaaat aaaccttaaa ggcaagtatc acagcttcat cttccattct  49680
accctaaaat taaggaccac aatctagatc agcattgctc taaatatgcc ataatatgtg  49740
acacttttgc acctggtatt tctacagcct tgaatacctt tgtttctttg tctacccttc  49800
tattcatctt ccagattcgt tttacctgtc attctcatgt tgatgtcttc tctgatctat  49860
tcccgcaacc tccaagcaaa gttgatcata tcctttgtct ttgtgacaac tcaggacctt  49920
atatattaaa cttataactt ttatcatcta tgtttatact agtgtgaaat tccctaagta  49980
caaaaactgt gtgttttatt tctagctctt tgaagcttag cataatgcct ggaatacagt  50040
aggctgcctt tagagctcac gtggtaccta attatttatg gatattaaca tctctgttat  50100
tcctatcaag ttttctctca tctagttgaa atggattaga ttttattttt actacatttt  50160
gaagagtcat acattagagc gtgtgtgtga atatgtgtcc atgaaagaaa atctgacaga  50220
ctgatcatct ttgaagataa ttcaaaagga tgaatggtta cacacaatta ataattactt  50280
tttaaaaagg tgaaactagg atatttcata tcttgaccaa gatataacca ctcctaggat  50340
aatagcaagg tgataaccca cttagcctgg ggtgtattga attatctttc ttgctggaca  50400
cttccatttc acttttaccc atcacatctc ttaaaacaca tgctgggaaa ttgacagaaa  50460
gtactctggt aatttgggga agataatggt gcaaataaag gggaatattt ctctgtattt  50520
ctaggaaaag tgaaaatatt cagtagataa gcaaaatgtt taattcagtg atgttcttac  50580
agttacaggt attctaaaga aactaatatc aattcatcag aaaattcaac atcgacctta  50640
tccacttgtt taattaatca aattttatca ctcaatagag catcacctga gatagtggga  50700
aaaggtaaga attaatattg acagtaaaaa gtcttctaaa atgtatacat ttaattacat  50760
ctctaaaaat tgttgtgata ttcattagca aaatttaatt aagaatgaat aggaaaaaca  50820
tttgactctt acagacataa ttatagtgtt aatatacaca gttcgcccat taacaacaca  50880
```

```
ggtttaaact acgcgttttc acttctatgc aaattttgtc catctgaact ggatgataaa  50940
cctgccggta agaatatctg acattttcta tatttggatt gaacagggcc aactgcagaa  51000
cttaagtgtg catgaatttg agaacacaca ggcagccctg taacaaattc cttaatatac  51060
caagggatga ctgtattata tgtaaaagca tttagaagta gatcagaaaa gagaatattt  51120
tcaataggaa attgacaaag aatatatgca ttaaagtaaa acagaaggaa atggtataaa  51180
tatgtaaata atataacttt gctttcattg caaaaggcaa actattatat catttaaaga  51240
ctttttgcct attataacac aaattataaa ttataattgc aaattgtact gctaaagatt  51300
tttttaacct attaaataga aaaagactaa aaatacatag agacgaggta gaggcaaaaa  51360
aggatttcac attgtatata ttgctggaag tgtatacgtt tgtaaatctt tctggagatt  51420
cattatcaat atatgttaag aacaaaaata tacttaccta cttagtctga aattctgcta  51480
ttattgatta atcttaagga aataaccagg aaactgcaaa aggacttatt tacagttata  51540
gtcatgataa acctaataga ataaaacaac aaaaaagaaa ttaaaacata agatactgaa  51600
taaacacatt tggaaactta ttcagcacat tactgtccag tcattaaagt tttgatatta  51660
aagaaatctt aacaacatgg aacaattgtt ataatatggt gttaactgtg tataccattt  51720
aacaatatga actagatttt taaatatata atggatataa tgaatataat gtatatgttt  51780
tgtgcaaatc tagaagatat ataaaaaagc ttgaggtgat cttctgtgtg taatgtgatt  51840
acagataatt tttacttgtt tgtgcttttc tgtatgatat ggcttgactg tgtccccact  51900
caaatatcac cttgattgta ataatctcca catgccaaga gtggggccag gtagagataa  51960
ttgaattttg gggcggtttt cccccatact gttctcgtgg taatgaagaa gtctcacaag  52020
atctgatgat tttataaatg agagttcccc tgcaaaagct ctcttgcctg ccaccatgta  52080
agacatggct ttgctcttcc ttcatcttcc gccatgattg tgaggccccc cagccatgag  52140
gaactatgag tccattagac ccttttcctt tataaattac ccagtctcag gtatgtattt  52200
attagcagca taagaatgga ctaatacacc atattgtcaa agtttgcaaa gtgaatataa  52260
attacttgta cttgtaaatt aaaaaaaaat aagtagaata attaagagtt tacaagtagt  52320
taaatttgta atagaaatgc taaaattaat gtttaaaatg aaacactctc ttatctacat  52380
aggttgttta aaggaatctg ggtcatacat gtggatatat gtgttcatgg gtaatatgct  52440
tcgtggaata ggggagactc ccatagtacc attggggctt tcttacattg atgatttcgc  52500
taaagaagga cattcttctt tgtatttagg taatgtacac aaaatattaa attgtatgat  52560
cactttccct ttgtctactt ttgaaatagt agagttacta aacttattat tttacctatt  52620
agaacatata tttgggtata tgtattgtat catatttctt ttaaaaacat ggtgaataag  52680
aaccatgcat tcttggcatc tagtaaaatt gctttataat attttcaggt atattgaatg  52740
caatagcaat gattggtcca atcattggct ttaccctggg atctctgttt tctaaaatgt  52800
acgtggatat tggatatgta gatctaagta agtacaacca gaacaaggta ccatgataac  52860
gtctttctaa gcacacatgc gaaaaacatt ttttcaaata actgaattca ctctttcaat  52920
agtcctttgc ttaatataat tagaaagtta caagtaggaa ataaatgtat tactaatcag  52980
aataaatata aaatccagct cctatttata ctatctttat aactaagtgt aaaatgagag  53040
aatgtaaaca aatttatttt catgagcttg gtccaaaata accaaatgta aaatgtctcc  53100
ctcccaaact gactgtccag tcaagtaaat tttatttttc agttgatggt ggcttggatg  53160
ttgatgtgta caacttaaag tttgctttgc taaagtcttc ttgtggctgc tgcattgatt  53220
```

```
tatggctgga gtcatttgag agacttcact gtgtatttta tggtcatttt ccctggtcct  53280
agcagagggc ttggcgtatg gcaatgttca gtaagtactt gttgaacaaa ggaataaagc  53340
agaggacaca taaataaaat ctatgatttt cttcttcatt ctcagagcat actttccttc  53400
ttatctcata gatgaaagag atgccatgtt ataaaaactg tctcaacttc aggccctttt  53460
ccctaaaaat attcttgcac catatctatc tttatcttct ttttcttttt tgcagctcag  53520
tggaaaatat atacatctgt atccaatgtt gatagatcta gctggagctt agattctccc  53580
ttcccgcttc tttatctcca tcttctcttt tattcagcaa acacacccaa gtatttccca  53640
tctttatatg tagatacagt tttttatacc cccacacaac tttccagctg aatccttttt  53700
ttattcctct ttagaaccaa gcacctagga aaatatcagc taaattagct aagatatctc  53760
accttctcac ctcccatcca cttctaaatc cagtataatc tgcttctgtt attagtgaaa  53820
cacaatcaat ttctacctac tttactatag atttgtaaat gggtatattt ctatcatttg  53880
cgttaattga tatttccagt gcttcttcat ccattttccc tccttagata tcttattagt  53940
acctaaagca caatatgtca aaatctgatc tcatcacctt acctccaacc ccactgtatt  54000
ccctatattc ctccttttga tgaatatcca taccttattc aattattgac tgagttactg  54060
tgccctgtaa tctcacattt ctctgcattt acacttggta aaacttttcc ctctttttca  54120
tttgcatagt tcttgaagcc tcttccaaaa tgtggatcct cttagagaag ccttacttca  54180
ccactttcca ttagtctcaa attaatagcc aagagcatgc ctttattgta acccttctca  54240
caatgagcta ttaatatttg tgtgcttact tgccatctct ttaccacatg acagaatggc  54300
atgttcttag caaataataa ttagttaagt ttgtgaataa ataaatatga ttttccacct  54360
cattaggcct tcaatagatc attccaaaga gatcaaagga ttcatttcca agatgggata  54420
gacatcacag tgggccagca acagccaaaa acttgaaagt gtttgctaat ctaaaactat  54480
aaagaaaata cttgataaaa tgttttacat gttcaatttt agacatatgc cttagagtag  54540
ctacacatta tgtacattat ttctactcat tcaactccag tttcatcact gctttatcac  54600
gaagagtaca gaaatacgtg gtaaatgtcc ttaggttaat tattttataa gctctctaaa  54660
taagaaatta ttacattatt tgagaattca tcaccataca atttctaaca ttgaatgttc  54720
agatatcatt atatcttctc ttattcagtg atgagtatga gcttcactta caaagtatac  54780
tttggcaaac tccaatgcct aaaggagctg aagacataaa aataaatgag taaagagtgc  54840
caggaacagg aatttagggt gtgatggtta gaataggaga attcttttgg ttgtgaactg  54900
ctctccccat gcatccaaaa gcacttgtgt tcctcagctc tggcctattc ttttaatgca  54960
caaatttagg ccctgcattg gcaaggactt ctgattggtt tccaagaaaa tccaaacacc  55020
aaaatttttg tgtagaattt ttcaattttt aagactgtga gtgagccaag aaaaactttt  55080
tctcacgtcc tatctagcgc gattatgacc cttagttact atgtgtagaa cagtgaaaga  55140
acagaaaaaa aagtcatcaa aattacattt gtcacaggtg atgaataaat actttgcatg  55200
tagatggagt cactgattta accaatcatt tcctgaagtc tgagttgttg attatgacat  55260
ggtatgatca tataaatcaa atttaaaccc agatctgtgc atacttgaaa ataattattt  55320
ctaggtagtt tgttatcaag tcaatgttat cttatattag tgagttttct tatagattag  55380
agtaatggca ccatttaatc gtgccacaaa cttctgtggt gtgtgtttct gtatgcatat  55440
gctttttttat ttcttattat ttttctttta ttatggtaag aacaattaaa atgacatcta  55500
ccttcttaac aggttttgaa acatacagtg gacccatgaa caataggttt aaattatgct  55560
cgtccactta tgcacagact tttttcaata aatatattga aaaaatttgg ggagatttgt  55620
```

```
gaaaatttga gaaaatttat agatgaattg catagtgtag aagtaaagga aaccctaaga  55680
aaaaggtata tcatgagtgc ataaagtatg tttagatact ccactatttt atcatttact  55740
accataaaat atacacaaat ctattataag aaattaaact tattagaggg tacaagatgg  55800
ccaactagac acactcagga agcaccactt ccactgagga agcccaaaat attgaataaa  55860
ctaacatact tcgagcatat cttttgagag aaaacactga aagtcaatag agaggtgaca  55920
cagacactga ggctgaagag agagaaagct ggaaacccag tgcagggttg ttgaacacca  55980
gagatagttt ccagccctga gtggctccta gctaaggggt gagtaaagtg gcagtgggac  56040
agcctactct cactgttgac atctgggatc ctacctacaa gagaacccac gacccccaga  56100
gacattggaa caggcagggg catctgccca gagagtaggc agaaatagaa ctacagccag  56160
ccttgaaccc agggggtttt gcatgttggg tagctgcagc agaacgcagc cataggcgcc  56220
caacatccaa ggctctcttt cttccaccaa gtagctctca actcacctga cttctgagcg  56280
aagagacagc ggggccaact ttcctgtgag ctgggacaca tctgtattgt aggcccttct  56340
gcccgccagt ccctcccagt actcctgcct ggccacacct gcaagaatat gtgcacagca  56400
cagcctccac tgctcagcct gagggttttt tcaaggaccc ccacctgagt acttcctcag  56460
tatccttgga gcacttcaga tcccccagtg tagctactgc ctgaaccaga ggggccagac  56520
agtggagaca caggctagtc ccaaaacccc agggctgcag tgcatagctt gggagtgtga  56580
gctgagattg gtgcccagca ctcaagcaga ggaagaattc tgaatctcag aacactgaga  56640
ggggtgagat gcacgggttc atgggccagt gcagaatgag acatgcctca tttcataggc  56700
ccagtccagg aaggctgtgt cctgtctgcc agctgctgcc tctgcctaag ggagctccat  56760
ggctcagaac agtttcctaa caaaagaaat gcaagtgtgg caccagtgac cagagcggga  56820
gattgggggg gtgtccccta tggcccaggc acaggcctgt taagggggtc atctctcttg  56880
cccgctgcca caagcactgt tgtaaacaca ctgaaaaaca aaagagttat gtccccgagt  56940
aacagcttat ctgccagcca ttactcttaa gcaccattta ctggatcaca gctcaattta  57000
aaacatctgc ctatatattt gagactgtac ctcactctgt tacccaggct agagcgcaga  57060
gaagcaatcg tagctcactg cagcctcaag ctcctaggct caagccattc tcccacctca  57120
gccttctgag tagctgggac tacaggcaca caccactaca cttggctaat atgtgttatt  57180
ttctgtaaag acagggtttt ccatgttgcc caggctgatc tcaaacttct ggcctcaagt  57240
gatcctccca ccttagcctg gcaaagtgct ggaattacag gcttgagcca ctgtgcctga  57300
cttcaaaaat agtttgtcag tatacattgc atatgaaact gagagcaaga atctagctat  57360
aaataaaaat attgtgcaga gtcttatccc agaaattaaa ccaactgacc atactcaact  57420
tataccacag ttaaaggaac accattcctt caagatgaaa aagaatcaac aagaaatctg  57480
gcaattcaaa aagtaagaat gtaccttaac cttcaaatgg gtgcatttga gctctccagc  57540
gatggttctt aaccacattg gaatgactaa aatgacagac aggcaattcg gaatctggat  57600
ggcaagaaag ctcattgaga ttcaggaaag tgctgaaaca caatttaagg aattcaataa  57660
ttccagtaga atgatccaaa agctgaaaga cataatagcc attaaaaaaa cactacttct  57720
ggaattaaaa aaaatactac atggatttga taatacatcc agacctttag caacagaaca  57780
taccaaagag agaaaagaat ctcagagctt aaaaaccagt ttttataatc cactccatca  57840
gacaaaaaga aagaaagaaa aaaaaacata aaaatgaaga aaacttctag gaatttggtt  57900
tccttctgta aagaaaccaa gcctatgatt cattggaatt cctgagagag aaaaagagag  57960
```

```
agtaaacaac ttgtaaaacg tatttgcaga tatagtccat gaaaatatcc tcaaacttgc  58020
tagagagatt gatatgcaaa ttcctaaatt acagagaacc cctttgagat gctataaaga  58080
tgacaatccc caaggcatct actcattaga ttccccaaag tccacatgaa agaaataaat  58140
attttaagat ttttttgggg ggcagctaga gagatggatc aagtcactgt caaggggaac  58200
cccatcaatc ttgcagaaca cctttgagca aaaaccatac aagccagaag agattgggga  58260
cctattttca gcacccttaa agaaaagaaa tttcaaccaa aaatttaata tcccaccaaa  58320
ttaattttgt aagtgaaaga gaactaaact ccttctcata caagcaaaca ttgaggaaat  58380
ttcttatcac taaaccagcc ttataacagg tctctagaag agtgctaaac atggaaacaa  58440
aagattaata cttgccacaa caaatactca cttaaatagg tagcccagac acataaagca  58500
actatacaac caagtctatg aaacaaccag ctaacaacat gatgccatga tcaaaatctc  58560
acgtatcaat aataaccctg aatgtaaaca ggctaaatgc cccaagtaaa agacactgag  58620
tgacaagctt cataagtaga caaaacttag ccttctgttg tctttaaaag acacatctta  58680
catgtacaat acccacagga tcaaagtaaa ggaacggaaa gagatctatc catgcaaaca  58740
gaaaacaaaa cagggcagta atcactattc ttatatcaga taaaacagac attaaaccaa  58800
aaaccatcaa gaaggacaaa gaagggtatt acataaggat aaagtgttcc attaaacgag  58860
aagacttaac tattctaaat atatatgcag tcaaaagtgg aggacccaga tttacaaaaa  58920
agattcttag agacctaagg aaactaaaaa cagacagcca caccatgata gtggaagact  58980
tcaacaactc actgacagtg ttagatatcg aagcagaaaa ttaaaatgta aattttggac  59040
ttaaactcaa ctctcaacca actggatcca aaaacatcct acagaatact ccacccagca  59100
ctatcagaat atgctttctt ctcatctgca tatagattgt attctaaaat caatcatatg  59160
ctcagtcata aagtctcaat acattcaaaa aattaaaaga ttttgagtac attcttgaac  59220
aaaagtgcaa taaaaataga aatcaatacc aaaaagattt cttaaaacca cccaaaagta  59280
tggtaattca acaacttttc ctgaataatt cttggtttaa gaatgaaagt aaaaccgttt  59340
ttgacattaa ataaaataga gacacacctc actaaaatct ttgggatcta tctaaagcag  59400
tgttaagagg aagtttacaa tgctaaaggc cttcatcaag aaggcagaga gatttcaaat  59460
taacaattta acattgcact tacactaact agaaaaaaaa aggacaaccc caaagcaaac  59520
tgaaaataaa taacgaaaat cagaatgaaa ttgtgatgca aaatgtatac aaaagataaa  59580
taaaaccaag agtttgttat tcaaaagaat acaaaaagat taatagactg ttaactagat  59640
taacaaggaa aaaaaggaga cccaattaag cacaatcgga aatgacaaag atcacattac  59700
aactcccata gaaatgcatt acaaatgccc ctctgcacac aaattagaaa atctagagga  59760
agtagagtca ttcttggaaa caacctccaa agattaaacc agaaaaaaag tgaaaacctg  59820
aacagaccga taacaagtta tcaaattgaa ttagtaataa aaaacctact gaccaaaaaa  59880
aaagccctgg accagatgga ttctcagcca aattctacta attctaattt tattctaaca  59940
taaaagttcg ctttttttaaa gttaaacttc aaatttaagc acagaaacac atatgtacct  60000
catattatct catctacagt caagagaagt gaaaacaaat gtgaagatgt actattaaag  60060
cataacttta tacaattgac tgtaatatat acgttactgc tgtaataatt tcatagcacc  60120
tcctgtaatt gtagtaataa ggttgtgttg aaagcacctg cttaaaacac catgtgacac  60180
taattatctc cacatgaaca gttcctctct ccaataaatt gcggattgca gcaaaatctg  60240
attgtgattc ttgtgcgttt ttatactgtt tagtgcaata ctgtcaactt tgaataacac  60300
cgttggagcc atatgaattg ccactagtga tgctgaaact gctcctaaga aactgagaaa  60360
```

agtcacgaca ttacaagaaa aagttgtatt gcttgatata taatgcagat tgaggtcttc 60420
agctgcccat tgtttcaata caaatgaatc cagcataaag atcattgtaa aaaacaaaaa 60480
aagggaaaaa aaaaggaaat tcatgatggc attgctgagt ctatgccagc aggcacaaaa 60540
tcttgcactt ttagtaatat accgtcttat ctcatattga aaatgaaatt gttatatggc 60600
tgcaaacttt tataagaaag gcataaccac agactttaat gtgatttgag aaaaagtgaa 60660
gttattatat gaccatttaa agcaaaggaa ggtgagggat ctaaaactgg agaaactaat 60720
gcaagcaaag gatggtttga taattttaga aaatgatttg ggtttaaaaa ttttcaaaat 60780
aacagaagca gcagcttctg ccaaatgaga gaaagtgaac aagttttcag attccactaa 60840
gaaaatcatt gagaaagcat atctgcatga gcaggttttt aatgcagatg aaagtgtcct 60900
atcctgggga aaagaaagcc acgaaggacg tttattaata aagaagagaa gtgagcacca 60960
ggatttaagg caggaaggga tgaggtaagt ctactattct gtacaaataa ggtcaggctt 61020
attatcaaaa ctgctagtat ctacaaagtt gataagtccc aaaccttgaa ggcaaaagat 61080
aaaaatcaac tgctagtctt ccagtcatac aaaaggaagg tctgaacaat tagtactctt 61140
tttcagaatt gtttccatca atgccttgtt cctgaagaca ggaagtagct tgacagtaag 61200
ggactgcctt tacagttctt ttcatatcag tcgatgcccc tggtcaccta gaaagcccat 61260
aagttcaaca tcaaaggcat tgtagtgatc tatttcttcc accacaacat ctctaattca 61320
gcctctagat catggagtca taagaaactt taaaggatca ttacagatga tactctaacg 61380
aaaggattat cagtgctatc aaagaaaatc ctgataggca gaacatcata aaagactaga 61440
agaattacac catttaagat gctattgtta tagggaaaaa aaaaagtgaa agtcattaag 61500
tgcaaaacaa tacatttcta ccagagaaaa ttttgttcag atgttgtgca taaattcata 61560
ggattaacaa catggccaat caagaaaatt atgaaagaga ttatggatat ggaagaaaaa 61620
gtgaggagta aagaatttca agatatcggt attggagaaa ttcaagagct aattcatacc 61680
tcatcaggga agttaacaga agatgacctg atggagatga gtgcctgcga actagtgtca 61740
gatgatgggg aaggagacat agaagcagca gtgccagaaa caaattgtta ttaggcaatc 61800
tagcagaagg attctgataa ttcaagactg tttttggctt cttttataac agggactctt 61860
gtctaatgtg ggcactgaaa ctaaagcatg tgttggaaga aggattagtt ccatttagaa 61920
aaatttttag agaaatgaca aaaccacaaa gtcaaataga aattatggcg tatttatgaa 61980
atagttactg aatgtacttg cctcttttgc cttccctcta cctcctccac ctcttccacc 62040
tcttctaccc tagtgaaagc aagaccagtg cctcccattc cttctcctcc tcagcctact 62100
caatgtgaag agatgagaaa gatcttatga tggtccactt caacttaata gtaaatatgt 62160
tttatcttcc ctgtgatttt ctttataaca ttttttctct agcttacttt atattaagaa 62220
tactatatat aatacatata acatacaaaa catgtgttaa tcaactgttt atgttattgg 62280
taaggattct gatcaacagt agctggtatg atttggatct gtgttcccgc caaagtcatg 62340
tagaattgta atccccaatg acggaggtgg ggcctggtgg gaggtgattg ggtgataaag 62400
gtagtttctc atgaatagtt taacaccatc ccccttgatg ctgatctcat gatactgagt 62460
gaattctcat gagatttatt tgctcaaaag tgtgtaatac ctcccccctc tcttcttcct 62520
gtagagactg cagaactgca taactgaaac tttataccca ttgactaaca actccctgct 62580
tccccttccc cttaatcact ggcaataacc attctactct ttgcttctgt gagtgttact 62640
gttttatgtt cctcacatga atgtaatcat gtagtatatg tccttctgta actggttcat 62700
tttgcctaat gtcctcaaag ttcatccaag ttatcacata ttgcagaata tccttctttt 62760
taaagactga ataatattcc attgtatgtc tatacaatat tttctttatc catttatccc 62820
tcagcagaca tgaggttgtt tttacagcta gctattatga atagtgctgc aatgaacgtg 62880
caaatgcaaa tggtctcttc aagataatga tttcaattct tttatatatg tacccagaag 62940
tgggattgct gggtcatatg agagttctgt atttaatttt tgaggaatct ttataatacc 63000
ttttatactg gctgtacctt tttgtattct accagcagtg taccgtgttc aaatatctcc 63060
acattcttgc aaacactttc tttcttaaat gatagccatt ctacaggtgt aaggtgtagg 63120
aaaagagtgg agttgtgctt ttgatttgca tttccctgat atgcaatgtt gaaaatcttt 63180
ttattgacct gttgttcatt tgtgtgtctt ctttggagaa atttctattc aggtatgtag 63240
cctaattgtt ttttcaaatt aatttttttt ttttgagtca ctctcactct gtcacccagg 63300
ctggagtgca gttgtgtgat ctcagctcac tgcaatctct gcctgccagg ttccagtgat 63360
tatccagcct cagcctccag agtatctggg attacaggtg cctccaccac acctggctaa 63420
tttttgtatt tttagtagag atgggatttc accatgttgg cctggctggt ctcaaactcc 63480
tgacctcagg tgatccaatt tgtcttggcc tcccaaagtg ctgggattac aggttatcag 63540
ccactgactg acatatataa aattgtattt ttatcatgta cactctaatg ttttgaaata 63600
catatataag tggaatagtt aaatttagct aattaacaaa tgcattatct tacatagtta 63660
cttttgtagt ggaaacactt aacatctact ctctcagcat atttcaaaaa tacaacatat 63720
tgtggttaag aatagtcacc ctgctgcata ataaatctct gcaatttttt cctcctaatt 63780
gtaattatgt atgctttgac cagtatctcc tcatgtggga gatcagtcag agtggtggaa 63840
gaagctatag ggaaggaagc aggcctttag aaaggtcaga aggctctgca aaacttcagg 63900
ggagactaag ctgaagatag ctgttctctt accctgaggc agagcacaag aaataggtat 63960
aaggaagtat aggggaattt atctaaatag gcttgtctac ccatgttgtc cagaaactga 64020
cctttgacca tccgtacacg tgactgttcc cagtaagggg gaacaataat gttaattaca 64080
cacagattgt gttggctcca gcctttcggc attatgtctg tactaaataa aagtgagcag 64140
ctccagcttg ttgggactgc tactcactct ttggcagtcc cctagccact ctttcaccac 64200
atacctgtgt ctgagtactc ctttcatctg ttggtaggcc agggtctacc aggatggacc 64260
aggcatcctc aactccactg ttctcccaac cacctggctt ctggtagcca ccattctact 64320
cactaataac taattaattt ttatttcaat agcttttggg gtagatgttg tttttcgtta 64380
catgggtgaa ttctataatg ataaattttg atattttaca tacctgagta atgtacattg 64440
tacccaatat gtagtttttt tatccctcag tccccttcca tctttcccct tctgagcctc 64500
ctaaatccac cacatcaatc tgtatgtctt tgtatcttca tggcttagct cccaatgata 64560
agtgagaaca tacagtattt ggttttccat tcctgagtta cttcacttag aataatgtcc 64620
tccagttcca tccaagttcc tgcaaaattt ttcatcgtta ttattttttt gctattgagt 64680
tgtaggattt ccccgtgtgc tttagaaatt aacccctttt catatataaa tgatttataa 64740
tattttattt tattctgcat atttcttttt taccccattt attgtctctg ttctgttcca 64800
ttggtctata tttctgtctt tatgctggta ccatattata ttaattacta tagctttaaa 64860
atacattttg taattaggaa atatgaggca gctttattct ttctcaatgc ttttttggct 64920
atttgatgtc cttcttggtt ccatatgtat tttagaattg tttgttatat ttttgtaaaa 64980
atactattgg gcttttgata ggtattgtat tgaatcttta catatatttg ggtagtatgg 65040
acatttacta ttaataagtc cttcaattat taacacagaa tgtctttcta attatttatg 65100

```
gcttctttat ttcctcagtg tcttgaagta tttcatgcac aagtctttca ccttcttaaa  65160
tttatttttg tgttttattc tttatgattt tagtgtaaat ggaattgctt tcctaatgtc  65220
ttttcaaata gtacttggtt aattcataga aatataagta atatcttata attattttgt  65280
atcctgcaac tttacagaat gtgtttattc aattctaaca ggtgtgtgtg tgtgtgcatg  65340
tgtcatcttt agggttttct atatacaaaa tcatgccatc tgcaagtaga ggcaatttta  65400
cttctttctt tcaagtttga atgtctttta tttctttttc ttggttaatt gctctggcat  65460
aaaatggcag gactgtgttg aatagaagtg atgagaatgg ccattcttcc tttgttcctg  65520
aaagctttct gtttttcact cttgaattta atgctagctg tgagcttttt aaatatgcac  65580
ttcattttgt tgaggcaatt tttatctatt cctagcttgt tgaaagtttt tatcacaaaa  65640
cattgttgga ttttatcaaa tgctgtttaa catctgcata tttgatcatg tagattttgt  65700
cctttttttg ttaatgtgtt acattacgct tggtgatatt tgttaaactt agcatttcag  65760
gtataaatcc cccttgaata tagtgtagta tccttttttat atgctattaa atttggttta  65820
ctagtattgt ttgaggattt tctcctctgt cttcatcaga tatattggtt tgtagttttc  65880
ttccttttgg tgtctttgtc tggctttggt atcagaataa tgctggcctt ataaaattag  65940
tttgaagatg ttctcttctc ttcaattttt ggcaagagat tggaatggat tgccattaat  66000
atttcttta gctatttagt aacacgcacc agtaaagcca tctggtccta agttttttgt  66060
tgagaagtat ttgattatta attcaatatt tttactggtt gtaaatctct ttatattttc  66120
tatattttct gtgttttatg tctccaggaa tttatttttt ctttcttatc taatttttga  66180
tgtataattt ctcatagtaa tctcttatga ttgttttatt tttctagcat caattaaatg  66240
tctctacttt cagctcttat tttgtttgtt tgagtctttt ctcttttgct tagtctagtt  66300
taaagtttgt caattttgcc tctctttcaa aaagatcaac acttagttgt gttgatattt  66360
tttctaatgt tttttttcc atattcttta ttgtatttat ttcttctcta atcttttttt  66420
ctcctgctaa ctttggcctt agtttgtttt tctttttata attttgtgag gtgtaaaata  66480
ggttgttagt ttaagataat tctttacttt ttactagcat aattatgtga tatttatcag  66540
tgtgtactga gagcaaacaa tgccagatgc tactagtgac cataaattag agaaataacc  66600
tatgtttttt ggatatggaa atgaaattta ccctacaaat gtagatattt tttactgaac  66660
acttcctctt actactgttc ttgctgcatc tcacatttta gaatgttttg tttttgattc  66720
tcttcgtatc taaatatttt ctaatttccc ttttgatttc tttgacaatt taattattga  66780
aaagtttgtt agtatccata tttttaaaat tttctacttt tctttttgat actaatttcc  66840
agttttattc cattgtagtt agaaaagata attggtatga ttttaatttt aaatttatca  66900
agacctgttg catgatgtaa catgtggtct atcttagaaa atattccatt tctatttgaa  66960
aagaatatac attctgtttt tattgagtga agtattctct atgtgtctgt tacgttcaat  67020
tggtctataa tgttgttgaa gtcctctgtt tcctcattga ttttctctct agtcattcta  67080
tttataattg aaagtgagat attatgaagt cagcctacta tggagggcta actgtaatac  67140
actattttat ataagagact ggagcatcct tggattttgg tatccatagg gagtcctaga  67200
accattgttc acagatacca agagatgatt ttattgtatt tctctatatt tctcttttca  67260
gttctgtcca tgtttgcttt atagcttttg ggtctttgag attgggtgaa tatattgggt  67320
tgtatattct tggtgaatta acttaaaaaa tcattttata atgtcctttt tgcaacttga  67380
gacagttttt tacttaaact ctttttcttt ctttgacaaa tagttaggtt gcaaattttc  67440
```

```
caaacttgta tgctctgctt cccctttaaa tataactttc aactttaggt catttctttg  67500
ctctcatatc tgagcattgc atgttagaag cagccaacct atatccttaa tgctttactg  67560
cttagaaatt tcttccatca gatgttctaa gtcattgctc ttttttttta ttttggagac  67620
agagtctcac tctgtggccc aggctggagt gcagtggtgc gatctcggct cactacaagc  67680
tccacctccc aggttcacac tattctcctg tttctgcctc ccaagtagct gggactacag  67740
gtgcccacca cgatgcctgg ctaatttttt tgtattttta gtagagatgg ggtttcaccg  67800
tgttagccag gttggtctcg atctcctgac cttgtgatcc acccaccttg gcctcccaaa  67860
gtgctgggat tacaggcgtg agccaccgtg cccggccaag tcatcaccct ttatttcaga  67920
cttccacaga tcccctaggg tatgaacaaa atgcagccaa gtactttgcc cgacaccatg  67980
cccggcttat tttgtacttt attagtggag acggggtttc tccatgttgg tcaggctggt  68040
ctcaaactcc cgacctcaga tgatccaccc gtctcagcct cccaaagtgc tgggatgaca  68100
ggcgtgagcc accgcgcctg gcctatttta ttttctatag cctcataaca gaggtgagac  68160
tagtgatttt agagccacac ttcctggctt ctgtttttat tattttaatt atttattatt  68220
attattatta attttgtttt tttggggggg ttgttttgtt ttgctaaggc ataacaagag  68280
tgacttttgc tctagctccc aataactgtc atttctattt gagacctttt cagcatgaac  68340
ttcattgtcc atgtcacgat ctgcattttg gtcataatca tttatcagtt tccaagaagt  68400
ttcaaacttt ccttcatttt cttatcttct tctgagtcct ccaagctctt gtaagctctg  68460
ctcattacct agttccaaag tcaagtccac attttcaggt atccttatag caatgtccca  68520
cttcttggta acaattttct gtgttaggcc attctggcat tcttacacaa gaatgcatga  68580
gactggctaa tttatcaagt aaagaggttt aattggctta tgattctgca agctgtacag  68640
gcatggcact ggcattatct cagattctga ggagacccca aggagctttt actcctggca  68700
gaagttaaag caggagcagg cacatcacat gttgagagaa agagcaaggg ggaggcaagg  68760
tgccacacac tttttaagca atcagatctt ctcctgagaa ctcatacact attgcaagga  68820
cagcaccaag caatgaagga tcaaccccca tgacccaaac acctcccacc aggccctacc  68880
tccaacattg gatattacat ttcagcagga gatttgaaca agacaaatac ccaaaccata  68940
tcagcctcca agtcttcatg gactggtatt gtataggaga aaactttctt cattcaaccc  69000
cagcagagcg tctgtgggcc tctcaaattt tgattctttt ttaaactgct atctttttgt  69060
taggaacttt cagaatctag agtatgtagg gtctcatgag cacttttaga cagtggacag  69120
agaagcccgt cacttggtca actcccagaa aattttgaat atttcacatg ctatccaatt  69180
ttttccttcc caaggagaat ttgaaaactg aggtgttttc tttgtttttt gtttgtttgt  69240
ttgtttttct tttcttttt acctcctcac tctgcataga tctgggagca gggaggagct  69300
gtagcaagtg ctcatgtgct aatttaagcc accattttg tgctctttgt agcccattgg  69360
aagcaagcat atgcctagcc ccaagatagg caagacaatg accagctgct ggagttggac  69420
acagaaaaga tgaaatgtta ggtttgtggt cgaaatattt ccctccccat agagaagctg  69480
gagttaagtt tttgtttcta attttttta acttggtcat tctgccctaa gctatgggcc  69540
aggagctatg ggaatgctta catactagtt caagctgcct tctttatttt ccgtagcctc  69600
caaaggtctg gtatatgctg agtcctgtca acacttcaag ataggtgata tagaagacag  69660
tcgcaagggt agtacctgaa aagttacagt tttggatgtg cagtctcact ctgtctctcc  69720
acagggataa gctggagatg cagttttctt acattcagtc tatgttgagc cagggaatag  69780
agctattgca agtgttcata ggcacttgca aatttctagt tcctcttgaa tgcatggtat  69840
```

```
tataatgagg agaggaacag caaagaggtg tctccaattt tcttaaaagt gtcaatgtag  69900
ctaatattgc acttccctgg ggtacaatgg cctgtcaact agcttctgga ttttccacta  69960
atggaattga tcgctgtata attgttgaat aaaatattgt tgaaagaaaa aagggtccag  70020
tccttcctat taggctatct tgctgataac tcatattggc tttttttatt acttagattg  70080
tttattttat acctgttaaa agagtgcatt tacacttgag atatagcatt tacataatac  70140
tcttattcat gatttaaaga aaaatatgac tgaaataaaa tggttaaatt atccttaact  70200
tttagagtct aactcttcag ggttactttt aaactcatat tttcactgta ttttcttatc  70260
ctctgtgctg tcaggagagt tggaaatgct tatttcaggc atggtgggaa gccccttat   70320
tgactcagta gatttcttgc aaactgctaa aatttcattg ctgacccttt cttgatttta  70380
ttagcttgtg ccaatagaca ttttcagaca acaatgagac gtcatagttc ttccacaggt  70440
agtaattaaa cagtctgcaa gcttaaatgt ccagtgatag aaactgtcca gtcatgtaat  70500
cagaaaagcc atcaagtgca cacaagctca ggcaatgaca acaatatcat gactgattcc  70560
tagacagtat ctgttgcatt atgtcatcaa atgttagact gatcctagtc tcagagatga  70620
caaaaaatta aaagaaaaaa atcgtgtctt ggaattgagg aaatgtagtt tactttcttc  70680
ataccattat ttccctgaac ctattgtatt tcaaaatgat ttttgactgg cttctataat  70740
tatttattct aggcactatc aggataactc ctactgattc tcgatgggtt ggagcttggt  70800
ggcttaattt ccttgtgtct ggactattct ccattatttc ttccatacca ttctttttct  70860
tgccccaaac tccaaataaa ccacaaaaag aaagaaaagc ttcactgtct ttgcatgtgc  70920
tggaaacaaa tgatgaaaag gatcaaacag ctaatttgac caatcaagga aaaaatatta  70980
ccaaaaatgt gactggtaag tatttaacat tcattgtcaa tttggagttg ttaatctcaa  71040
tgaaaaggaa gaatgagtat tccaaaataa taaagcatac ccaactcatc tggagttggc  71100
tttcttttgc actaaattta gataaattat ttttctaaaa ctcctattaa agttaacata  71160
tatgtcttga gcacataaca agtggaagag aattaggttt gtacttttta gcagggagaa  71220
accaacaaaa gtttacaaac atccattttt tatgagccaa atagtaaata ttaattttag  71280
tattatatgg tctaaactgg gagagttcaa agaattataa tatttcattc cttcatttat  71340
tcaacaagta gtaccaggaa ctgtactatg ccctggtaat aaaacattac ctctattttt  71400
caagaaccta gtgggtgatg ctgagaaata tatagacaat agcaatatag tgccttaagt  71460
attatggtga aattaaactt aactattatc aggtgtagag atggattaag gagaaggaag  71520
tcgggagaag tttctcccta tgtaattaga gtaatattta ttttggtaat tatctatcta  71580
tctatcttat ctaaatattc aaaataaagt ggaagcaaag gtggtagtta agataattag  71640
actaagtaat gtaaattagg atgcatcagc atttgacagt gcctcctctt ttgaatataa  71700
accctgggac taatggagaa ccattgagag tcaataaaca aagagaatga cttggcagta  71760
gccagagcaa gatatgtgaa tcagtgaggt gttgacagca gttttcagat ttgggagaaa  71820
tggtgaaata gccaaagcaa tgcaacactt aaaccctcag catctttttc aagttttctt  71880
taaagtaaga tgacaaattc tccagtgtag cctaggttct tcctttcatc aggtctttta  71940
cttattactt tattgctatt ttctcctttc tatcacacta acccaagagc agtggtgttc  72000
tggtactctt tatattggct catagcagag gactgttaag tttcagctac attggtaggt  72060
tgaaattgtt catggcaaga gaattaccat gatttattac catggaaatt gggatatact  72120
acaagtagaa gtttgttttc ctaagaatca gatgttaaac atttatgttt ttaaaattta  72180
```

acattcacac taaaagtact ataccaataa ttttcatttt gtatatgatg tttctactgt 72240
accaaatcaa atctttaaaa aatagtagat tgtctaaacc tataaggagc ggggttgact 72300
gtgatccaaa cagaacagag aggataatga agttgtaaaa ataggacaat tgtagacata 72360
atctctatta tgaacagttt ttgtaggtgt gaccctaaga aagaggatct taagtatgta 72420
tctattagga atggataaaa taagaatata tagtcagaaa aaatattgaa tttattccat 72480
atgctcttga atagaactaa aactgattag aatgaaaaga tgatttcagt tcattacaaa 72540
aacagtgtgt aaacaatgag aacttttcaa aagtggagga aattgcttcc taaggtactt 72600
agtttaatgc cacttaagtt gtttattgat ccacttatta atgatatata gtagatcatg 72660
actatacaga agtttacact ggatgacatt gaatttctca tcctcaaaaa tgcaacgctt 72720
gtgtgaatgt atatactcca tttctgttga agaaaggcca caactcactt ataatactta 72780
caaatcaggg atggtttttc atgactgggg agacctgtgg agagaaatgt ggcacttttg 72840
cccaagaatt ttaaatgttg tttattccca ctatacattt tcttatctct tcttttttc 72900
ttttctgttt cttttctcta actccttcta ctccttattt caagcagatg caactgtttc 72960
gtagctgaca ttaaatggat gtcttagttc tgaccatatc taatgaaaat ctttagagat 73020
ttaaatagag aaaaatattt caaagtccgt atcatccaac tctcagtaac catatcttgg 73080
ctctgtcttg atgaactctg atacttccta ctgtttttct aagtagttcc ttctactttt 73140
aagtcctatt acagctagtt gacctggtga tcacagatcc aaatgacata atttctacca 73200
tgaacagaag ttagaagttt gttaccacag ctgtttgtag ggataggtgg ttgtattatt 73260
actattataa tactacttgg gacacaatat tatcccctgg ctgctttcct tgtatcttaa 73320
gacagagggt taataatatt gccaaattta ctgagaaagt atgttatggt agaagagctg 73380
tatactagag aaacaggagg tctgagtcct catactaaat taatctttaa gaattttgaa 73440
cctcaatggt cttatttctg tgagttttga attatgctgt ctttacattt ccatttaata 73500
gttatatttt taatataata cttatatcat taagtactaa taaataagaa acatcatatg 73560
tcttattcac tttttgtttg tttgtttttg ggttttttttg tttgtttgtt tgtttgtttg 73620
tttgagatgg agtcttgttg ctctattgcc taggctggag tgcagtgtca ccatctcagc 73680
tcactgcaac cttcgcctcc ctaattcaag caattctcct gcctcagcct cccaagtagc 73740
taagattaca ggtgtgtgcc atcgtgctgg ccaatgtttg tatttttagt agagttgggg 73800
tttcaccatg ttggccaggc tggtctcgaa ttcctgaccc caggtgatcc atctgcctcg 73860
gcctcccaaa gtgctaggat tacaggagtg agccactgtg cccggccttc acttttgttt 73920
tttgaacaat tagcatattg tctggtaccc agttgaaaac ctaacatttg ctgaatgaat 73980
gaataagtga attaatatgt ttgcaatagt attgtaaagt acccaggata accaaatatt 74040
aagtgaagaa agcaagttac aaaacagcac ttacgtatga ccctatttga gggtaaaata 74100
aactaaacta ataaatatta atattcgtat ggaaaatatt gaaagaatat atttaaaagc 74160
tgtgaacagc ctgtggtatt gcaggctatt ctcactcttt gtgttatgtg tttatagaat 74220
tttaaatctt acatgactta cgttcacaaa ttttagatat aaatgtatat ttaagttgca 74280
ttcaaatatt ttctttattt ttacaatttt acaggttttt tccagtcttt taaaagcatc 74340
cttactaatc ccctgtatgt tatgtttgtg cttttgacgt tgttacaagt aagcagctat 74400
attggtgctt ttacttatgt cttcaaatac gtagagcaac agtatggtca gccttcatct 74460
aaggctaaca tcttattggg taagacatat tttttacttg tgtgcttaat aagtgaaata 74520
atactaaata ctgtattcca agtggtattt tattgtgaaa gtgattttgt attttagtaa 74580

```
tacaggataa gtataatttt cttgtattct ttctcaaatg ttattaaaca tataaaactt  74640
gtgatgtcac tattgctctg catttgaagt tgcatcttat tttagatgag ttcctgaaaa  74700
aaatgttgca aataaatgga caatttagag gtagtatctg tataattgga tcttataatt  74760
tagtgctaag atctgagaca aaccctttttg taattataat cattataatt ctataattta  74820
tggactttga aatcaagact cagttactta caaaaaatatg acactaatag ttccaaaaag  74880
agtatcgatt taaatacatc aaaatatgca taattcaaaa caaatatatt ttacagagta  74940
tttttgcta caatatctat tttcaatggc acatttagat gtgcttatta aggaaagttt  75000
ccttgtatta ttcttcccac aactctagta ttgtagacac attatagaaa ttcaatataa  75060
atatatgatg aattaaacaa cttatcatgt ggtatgtaac taggtcataa gtaaacaaga  75120
aaatgaatgt actgaagcag gagaccaagc ttccagataa tctctttgtt gatcttaaga  75180
taaaagttta aaatcgaaaa ataatgtttt gactcccagt aacctagcct gagctttttc  75240
ctagagaaga cttcatcttt gttaactctt attagacaaa gatatggaaa agttatagga  75300
gggattaaac attattaatc ctgtatgtag agcgatttgt cagttcaggt tctgtatgtt  75360
ttttaataaa tgacaaagat atattaattt ttatgttgtt aagctctggg cagatttagt  75420
gtgagttact gagggttaga actctatctg agagaggcaa aaggctttag atgaagttcc  75480
ataggcagaa agatggtgtt ttgttgttgt ttatttccag aaaaacaaaa ttgcctcata  75540
gaaattatct gctccaacaa atatcctcag ccacactgcc ttttgctatt gaggaaacca  75600
aactgtcatc attggcagga acaaattaca cagatcccct accaccatac tgctatatca  75660
ttcttctttt taaaaagtaa taagattggc attctactat aaagatacat gcacacatat  75720
gtttattgca gcactatttg caatagcaaa gacttggaac caacccaaat gaccaccaat  75780
catagactgg ataaagaaaa tgtggcacat gtgtaccatg gaatactatg cagccataaa  75840
aaagaatgag tttatgtcct ttgcagggac atggatgaag ctggaaacca tcattctcag  75900
caaactaaca caggaacaga aaaccaaaca ctgcatgttc ccactcataa gtgggagttg  75960
aacaatgaga acacatggac acagggaggg gaacatcaca caccggggac tgttgagggg  76020
tgggaagcaa ggggaggaag aacattagga caaataccta atgcattcag gggttaaaac  76080
ctagatgaca gtttgatagg tgcagcaaac caccatggca catgtatatg tatgtaacaa  76140
acatgcacat tctgcacatg tatcccagaa cttaaagtaa aattttaaaa agaagcaata  76200
atattgaata aatttgattg acatacattg tgtttcatct ataaagacat atcagaaaac  76260
tcatatatga ttacaacttt ttttcttttt tttctaggag tcataaccat acctattttt  76320
gcaagtggaa tgtttttagg aggatatatc attaaaaaat tcaaactgaa caccgttgga  76380
attgccaaat tctcatgttt tactgctgtg atgtcattgt ccttttacct attatatttt  76440
ttcatactct gtgaaaacaa atcagttgcc ggactaacca tgacctatga tgggtttgta  76500
tatatcacta tatcaattgc ataatatgtt aaccatcaaa ttaagagtct ctgtataagt  76560
aatataaggc agaaaacaat tttaactaaa ctttctttaa gttaagagaa atttcaattt  76620
taaaattttt aaaatatctg tttcttaaga cctcaaacac attcttttat tcctccacta  76680
aagagaagca acataggttg taataataat aactattatt tatgtggtac ttacaattag  76740
tagtgggtac ttttatcatt attttatgaa tgggaaaagt aaggcttaga gaaatacatg  76800
gattacacag ctagcattat taagattcta actcaaattt gagtttttta agtccaaaac  76860
tcttagtctt aaccaccact gtaatcttgg atggatcata agagttacat aaatggcatt  76920
```

-continued

```
agccaaaagt gactaaacaa cttttatcta cagttcatat cgatgttcaa caactatctt  76980
aacaaaagaa cacttttaat gttgtactga attttctttt ttgcaagcta atattgtttt  77040
tttctgatat tatctacatt ggaagtagca ttaagaaata ttctatatat aattgcatat  77100
tagacattga agaatcttta cttttccatg attaccatgt atagcaaagt atttttagtg  77160
caacagtctc cacctcaaat caagggcaag aatcctatgc agttttctga taatttcctg  77220
aatatagcca acaatttaag cttaggaagg ttcacattca agcaacaagc agagatgctc  77280
agatcacaat tcagtaacca tgttctttag tgctgcttac tactggtgct gagctttcaa  77340
agtctggatc ccatgaggtg ttggttttaa cttgtcaaat attcccacat tttcttctat  77400
aaacattgtg ctattcttgg aggcttgcca aggttatctg aaattgtttc cctgcacact  77460
gctaattctg aactgttatt ggtatctcct atccaccatc aactactgta gtaaattaaa  77520
atacattgtc ctagaatact gaattttaga ggtaaaagaa ccttagagat gatgcaatcc  77580
aacccttgta ttatactttc ctttattatt gaagagtcag aaaaaatgta acatgttgaa  77640
gtcacacaat gtctttagac tctagactga tcctatgtca caccccttagt tcaaaagcct  77700
tcttggttgt aaggacaggc cagtttcttg acaacaaggt tagtcactgt acaaagtata  77760
caaaagatgg cagcagagtt aaacagaatt tgtttcattt aataaaattt tattaagcct  77820
ttccttaaag gtaaatatta aggatatttg taggatacat cagttccctc atgggactca  77880
taatctaatg ataaataata taattaatgg attcaacatt cataaaatcc tgcgactggg  77940
ataagttttt ttttaagtat gaattattgc agaggtctcg gaatgtgttc tgaatatctc  78000
taaggatccc tgagacttta tcaaggggtg cacaacttca aaactatttt tataataata  78060
ctaagacatt atttgccttt ttattctcat gctatcctga cagtatagtg atattttcta  78120
atgctccaag gtatgttatt aattcattaa tctgactgct aaaatatgtg tgcttatgta  78180
cttttgtgta ttaaaatttt cttagtatta ctttctaata tagtacatgt caagaggtac  78240
aacttaattt aacaaaatcc ctttggaaca agccctcaat cttttataag agtgtgaagg  78300
acttctgaga accaattttt tttccaaaaa aaaaaaaaac cctgtgaggt tggcattatt  78360
atctatgact tacaaatggc aaaactgatt ttagaaagaa gtgccagaat taatataaac  78420
acagatgtga ctgattgcaa tatctggact gggtcattgt cttagtccat tcaggctgca  78480
aagttctagg tagcttatta atacacagaa attaattttt caagattcta aaggctggaa  78540
catgtaagac caaggtgatg gcacttttgg tgtctaggaa gggcccattt cttaatttat  78600
agacggtacc ttctcattgt gtccaggcat ggtggatggg gcaggcaaag ggtcagtaat  78660
tccattcatg agtactcatc ctcatgacct tatcactttc tagaggcctg acttcataaa  78720
gtcttcatat acgagattag ttttcaatct atgaatttgg gggccacaaa cattctgact  78780
atagtagtca taaaccattc tacttaacca ctccaagtag tatttcctca agcagaatat  78840
gctttttaat aaaattattg ataatgtagt ttctgaagta tgaatcttag tttttcattt  78900
aaattatgtg ctcattcaaa gataacacat caatcctcaa ttattatcaa attaaacatt  78960
tgaaagaaaa taattttttta aatgtttaag cagaaatgaa ttatacaaaa aatatatttt  79020
ataattttag ctatgttata atcatatttt ataatttata accatttcat aaaggaaatc  79080
agtataaagt atactatagt tttatttcaa aaatatactg agcttttcta gccttttttca  79140
actgattcta ttcttgattt ttcattttgt agaggttctg ctttaagcat gtctgttttt  79200
ttcttacata ttaaaataga gatttttaaa ttcaacctag ttaaatagca ttcgtagact  79260
cacaagactt tacagtgagc tgaaaggaat gtcagtctaa tgtcatcacc ttactgaaga  79320
```

gaaactcagt ctcagaaaaa agatgtaact tatctaatgt gaagtttctt catagaatta 79380
taacaacttc ttgtctaagt cctacttaac atctttggtt tatttttaca ttttgctttt 79440
tctaggtcac aagtcatgta ttggcaaaga tggagagcgt aaaataaata agcattaaaa 79500
aaaactttgc catttcgtca tcatcaaagc aaatttcttc atataaagaa aaattcttta 79560
tctacttttt ttccctcttt ctctgctttc actttacttc ttccttctcc tccccttctt 79620
tgtctttttc ttctctctct ctctttttga tatatgtcta tcatatattt ccagaaataa 79680
tccagtgaca tctcatagag atgtaccact ttcttattgc aactcagact gcaattgtga 79740
tgaaagtcaa tgggaaccag tctgtggaaa caatggaata acttacatct caccctgtct 79800
agcaggttgc aaatcttcaa gtggcaataa aaagcctata gtgagtatta gtttttactt 79860
tcctctcctt attcaaaagc acagattaga ttgaacaatt ttttaccaaa tatttctgta 79920
actaaggact ccattaaaaa gataaaagag aaagtttcca gtattatctg ttattgtgat 79980
gggtgtgatg tataaacaaa gttttatata aaagtctgct tagggcacaa tcaggttttt 80040
ctgttacttg aattctaatt ggagatcacc ccactttttt cctttgagat tgtaagacta 80100
tgacctttta gaatttgaat gcatttagaa tatctaagaa gcacctcatt tgactaaagc 80160
ctataatttt cattaagttg gaattacttt atccctcaga attcaggaaa atgagttaac 80220
ccattgtcag cacttcctat cttactaaga caacagtcaa tatgcaatgt tatatacaga 80280
ttctgatctg tttagctctg ggatcactac ccttttttact ttttaagaaa ttaatcaagg 80340
cttcatgctc acttgactgc cctattcttg attttctatt ttgatttttc caaagctggc 80400
acttctaccc aagataatgt agtatcctgc tcacctaatg tcaatatgtc ccatagaaat 80460
gtcatttatt ccgtcctgca aaacctttct ttccatgtga actacagttt ttctctaatc 80520
tcctgggtag ctacctgtca ctgggaatgg gttatggtgt ttcccatacc tacaatccac 80580
tcaacatctc acaaagttgt gtaatgtttt cctaggaact tttactatta ccaacattac 80640
taaaacagtc aactataatt attgctctct gccacaccct tctgtgtttg atttttaaac 80700
attctccatc tactcttgcc catggatcta cctaccaatt ataataagga atggcatgta 80760
gaattttaaa gaataaagca tcctggactt tttgaagaaa ggccacaact ttaataaact 80820
tgcacaaata tggcccaaag actacttaaa agcccacatc ttagtcatgg caacaatgaa 80880
tcttttgtgc agttgtttcc ttttcctttg ctgtttattt ttattttgct gtttttttaaa 80940
aaaataattt aactcttatt ttaggtaaag gggatacaaa tgaatttgtg ttagatgggt 81000
atattgtgat aagctaaagt ttagggtaca atcattccca tcccccaggt agtgagcata 81060
atacccaata agtggctttt tagtacttgc tgttttttat ctctccactc tagtagtctg 81120
taatatgtat ttttcctgtc cttatattcg tgtggaccca gtgattagct tccacttata 81180
agtgagaaca tgtggcatct ggttttctgt tcctatgtta attcacttaa gataatgacc 81240
tccagctgca tccaggttgc tgcaagggac attatttcat ccttcttttg gccatgtagt 81300
attccattgt ctatatgtac cacatttctt tatctaattc actgttgacg ggcacccagg 81360
ttgagaccgt gtctttgcta ttgtgaatag agctgtgatg accatagaag tatataagta 81420
gatgtgtttt tggtagaaga atttattttc ctttgggtat atacccggta gtgggattgc 81480
tgagttgaat ggtagttctg tttaagttct ttgggaaatc tcgaaactac tttacacagt 81540
gactgaacta atttacattc ctaccaacat aggataagca ttccctttct tctgcagcct 81600
tgccagcgtc tgttttttta atgttttgaa ccagtcagcc cttctgactg gtgtgagatg 81660

```
gtatctcctt gggattttga tttgcatttt tttgatgatt agtgatgtta aacattttta  81720
tgtgtttgtt agctgcttgt atgtcttctt ttgagaagtg tctgttcatg tcctttgtct  81780
actttttaat attgtttttg ttttttgctt gttgaattgt tcaagtttct tatagattct  81840
ggatattagt cctgtgttag atgcatggtt tgcaaaggtt ttctcccatt ccatagattg  81900
tcttttcact ctgttgatta tttttgttgt gcagaagctc attagtttaa ttatatccca  81960
cttgtccatt ttttttgttg caattgcttt tgagaactta gtcacaaatt ttttgccaag  82020
gccaatatcc agaatctttt cttggttttc ttcagtggtt tttatagttt taggttttac  82080
atttcagtct gtaatacatt ttgattaaat tttttatatg aaaagaaggg gtccagtttc  82140
atttctctgc atagttagcc agttattcca gcaccattta ctgaataatg agtactttcc  82200
ccattgcatt ctttttgcta acttcattga agatcagatg gttttaggtg tgtggctttg  82260
cttctgggtt ctctattctg ttcctttagt ctaggtgtct gtttttgaac cagtactatg  82320
ctgtttggtt actgtggcct tgcagtatag tttgatatca ggtaatggga tgcctctcac  82380
tttgttcttt atgcttagga ttgctttgac tattcagtct ctttttttcct atggaatttt  82440
acaatagttt tattctaatt cagtgaaaaa tcatgccggt tgtttgataa gaataccatt  82500
gaatctgtag attgctttgg gcagtataga cagtttaatg ataatttttc taccaatcca  82560
tgagagtaga atgtttttcc acttgtttgt gtcacctata atttctttca tcagggtttg  82620
tatttatcct agtagagatc tttcacttcc ttggtttaaa tgtattccta ggtatttaat  82680
ttattgtagt tattctaaat ggaattgcat tattgatttg ggtatcagtt taactgttat  82740
cggtgtatag aaatgctact aatttttttc cattgatttt gtattctgaa actttattag  82800
agtatgttgt cagttctagg aggcttttgg cagagtattt agggtttttt tttaattaat  82860
taatttattt atttttaatt atactttaag ttttagggta catgtgcaca ttgtgcaggt  82920
tagttacata tgtatacatg tgccatgctg gtgcactgaa cccactaact cgtcatctag  82980
cattaggtat atctcccaat gctatccctc ccccctcctc ccaccccaca acagtcccca  83040
gagtgtgata ttccccttcc tgtgtccatg tgatctcatt gttcaattcc cacctatgag  83100
tgagaatatg cggtgtttgg ttttttgttc ttgcaacagt ttactgagaa tgatgttttc  83160
cagtttcatc catgtcccta caaaggacat gaactcatca ttttttatgg ctgcatagta  83220
ttccatggtg tatatgtgcc acattttctt aatccagtct atcactgttg gacatttggg  83280
tgggttccaa gtctttgcta ttgtgaataa tgccacaata aacatacgtg tgcatgtgtc  83340
tttatagcag catgatttac agtcatttgg gtatataccc agtaatggga tggctgggtc  83400
aaatggtatt tccagttcta gatctctgag gaatcgccac actgacttcc acaatggtta  83460
aactagttta cagtcccacc aacagtgtaa aagtgttcct atttctccac atcctctcca  83520
gcacctgttg tttcctgact ttttaatgat tgccattcta actggtgtga gatggtatct  83580
cattgtggtt ttgatttgca tttctctgat ggccagtgat gatgagcatt ttttcatgtg  83640
tttttggct gcataagtgt cttcttttga gaagtgtctg ttcatgtcct tcgcccactt  83700
tttgatgggg tttttttgttt ttttcttgta aatctgttgg agttaattgt agattctgga  83760
tattagccct ttgtcagatg agtaggttgt gaaaattttc tcccattttg taggttgcct  83820
gttcactctg atggtagttt tttttgctgt gcagaagctc tttagtttaa ttagatccca  83880
tttgtcaatt ttgtcttttg ttgccattgc ttttggtgtt ttagacatga attccttgcc  83940
catgcctatg tcctgaatgg taatgcctag gttttcttct agggttttta tggttttagg  84000
tctaacgttt aagtctttaa tccatcttga attgattttt gtataaggtg taaggaaggg  84060
```

atccagtttc agctttctac atatggctag ccagttttcc cagcaccatt tattaaatag 84120
ggaatccttt ccccattgct tgtttttctc aggtttgtca aagatcagat agttgtagat 84180
atgcggcatt atttctgagg gctctgttct gttccattga tctatatctc tgttttggta 84240
ccagtaccat gctgttttgg ttactgtagc cttgtagtat agtttgaagt caggtagtgt 84300
gatgatgcct ccagctttgt tcttttggct taggattgac ttggcgatgt gggctctttt 84360
ttggttccat atgaacttta aagtattttc caattctgtg aagaaagtca ttggtagctt 84420
gatggggatg acattgaatc tgtaaattac cttgggcagt atggccattt tcacgatatt 84480
gattcttcct acccatgagc atggaatgtt cttccatttg tttgtatcct cttttatttc 84540
cttgagcagt ggtttgtagt tctccttgaa gaggtccttc acatcgcttg taagttggat 84600
tcctaggtat tttattctct ttaaagcaat tgtgaatggg agttcactca tgatttggct 84660
ctctgtttgt ctgttgttgg tgtataggaa tgcttgtgat tttgtacat tgattttgta 84720
tcctgagact ttgctgaagt tgcttatcag tttaaggaga ttttgggctg agacaatggg 84780
gttttctaga tatacaatca tgtcatctgc aaacagggac aatttgactt cctcttttcc 84840
taattgaata ccatttattt ccttctcctg cctaattgcc ctggccagaa cttccaacac 84900
tctgttgaat aggagtggtg agagagggca tccctgtttt gtgccagttt tcaaacggaa 84960
tgcttccagt ttttgcccat tcagtatgat attggctgtg ggtttgtcat agatagctct 85020
tattattttg aaatacgtcc catcaatacc taatttattg agagttttta gcatgaagtg 85080
ttgttgcatt ttgtcaaagg ctttttctgc atctattgag ataatcatgt ggtttttgtc 85140
tttggctctg tttatatgct ggattacatt tattgatttg tgtatattga accagccttg 85200
catcccaggg atgaagccca cttgatcatg gtggataagc ttttggatgt gctgctggat 85260
tcattttgcc agtattttat tgaggatttt tgcatcaatg ttcatcaagg atattggtct 85320
aagattctct ttttttgttg tgtctctgcc tggctttggt atcagaatga tgctggcctc 85380
ataaaatgag ttagggagga ttccctcttt ttctattgac tggaatagtt tcagaaggaa 85440
tggtaccagt tcctccttgt acctctggta gaattcagct gtgaatccat ctggtcctgg 85500
actcttttg gttggtaagc tactgattat tgccacaatt tcagatcctg ttattggtct 85560
attcagagat tcaacatctt cctgatttag tcttcggaga gtgtatatgt caaggaattt 85620
atccatttct tctagatttt ctagtttatt tgcgtagagg tgtttgtagt attctctgat 85680
ggtagtttgt atttctgtgg gatcggtggt gatatcccct ttatcgtttt ttattgtgtc 85740
tattagattc ttctctcttt ttttctttat tagtcttgct agcggtctat caattttgtt 85800
gatcctttca aaaaaccagc tcctggattc actaattttt tgaaggtttt tttttgtgtc 85860
tctatttcct tcagttctgc tctgatttta gttatttctt gccttctgct agcttttgaa 85920
tgtgtttgct cttgcttttc tagttctttt aattgtgatg ttagggtgtc aattttggat 85980
ctttcctgct ttctcttgtg ggcatttagt gctataaatt tccctctaca cactgctttg 86040
aatgcgtccc agagattctg gtatgtcgtg tctttgttct cgttggtttc aaagaacatc 86100
tttatttctg ccttcatttc gttatgtacc cagtagtcat tcaggagcag gttgttcagt 86160
ttccatgtag ttgagcggtt ttgagtgaga ttcttaatcc tgagttctag tttgattgca 86220
ctgtggtctg agagatagtt tgttataatt tctgttcttt tccatttgct gaggagagct 86280
ttacttccca gtatgtggtc agttttggaa taggtgtggt gtggtgctga aaaaaatgta 86340
tattctgttg atttggggtg gagagttctg tagatgtcta ttaggtccgc ttggtgcaga 86400
gctgagttca attcctgggt atccttgttg actttctgtc tcattgatct gtctaatgtt 86460
gacagtgggg tgttaaagtc tcccattatt aatgtgtggg agtctaagtc tctttgtagg 86520
tcactcagga cttgctttat gaatcttggt gctcctgtat tgggtgcata tatatttagg 86580
atagttagct cttcttgttg aattgatccc tttaccatta tgtaatggcc ttctttgtct 86640
cttttgatct ttgttgtttt aaagtctgtt ttatcagaga ctaggattgc aacccctaac 86700 ttttttgtt ttccatttgc ttggtagatc ttcctccatc cttttatttt gagcctatgt 86760
gtgtctctgc acgtgagatg ggtctcctga atacagcaca ctgatgggtc ttgactcttt 86820
atccaatttg ccagtctgtg tcttttaatt ggagcattta gtccatttac atttaaagtt 86880
aatattgtta tgtgtgaatt tgatcctgtc tttatgatgt tagctggtta ttttgctctt 86940
tagttgacgc agtttcttcc tagtcttgat ggtctttaca ttttgccatg attttgcagt 87000
ggctggtacc agttgttcct ttccatgttt agcgcttcct tcaggagctc ttgtagggca 87060
ggcctggtgg tgacagaatc tctcagcatt tgcttgtctg taaagtattt tatttctcct 87120
tcgcttatga agcttagttt ggctggatat gaaattctgg gttgaaaatt cttgtcttta 87180
agaatgttga atattggccc ccactctctt ctggcttata gggtttctgc cgagagatcc 87240
gctgttagtc tgatgggctt ccctttgagg gtaacccgac ctttctctct ggctgccctt 87300
aacatttttt ccttcatttc aactttggtg aatctgacaa ttatgtgtct tggagttgct 87360
cttctcaagg agtatctttg tggcattctc tgtatttcct gaatctgaac gttggcctgc 87420
cttgctagat tggggaagtt ctcctggata atatcctgca gagtgttttc caacttggtt 87480
ccattctccc catcactttc aggtacacca atcagacgta gatttggtct tttcacatag 87540
tcccatattt cttggaggct ttgctcgttt ctttttattc tttttctct aaacttccct 87600 tctcacttca tttcattcat ttcatcttcc attgctgata ccctttcttc cagttgatcg 87660
catcggctcc tgaggcttct gcattctcca cgtagttctc gagccttggt tttcagctcc 87720
atcagctcct ttaagcactt ctctgtattg gttattctag ttatacattc ttctaaattt 87780
ttttcaaagt tttcaacttc tttgcctttg gtttgaatgt cctcctgtag ctcagagtaa 87840
tttgatcgtc tgaagccttc tctcagctcg tcaaagtcat tctccatcca gctttgttcc 87900
attgctggtg aggaactgca ttcctttgga ggaggagagg tgctctgctt tctatagttt 87960
ccagtttttc tgttctgttt tttccccatc tttgtggttt tatgtacttt tggtctttga 88020
tgatggtgat gtacagatgg gttttcggtg tggatgtcgt ttctgtttgt tagttttcct 88080
tctaacagac aggaccctca gctgcaggtc tgttggaata ccctgccgtg tgaggtgtca 88140
gtgtgcccct gctggggcgt gcctcccagt taggctgctc aggggtcagg ggtcagggac 88200
ccacttgagg aggcagtgtg cccgttctca gatctccagc tgcgtgccgg gagaaccact 88260
gctctcttca aagctgtcag acagggacat ttaagtctgc agaggttact gctgtctttt 88320
tgtttgtctg tgccctgccc ccagaggtgg agcctacaga ggcaggcagg cctccttgag 88380
ctgtggtggg ctccgcccac ttcgagcttc caggccgctt tgtttttcct aatcaagcct 88440
gggcaatggc gggcgcccct cccccagcct cgctgccgcc ttgcagtttg atctcagact 88500
gctgtgctag caatcagcga gactccatgg gcgtaggacc ctccaagaca ggtgcgggat 88560
gtaatctcgt ggtgcgccgt tttttaagcc cctcggaaaa gcgcagtatt cgggtgggag 88620
tgacccgatt ttccaggtgc tgtccgtcac ccctttcttt gactgggaaa gggaactccc 88680 tgacccottg cgcttcccaa gccaggcaat gcctcgccct gcttcggctc acgcacggtg 88740
cgcgcaccca ctgacctgcg cccactgtct ggcactccct agtgagatga acccggtacc 88800

```
tcagatggaa atgcagaaat cacccgtctt ctgcgtcgct cacgctggga gctgtagacc  88860
ggagctgttc ctattcggcc atcttggctc ctccaaccag ggtttttgag atatagaatc  88920
atatcatagt gcagagagat aatgtgagtt catttcctat ttgtcagtgt tttatttctg  88980
tctctttcct gattgatctg tctaggattt ccagtactat gttgaatagg agtggtgaga  89040
gtgggcattc atgctttgct cctgttctta agaagaatgc ttccagcttt tgcacattat  89100
atatgaagtt ggctgtggtt ttatcataga tggctcttat tattttgagc tatgttcctt  89160
caatgcccag tttgttgaag aactttatca taaaaggatg gtggatttta ttgaaagctt  89220
tttctgcatc tggtgaaatg ctcatatact gtttatccta aattccattt atgtagtgaa  89280
tcacatttat tgattgtgta tactggacca tccttacatc tcaaaaataa agcctacttg  89340
gtcatgatga attcactttt tgatgtgctg ctggattcag tttgctagtg ttttgttgag  89400
gaattttgca cctatatgca tctatattca tctatattca ccagggatat tggcctgttg  89460
gtttgttttt gatgttgttg ttgtttttgt gtcttgctat attttggtac caggatgatt  89520
ctggcttcaa aaaaatcagt taagaaagag tccttctttc tcaatttttc agaataattt  89580
agtacagtgg gtactcactc ttttttgtat ttccagtaga atttggctat gaatgcattt  89640
ggtctagggc ttttattgat aggcaggttt tttcagtact gattcaaatt tggaactcta  89700
tattagtgtt cagggtttca attactcttt gttcgtcttg gatggttgtt ggatggttca  89760
ttttggatgg ttggataaga atgacccagt taatacatgc tccctctttg cacactagcg  89820
aaggcctgaa agtgatagaa tattagaacc ctaaaaagaa ttgtgtctac cacaagacat  89880
aatcttcatt atactggcaa tgactatgcc atttggggac tattgcaaag tttttattat  89940
ttatttattt gtgtatttat ttatttatta ctaaatcctc aataatgaac catcacttct  90000
taaaatagtg ttctttgtac caaagcttag ttttattgac caatacactt gttccataaa  90060
aaattcctct atattattcc tagtgaaaaa aaatagtaag aactgtaagt ttggcagaac  90120
tgtagatgta tagatttaaa ttcttctaca attcttcctt caataattga tctttagcat  90180
taatagattc aacgtgaggt tcccttaaac tttagcctag atttagaaca gaatttatta  90240
aagccacctg tctatataaa ctgttcaact gattaaaaat ctgaaatcac ttgtttctac  90300
attttccact tctgtgctct aaacactagt ggggcattct gttgtgttta acctctctgg  90360
taataatatc atctgtcatt gtatccttgg attttgttta tgcctgctaa attaaaattt  90420
tagcatctct acctgtctct atttttcctg gactcagtgc cattttcatg ggtgactcca  90480
gttaaatttt gattactccc aaactgctaa attatctgaa ttctttggat aattcctcct  90540
cagggcatgt ctctgaaact tagagattgt ccaaaagagt atgtgctctg cagagggtaa  90600
aagggaatgg aaaataatta ttaaagagaa tctatagtga tgagaaaatt gtatacagag  90660
ttctaggcac taatttcttt gtttcttagt tttaaaatta agaatgaact aaatgtcaat  90720
catgaattac attgtcttat atagaaagaa atccacaaaa ctattttacc ttttatctct  90780
taagcaactg tatttttaga atcttcttaa actgtaaata tattagtttg aacaagtgag  90840
acttcactaa atataatgca atgtatttgc agcactgtta ggtcttgcaa atttcttatg  90900
tcatatttta tacacaacgc ttaaggtgtt ttacaactgc agttgtttgg aagtaactgg  90960
tctccagaac agaaattact cagcccattt gggtgaatgc ccaagagatg atgcttgtac  91020
aaggaaattt tacttttttg ttgcaataca agtcttgaat ttattttttct ctgcacttgg  91080
aggcacctca catgtcatgc tgattgttaa gtaagtatga cttttaaaaa cattttcata  91140
```

tgcatgagac tataaacaca cctaatgata tgcatatttt tacataatat actgggaatt 91200
caaattcata tttcatcaaa ttttaatttt ctgagaattc attttattaa aattactatg 91260
aactctcaag gctgtaatta ataattttgc ctctaattct tccattaaaa gtccagattc 91320
catacgtttc ttctcttact aagaatctga agacacagac tgacaattct ctcagttgta 91380
aaagaatcgc cctaggatcc taaaagaact tgttgaattt tgagttgcct tacatcctaa 91440
tgagagatgc cttgcatctc tcagggtaaa tctattgatt tcactaaaat aaagcatttg 91500
aaaactagat ataaaatatg ctccatttga taacattcca aaacttttaa tcgactcaca 91560
gcatgacttt tataataccc ttgtagaaaa ataaaaaaat acacaggaag aattagttcc 91620
tttcttggct cattagaaaa gatacaatgc ttggtgaata ttacatggta aatgaaacca 91680
ataagatact tgttgtcata cagctttcaa aattacagga aagactggtg tgagataaat 91740
aatcttaaaa tcaaagcaca tatttataaa ttgttctgag tcctcatcag gaaaaagatt 91800
tccctaaaaa gaaagattca aaaggaaagt taatttagga ttgaggtggg gggctgtgaa 91860
gaagaggatt cagagtacat ctcaaaataa gtaacattta ttctaaaggt ctaaagaaaa 91920
agccaaatga aagggtttcc aggagagggt cttggtgctg acgccttaat acaggaaaga 91980
gctggtgtgt ttgagaaatg aaaagaagct ggcagattga aacatactga atgagaggtt 92040
gtgacacatg ataagattgg agagttagga agggtgcagg taatgcatgc cctactggcc 92100
aagttgattc aatcacctaa aacttgtaac atgtaaataa ttgcttttag atcttaaaaa 92160
tatacatgtg taagtatagt gacctgggtt aacattcaat tgtactttta aaacttacat 92220
tgttgatcat aagttcactg tcagccaaca gcatgacatg gtagagatga aaaaaaaaag 92280
catttttaac atttgttaac attagtatca acctgtaaat tgaatttaca gttgtttaat 92340
tttgaccctg actgcaaatc ttatcaaatt atttatacta aatatgccac agatatagct 92400
ccatcttaat ataaaatgtt gtctactcaa aaggagaagt ctttcatatt tgccaaatta 92460
aattcattaa catattaaaa ataaccttaa aattaaataa tagtctgcat atcaacaggt 92520
tttagctttt tattttaaac tcatgagttt gaaaaaacac tgttccatca tcgatgataa 92580
caatatcata tctgtttcag aaattgatta aatcagcatt acaacttgtc aaaaatattt 92640
aactcttgct agcctttgat tttattgaaa taagcatttt gtgaatatga ctacagaata 92700
aaaatataaa tttcagtttg ttaatagttt tctaatgctt aacactatga agctattttt 92760
taaacttgat taagtaggca gaaggacatc catttattca atatgtattc atttttttatg 92820
tcaggcatag ttgtatgcac tgaggatgca actgtgaaca aaagtgatag aactttataa 92880
gcttttagta tgggtgggga atgaaggaat gaatgtgtgt agcagaaaac acagtaaaca 92940
aataagtgag taaacatcta aaatagagta agtgtgaagc actagaaaga taaataaatc 93000
acagttaaga aaatagaaaa aaatgagaaa ataggcaaga gatactagtt cagatatggt 93060
gctttggaag tcctttgagt aaagacctga atgaagagat agaaaataaa ggtacaagcc 93120
atgctaaatg gagacatagg aggaacaatc caggcaaggt agaagaaagg tcagcgtcct 93180
ggtgtgaagt atagttgaca tgtacaaggt ccaaaaacgt gtgtaaggag gagagaggtg 93240
acaagtgcag caagagagct agcctagttc agatcctatg ggtcacagga aagactttga 93300
aatatattct aaatgtgttg aaagcccaag ggatttaag cattagtatt tgcaaagatg 93360
ccttacataa ctagaagatc actctggctg tgggtagaaa gtgtgttttg tgaaaacaat 93420
agtgaagtca gggaaaacag aaggcttgaa ttgttcttct caagatggaa gcttgattga 93480
gaatgctgat aataggaaaa tatgaagtaa atgaaatgag taaatgaaac aaatatgagt 93540

```
ctcagttgtt ttgctttatt ttattatatt tatttattta tttttgagag acagtcttgc  93600
tctgtcaccc aggctggagt gcagtagcac aaccttggat tgctgcaacc ctccgcctcc  93660
caggttcaaa cgatgctcct gcctcaacct cctaagtagc tggaattaca ggtgcacgcc  93720
accgtgcctg actaattttt gtatttttag taggacctgg ttttaccacg ttggccaggc  93780
tggtctcaaa ctcctgacct caagtgatct gctagcctct gcctctcaaa gtgctgggat  93840
tacaggcctg agccacagca cctggccttt gttttatttt ttaatgcaaa gccagtaggg  93900
tttgctgaga cattgaatgt ggcatgtgag aaagataatt taaggataat cccaaagttc  93960
tggcttgagt tctggaagga tggtggtact attgaacaaa atgggaaaga ctaagaaagg  94020
gtagattggg aaagtgaaaa agcaagaatt tgttctatct ctataaagct gagcagcctg  94080
ttcaatatct agcaatgtca tatatgcaat ccaacaggag aaaccttgat gccagagcca  94140
taaattttag agtcagcaac gtacagatgg tatttatttt tatttttact tatttattta  94200
tttagagaca aggtctcatt ttgttgtcca ggctgaagta taatggcatg attatagctc  94260
actgtaacct tgaatgcctg tattcaagca atcccccaag gcggtattaa aatccatgga  94320
actaatgaga tcttctaggg actgagtaca gatagaaaca agatcctagg atcagttctc  94380
aatcactcta atttaaagat cactaatagg agaaaccaat aaagaaaact gaggaggttt  94440
catgagaaaa actaggaaag agcgttgtcc tcaaactaat aaagcatatg tcaaaaagag  94500
cataagtaac tgtgtcaagg gctgctgaga gttcacagga gttgaacctg ggaggcggag  94560
gctgcagtga gccaagatcg ctccactgca ctccagcctg ggagacagag caagactggt  94620
ctaaaaaaaa aaaaaaagaa aagaaaacca caaaccaata tccctgatga acatatgaaa  94680
aaattatcaa taaaacacta gcaaatcaaa tccgatggca cataagaaaa attttataac  94740
atgatcaagt tgtttttatt ctagggatga agggttggtt caacatatat aaatcaataa  94800
atgtgatttg ccacatagaa taaactaaaa accaaaacca tttgataaga caaaattaaa  94860
aacaaaaacc atatgatcat ctcaatagat gcagaaaaat tatttgataa aatttaacat  94920
ctttcatgac aaaaatcctc aacaatctgg gcatcaaagg aacatacctc aaaataataa  94980
aagctatgta tgacaaaccc actgccaact tcatactgaa aggaaaaaag ttgaaagcat  95040
tctcctgaga cctgaaacaa gacaagtgtg tctattttca ctactcttac tgcacatagt  95100
atgggaagtc ctagctagag caatcaggca atagaaagaa agaaaaggta tccaaattag  95160
aaaagaggaa ctcaaataaa ctctgttcac tgatgatatg caacaataac aacaaaaata  95220
gactaatggg acttaaacta aaaatttcct gcacagcaat ggaaataatc aacagagtaa  95280
acagacaacc tacaggaagg gaaaaaatat ttacaaacaa tacatctgac aaagggctaa  95340
tatccttaat ctataagaaa tacaaaaaaa ctcatcaaga aaaaaattat taaaaatagg  95400
gtaaatgata cgaccagcat gtttcaaaag acaaacagtc aacaaacaac aaacatatga  95460
caaaatgctc aatatcacta atcatcagag aaatgaaaat taaagctaca gtgagattcc  95520
attttatacc agtcagaacg gccattacta aaaagtcaaa aagcaagata ctggtaagaa  95580
tgttgaggaa aaggaatgct tatatactgt tgagaatata aattagtaca acctttatga  95640
aaaacaatgt ggagattttt caagtatctg aaaatagaag taccatttga cccagcaatc  95700
caactattgg atatctacca aaaggaaagt aaatcatttt atgaaaaaga ctcatgctct  95760
ttcacactta ttataacact gactagacca caaaaaatca gtatcttcag aggcataata  95820
aagtctgttc taaccacttc ctcataggat tttcataagt accatatgag aaaatatttt  95880
```

```
aagccatctt gaaatcatga tgcattgaat aaataaggga ataattatta ttattgctca  95940
agtgtttgcc ttttaaaaca attaaaatat aattttatat aatggggcca ttcaactgtg  96000
agcttaattc tatcatggag aaaaacaaca caggagaagg tttaatgttg tttcgttttg  96060
atattttaat gatatttaat gtttctttgc ctttgtcttg tttcagaatt gttcaacctg  96120
aattgaaatc acttgcactg ggtttccact caatggttat acgagcacta ggtatgatga  96180
aaaaaaaaaa aaaaaaaaaa aaaaatatat atatatatat atatatatat atatacacac  96240
acacatacat atattaaatt taagttataa atattaatgt caaggattaa agactgtaat  96300
gaatctttaa ttatgatagt aaataaaatt agtatccttt ctatttctgt gataaataaa  96360
aacaataaga gacagagtaa aattgagtga tggacctaaa ggagaattcg attgttaatt  96420
atacataaag tcaatctgtt aagactaagg aattattgta tttgtattac actctttcaa  96480
acacaaagat agatggtcct ccaaattttt cttttttttc agaaaaaataa gaatatttcc  96540
tcccagtagg cagagtgaag ggcctaactt ctaaactgtg gcatgattta ggcaaggcct  96600
aaagctagct tgggaagcgt gggaatctgg tcagagaatc tggccaggct atggccaaat  96660
tacaatgaag aaattgtcta agaagcgtat ttgatgataa agtcacaaat cctcaaagtt  96720
aaaaaagaag aaatataaag ggaatagaag agaggaaatg agatgctata gtattctgtt  96780
ggttttcttc cctccgttcc gttttgtgtg tctctaatct cccagactct gtacattctg  96840
gcaggtttct accttcagtt tcaatggaga tacctctctg ctagaacctg ggtgacaaaa  96900
gcttaaagta acatctgggt tgttagtact ccttctcata tgtagaaatg agactatgag  96960
aatggagtaa aattttttt agcaatagaa aataggaaaa aaaatgagtt tcaccattct  97020
aattctgagt atcctatttc gatgtatcca atctgtggca cgatggaacc taaatgcacc  97080
tatggaaaaa atacacattt agtacaaaac tttcaattca taaacaattg tcttgaatac  97140
aataaacgtg taaattgtgg aaggcctata tatttacctg aaaaagtcat ttagaaaata  97200
ggttatgagt tttaaaattg tagtgattag gacaaagttt attacttaaa acaatccatt  97260
acgtttgttc aaatcagtgg cattatgtgg ggaaaataaa ctgttagcat atatttttca  97320
tttttcaaag ggtggctgtg atttttgaaa cctgaaaatt tctcactcat ttcctcagta  97380
ccgggttttc tcagatacat tggcctcagt cccttgtcat tttaatattt ctcactctca  97440
aaaaattgag actgaggaaa actaaatgga attagtaaaa ttgtgatata tcaatcacta  97500
tcattttatc catggcaaaa taaattctga aaattattca ccacaataca aaaaaaaaca  97560
aagtaaagtt atgaacactt tagttgcacc atcttaagga cagttctcta ctggcgtgtc  97620
cctaaaattc ttcatcaaat tacctttgcc tagaaccagg agtgaatctc agagttcatt  97680
aaaacagcag tggaagcaga tggacactta ttatataaac aacatatctg tctgtgaaaa  97740
gccttgcatt ctgctaaatc atgagctaca aataaaaatt aactaagaaa aagaccactg  97800
aaaacttatc attgtgatca gaacactaac acaaacaaaa ttcagtacca caagccctaa  97860
cttagcctaa gctgcttcag gaggtattta caaatgcaca aaatcaattg tagaaaatca  97920
ctggactgtg agctctaatg acatcaataa gtgggaagta gatgtctgag cccagaaaaa  97980
agtacaacct gccaaaagct aagcactctc tgaagctcag cctatactta tctggggagg  98040
gagttctgat gaagcactca cttttaaatt ctcttaaaat aatgttaaaa aaaaaaaaag  98100
tctgctttta cagcaattga gccaagatct tttcctttc cccataaaat tgtaattcta  98160
ctccatttca ggtttctttg cctaagaaaa atcccatatt aaccaacata acttccaagt  98220
tttactaaca acattctcct ttttaccatt caggcttaag ttaattgtta tcataagaag  98280
```

```
aacagagtat atatgcatgt atgtagggag ggtacgagta ggtaaaaggt gtcaatgaca  98340
ttactacatg atttgggtct ttgagatttc taataatctt tattattggg tagatgcaga  98400
acaaaataat aaacgaatcc tccaaatttt tgaactttta tttaatcaaa atatatcaat  98460
gtggaatatc atgcagttac atttaaaata tgttccctaa actgacatct tctcttctcc  98520
tattacagga ggaattctag ctccaatata ttttggggct ctgattgata caacgtgtat  98580
aaagtggtcc accaacaact gtggcacacg tgggtcatgt aggacatata attccacatc  98640
attttcgtaa gttgtcataa atatatttca ttatttttc tttgactata ttaattccta  98700
aaaaatatca ttttcattat ataataatat taataatgat agccaccatt taatgaaaac  98760
tgactttgca tgcagtatgg tatcaagcaa tctcgtatct cattttagta ctcatagaaa  98820
ctataggaaa tggatatttt cttctattct gttatatacg aagaaactgt gattcaagga  98880
taataaccaa cttgtcaaaa atcagagata atagaaaatg gctaggattt gtatgtgaat  98940
cttttttgtt tccaaaactc tcctcatgtc agtatatata aggataaata tacacatgta  99000
aatatagaca cagacatata tatatgcatg tgtgtgtatt cgattgcctc tgacttctct  99060
agaaagaaac agaatgacta gctggggctc tggtcatatg tcaattaaga aaaaacggga  99120
aaatatgttt ctatattact ctattcgtgg ggagagatat tccgtaagtg acatgaagat  99180
aactgcatgg gcatctggaa aaacaaaaag ctacaattat actttacctc tttaaaaaaa  99240
aactaatttc aaattcatat attgacaaat tatacacttt gaaatgtgaa actacatgta  99300
ttaaaactca tagtataatt tctttcaatt atctacgaag cagaaactaa gtatgaccca  99360
aatgcccaaa accataatag aaaaaaagac aaaatattta taaaatctgc atcattaaac  99420
tttgaaaagg aaatttcaaa gtgaaagtat aaattaggag aataatttgc aacttgtaac  99480
acagacacag gcaaatatcc cgaatatata cggaactctt aaacatcagc aaaaaaacca  99540
tccaatgctg gcaaggatgc aaaacaacag gaatttcctt taatttttct ttcattgctg  99600
gtggatatgt aaaaaatagt acagccatgg tagaagacag tctggaagtt tcttacaaag  99660
aaaaacacag gcttatgata ctgttaagta atcatgcacc taggtattta cctaagttag  99720
atgaaaacat gaccccacaa aaacctgcac ttgcatatga aaaaatggaa gcaaacaaga  99780
tgtctttcaa taggtgaatg gatagccaaa ctggggtata ttcatacaat agaaaattat  99840
tcagcaataa aaagaagtga cctatcaact cacaaaaaga caagaaagaa attaaatgca  99900
tgtagctaag tgaaagaagg cagtctaaag aagcttctgg gcctggtgca gtggcccatg  99960
cctgtaatct aggcactttg ggaggccaag gtgggaggat tcatgaggcc aggatttcaa 100020
gaccagcctg gacaacatga caaaaccctg tctctactaa aaatacaaaa attagccagt 100080
cacggtggtg cacatctgta atttcagcta cttgggaggc taaagcacaa gaatcccttg 100140
aacccaggag gcggaggttg cagtaagcca agctcatggc actgctctcc ggcctggctg 100200
acagagcgag actctgtctc aaaaaaagaa aaaaaaagaa cattaaaaaa aattaaagaa 100260
gcttctgact gtattattct aactgtatga ccttttgtaa aagggccaaa ctatgaagac 100320
aatgaaacat cagtggttgc taggagctca gtggggagaa gataaggatg agtaggtgga 100380
gcacagggca ttttaagggt ggtgaaatga ttttatatga tattatcatg ttggatacat 100440
gatgttatgt atttgtcaaa cctatggacc catacccata caacatacaa accacataaa 100500
aagcaaactc taatctaaaa tatgaattta ataataatgc attcatattg gttcatcaat 100560
tgtaacaaag ttacacacta atacaaactg ttaatgatag gggaaactgt atgtgtgggg 100620
```

cggggagtat atgggacttc atactttctg tacagttttt ctgtaaatct aaaatttctg 100680
taaaaagtat gttctattaa aaaaaatcaa gtatctccca aagaaaaaat cacgaatggc 100740
tattaaatat ataaaaagat gctcaaatta attgataatg acaggattgc aattaaaact 100800
cacccaaatt gtcaaccatc aaaaatgtta agtagacatt gtcttggcaa aagtacagaa 100860
ctttgagcca gcagcaaact tctagaaatt tatcctacag ataactatac tcccaaatag 100920
ataaaatggc acatatataa gattacatac atgtgtatgg caacattgtt tatgatggca 100980
aaatattgga agcaacttaa atatctcttg ataagggagt aattagataa atagttctac 101040
ctgcaggaaa atgaatagtc tgatgtcttg aaaaaagaag aaaaaattat ttgtttacta 101100
atatggaacc ttcttcaaga catattttta tatgaaaaaa aagaaccatg aagaatgtgt 101160
atggagcatg ctatcattta tatgaaagtg gaggtttatt agttcaggat acatctctgg 101220
agtaaagacc taggatcaaa tttaccaaac agactctctt ccatttaatg tgtaaattca 101280
ctatctaaaa tccccagcag ataaaatgat ccaacttttt ccagaattgt accccacaga 101340
cattctcaca aatttattta aatattaatg acagaaaatg tctcacaaaa tgggagaaag 101400
aaatgaaaag aaattacaaa tgaaaacttc ataaatttat cttaatgact ttatttaaga 101460
atgtgttcat tttttattga aatcatcatg tatttccagg acacctggca agatgctcct 101520
cagaatttcc ccaaagcaat gaccacaact tcaagtatta atgtaacatt ttgagatggc 101580
tttataatgg tttgagtata aaaagaccct aaaactattt tttaagccat actagttcct 101640
ttttgttcag tgaaggttta gttagaacta aaatggaatt taaaaatatt ttatgttaat 101700
tgatttatta atgcattctt cttgttgaac aactggtata gtatccaaat ttttaatata 101760
ctgcaaagac cattgtgata acattatata gtgtatatgt gtactatata tatttaatat 101820
gcatatatat gcatatataa gacagacata ttatatatat gttattcttg tgtactttaa 101880
tttatgctca tcccaagact ttaagattta aagggtcggt ctttgtacat ccccacatat 101940
ttatcatttt cttttctctg atttcttctt gcatgtcaga ttctatctag ggtcattttc 102000
cttctgatta aagtcgattt ttaaaaatgt ctttcagtga gctctttagt ggcaaattgc 102060
caatttaaat ttctctggaa ggaactttag ttcaactgta tacttaaaag aaatgtacaa 102120
ggtatagaat tctaaattga caactatttt ctcttgtcag attgaagata ttactctatt 102180
gtcttctaag ttccatttta ctcttgataa gtaagctgtt gtctgttttc ttgttccttt 102240
aaggtaacct cactcctctg tggattcttt aaatatcttg tcttaatccc tggaatctgt 102300
aattacacta tgttcaggtt gcagatggaa taagtttgct aattagctga actcaagata 102360
agaaaattat ttggttgggc ccaatataac cacaaatatc ctaaaaaata aaaagaggag 102420
gtcagaagga tgtgatgtga gaaagactca gtctattgtt gctgggtttg aagatggaag 102480
aaaggggcca ggagccgagg aatgtaggtg gcctctagaa gtgagaaaaa gcgaaggaac 102540
agcttatttc ctggaggtcc cagaaaggaa tacagccctg ctgatacctt gattttagcc 102600
aactaagaca agtattaggc ttctaactgc caggaaatgc tccgggctta gctcacacac 102660
ccttttcttt cataaagttc acaccattcc aaccagctgg aaatgaccaa ccctctttgg 102720
gacttaccac attgtagcta actcatggcc cttatcactt tccttttggt cacttgtgtt 102780
ctttgcttga ttgtgtaaag tggaatttaa aaaaaaaaaa agagcagtgc atttaccaat 102840
gaatacataa aaagttaaat tgttacctta agaatttttt aaataaactc aattttagag 102900
agttttagga tcacagtaaa attgaggaga aattacagag atttcccaca taccacctgc 102960
cccacacatg catagcctat cctaccatca atgtctccca acaaagggtg atacagttgt 103020
tacaaatgat gaaacaacat taacacatct ttatctccca gagtccacag tttacattag 103080
gtttcactct tgacattgta cttttatggg tttggacaaa tgcataatga catatatcca 103140
ccattacagt attatacaaa gtagtttctc taccctaaaa atcctctgct ctgcctattc 103200
attccttcct cctctaaaac ccctggagac cactgtgctt tttactgttt tcatagtttt 103260
gcgttttcca gaatcataca gtatgtagca tttttagact agcttattta acttaatcac 103320
atgcatttaa atttcctcca ggtgtttcaa ttgcttgata gctcatttct ttttattgct 103380
gaataatatt ccattgtcta gatgtataac agattattta tatattcacc tactgagggc 103440
atcttgatgg cttccaagtt tcatgtttct ttgatgatat atatgaagat gtttgattct 103500
gttatattaa ccctggatcc tgtgtcctga aaccttgcaa taattgctta ttagttccaa 103560
gtgtgttttt gtctgttatt ttaaactttc tacttagaca attatgtcat attgcaaaca 103620
aagacaattt ctttcttttc aatctatata catttcattt tcttttcttt ttaaaaatta 103680
cattaattac gactcccagt accatgttga aaaacagtgg tgagagggga cgtttttgac 103740
ttgttcctga ccttagtggg aagactttga gtttctcact attaagtatg aagttagatg 103800
tagggttttg gcagatattt ttgatcaagt tgaggaggtt ctcccctatt ccaagtttaa 103860
tgggagtttt tattataaat gagtgtttga ttttgcaaat tcacttttct agatctattg 103920
atgtgatcat gtcattttat tattcttctt tagcctgtta atgtaatgaa ctgtaagaat 103980 tcatttttgaa tgttgaacca gtcttggaaa cctgagggaa atcccactta gtcatgatgt 104040
atactatatt tatacattgt tggattcaat ctgatatttt ttgagaattt ttgcgtctat 104100
gttcatgaga gaagttgctc tgtagtattc tttttttttt tttttttttt tttggagaca 104160
tagttttgct cttgttaccc aggctggagg gcaatggtgc gatcatggct caccgcaacc 104220
tccgcttccc aggttcaagc gattctcctg cctcagcctc ccgagtagct gggattacag 104280
gcatgcacca ccatacccgg ctaattttgt acttttagta gagacaaggt ttctccacgt 104340
tggtcaggct ggtctcgaac tcctgacctc aggtgatccg cccacctcgg cctctcaaag 104400
tgctggcatt gcaggtgtga gtcaccatgc ccagccctct gtagtattct tttcttgtaa 104460
tgtctttgtc tgattttgtt attaggataa tgctagcctc acagaatgaa ataggaagta 104520
cttctgctgc tgctatcatc tgaagaagat tgtaatgatt tggtataatt tcttacttaa 104580
gtgtttgata gaattcacca atgaacctat cttaatttga tgctttcttt tttattatta 104640
ttattatact ttaagttcta gggtacatgt gcacaatgtg ctggtttgtt acataggtat 104700
acatgtgcca tgttggtgta ctgcacccat taactactca tttacattag gtatatctct 104760
cagtgctatc cctccccccct ccccccaccc cacgacaggc cccagtgtgt gatgttcccc 104820
ttcctgtgtc caagtgttct cactgttcaa ttcccaccta tgagtgaaaa catgtggcat 104880
ttggtttttt tgtccttgtg atagtttgct gagaatgatg gtttccagct tcatccatgt 104940
ccctacaaag gacatgaact catccttttt tatggctgca tagtattcca tggtttatat 105000
gtgctacatt ttcttaatcc agtctatcac tgatggacat ttgggttggt tccaagtctt 105060
tgctattgtg aatagtgcag caataaacaa acttggcttt ttggctaata tcaagtatag 105120
tatctgttct tttcagttta gtttgatgct ttctgtttta gaaggttatt aaatatggat 105180
tcatttttag agagttctat cctccttcaa tgcctggggt tccatgagga aatcagagct 105240
ttttcccaaa aatggtacct cctatttttc ccaaggactc ctcgtctgtt agaaatgaac 105300
ttagttcctt tcatgtggtc atcaagaggg gcaaaaagac agactgagga aataattcac 105360
tcaagtgaga aaaataaata aataaaaact tctcaaaaaa acaagatcca agaagagaaa 105420
aagcacaaag gtcttgtata tagatatata cacacacaga cacacacaca tatatataca 105480
tatatgtata tatgtgtgta tatatgtata tgctatatat acatgtatat atgtgtatgt 105540
atatatacac acaaacgtat atgtgtgtct gtaaagagag agggagagcg agagagagta 105600
tgggagagca cttggatatc catttttaat taagctgact tttagctata gtgcccttta 105660
aaaaaaatcc tttatatctc ttattatctg actttagcaa ggccaaacag ccagtatttc 105720
tggcttttga acttctttag aaatagtaat ctcctaggtg aaataaataa gccttaactg 105780
aggttgtaac ttaaccatga gtgtatgagg tattttcaaa taggtggtaa gcagttttta 105840
caagatctag aatcttcaaa ggtaactcac agaaacgaaa attcaagaag ggaagccaga 105900
agttggtcat ggaggagcag agaatcaaca aatggaaaaa gccacaagaa tatcaaatca 105960
gaaagcattc attccctggg ccaagaattg agtcccaggc caccattgtg aaaagacaaa 106020
ctcttagctt ctgagctata gcattggata gtcttcatta cctttcccag aaggattcca 106080
gtgcaaccga tttcaagctt gcaaaggctt ttaactgctc gagataattt ttagagctaa 106140
ctatgacatt aactacaaaa ttcctgtcct ctagatggca gagaccaaga gtaagtactg 106200
ccacatagtt acaagatcaa gctcccacgg acataaaaca agatgagagg gaaacctcat 106260
ccagtatagg tttcaggaac acacagcaaa gtttgtaacc gaccagccca agaggctggc 106320
ttaaaaagta ggcttatagg aatcctaagc ctactttcta cattctttcc tatgacaccc 106380
ctctccatta cagaacaaca ctaaaagaca aattcttagc acaaagtaca ccagatttgc 106440
taaagcctaa gactagtctc aaaaattcat ttttctatta atcagaccac acacacacag 106500
agagagagag agagagacag aaagacagag agacagagag acagagaaag acagagacag 106560
agacagagag acagagacca gaagcttggc tggtaacaaa ttcttacccc ttttgccagc 106620
ataccacgtt tctgggttcc ctttctctgc agcttccaga agaatgaagt ggcttttgat 106680
gaccctgctc attgcaccat agctttgggg gccaagccac tttacaaaag aaaattatcc 106740
ttttctgttt tataaaacta taggcaaaag cttctcattt ttgcaagatg ctgcccaatg 106800
ggctgcatga ggaaccaaat taacattttc caccccagcc tagcaaaata cacataacaa 106860
aacagacatt tgtcacctca ttcagcaccc aatattgacc tggcgaggct caaactttct 106920
ttcattggtc cctatcatct ctgatccact caagatgtgg agggctaaac tccaactgag 106980
aattcaggtc tctgggcaag atgaagaagt ggacagtcac cccgactcag gcctttttga 107040
gcttccttca ggactcactg aatgtgacca gacaaataat gagggttttc tgagttaggt 107100
gtcctagact tccatcagta gttcctttag aggtctcctc cacatataca aatacacaca 107160
acaaagacaa gacagacaga aggccttcca aaccacgact tctaaccaag aattccgagt 107220
cttcctccca aacgaacctt ctattctcca cctgagaatt ctccctaaaa tcttcttgat 107280
tgaagagaaa tctcctgaac caagacttcc tactaattag agctaaccaa cacctccaaa 107340
ggagctgaac tgagacctca aaaaaaaaac aaacaaacaa aaaaaaaaaa acaagagccc 107400
caaaggagcc aaaccaaggc ccctaaagaa gccaaatcat gatccccaaa ggagccaaac 107460
caactgggag aagaaaggag gagttggcag tgcctagaat actcaccaaa ttagtttgga 107520
gacagacatc atttccagga actatttctc cattgcaatt aaatccatgc acattgggtc 107580
agcagcaccc tgccagtaga gacagtgcca gagtcagccc acagtccaag agaactaggc 107640
agccacttgg gctggcctct ggatccatca ccagagcagg gctactgaac catgggcagg 107700
taggcacaaa ggcaatccca gatgagaccc ctagtgtgta accacctaac gggttcacct 107760
tgcccactgc ctagacagag cttatttatc aagaaagatc ttacttatca aaacagagaa 107820
attgcaataa agagtaattc atgcagagcc agctgtgcag tacaccagag ttttgttatt 107880
attcaaatca gtctctctga gaatttgagg actggagttt ttaaagataa tttggtgggt 107940
aggggggcca gtgagtcaag agttctgatt ggtcaggtga gagatgaaat catagggagt 108000
tgatactgtc ctctcgtgct gagtcacttc ctgggagggg gccacaggat gagataggcc 108060
agtttatcaa tctgggtggt gtgagctcat ctgtgaagtt caggatctgc aaaatatatc 108120
aagtattgat cttaggtttt acaatagtgc tgttatcctc aggagcaatt tggttagagt 108180
cagaatcttg tagcctccag atgcattact cctaaatcat aatttctaat cttttggcta 108240
attcgttagt cctacaaagg tagtctgttt cccaggcaag aagctggttt gttttgggaa 108300
aggactgtta ctgtcttggt tttaaactcg aagctataaa ctaaatttct cccagaatta 108360
gttcggctta cacccagaaa tcaacaagaa cagcttggag gatagaagca agatggagtt 108420
ggttaggtca gctctctttc agtctcggtt atagttttgc agtgaaaatt tcataagcat 108480
ttagtgcaat aaactttcca ctttatgctg ttgaagctat atcctagagg ttttaaaata 108540
ctttgtctcg attttcattt gtttaaaaca aaaaaattgt gttctgctct aattttgtta 108600
tttacccaaa agtaattcag gaccaagtta tacagatttc ttgtaattgt gtagtttcaa 108660
gagttgctct tgatactgat ttctattttt attctgctgt ggttcatgaa gatgtttgtt 108720
ataactctga ttttttaaaa aatttattgt gacttatgac ttagaatgtg gttagtttta 108780
gagaatgttt tatgaacaga taaaaaatgc attttctctg atttttgggt gaagtattct 108840
ctagatatct attagatcca cttggtaaag agtctacttc aagtcgaatt tttttttttt 108900
ttttttagct tttggccttg atgatgtgcc tgcctagtgc tgtcagtctg gtgtcgaagc 108960
ttattactca ttgtattact ttctatctct ttgcttaggt ctggtagtat ttattttata 109020
aatatgattg cttcagtatt gagtgtgtat atatttagat tagttaaatc ttgttgaatt 109080
aaatgcttta tcattatgta atgcacttac ttggtttttt ttaaactgtt gtttgtttaa 109140
ggtctgtttt atttgataca aagagaggaa tttcagctta tttttgcttt ccatttgaaa 109200
gatagatctt tcttcattct tttactttaa gtctatgggt gtccttacat acgagatgga 109260
ttccttaagg gcagcagaag gttgcctttt tttttttaat ccactttgct actctatgtc 109320
ttttatatga agcatttagg caatttacat tcaaagttaa tattgatatg tgagattttg 109380
tacctctcat actgttgtta gctagttgct ttatagttgc aattgtgtag ttacttaata 109440
ggatctgtag gctttgtaat tatgggtgct tttatagtag caagtattgg tctgtttttt 109500
cctgttttga actcctttga gcattttttc taaaactgat ctggtggtga catatttcct 109560
tagtgtttac tggtctggga aatattttat ttctacttta ttcacaaatc ttcatttggg 109620
aagttatgaa gttcttggct gtcattatta tttttctttt gtaagtctaa caataggccc 109680
ccagtctctt ctagcttgta atgtatctgc tgggaagttc acctttagtc taatggtatt 109740
tccttcataa ataatttggc ccttttctct agctgccgtt aggatttgtt ttttcatgtt 109800
gaacttaggc aatctgatga ctatattcat atagtatctg aatggttgtt ttgtatagta 109860
tctcatacta tagtatgttt tgtatagtat ctcatacact gttgcaccca caacagtgta 109920
cagtggagag agtgggaaat taccctctat ccagattcat tcctgagtgt tggtactgcc 109980
tccttcagta attggtgctg tgcccatgtt ctctttgtcc caggggaagc tatagtgggc 110040
tacagtcccc actcttttag gggaagaaca cattgagggt tagatctcca gaggtcctgc 110100
tgtctcccca aagtccactg acccctgtgc ctaccaaagt cagagcagtt tgttggacat 110160
gtttgccagg aattgggtgg catggtgact caaagatgga gaatcctcag gcagggcggt 110220
ggcataccat agatgcacca acagtatggc acatctttcc tttagataga aaggtggtgc 110280
agctgtacct gtgcaggctg gccacctagt tgtctatccc tggggagttc ccaaattgcc 110340
accaatagca ttaccctgca tcaagagggc agaggaaatt cctaacaatt tggtggtcag 110400
cagattatca gagatgtgag gggagcagag aagcactttc agctaaattt tcacagggtt 110460
ctctgggggt tgattattac caggctttta ccgcttttct ttactacacc acagctgctt 110520
cttatgggca ctataacagt tcctggctct ctttctcagt tttttatttg gtacttcttt 110580
attcaccagt aactttgatc ttctttctga ggagaactgt aatttgatgt ccctggtcag 110640
ccatcttgaa aagaacttga cttatttttt tatcagtggc agcatgatat atcttcctcc 110700
atctaattac ttttaatcta tacatctata agtagatctc ttagagacta catatagttt 110760
gtttcttctt tttaatcctt taacaaactc agtcttttaa ttggtggatt tagatcattg 110820
acattaaaag tgactactga tgttgtgaga ccaatgttga ttataatttt actattgtct 110880
atttgttata cttgttcttt gatcctattt ttgtcttcta ttctttttttc ttctgttgtg 110940
ttcttaacta aatagtctat atgactctga ttttatatga ctatataatc ataacttttt 111000
atgttacctt tctttatgta tatcaagttt ctgacctata tgagtctctc taaaaagctt 111060
ctcttaacat ttcttacaag gaagatgtac tggaaaaaca tttcttcaat tgttgtttgt 111120
ctgagaatgt gtttatttct actttacttt taaaagaatt tcacagagta cagaatttta 111180
agttggtgat tttttctct taagacttta aatatttcac tccactctct tcttgcttgc 111240
atggtttctg aagagaagtc tattttctcc cctatagata aaatttgttt ttccttctgg 111300
ttagtttcag gataaagttt tctttatctt tgactttctg taatttgaaa ataacacacc 111360
tacacgtagt ttttctggtc aataataact tatttgtata tttaaaaata acttaggaag 111420
tgtagttgaa ttgtttgtaa ctcaaaggac aaatccttag cattttctga gtttcctgaa 111480
tctgtgatat agtgtctgac attaatttaa gagaaattct tagtaatttt tttttttttg 111540
agatggagtc tcactctgtt gcccaggctg gagtgcaatg gcatgatctt ggctcactgc 111600
aacccccgcc tcccgagttc aagtgattct cctgcctcag cctcctgagt agctgggata 111660
acaggcaccc gccaccacgc ccagctagtt tttgtatttt tggtatagac ggggtttcac 111720
catgttggtc aggctggtct ctaactcctg acctcgtgat ctgcctgcct cagtctccca 111780
aagtgctggg attacaggca tgatccactg cacctggcca gtaattattt tttaaaaatg 111840
tttcttttgc tccttttctc tttgttttcc ttctaacctt tccattacac ccacttatat 111900
aattgtctca aaatttttat atgatttcaa ttgatttact ttttagtctt gtttctcttt 111960
gcttttcagt tttggaggtt ttcattgata tatcctcaaa ttagagagtc ttcatcagtt 112020
gtgttctatc tactaataag cccatcaaag gcattcttta tttctgctac agaatttttt 112080
atttttagca ttttcttggg ttcttaaaat ttttattttt atacttacat tgtccatctg 112140
ttattgaatg ctgtctacct tattgattag aacacttaac atattaatca tagttgtttt 112200
aaattccatt ttgaaaattt ccacgtcccg gacatatcta ggtctggttt aaagcttact 112260
tattcctttc aatctatgtt tttttttca cttttggtat gactggcaat ttttttcatt 112320
acagttaagc ataatgcatt aggtaaaagg aactgctttg ataagccttt attaatatgg 112380
tgtaaggtgc tggagaaggg gtagcattct acaggcctac atttaggttt tattatttta 112440
gttataatcc agtaacctct ggattataaa tttcaaacat acttctcagt ttctcctccc 112500
agctgtaggt ggggcaggat ggcttaacag ggcttgagtt gtatattttt ctcgttttat 112560
gaagaaggcc agaggcaact agagtatagt ttctatggct tcataaccct attacaataa 112620
taaaatatct atcgttatgc cccaataaaa agaattatta gaattattgt cttaatattt 112680
tatttataat tttttttctt taggatctgg atactggaga aaatgtttta agttattaca 112740
cacaatttaa actgatttat tgttttattt tctctatttc tacagaaggg tctacttggg 112800
cttgtcttca atgttaagag tctcatcact tgttttatat attatattaa tttatgccat 112860
gaagaaaaaa tatcaagaga aagatatcaa tgcatcagaa aatggaagtg tcatggatga 112920
agcaaactta gaatccttaa ataaaaataa acattttgtc ccttctgctg gggcagatag 112980
tgaaacacat tgttaagggg agaaaaaaag ccacttctgc ttctgtgttt ccaaacagca 113040
ttgcattgat tcagtaagat gttatttttg aggagttcct ggtcctttca ctaagaattt 113100
ccacatcttt tatggtggaa gtataaataa gcctatgaac ttataataaa acaaactgta 113160
ggtagaaaaa atgagagtac tcattgttac attatagcta catatttgtg gttaaggtta 113220
gactatatga tccatacaaa ttaaagtgag agacatggtt actgtgtaat aaaagaaaaa 113280
atacttgttc aggtaattct aattcttaat aaaacaaatg agtatcatac aggtagaggt 113340
taaaaaggag gagctagatt catatcctaa gtaaagagaa atgcctagtg tctattttat 113400
taaacaaaca aacacagagt ttgaactata atactaaggc ctgaagtcta gcttggatat 113460
atgctacaat aatatctgtt actcacataa aattatatat ttcacagact ttatcaatgt 113520
ataattaaca attatcttgt ttaagtaaat ttagaataca tttaagtatt gtggaagaaa 113580
taaagacatt ccaatatttg caagctgtga ttgtcaaaca acatattaca ttatgtgtta 113640
agtttccagt gggcccacgg taatgtatta ggaaaaattg actttgacta atgtagccac 113700
tctcatactt atcttagcta gatttcctag atcatttgcc gcaccttcta cgtcagcact 113760
tgcttcttca ctttgtactt agataatgaa accagcttct ttttttaaac cccgtgaaac 113820
aaattctaca gctttttttc ttttgcagct ttcccacgtc tcttagtcat catagaatga 113880
cagagagtta tgtccttgct ctagattaga tttggcctaa gggaacattg tggctgcttt 113940
gttcttcaat ccaggctact gaagttttct ccatgttagc cataagtctg tttcactttg 114000
ttattatttg tgtgttcact gaagtaggac tcttaattat cttcaagtac tttatttttg 114060
cattcacaac ttggctaact gctgaatgca agatgcttag ttttgactta ccttggctct 114120
tgatatgcct tcctcactaa acttaatcat ttctaaaatt tgacttaaaa tgagagatat 114180
gtgactcttt ctttcactca aacacctaga ggtcattgta aggttattat ttggcttaat 114240
ttctatgttg ttctgtctca ggacatagga aggcccaagg ggatggagag agatgtagca 114300
atagctggtt ggtggagcat tcagaacaca cacaacttta ttgattaagt tccacgtatt 114360
atatgggtat ggatagtggc aagtcaaatc aattacaata gtaacatcaa agatcactaa 114420
ccacaggtca ctatcacaga tacaataaca atgaataagt ctgaaatatt gtgagaatta 114480
gtaaaatgtg acacagagac ataaagtgag cacatatttt tgaaaaaatg atgtcaatag 114540
acttgtttga tgcaggattg ccacaaactt ccaatttgaa aacaaaaaac aaacaaaaaa 114600
aacaccaaaa tatgtgaagt gcaataaagt gaagttcaat aaaatgaagt atgccaggaa 114660
taaaaactag caggatcaca ggatcaacct ctacttaaaa gtattagaaa tatggaggta 114720
aatagaagaa atagctaaaa agagttgtaa atgcttgcct ctggaaagca gtaataataa 114780
gcagagaaaa actcattttc aatatgagat ttttgatata atcttatttt tacaactttg 114840

```
tgcataaatg gctttggtaa aaattaaaaa tcaatcatca gactggtatg tctcttatta 114900

atcaacaata aacaataata ttgataccca ggtactacac tgagagcctt gggtgagcct 114960

ccaagtcttg ctggcttcag ataccagaaa gatcacaggg gttaatgcac taagcagact 115020

cttgaggtcc ctgattccag gacttgactc tgggatagca tttctgaacc tgccctcggc 115080

cagaggggag cccattgttc tgaagtttga atcccacctc aggcagaatt caatagaagc 115140

tgattaaagt gcccttgggc cttaaggaaa cattggcagt agtctagcag tactccctgt 115200

gggcctgaag tgttgtggct atgggttgag gctcctttgt atttggaaat gcgagggaag 115260

agtgggaaag acggtcttgt ggtttgcgtg ccacctcagc cacaatatga tagaacacca 115320

ggtagacttt acgagttttg gctctagtct ctgactcctg gatggcatct ctggacccac 115380

atgggacctg ggggacctcg ccaccctgaa aggaaggaca caggccttgc tggcttttct 115440

gcctgctgat tgtagagccc catggccttg agcaaacatt ggcagtagtc agggagtaat 115500

tacagcagac cttgggcaag actcataaat gtgctggctt caggtgtaac ccaatgtagt 115560

catagttctg gatgccacag aggtgcttac gccactccaa acc                   115603


<210> SEQ ID NO 73
<211> LENGTH: 691
<212> TYPE: PRT
<213> ORGANISM: Homo sapiens

<400> SEQUENCE: 73

Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
            100                 105                 110

Leu Pro His Phe Phe Met Gly Tyr Tyr Arg Tyr Ser Lys Glu Thr Asn
        115                 120                 125

Ile Asn Ser Ser Glu Asn Ser Thr Ser Thr Leu Ser Thr Cys Leu Ile
    130                 135                 140

Asn Gln Ile Leu Ser Leu Asn Arg Ala Ser Pro Glu Ile Val Gly Lys
145                 150                 155                 160

Gly Cys Leu Lys Glu Ser Gly Ser Tyr Met Trp Ile Tyr Val Phe Met
                165                 170                 175

Gly Asn Met Leu Arg Gly Ile Gly Glu Thr Pro Ile Val Pro Leu Gly
            180                 185                 190

Leu Ser Tyr Ile Asp Asp Phe Ala Lys Glu Gly His Ser Ser Leu Tyr
        195                 200                 205
```

```
Leu Gly Ile Leu Asn Ala Ile Ala Met Ile Gly Pro Ile Ile Gly Phe
    210                 215                 220

Thr Leu Gly Ser Leu Phe Ser Lys Met Tyr Val Asp Ile Gly Tyr Val
225                 230                 235                 240

Asp Leu Ser Thr Ile Arg Ile Thr Pro Thr Asp Ser Arg Trp Val Gly
                245                 250                 255

Ala Trp Trp Leu Asn Phe Leu Val Ser Gly Leu Phe Ser Ile Ile Ser
            260                 265                 270

Ser Ile Pro Phe Phe Phe Leu Pro Gln Thr Pro Asn Lys Pro Gln Lys
        275                 280                 285

Glu Arg Lys Ala Ser Leu Ser Leu His Val Leu Glu Thr Asn Asp Glu
    290                 295                 300

Lys Asp Gln Thr Ala Asn Leu Thr Asn Gln Gly Lys Asn Ile Thr Lys
305                 310                 315                 320

Asn Val Thr Gly Phe Phe Gln Ser Phe Lys Ser Ile Leu Thr Asn Pro
                325                 330                 335

Leu Tyr Val Met Phe Val Leu Leu Thr Leu Leu Gln Val Ser Ser Tyr
            340                 345                 350

Ile Gly Ala Phe Thr Tyr Val Phe Lys Tyr Val Glu Gln Gln Tyr Gly
        355                 360                 365

Gln Pro Ser Ser Lys Ala Asn Ile Leu Leu Gly Val Ile Thr Ile Pro
    370                 375                 380

Ile Phe Ala Ser Gly Met Phe Leu Gly Gly Tyr Ile Ile Lys Lys Phe
385                 390                 395                 400

Lys Leu Asn Thr Val Gly Ile Ala Lys Phe Ser Cys Phe Thr Ala Val
                405                 410                 415

Met Ser Leu Ser Phe Tyr Leu Leu Tyr Phe Phe Ile Leu Cys Glu Asn
            420                 425                 430

Lys Ser Val Ala Gly Leu Thr Met Thr Tyr Asp Gly Asn Asn Pro Val
        435                 440                 445

Thr Ser His Arg Asp Val Pro Leu Ser Tyr Cys Asn Ser Asp Cys Asn
    450                 455                 460

Cys Asp Glu Ser Gln Trp Glu Pro Val Cys Gly Asn Asn Gly Ile Thr
465                 470                 475                 480

Tyr Ile Ser Pro Cys Leu Ala Gly Cys Lys Ser Ser Ser Gly Asn Lys
                485                 490                 495

Lys Pro Ile Val Phe Tyr Asn Cys Ser Cys Leu Glu Val Thr Gly Leu
            500                 505                 510

Gln Asn Arg Asn Tyr Ser Ala His Leu Gly Glu Cys Pro Arg Asp Asp
        515                 520                 525

Ala Cys Thr Arg Lys Phe Tyr Phe Phe Val Ala Ile Gln Val Leu Asn
    530                 535                 540

Leu Phe Phe Ser Ala Leu Gly Gly Thr Ser His Val Met Leu Ile Val
545                 550                 555                 560

Lys Ile Val Gln Pro Glu Leu Lys Ser Leu Ala Leu Gly Phe His Ser
                565                 570                 575

Met Val Ile Arg Ala Leu Gly Gly Ile Leu Ala Pro Ile Tyr Phe Gly
            580                 585                 590

Ala Leu Ile Asp Thr Thr Cys Ile Lys Trp Ser Thr Asn Asn Cys Gly
        595                 600                 605

Thr Arg Gly Ser Cys Arg Thr Tyr Asn Ser Thr Ser Phe Ser Arg Val
    610                 615                 620

Tyr Leu Gly Leu Ser Ser Met Leu Arg Val Ser Ser Leu Val Leu Tyr
```

-continued

```
625                 630                 635                 640

Ile Ile Leu Ile Tyr Ala Met Lys Lys Lys Tyr Gln Glu Lys Asp Ile
                645                 650                 655

Asn Ala Ser Glu Asn Gly Ser Val Met Asp Glu Ala Asn Leu Glu Ser
            660                 665                 670

Leu Asn Lys Asn Lys His Phe Val Pro Ser Ala Gly Ala Asp Ser Glu
        675                 680                 685

Thr His Cys
    690
```